(12) United States Patent
Wang et al.

(10) Patent No.: US 10,815,476 B2
(45) Date of Patent: Oct. 27, 2020

(54) METHODS AND COMPOSITIONS FOR SYNTHETIC RNA ENDONUCLEASES

(71) Applicant: The University of North Carolina at Chapel Hill, Chapel Hill, NC (US)

(72) Inventors: Zefeng Wang, Chapel Hill, NC (US); Rajarshi Choudhury, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 16/021,892

(22) Filed: Jun. 28, 2018

(65) Prior Publication Data

US 2019/0153429 A1  May 23, 2019

Related U.S. Application Data

(60) Continuation of application No. 15/602,546, filed on May 23, 2017, now abandoned, which is a continuation of application No. 15/353,485, filed on Nov. 16, 2016, now abandoned, which is a division of application No. 13/805,240, filed as application No. PCT/US2011/040933 on Jun. 17, 2011, now Pat. No. 9,499,805.

(60) Provisional application No. 61/356,340, filed on Jun. 18, 2010.

(51) Int. Cl.
| | |
|---|---|
| *C12N 15/10* | (2006.01) |
| *C12Q 1/44* | (2006.01) |
| *C12N 15/86* | (2006.01) |
| *C12N 9/22* | (2006.01) |
| *C12N 9/16* | (2006.01) |
| *A61K 38/46* | (2006.01) |
| *C12N 7/00* | (2006.01) |

(52) U.S. Cl.
CPC .......... *C12N 15/102* (2013.01); *A61K 38/465* (2013.01); *C12N 7/00* (2013.01); *C12N 9/16* (2013.01); *C12N 9/22* (2013.01); *C12N 15/86* (2013.01); *C12Q 1/44* (2013.01); *C07K 2319/85* (2013.01); *C12N 2750/14143* (2013.01); *G01N 2333/08* (2013.01); *G01N 2333/922* (2013.01); *Y02A 50/409* (2018.01); *Y02A 50/411* (2018.01); *Y02A 50/414* (2018.01)

(58) Field of Classification Search
CPC ........ C12N 15/102; C12N 15/86; C12N 7/00; C12N 9/16; C12N 9/22; C12N 2750/14143; A61K 38/465; C12Q 1/44; Y02A 50/409; Y02A 50/414; Y02A 50/411; G01N 2333/922; G01N 2333/08; C07K 2319/85

See application file for complete search history.

(56) References Cited

U.S. PATENT DOCUMENTS

| | | |
|---|---|---|
| 2003/0219382 A1 | 11/2003 | Young et al. |
| 2009/0081756 A1 | 3/2009 | Katahira |
| 2013/0129701 A1 | 5/2013 | Wang et al. |
| 2013/0323813 A1 | 12/2013 | Filipovska et al. |

OTHER PUBLICATIONS

Gibbs, C., Clinical and Experimental Pharmacology and Physiology 30:598-603, 2003.*
Silva et al., Current Gene Therapy 11:11-27, 2011.*
Adams et al. "PHENIX: a comprehensive Python-based system for macromolecular structure solution" *Acta Crystallographica Section D: Biological Crystallography* D66:213-221 (2010).
Arambula et al. "A simple ligand that selectively targets CUG trinucleotide repeats and inhibits MBNL protein binding" PNAS 106(38):16068-16073 (2009).
Argos, Patrick "An Investigation of Oligopeptides Linking Domains in Protein Tertiary Structures and Possible Candidates for General Gene Fusion" *Journal of Molecular Biology* 211:943-958 (1990).
Auweter et al. "Sequence-specific binding of single-stranded RNA: is there a code for recognition?" *Nucleic Acids Research* 34(17):4943-4959 (2006).
Bartel "MicroRNA Target Recognition and Regulatory Functions" *Cell* 136(2):215-233 (2009).
Branden et al. "Prediction, Engineering, and Design of Protein Structures" *Introduction to Protein Structure* Chapter 16 (p. 247) (1991).
Brukner et al. "Cellular Proteins Prevent Antisense Phosphorothioate Oligonucleotide (SdT18) to Target Sense RNA (rA18): Development of a New in Vitro Assay" *Biochemistry* 39:11463-11466 (2000).
Bugiani et al. "Clinical and molecular findings in children with complex I deficiency" *Biochimica et Biophysica Acta* 1659:136-147 (2004).
Carthew et al. "Origins and Mechanisms of miRNAs and siRNAs" *Cell* 136(4):642-655 (2009).
Cassiday et al. "In Vivo Recognition of an RNA Aptamer by Its Transcription Factor Target" *Biochemistry* 40:2433-2438 (2001).
Cathomen et al. "Zinc-finger Nucleases: The Next Generation Emerges" *Molecular Therapy* 16(7):1200-1207 (2008).
Champoux et al. "Ribonuclease H: Properties, Substrate Specificity, and Roles in Retroviral Reverse Transcription" *FEBS Journal* 276(6):1506-1516 (2009).
Charlet et al. "Loss of the Muscle-Specific Chloride Channel in Type 1 Myotonic Dystrophy Due to Misregulated Alternative Splicing" *Molecular Cell* 10:45-53 (2002).
Chen et al. "Identification of Synaptic Targets of *Drosophila* Pumili" *PLoS Computational Biology* 4(2):e1000026 (2008).
Cheong et al. "Engineering RNA sequence specificity of Pumilio repeats" *Proceedings of the National Academy of Sciences* 103(37):13635-13639 (2006).

(Continued)

*Primary Examiner* — Delia M Ramirez
(74) *Attorney, Agent, or Firm* — Myers Bigel, P.A.

(57) ABSTRACT

The present invention provides sequence specific restriction enzymes for site-specific cleavage of RNA, as well as methods of their use.

19 Claims, 40 Drawing Sheets

Specification includes a Sequence Listing.

(56) References Cited

OTHER PUBLICATIONS

Chomyn, Anne "In vivo labeling and analysis of human mitochondrial translation products" *Methods in Enzymology* 264:197-211 (1996) (Publisher Summary Only).

Choo et al. "In vivo repression by a site-specific DNA-binding protein designed against an oncogenic sequence" *Nature* 372:642-645 (1994).

Choudhury et al. "Manipulation of RNA Using Engineered Proteins with Customized Specificity" *Systems Biology of RNA Binding Proteins, Advances in Experimental Medicine and Biology* 825(Chapter 6):199-225 (2014).

Crittenden et al. "A conserved RNA-binding protein controls germline stem cells in *Caenorhabditis elegans*" *Nature* 417:660-663 (2002).

Danna et al. "Specific Cleavage of Simian Virus 40 DNA by Restriction Endonuclease" *Proceedings of the National Academy of Sciences* 68(12):2913-2917 (1971).

Das et al. "Macromolecular Modeling with Rosetta" *Annual Review of Biochemistry* 77:363-382 (2008).

Dong et al. "Specific and Modular Binding Code for Cytosine Recognition in Pumilio/FBF (PUF) RNA-binding Domains" *The Journal of Biological Chemistry* 286(30):26732-26742 (2011).

Du et al. "Aberrant alternative splicing and extracellular matrix gene expression in mouse models of myotonic dystrophy" *Nature Structural & Molecular Biology* 17(2):187-193 (2010).

Dubnau et al. "The staufen/pumilio Pathway Is Involved in *Drosophila* Long-Term Memory" *Current Biology* 13:286-296 (2003).

Eberle et al. "SMG6 promotes endonucleolytic cleavage of nonsense mRNA in human cells" *Nature Structural & Molecular Biology* 16(1):49-55 (2009).

Edwards et al. "Structure of Pumilio Reveals Similarity between RNA and Peptide Binding Motifs" *Cell* 105:281-289 (2001).

Emsley et al. "Coot: model-building tools for molecular graphics" *Acta Crystallographica Section D: Biological Crystallography* D60:2126-2132 (2004).

Fardaei et al. "Three proteins, MBNL, MBLL and MBXL, co-localize in vivo with nuclear foci of expanded-repeat transcripts in DM1 and DM2 cells" *Human Molecular Genetics* 11(7):805-814 (2002).

Filipovska et al. "Building a Parallel Metabolism within the Cell" *ACS Chemical Biology* 3(1):51-63 (2008).

Filipovska et al. "A universal code for RNA recognition by PUF proteins" *Nature Chemical Biology* 7:425-427 (2011).

Fox et al. "Detecting ligands and dissecting nuclear receptor-signaling pathways using recombinant strains of the yeast *Saccharomyces cerevisiae*" *Nature Protocols* 3(4):637-645 (2008).

Gardlik et al. "Vectors and delivery systems in gene therapy" *Med Sci Monit* 11(4) RA110-121 (2005).

Gareiss et al. "Dynamic Combinatorial Selection of Molecules Capable of Inhibiting the (CUG) Repeat RNA—MBNL1 Interaction in vitro: Discovery of Lead Compounds Targeting Myotonic Dystrophy (DM1)" *Journal of the American Chemical Society* 130(48):16254-16261 (2008).

GenBank Accession No. AF315591.1 *Homo sapiens Pumilio 2 (PUMH2) mRNA, complete cds* Dec. 2, 2002.

GenBank Accession No. AF315592.1 *Homo sapiens Pumilio 1 (PUMH1) mRNA, complete cds* Dec. 2, 2002.

GenBank Accession No. XP_002952190.1 *hypothetical protein VOLCADRAFT_105407* [*Volvox carteri f. nagariensis*] Aug. 13, 2010 (2 pages).

George et al. "An analysis of protein domain linkers: their classification and role in protein folding" *Protein Engineering* 15(11):871-879 (2003).

Gerber et al. "Extensive Association of Functionally and Cytotopically Related mRNAs with PUF Family RNA-Binding Proteins in Yeast" *PLoS Biology* 2(3):0342-0354 (2004).

Gietz et al. "Transformation of Yeast by Lithium Acetate/Single-Stranded Carrier DNA/Polyethylene Glycol Method" *Methods in Enzymology* 350:87-96 (2002).

Glavan et al. "Structures of the PIN domains of SMG6 and SMG5 reveal a nuclease within the mRNA surveillance complex" *The EMBO Journal* 25:5117-5125 (2006).

Glisovic et al. "RNA-binding proteins and post-transcriptional gene regulation" *FEBS Letters* 582(14):1977-1986 (2008).

Griffith et al. "Measuring (β-Galactosidase Activity in Bacteria: Cell Growth, Permeabilization, and Enzyme Assays in 96-Well Arrays" *Biochemical and Biophysical Research Communications* 290:397-402 (2002).

Gupta et al. "Structures of Human Pumilio with Noncognate RNAs Reveal Molecular Mechanisms for Binding Promiscuity" *Structure* 16:549-557 (2008).

Harper et al. "VEGF-A splicing: the key to anti-angiogenic therapeutics?" *Nature Reviews Cancer* 8(11):880-887 (2008).

Hook et al. "RNA-protein interactions in the yeast three-hybrid system: Affinity, sensitivity, and enhanced library screening" *RNA* 11:227-233 (2005).

Horwich et al. "A leader peptide is sufficient to direct mitochondrial import of a chimeric protein" *The EMBO Journal* 4(5):1129-1135 (1985).

Houdebine "The methods to generate transgenic animals and to control transgene expression" *Journal of Biotechnology* 98:145-160 (2002).

Huntzinger et al. "SMG6 is the catalytic endonuclease that cleaves mRNAs containing nonsense codons in metazoan" *RNA* 14:2609-2617 (2008).

Inagaki et al. "Robust Systemic Transduction with AAV9 Vectors in Mice: Efficient Global Cardiac Gene Transfer Superior to That of AAV8" *Molecular Therapy* 14(1):45-53 (2006).

International Preliminary Report on Patentability corresponding to International Patent Application No. PCT/US2011/040933 (8 pages) (dated Jan. 3, 2013).

International Search Report and the Written Opinion of the International Searching Authority corresponding to International Patent Application No. PCT/US2011/040933 (11 page) (dated Feb. 10, 2012).

Iost et al. "The stability of *Escherichia coli* lacZ mRNA depends upon the simultaneity of its synthesis and translation" *The EMBO Journal* 14(13):3252-3261 (1995).

Isaacs et al. "Engineered riboregulators enable post-transcriptional control of gene expression" *Nature Biotechnology* 22(7): 841-847 (2004).

Isaacs et al. "RNA synthetic biology" *Nature Biotechnology* 24(5):545-554 (2006).

Ito et al. "Toward a protein-protein interaction map of the budding yeast: A comprehensive system to examine two-hybrid interactions in all possible combinations between the yeast proteins" *Proceedings of the National Academy of Sciences* 97(3):1143-1147 (2000).

Janssen et al. "Spectrophotometric Assay for Complex I of the Respiratory Chain in Tissue Samples and Cultured Fibroblasts" *Clinical Chemistry* 53(4):729-734 (2007).

Jiang et al. "Myotonic dystrophy type 1 is associated with nuclear foci of mutant RNA, sequestration of muscleblind proteins and deregulated alternative splicing in neurons" *Human Molecular Genetics* 13(24):3079-3088 (2004).

Johnston, Daniel St. "Moving Messages: The Intracellular Localization of mRNAs" *Nature Reviews Molecular Cell Biology* 6:363-375 (2005).

Judge et al. "Overcoming the Innate Immune Response to Small Interfering RNA" *Human Gene Therapy* 19:111-124 (2008).

Kalsotra et al. "A postnatal switch of CELF and MBNL proteins reprograms alternative splicing in the developing heart" *Proceedings of the National Academy of Sciences* 105(51):20333-20338 (2008).

Kanadia et al. "Reversal of RNA missplicing and myotonia after muscleblind overexpression in a mouse poly(CUG) model for myotonic dystrophy" *Proceedings of the National Academy of Sciences* 103(31):11748-11753 (2006).

Kappel et al. "Regulating gene expression in transgenic animals" *Current Opinion in Biotechnology* 3:548-553 (1992).

Kedde et al. "A Pumilio-induced RNA structure switch in p27-3' UTR controls miR-221 and miR-222 accessibility" *Nature Cell Biology* 12(10):1014-1021 (2010).

(56) References Cited

OTHER PUBLICATIONS

Kimura et al. "Altered mRNA splicing of the skeletal muscle ryanodine receptor and sarcoplasmic/endoplasmic reticulum $Ca^{2+}$-ATPase in myotonic dystrophy type 1" *Human Molecular Genetics* 14(15):2189-2200 (2005).
Koh et al. "A single *C. elegans* PUF protein binds RNA in multiple modes" *RNA* 15:1090-1099 (2009).
Koh et al. "Stacking interactions in PUF-RNA complexes" *RNA* 17:718-727 (2011).
Kornegay et al. "Widespread Muscle Expression of an AAV9 Human Mini-dystrophin Vector After Intravenous Injection in Neonatal Dystrophin-deficient Dogs" *Molecular Therapy* 18(8):1501-1508 (2010).
Kujoth et al. "The Role of Mitochondrial DNA Mutations in Mammalian Aging" *PLoS Genetics* 3(2):0161-0173 (2007).
Kuyumcu-Martinez et al. "Increased steady state levels of CUGBP1 Myotonic Dystrophy 1 are due to PKC-mediated hyperphosphorylation" *Molecular Cell* 28(1):68-78 (2007).
Langlois et al. "Cytoplasmic and Nuclear Retained DMPK mRNAs Are Targets for RNA Interference in Myotonic Dystrophy Cells" *The Journal of Biological Chemistry* 280(17):16949-16954 (2005).
Lee et al. "Pathogenic mechanisms of myotonic dystrophy" *Biochemical Society Transactions* 37:1281-1286 (2009).
Letunic et al. "SMART 6: recent updates and new developments" *Nucleic Acids Research* 37:D229-D232 (2009).
Lewis et al. "Conserved Seed Pairing, Often Flanked by Adenosines, Indicates that Thousands of Human Genes are MicroRNA Targets" *Cell* 120:15-20 (2005).
Li et al. "Synthetic muscle promoters: activities exceeding naturally occurring regulatory sequences" *Nature Biotechnology* 17:241-245 (1999).
Liquori et al. "Myotonic Dystrophy Type 2 Caused by a CCTG Expansion in Intron 1 of ZNF9" *Science* 293:864-867 (2001).
Lu et al. "Alternate Modes of Cognate RNA Recognition by Human Pumilio Proteins" *Structure* 19(3):361-367 (2011).
Lund et al. "Substrate Selectivity of Exportin 5 and Dicer in the Biogenesis of MicroRNAs" *Cold Spring Harbor Symposia on Quantitative Biology* 71:59-66 (2006).
Lunde et al. "RNA-Binding Proteins: Modular Design for Efficient Function" *Nature Reviews* 8:479-490 (2007).
MacKay et al. "The prospects for designer single-stranded RNA-binding proteins" *Nature Structural & Molecular Biology* 18(3):256-261 (2011).
MacRae et al. "Ribonuclease revisited: structural insights into ribonuclease III family enzymes" *Current Opinion in Structural Biology* 17:138-145 (2007).
Mahadevan et al. "Myotonic Dystrophy Mutation: An Unstable CTG Repeat in the 3' Untranslated Region of the Gene" *Science* 255:1253-1255 (1992).
Malfatti et al. "Novel mutations of ND genes in complex I deficiency associated with mitochondrial encephalopathy" *Brain* 130:1894-1904 (2007).
Mankodi et al. "Myotonic Dystrophy in Transgenic Mice Expressing an Expanded CUG Repeat" *Science* 289:1769-1772 (2000).
Mankodi et al. "Expanded CUG Repeats Trigger Aberrant Splicing of ClC-1 Chloride Channel Pre-mRNA and Hyperexcitability of Skeletal Muscle in Myotonic Dystrophy" *Molecular Cell* 10:35-44 (2002).
McCoy et al. "Phaser crystallographic software" *Journal of Applied Crystallography* 40:658-674 (2007).
Miller et al. "Recruitment of human muscleblind proteins to $(CUG)_n$ expansions associated with myotonic dystrophy" *The EMBO Journal* 19(17):4439-4448 (2000).
Mulders et al. "Triplet-repeat oligonucleotide-mediated reversal of RNA toxicity in myotonic dystrophy" *Proceedings of the National Academy of Sciences* 106(33):13915-13920 (2009).
Mullins et al. "Transgenesis in Nonmurine Species" *Hypertension* 22(4):630-633 (1993).
Murtola et al. "PNAzymes That Are Artificial RNA Restriction Enzymes" *Journal of the American Chemical Society* 132(26):8984-8990 (2010).
Nilsen "The spliceosome: the most complex macromolecular machine in the cell?" *BioEssays* 25:1147-1149 (2003).
Nowotny et al. "Specific Recognition of RNA/DNA Hybrid and Enhancement of Human RNase H1 Activity by HBD" *The EMBO Journal* 27:1172-1181 (2008).
Opperman et al. "A single spacer nucleotide determines the specificities of two mRNA regulatory proteins" *Nature Structural & Molecular Biology* 12(11):945-951 (2005).
Otwinowski et al. "Processing of X-Ray Diffraction Data Collected in Oscillation Mode" *Methods in Enzymology* 276:307-326 (1997).
Ozawa et al. "Imaging dynamics of endogenous mitochondrial RNA in single living cells" *Nature Methods* 4(5):413-419 (2007).
Philips et al. "Disruption of Splicing Regulated by a CUG-Binding Protein in Myotonic Dystrophy" *Science* 280:737-741 (1998).
Phillips "The challenge of gene therapy and DNA delivery" *J. Pharm. Pharmacology* 53:1169-1174 (2001).
Prosite Accession No. PS50302 PUM Jan. 2004 (2 pages).
Qiu et al. "The anti-angiogenic isoforms of VEGF in health and disease" *Biochemical Society Transactions* 37(Pt. 6):1207-1213 (2009).
Quenault et al. "PUF proteins: repression, activation and mRNA localization" *Trends in Cell Biology* 21(2):104-112 (2011) (Abstract Only).
Rackham et al. "A network of orthogonal ribosome mRNA pairs" *Nature Chemical Biology* 1(3):159-166 (2005).
Sanjanwala et al. "DNA polymerase III gene of *Bacillus subtilis*" *Proceedings of the National Academy of Sciences* 86:4421-4424 (1989).
Savkur et al. "Aberrant regulation of insulin receptor alternative splicing is associated with insulin resistance in myotonic dystrophy" *Nature Genetics* 29:40-47 (2001).
Schultz et al. "SMART, a simple modular architecture research tool: Identification of signaling domains" *Proceedings of the National Academy of Sciences* 95:5857-5864 (1998).
Schwarz et al. "Asymmetry in the Assembly of the RNAi Enzyme Complex" *Cell* 115:199-208 (2003).
Schweers et al. "The *Drosophila melanogaster* Translational Repressor Pumilio Regulates Neuronal Excitability" *Genetics* 161:1177-1185 (2002).
Scott, William "Ribozymes" *Current Opinion in Structural Biology* 17:280-286 (2007).
Seffernick et al. "Melamine Deaminase and Atrazine Chlorohydrolase: 98 Percent Identical but Functionally Different" *Journal of Biological Bacteriology* 183(8):2405-2410 (2001).
Sengupta et al. "A three-hybrid system to detect RNA-protein interactions in vivo" *Proceedings of the National Academy of Sciences* 93:8496-8501 (1996).
Shukla et al. "Precise genome modification in the crop species *Zea mays* using zinc-finger nucleases" *Nature* 459:437-443 (2009).
Silverman, Scott "Survey and Summary in vitro selection, characterization, and application of deoxyribozymes that cleave RNA" *Nucleic Acids Research* 33(19):6151-6163 (2005).
Spassov et al. "Cloning and comparative sequence analysis of PUM1 and PUM2 genes, human members of the Pumilio family of RNA-binding proteins" *Gene* 299:195-204 (2002).
Spassov et al. "The PUF Family of RNA-binding Proteins: Does Evolutionarily Conserved Structure Equal Conserved Function?" *IUBMB Life* 55(7):359-366 (2003).
Stein, C.A. "Does antisense exist?" *Nature Medicine* 1(11):1119-1121 (1995).
Stumpf et al. "Analysis of RNA-Protein Interactions Using a Yeast Three-Hybrid System" *Methods in Enzymology* 449:295-315 (2008).
Takeshita et al. "Crystal structure of the PIN domain of human telomerase-associated protein EST1A" *Proteins* 68:980-989 (2007).
Takeuchi et al. "Innate immunity to virus infection" *Immunological Reviews* 227:75-86 (2009).
Tam et al. "The Puf family of RNA-binding proteins in plants: phylogeny, structural modeling, activity and subcellular localization" *BMC Plant Biology* 10(44):1-19 (2010).

(56) References Cited

OTHER PUBLICATIONS

Taylor et al. "Mitochondrial DNA Mutations in Human Disease" *Nature Reviews Genetics* 6(5):389-402 (2005).
Thomson et al. "Nop9 is an RNA binding protein present in pre-40S ribosomes and required for 18S rRNA synthesis in yeast" *RNA* 13:2165-2174 (2007).
Tilsner et al. "Live-cell imaging of viral RNA genomes using a Pumilio-based reporter" *The Plant Journal* 57:758-770 (2009).
Tomari et al. "Perspective: machines for RNAi" *Genes & Development* 19:517-529 (2005).
Turner et al. "The myotonic dystrophies: diagnosis and management" *Journal of Neurology, Neurosurgery, and Psychiatry* 81:358-367 (2010).
Tuschl et al. "Targeted mRNA degradation by double-stranded RNA in vitro" *Genes & Development* 13:3191-3197 (1999).
Ullu et al. "RNA interference in protozoan parasites" *Cellular Microbiology* 6(6):509-519 (2004).
Uniprot Accession No. C8SIZ9 "Cation Diffusion Facilitator Family Transporter" (1 page) (Nov. 3, 2009).
Unjprot Accession No. Q14671—PUM1_HUMAN *Pumilio homolog 1* (Feb. 1, 2004).
Uniprot Accession No. Q86US8—EST1A_HUMAN *Telomerase-binding protein EST1A* (May 23, 2004).
Wang et al. "Crystal Structure of a Pumilio Homology Domain" *Molecular Cell* 7:855-865 (2001).
Wang et al. "Adeno-associated virus serotype 8 efficiently delivers genes to muscle and heart" *Nature Biotechnology* 23(3):321-328 (2005).
Wang et al. "Alternative Isoform Regulation in Human Tissue Transcriptomes" *Nature* 456(7221):470-476 (2008).
Wang et al. "Engineering splicing factors with designed specificities" *Nature Methods* 6(11):825-832 (2009).
Wang et al. "Modular Recognition of RNA by a Human Pumilio-Homology Domain" *Cell* 6110:501-512 (2002).
Wang et al. "Structural basis for specific recognition of multiple mRNA targets by a PUF regulatory protein" *Proceedings of the National Academy of Sciences* 106(48):20186-20191 (2009).

Wang et al. "Systemic Human Minidystrophin Gene Transfer Improves Functions and Life Span of Dystrophin and Dystrophin/Utrophin-Deficient Mice" *Journal of Orthopaedic Research* 27:421-426 (2009).
Wang et al. "Correcting human mitochondrial mutations with targeted RNA import" *Proceedings of the National Academy of Sciences* 109(13):4840-4845 (2012).
Wang et al. "Engineered proteins with Pumilio/fem-3 mRNA binding factor scaffold to manipulate RNA metabolism" *FEBS Journal* 280:3755-3767 (2013).
Wheeler et al. "Myotonic dystrophy: RNA-mediated muscle disease" *Current Opinion in Neurology* 20(5):572-576 (2007) (Abstract Only).
Wheeler et al. "Reversal of RNA Dominance by Displacement of Protein Sequestered on Triplet Repeat RNA" *Science* 325:336-339 (2009).
Wickens et al. "A PUF family portrait: 3'UTR regulation as a way of life" *Trends in Genetics* 18(3):150-157 (2002).
Witkowski et al. "Conversion of a β-Ketoacyl Synthase to a Malonyl Decarboxylase by Replacement of the Active-Site Cysteine with Glutamine" *Biochemistry* 38:11643-11650 (1999).
Ye et al. "nanos and pumilio Are Essential for Dendrite Morphogenesis in *Drosophila* Peripheral Neurons" *Current Biology* 14:314-321 (2004).
Yoshida, Hiroshi "The Ribonuclease T1 Family" *Methods in Enzymology* 341:28-41 (2001).
Zamore et al. "The Pumilio protein binds RNA through a conserved domain that defines a new class of RNA-binding proteins" *RNA* 3:1421-1433 (1997).
Zenklusen et al. "Single-RNA counting reveals alternative modes of gene expression in yeast" *Nature Structural & Molecular Biology* 15(12):1263-1271 (2008).
Zhu et al. "Sustained Whole-Body Functional Rescue in Congestive Heart Failure and Muscular Dystrophy Hamsters by Systemic Gene Transfer" *Circulation* 112:2650-2659 (2005).
Zhu et al. "A 5' cytosine binding pocket in Puf3p specifies regulation of mitochondrial mRNAs" *Proceedings of the National Academy of Sciences* 106(48):20192-20197 (2009).
Zuckermann et al. "A Hybrid Sequence-Selective Ribonuclease S" *Journal of the American Chemical Society* 110(19):6592-6594 (1988).

\* cited by examiner

Fig. 1
A
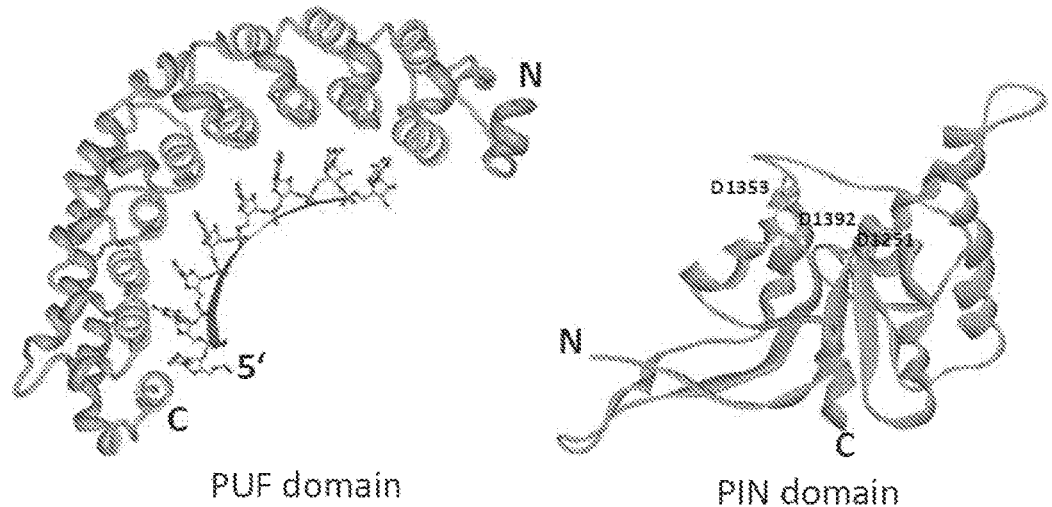
PUF domain    PIN domain
B 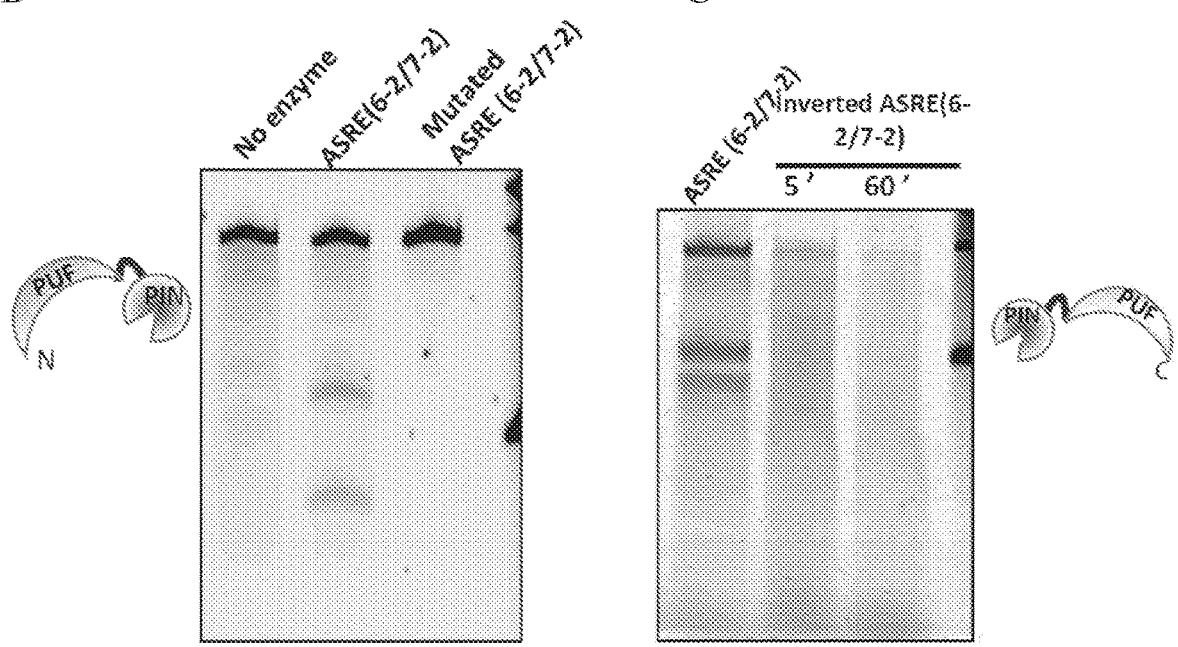 C

Fig. 2
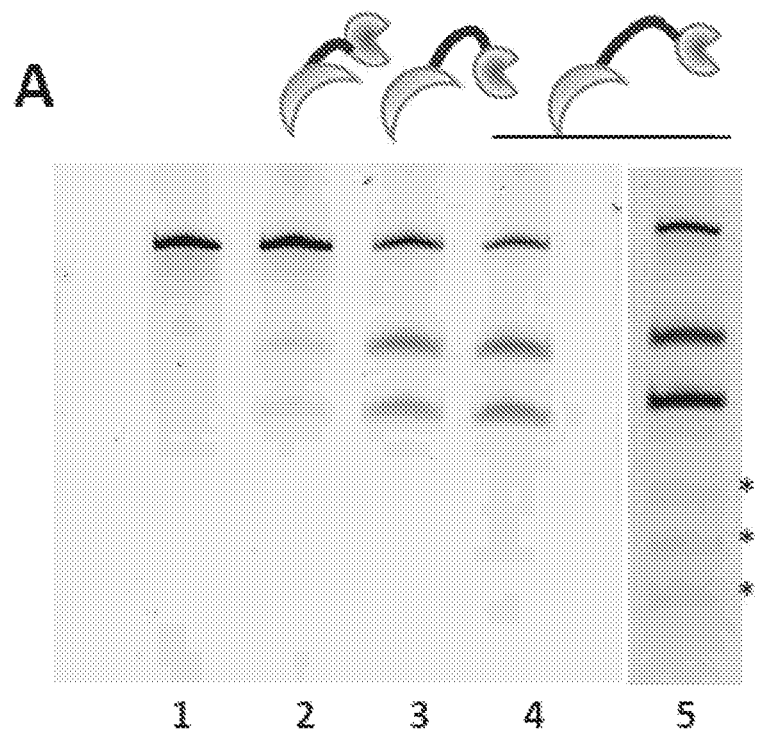
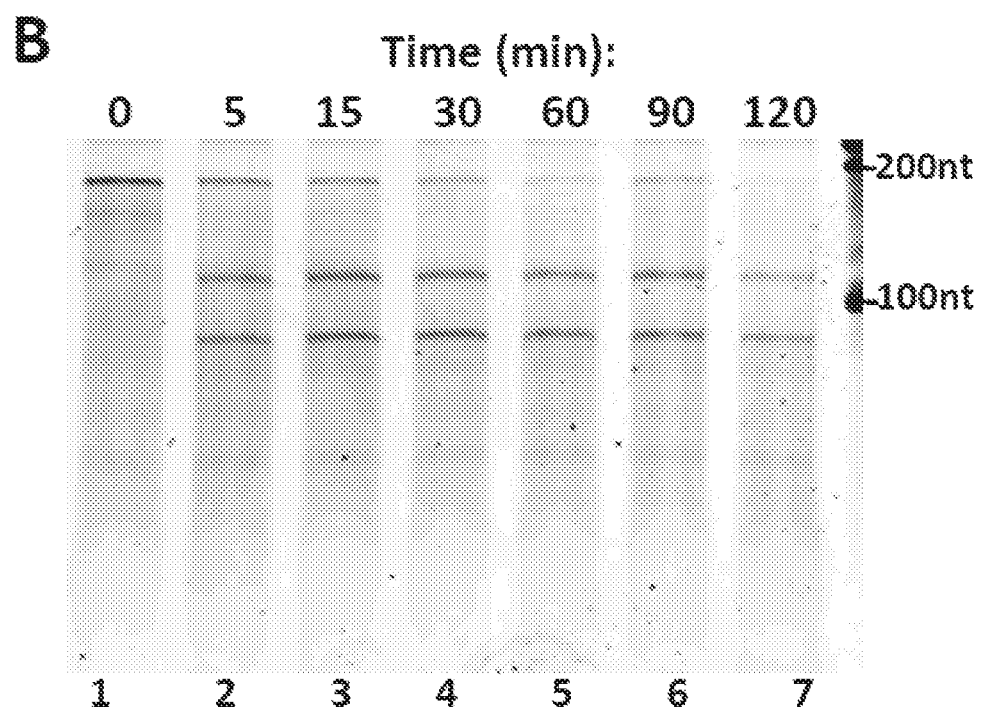

Fig. 2
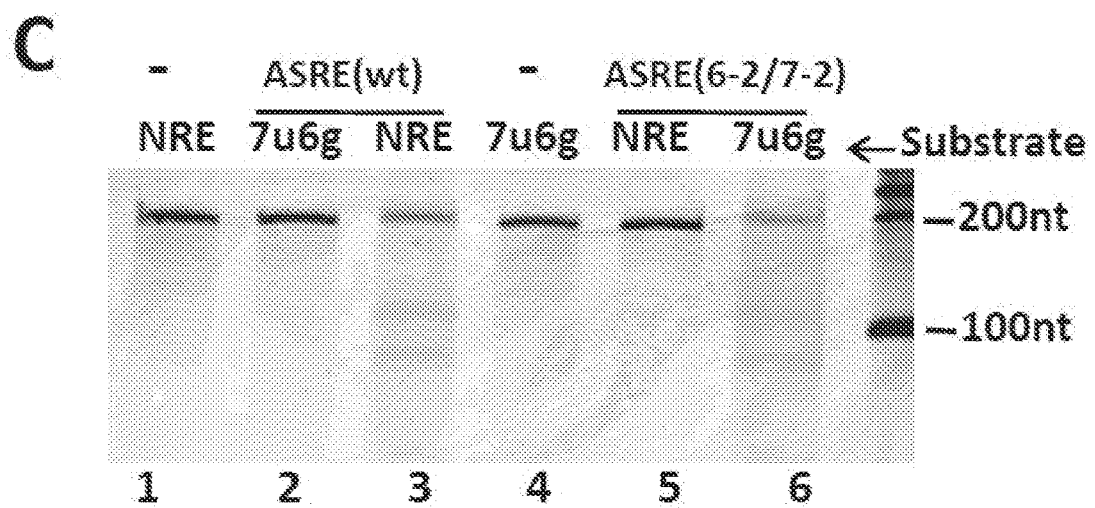
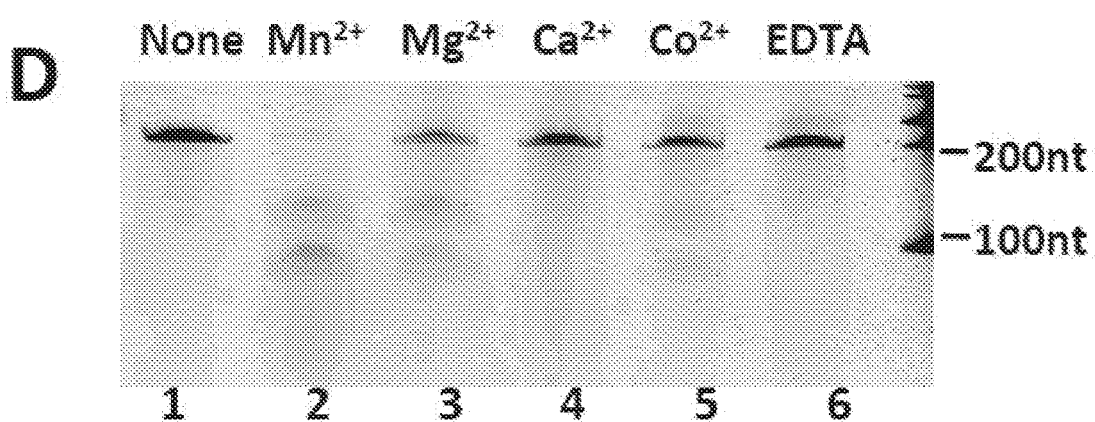
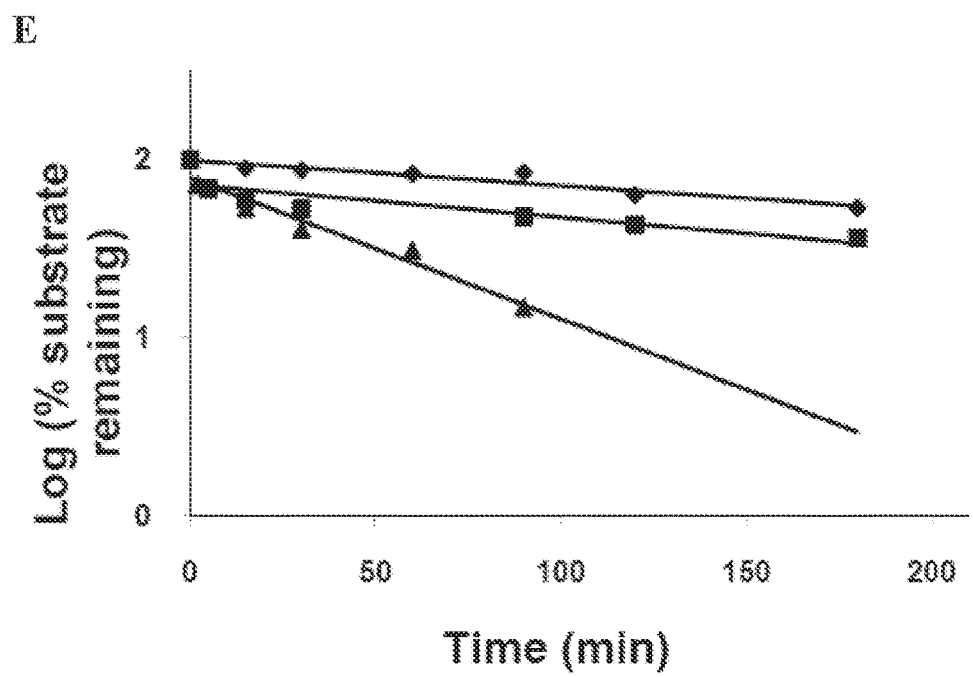

Fig. 3
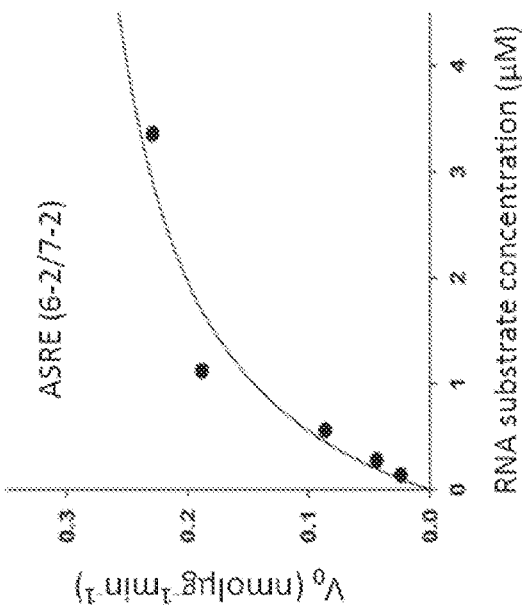
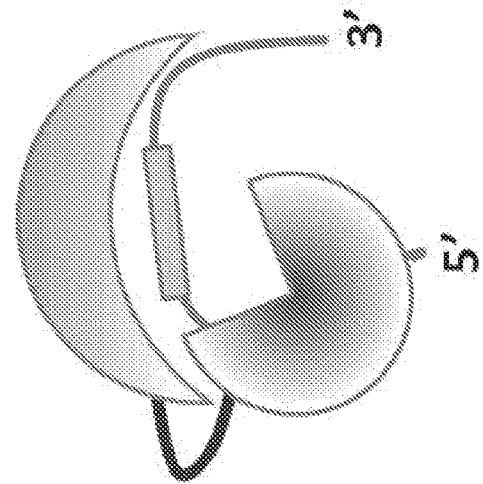
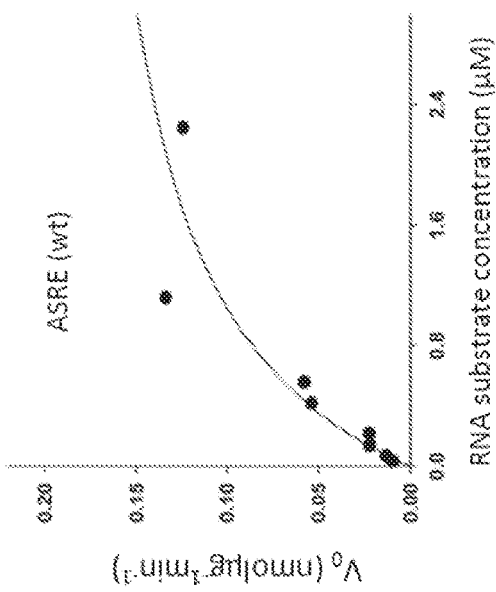
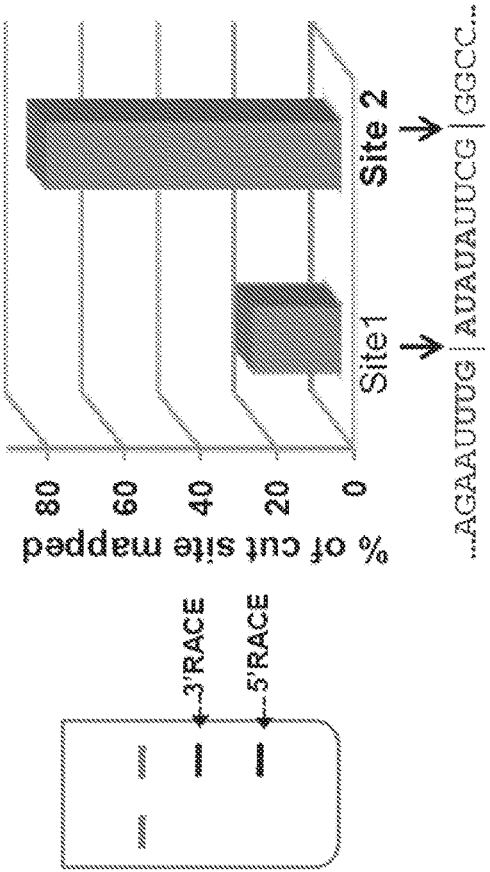

Fig. 5

```
                              10         20         30         40
hpum1            GRSRLLEDFRNNRYPNLQLREIAGHIMEFSQDQHGSRFIQLKLERA
Mpum1            GRSRLLEDFRNNRYPNLQLREIAGHIMEFSQDQHGSRFIQLKLERA
Ratpum1          GRSRLLEDFRNNRYPNLQLREIAGHIMEFSQDQHGSRFIQLKLERA
hpum2            GRSRLLEDFRNNRFPNLQLRDLIGHIVEFSQDQHGSRFIQQKLERA
Mpum2            GRSRLLEDFRNNRFPNLQLRDLIGHIVEFSQDQHGSRFIQQKLERA
Dspum1           GRSRLLEDFRNNRYPNLQLRDLANHIVEFSQDQHGSRFIQQKLERA
Clustal Consensus 110        120        130        140
hpum1            LALQMYGCRVIQKALEFIPSDQQ--NEMVRELDGHVLKCVKDQNGN
Mpum1            LALQMYGCRVIQKALEFIPSDQQVNEMVRELDGHVLKCVKDQNGN
Ratpum1          LALQMYGCRVIQKALEFIPSDQQVNEMVRELDGHVLKCVKDQNGN
hpum2            LALQMYGCRVIQKALESIPSDQQ--SEMVRELDGHVLKCVKDQNGN
Mpum2            LALQMYGCRVIQKALESIPSDQQVSEMVRELDGHVLKCVKDQNGN
Dspum1           LALQMYGCRVIQKALESIPFEQQ--QEIVMELDGHVLKCVKDQNGN
Clustal Consensus 210        220        230        240
hpum1            LEELHQHTEQLVQDQYGNYVIQHVLEHGRPEDKSKIVAEIRGNVLV
Mpum1            LEELHQHTEQLVQDQYGNYVIQHVLEHGRPEDKSKIVAEIRGNVLV
Ratpum1          LEELHQHTEQLVQDQYGNYVIQHVLEHGRPEDKSKIVAEIRGNVLV
hpum2            LEELHQHTEQLVQDQYGNYVIQHVLEHGRPEDKSKIVSEIRGKVLA
Mpum2            LEELHQHTEQLVQDQYGNYVIQHVLEHGRPEDKSKIVSEIRGKVLA
Dspum1           LDELHEHTEQLIQDQYGNYVIQHVLEHGKQEDKSILNSVRGKVLV
Clustal Consensus 310        320        330        340
hpum1            QKMIDVAEPGQRKIVMHKIRPHIATLRKYTYGKHILAKLEKYYMKN
Mpum1            QKMIDVAEPGQRKIVMHKIRPHIATLRKYTYGKHILAKLEKYYMKN
Ratpum1          QKMIDVAEPGQRKIVMHKIRPHIATLRKYTYGKHILAKLEKYYMKN
hpum2            QKMIDMAEPQQRKIMMHKIRPHITTLRKYTYGKHILAKLEKYYIKN
Mpum2            QKMIDMAEPQQRKIMMHKIRPHITTLRKYTYGKHILAKLEKYYLKN
Dspum1           QKMIDVSEPTQLKLMKIRKNMALRKYTYGKHIAKLEKYYMKN
Clustal Consensus 410        420        430        440
hpum1            ............................................VDLG.........
Mpum1            ..........................................VDLGPICGPPNG
Ratpum1          ..........................................VDLGPICGPPNG
hpum2            ..........................................PDLGPIGGPPNGML
Mpum2            ..........................................PDLGPIGGPPNGML
Dspum1           CSVQENGSAMVVEPSSPDASESSSVVSGAVNSSLGPIGPPTNGNV
Clustal Consensus
```

Fig. 6

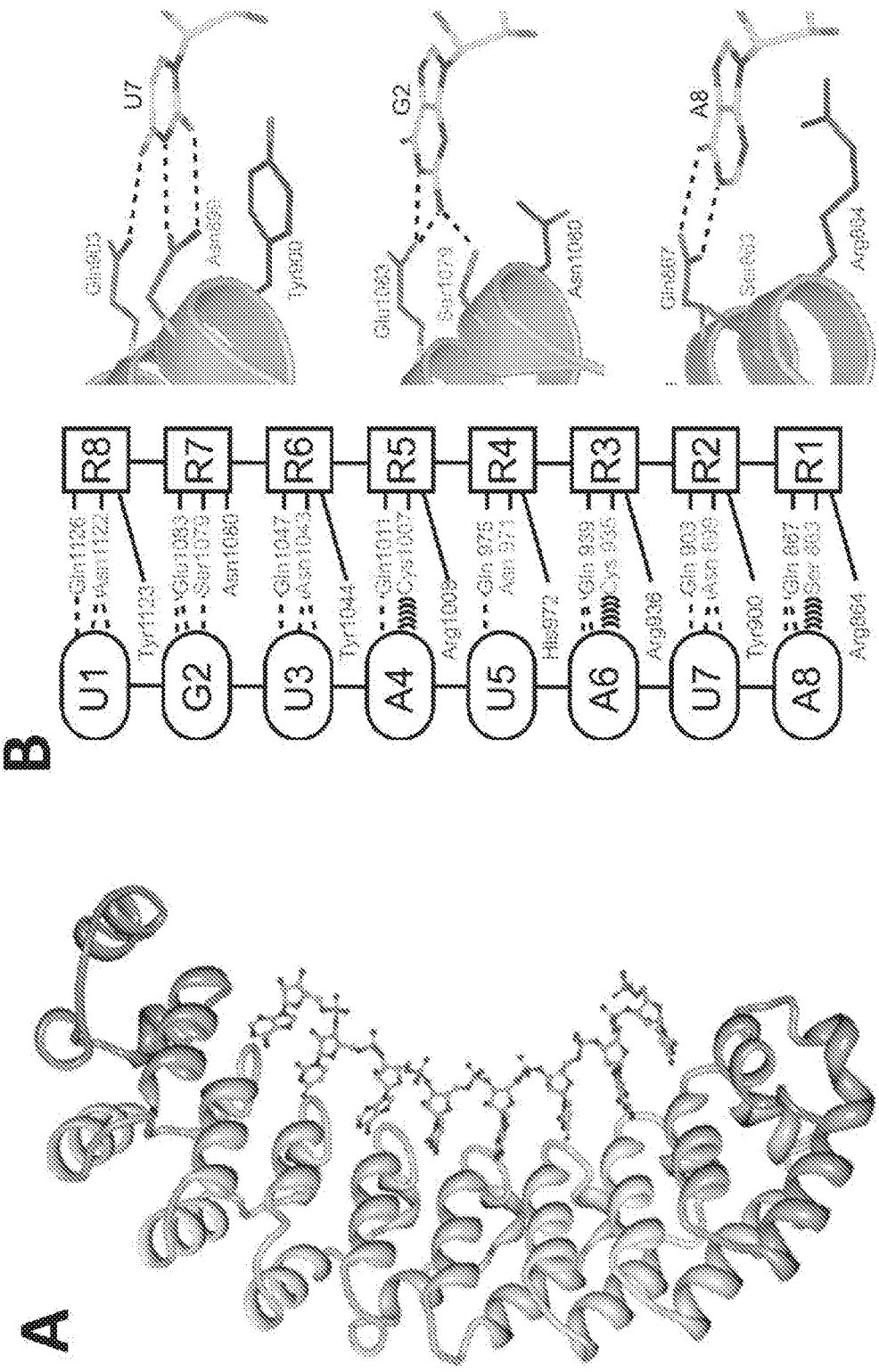

Fig. 8

```
hu_pin             QMELEIRPLFLVPDTNGFIDHLASLARL-L
Ms_pin             QMELEIRPLFLVPDTNGFIDHLASLARL-L
Ce_pin             -TTIVIHPEYLIPDTNVLIGDLQLMKNLLE
Dm_pin             -IYIEVRPRYLLPDTNCFIDCLEDFEKLST
Clustal Consensus    : :* :*:****  :*. *   :  .* hu_pin             ESRK---YILVVPLIVINELDGLAKGQETD
Ms_pin             ESRK---YILVVPLIVINELDGLAKGQETD
Ce_pin             TAQKNKKFQILVPTTVLDELQYIAKLSPLD
Dm_pin             EFKR---YTLIIPLTVVKELDGLSKGVKLD
Clustal Consensus   ::     : :::*   *:.**: ::*    * hu_pin             HRAGG--------YARVVQEKARKSIEFLEQ
Ms_pin             HRAGG--------YARVVQEKARKSIEFLER
Ce_pin             SKSNE-----AHDPERISKAKIAVAWLKE
Dm_pin             SYRSSKQTQRIHHFDEVSSRAKKSLEFIKS
Clustal Consensus    . .       :       .;*:  :: :::

hu_pin             RFESRDSCLRALTSRGNELESIAFRSEDIT
Ms_pin             RFESRDSCLRALTSRGNELESIAFRSEDIT
Ce_pin             QAKQKTGHLYTLTTTGKRLPTLSIVSEDLE
Dm_pin             ----AKGNVKCATTKGSFVNASVFAL--VE
Clustal Consensus          . :   *: *.  :  :     :

hu_pin             GQLGN-NDDLILSCCLHYCKDKAKDFMPAS
Ms_pin             GQLGN-NDDLILSCCLHYCKDKAKDYMPTS
Ce_pin             GHEMTTNDDMILNSALRWSESLPGSTAPSA
Dm_pin             EEYLS-NDDKILATAMAVSKTAKTEQCTDG
Clustal Consensus   .   . *** ** .:  .:     . . .

hu_pin             KEEPIRLLREVVLLTDDRNLRVKALTRNVP
Ms_pin             KEEPIRLLREVVLLTDDRNLRVKALTRNVP
Ce_pin             T----EISQKCVLITGDRGLTIKAIGNNFP
Dm_pin             K---CFIQTELVLITTDRNLRVKALSRNLA
Clustal Consensus  .    :  : **:* **.*  :**:  .*..

hu_pin             VRDIPAFLTWAQVG----
Ms_pin             VRDIPAFLTWAQVG----
Ce_pin             CRGISNFTKWIINV----
Dm_pin             VSALDEFLQWAKDCREST
Clustal Consensus    :    *    *
```

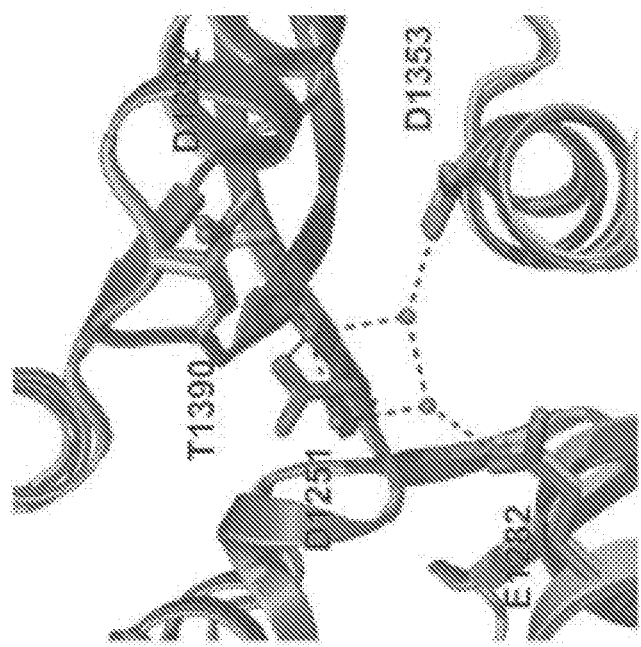
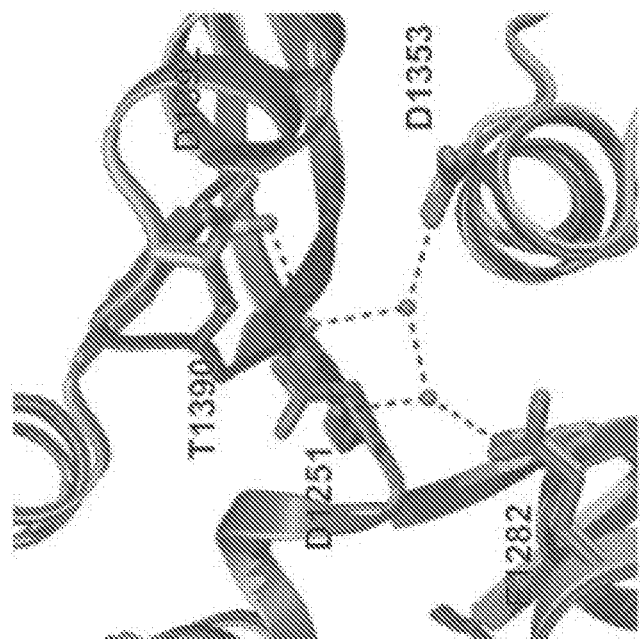
Fig. 9

Fig. 13
A
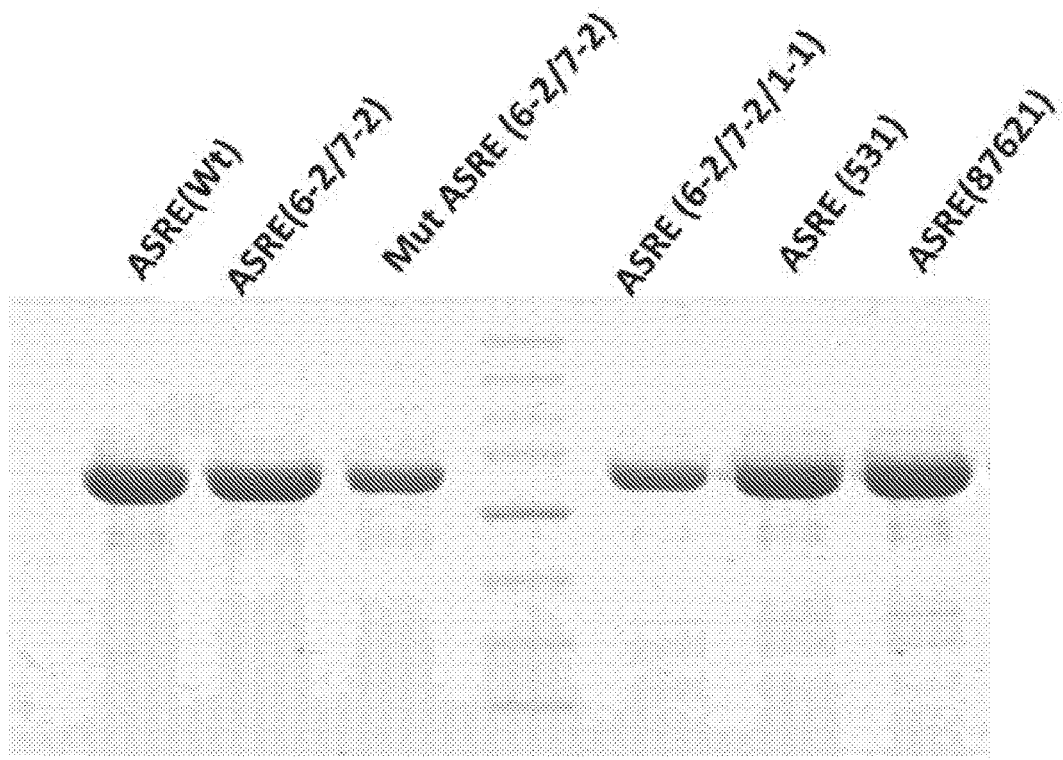
B
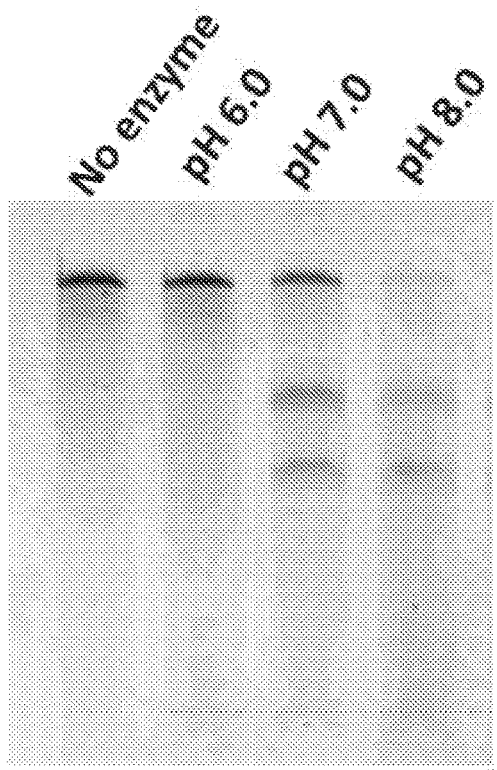

Fig. 15
A
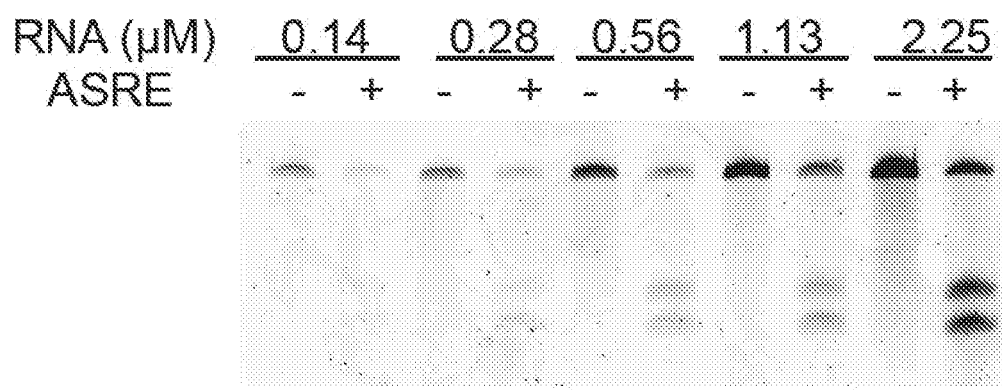
B
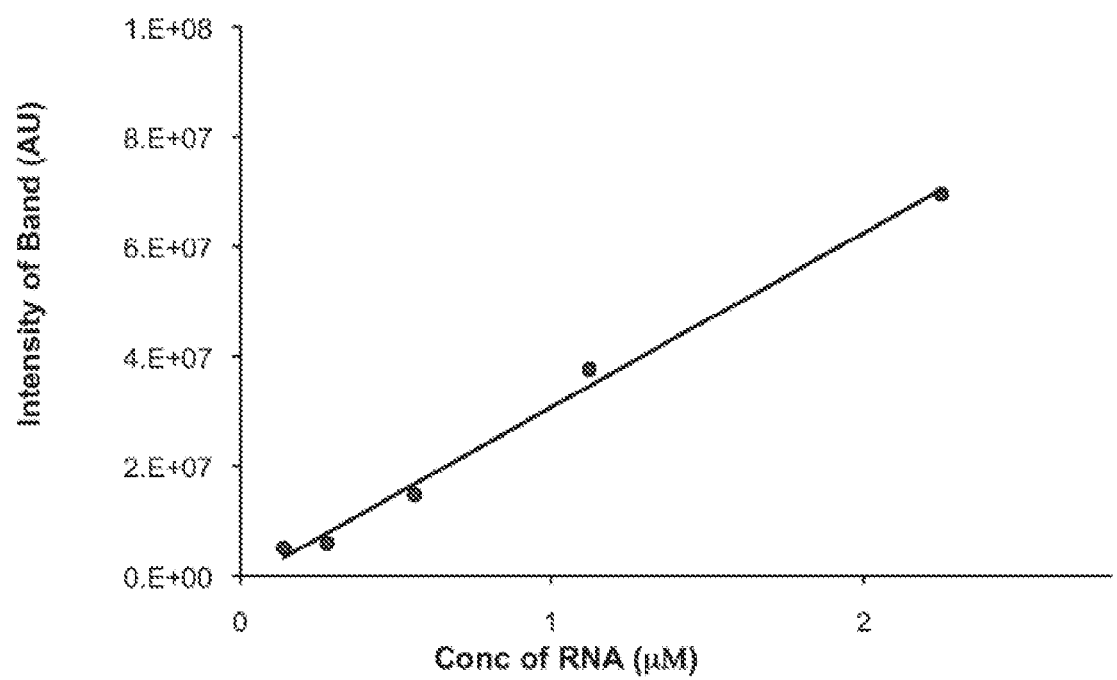

Fig. 20
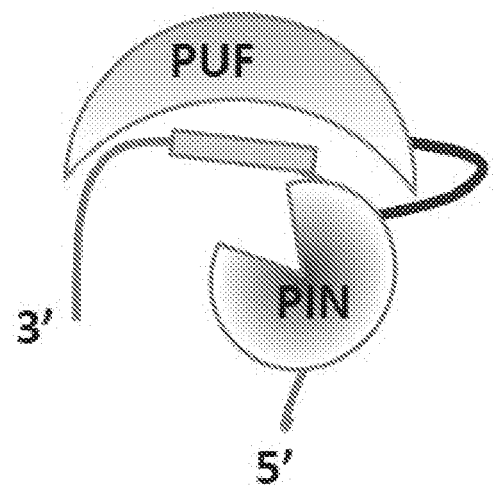
PUF-PIN
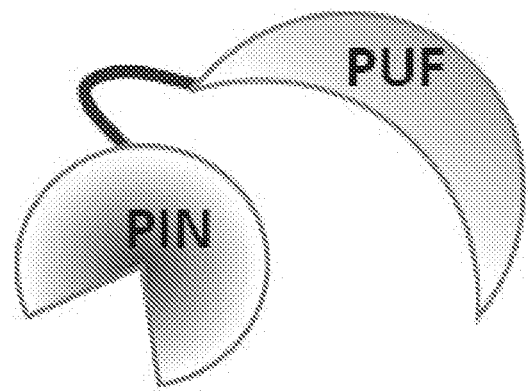
PIN-PUF
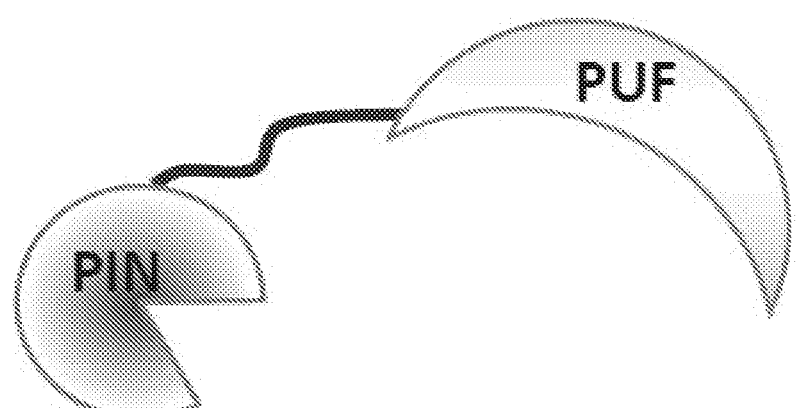
PIN-PUF

Fig. 21
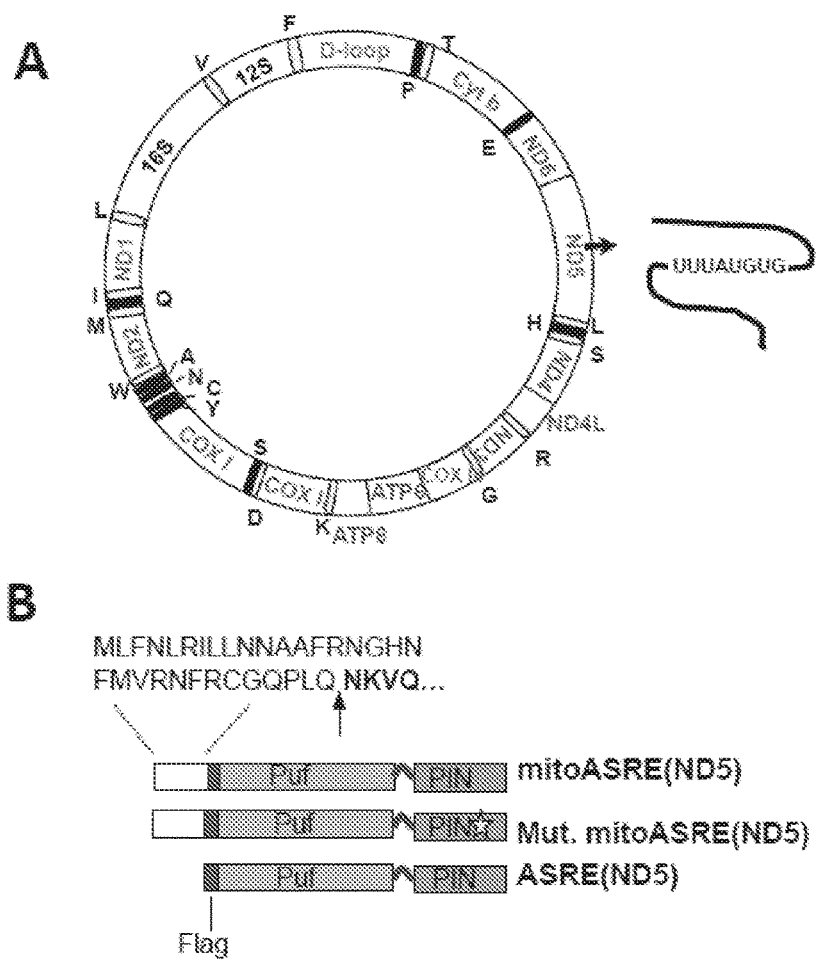
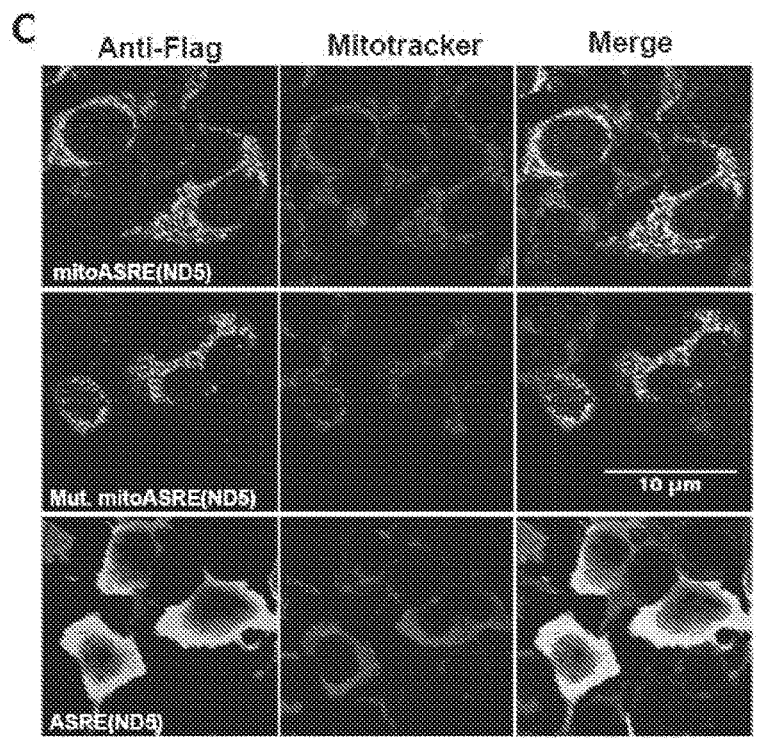

Fig. 21
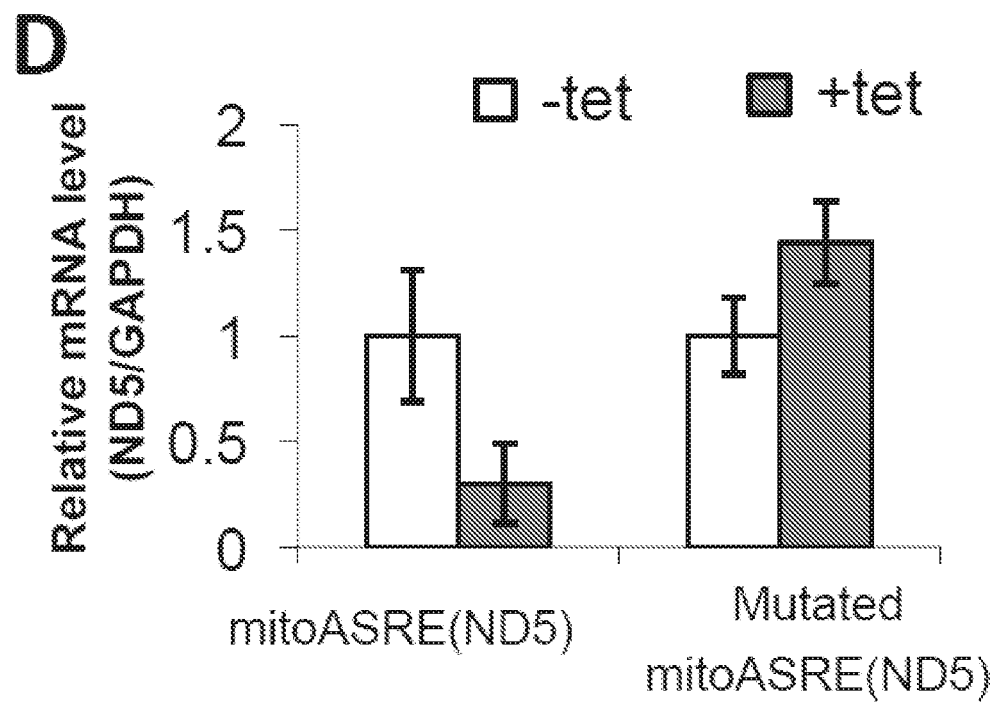
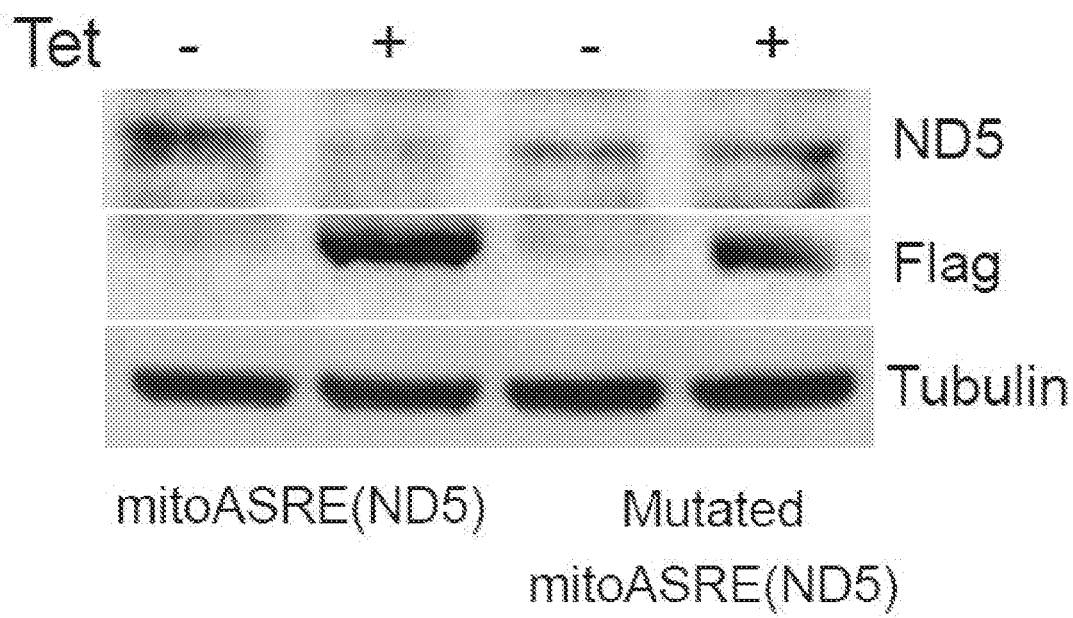

Fig. 27
A
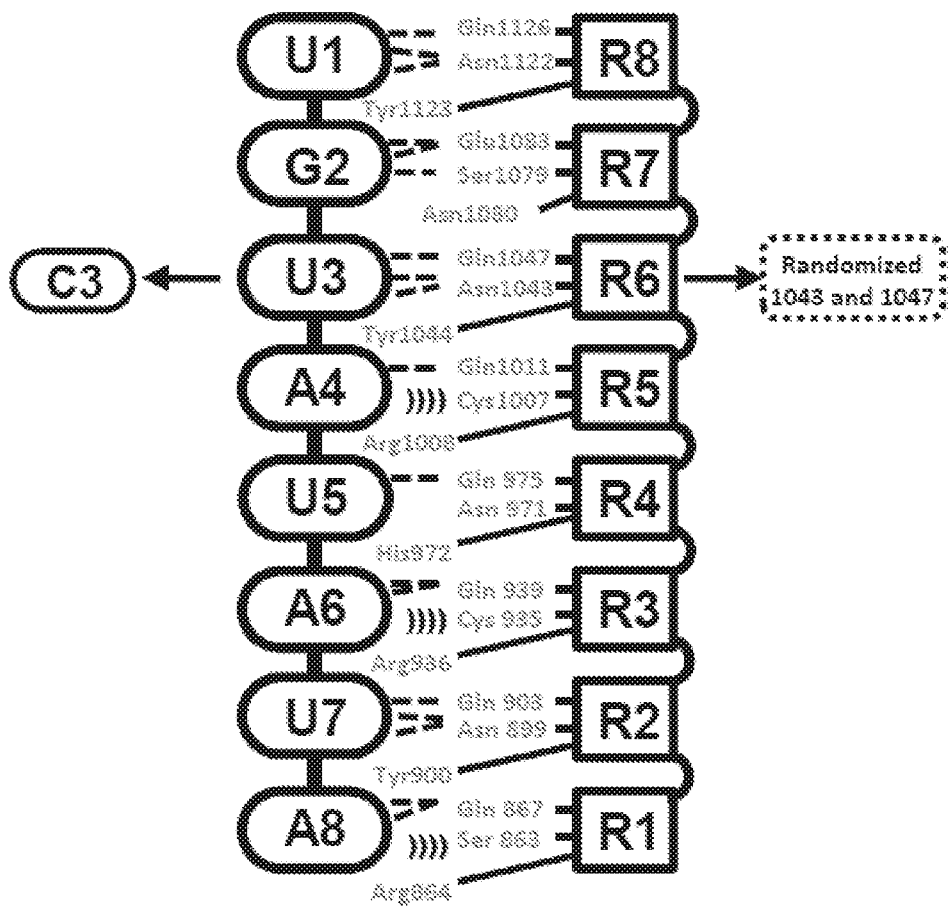
B
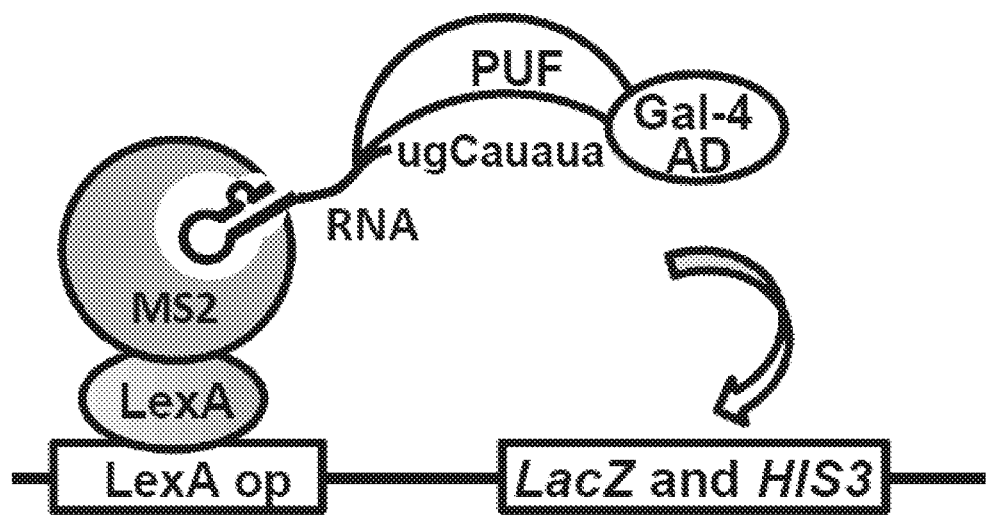

Fig. 27
C
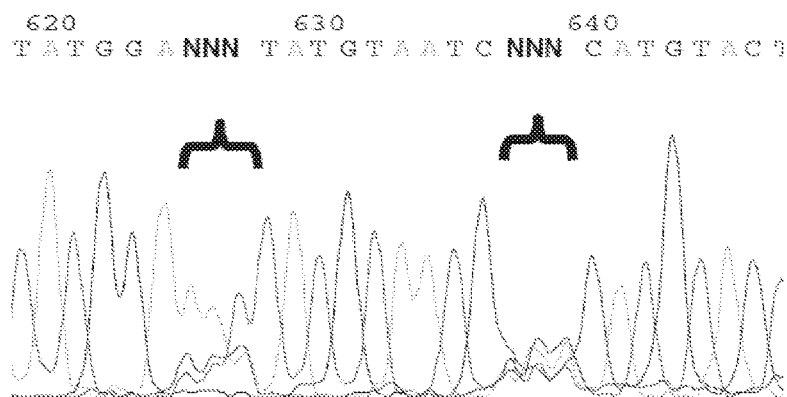
D
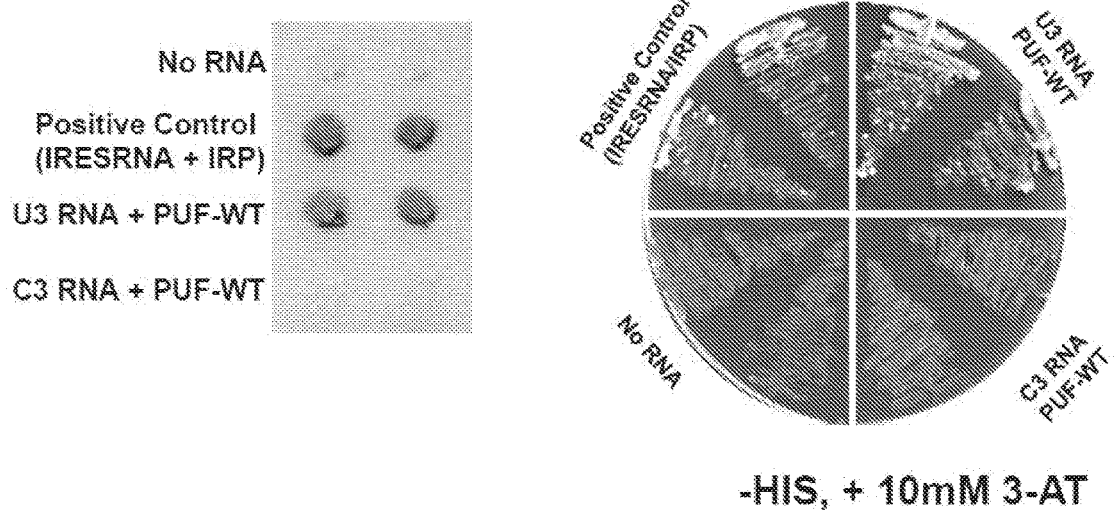
−HIS, + 10mM 3-AT
E
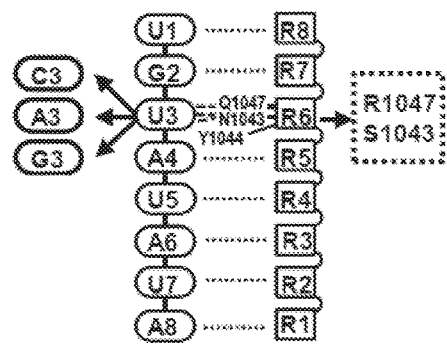
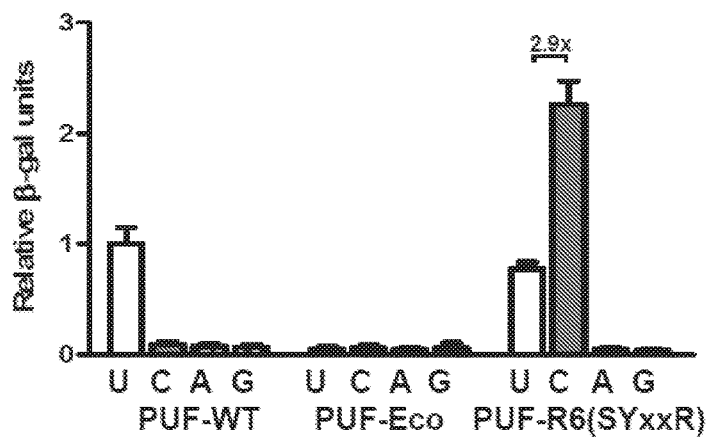

Fig. 28
A
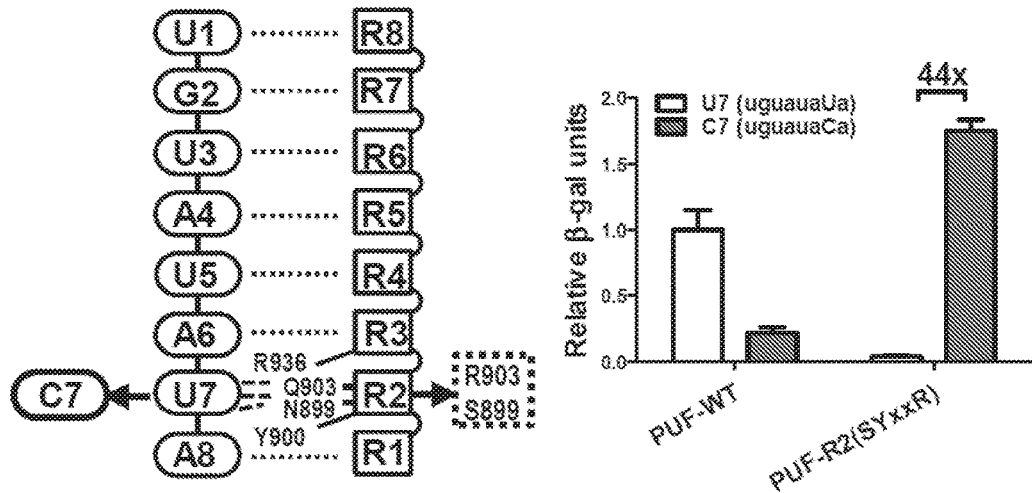
B
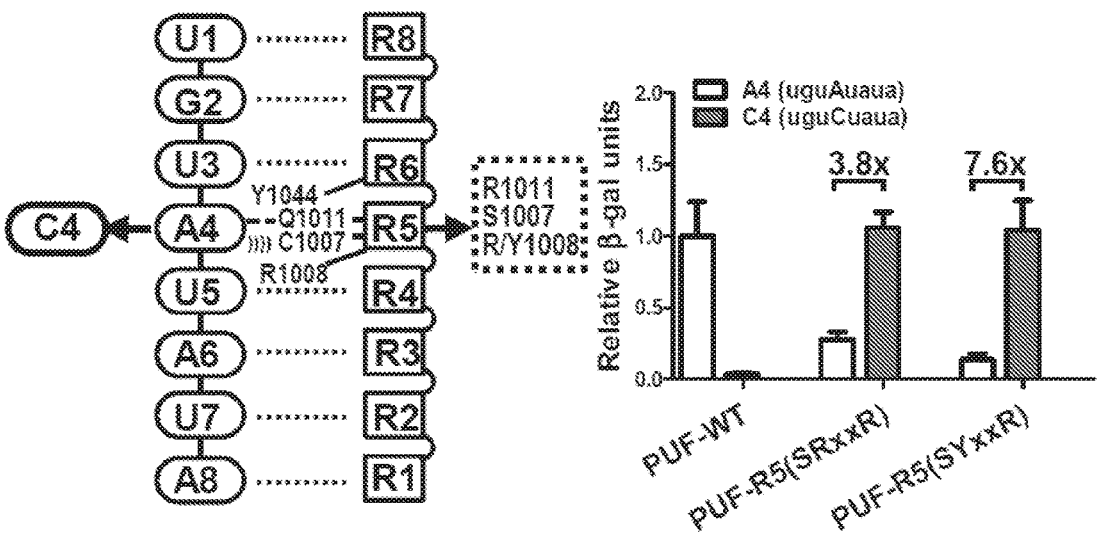
C
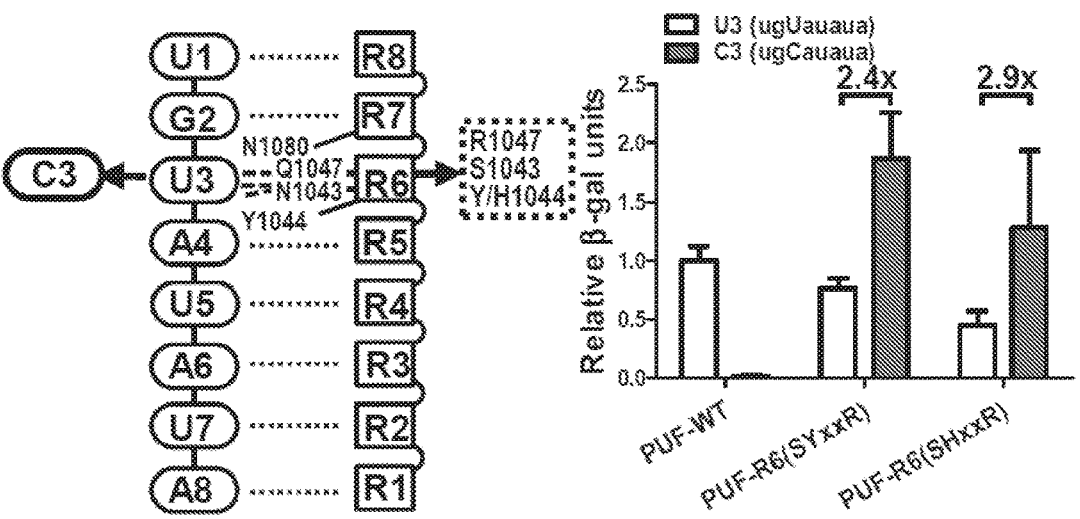

Fig. 28
D
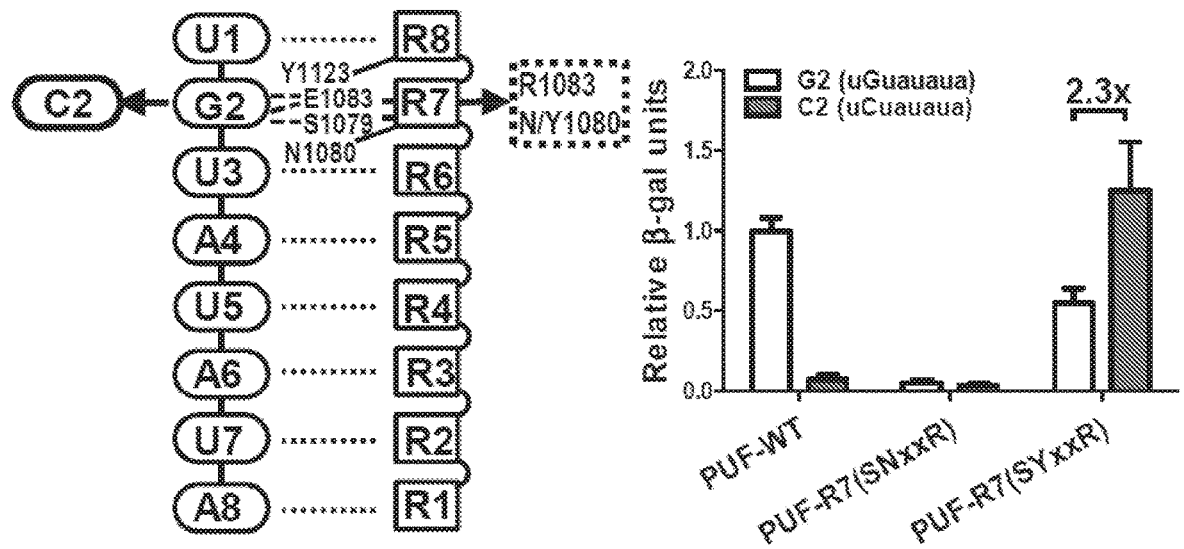
E
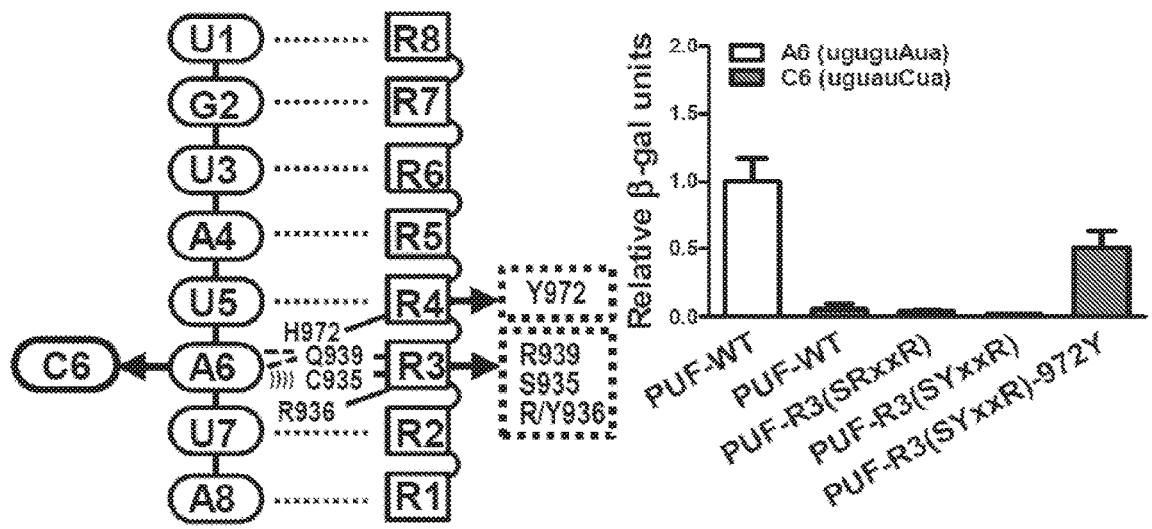

Fig. 29
A
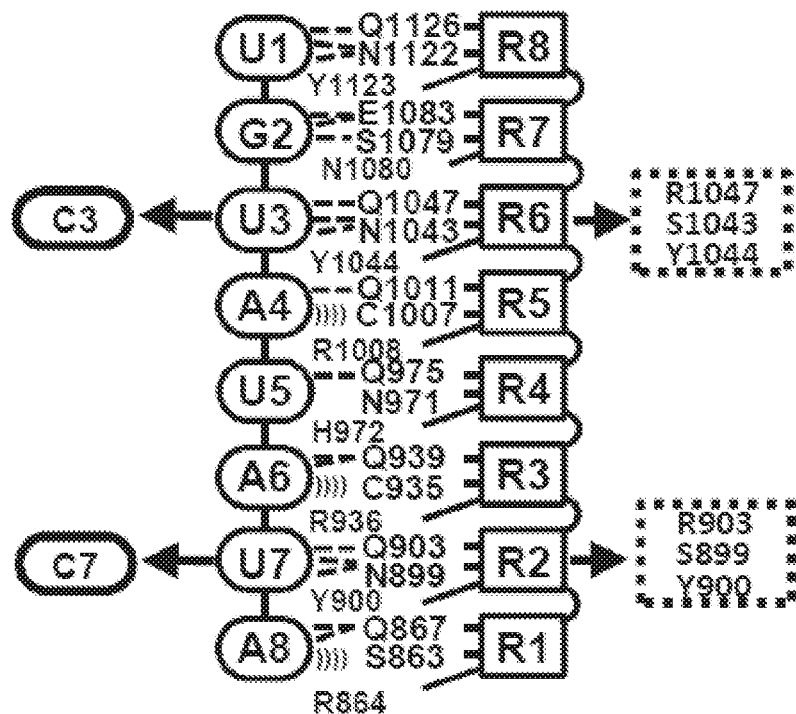
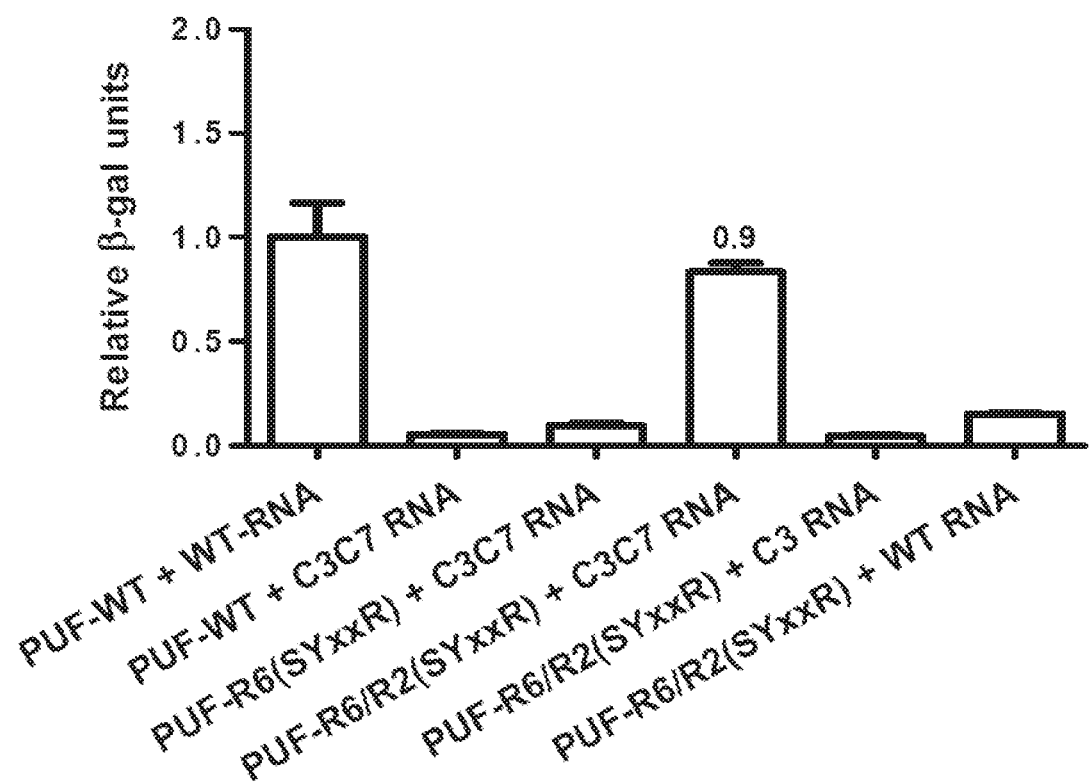

Fig. 29
B
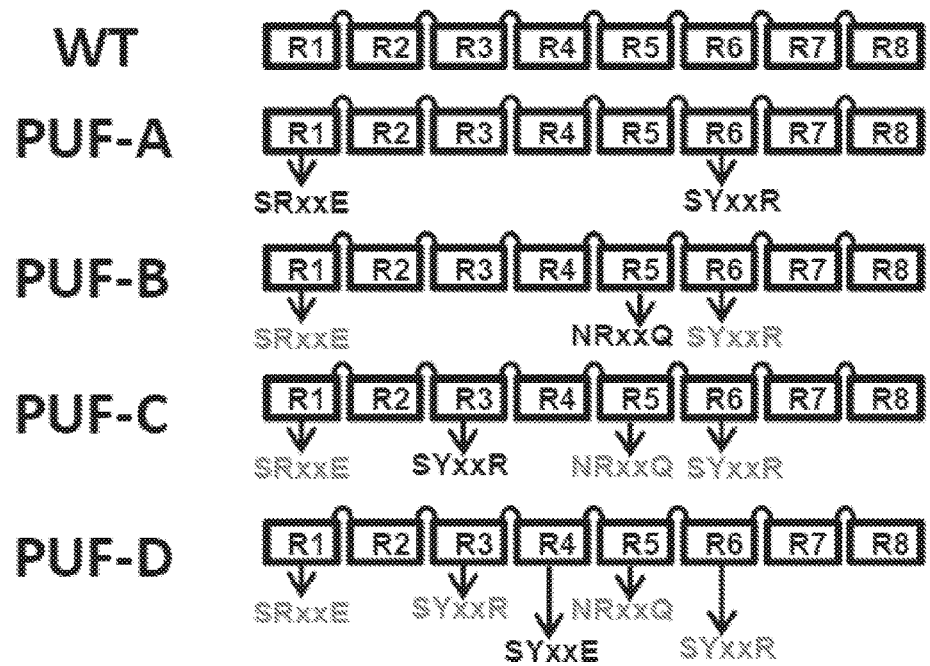
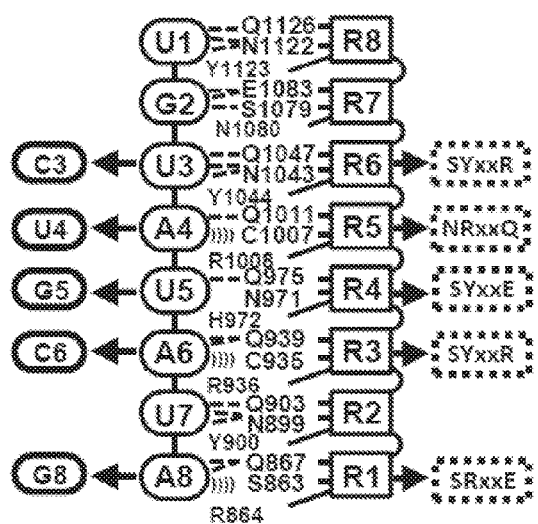
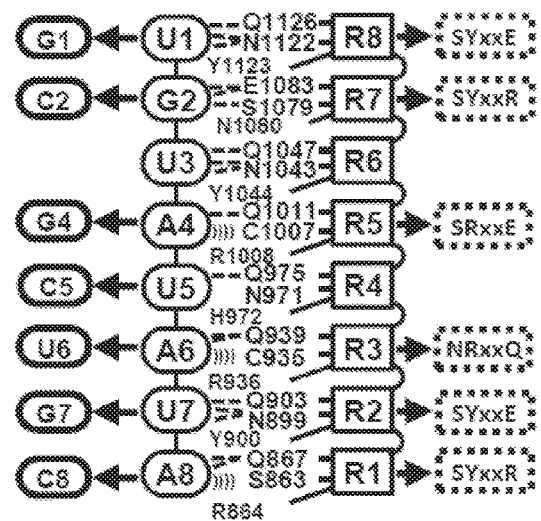

A

A

SEQUENCE LISTING

<160> NUMBER OF SEQ ID NOS: 149

<210> SEQ ID NO 1
<211> LENGTH: 5
<212> TYPE: PRT
<213> ORGANISM: Artificial
<220> FEATURE:
<223> OTHER INFORMATION: PUF domain RNA recognition code
<220> FEATURE:
<221> NAME/KEY: misc_feature
<222> LOCATION: (2)..(4)
<223> OTHER INFORMATION: Xaa can be any naturally occurring amino acid

<400> SEQUENCE: 1

Ser Xaa Xaa Xaa Glu
1               5

<210> SEQ ID NO 2
<211> LENGTH: 6
<212> TYPE: PRT
<213> ORGANISM: Artificial
<220> FEATURE:
<223> OTHER INFORMATION: PUF domain RNA recognition code
<220> FEATURE:
<221> NAME/KEY: misc_feature
<222> LOCATION: (3)..(5)
<223> OTHER INFORMATION: Xaa can be any naturally occurring amino acid

<400> SEQUENCE: 2

Cys Arg Xaa Xaa Xaa Gln
1               5

<210> SEQ ID NO 3
<211> LENGTH: 5
<212> TYPE: PRT
<213> ORGANISM: Artificial
<220> FEATURE:
<223> OTHER INFORMATION: PUF domain RNA recognition code
<220> FEATURE:
<221> NAME/KEY: misc_feature
<222> LOCATION: (2)..(4)
<223> OTHER INFORMATION: Xaa can be any naturally occurring amino acid

<400> SEQUENCE: 3

Asn Xaa Xaa Xaa Gln
1               5

<210> SEQ ID NO 4
<211> LENGTH: 5
<212> TYPE: PRT
<213> ORGANISM: Artificial
<220> FEATURE:
<223> OTHER INFORMATION: PUF domain RNA recognition code
<220> FEATURE:
<221> NAME/KEY: misc_feature
<222> LOCATION: (3)..(4)
<223> OTHER INFORMATION: Xaa can be any naturally occurring amino acid

<400> SEQUENCE: 4

Ser Tyr Xaa Xaa Arg
1               5

<210> SEQ ID NO 5
<211> LENGTH: 6
<212> TYPE: PRT
<213> ORGANISM: Artificial
<220> FEATURE:
<223> OTHER INFORMATION: PUF domain RNA recognition code

```
<220> FEATURE:
<221> NAME/KEY: misc_feature
<222> LOCATION: (3)..(5)
<223> OTHER INFORMATION: Xaa can be any naturally occurring amino acid

<400> SEQUENCE: 5

Ser Arg Xaa Xaa Xaa Gln
1               5

<210> SEQ ID NO 6
<211> LENGTH: 538
<212> TYPE: PRT
<213> ORGANISM: Artificial
<220> FEATURE:
<223> OTHER INFORMATION: Artificial sequence-specific RNA endonuclease
      (ASRE) sequence

<400> SEQUENCE: 6

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
            20                  25                  30

Gln His Gly Ser Arg Phe Ile Gln Leu Lys Leu Glu Arg Ala Thr Pro
        35                  40                  45

Ala Glu Arg Gln Leu Val Phe Asn Glu Ile Leu Gln Ala Ala Tyr Gln
    50                  55                  60

Leu Met Val Asp Val Phe Gly Asn Tyr Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Cys Arg Val Ile Gln
            100                 105                 110

Lys Ala Leu Glu Phe Ile Pro Ser Asp Gln Gln Asn Glu Met Val Arg
        115                 120                 125

Glu Leu Asp Gly His Val Leu Lys Cys Val Lys Asp Gln Asn Gly Asn
    130                 135                 140

His Val Val Gln Lys Cys Ile Glu Cys Val Gln Pro Gln Ser Leu Gln
145                 150                 155                 160

Phe Ile Ile Asp Ala Phe Lys Gly Gln Val Phe Ala Leu Ser Thr His
                165                 170                 175

Pro Tyr Gly Cys Arg Val Ile Gln Arg Ile Leu Glu His Cys Leu Pro
            180                 185                 190

Asp Gln Thr Leu Pro Ile Leu Glu Glu Leu His Gln His Thr Glu Gln
        195                 200                 205

Leu Val Gln Asp Gln Tyr Gly Ser Tyr Val Ile Glu His Val Leu Glu
    210                 215                 220

His Gly Arg Pro Glu Asp Lys Ser Lys Ile Val Ala Glu Ile Arg Gly
225                 230                 235                 240

Asn Val Leu Val Leu Ser Gln His Lys Phe Ala Asn Asn Val Val Gln
                245                 250                 255

Lys Cys Val Thr His Ala Ser Arg Thr Glu Arg Ala Val Leu Ile Asp
            260                 265                 270

Glu Val Cys Thr Met Asn Asp Gly Pro His Ser Ala Leu Tyr Thr Met
        275                 280                 285

Met Lys Asp Gln Tyr Ala Asn Tyr Val Val Gln Lys Met Ile Asp Val
    290                 295                 300

Ala Glu Pro Gly Gln Arg Lys Ile Val Met His Lys Ile Arg Pro His
```

```
                305                 310                 315                 320
Ile Ala Thr Leu Arg Lys Tyr Thr Tyr Gly Lys His Ile Leu Ala Lys
                    325                 330                 335

Leu Glu Lys Tyr Tyr Met Lys Asn Gly Val Asp Leu Gly Val Asp Thr
                    340                 345                 350

Gly Asn Gly Ser Gln Met Glu Leu Glu Ile Arg Pro Leu Phe Leu Val
                    355                 360                 365

Pro Asp Thr Asn Gly Phe Ile Asp His Leu Ala Ser Leu Ala Arg Leu
            370                 375                 380

Leu Glu Ser Arg Lys Tyr Ile Leu Val Val Pro Leu Ile Val Ile Asn
385                 390                 395                 400

Glu Leu Asp Gly Leu Ala Lys Gly Gln Glu Thr Asp His Arg Ala Gly
                    405                 410                 415

Gly Tyr Ala Arg Val Val Gln Glu Lys Ala Arg Lys Ser Ile Glu Phe
                    420                 425                 430

Leu Glu Gln Arg Phe Glu Ser Arg Asp Ser Cys Leu Arg Ala Leu Thr
                    435                 440                 445

Ser Arg Gly Asn Glu Leu Glu Ser Ile Ala Phe Arg Ser Glu Asp Ile
            450                 455                 460

Thr Gly Gln Leu Gly Asn Asn Asp Asp Leu Ile Leu Ser Cys Cys Leu
465                 470                 475                 480

His Tyr Cys Lys Asp Lys Ala Lys Asp Phe Met Pro Ala Ser Lys Glu
                    485                 490                 495

Glu Pro Ile Arg Leu Leu Arg Glu Val Val Leu Leu Thr Asp Asp Arg
                    500                 505                 510

Asn Leu Arg Val Lys Ala Leu Thr Arg Asn Val Pro Val Arg Asp Ile
            515                 520                 525

Pro Ala Phe Leu Thr Trp Ala Gln Val Gly
            530                 535

<210> SEQ ID NO 7
<211> LENGTH: 538
<212> TYPE: PRT
<213> ORGANISM: Artificial
<220> FEATURE:
<223> OTHER INFORMATION: Artificial sequence-specific RNA endonuclease
      (ASRE) sequence

<400> SEQUENCE: 7

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
                    20                  25                  30

Gln His Gly Ser Arg Phe Ile Gln Leu Lys Leu Glu Arg Ala Thr Pro
            35                  40                  45

Ala Glu Arg Gln Leu Val Phe Asn Glu Ile Leu Gln Ala Ala Tyr Gln
    50                  55                  60

Leu Met Val Asp Val Phe Gly Asn Tyr Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Cys Arg Val Ile Gln
            100                 105                 110

Lys Ala Leu Glu Phe Ile Pro Ser Asp Gln Gln Asn Glu Met Val Arg
        115                 120                 125
```

```
Glu Leu Asp Gly His Val Leu Lys Cys Val Lys Asp Gln Asn Gly Asn
130                 135                 140

His Val Gln Lys Cys Ile Glu Cys Val Gln Pro Gln Ser Leu Gln
145                 150                 155                 160

Phe Ile Ile Asp Ala Phe Lys Gly Gln Val Phe Ala Leu Ser Thr His
                165                 170                 175

Pro Tyr Gly Cys Arg Val Ile Gln Arg Ile Leu Glu His Cys Leu Pro
            180                 185                 190

Asp Gln Thr Leu Pro Ile Leu Glu Glu Leu His Gln His Thr Glu Gln
        195                 200                 205

Leu Val Gln Asp Gln Tyr Gly Asn Tyr Val Ile Gln His Val Leu Glu
210                 215                 220

His Gly Arg Pro Glu Asp Lys Ser Lys Ile Val Ala Glu Ile Arg Gly
225                 230                 235                 240

Asn Val Leu Val Leu Ser Gln His Lys Phe Ala Ser Asn Val Val Glu
                245                 250                 255

Lys Cys Val Thr His Ala Ser Arg Thr Glu Arg Ala Val Leu Ile Asp
            260                 265                 270

Glu Val Cys Thr Met Asn Asp Gly Pro His Ser Ala Leu Tyr Thr Met
        275                 280                 285

Met Lys Asp Gln Tyr Ala Asn Tyr Val Val Gln Lys Met Ile Asp Val
290                 295                 300

Ala Glu Pro Gly Gln Arg Lys Ile Val Met His Lys Ile Arg Pro His
305                 310                 315                 320

Ile Ala Thr Leu Arg Lys Tyr Thr Tyr Gly Lys His Ile Leu Ala Lys
                325                 330                 335

Leu Glu Lys Tyr Tyr Met Lys Asn Gly Val Asp Leu Gly Val Asp Thr
            340                 345                 350

Gly Asn Gly Ser Gln Met Glu Leu Glu Ile Arg Pro Leu Phe Leu Val
        355                 360                 365

Pro Asp Thr Asn Gly Phe Ile Asp His Leu Ala Ser Leu Ala Arg Leu
370                 375                 380

Leu Glu Ser Arg Lys Tyr Ile Leu Val Val Pro Leu Ile Val Ile Asn
385                 390                 395                 400

Glu Leu Asp Gly Leu Ala Lys Gly Gln Glu Thr Asp His Arg Ala Gly
                405                 410                 415

Gly Tyr Ala Arg Val Val Gln Glu Lys Ala Arg Lys Ser Ile Glu Phe
            420                 425                 430

Leu Glu Gln Arg Phe Glu Ser Arg Asp Ser Cys Leu Arg Ala Leu Thr
        435                 440                 445

Ser Arg Gly Asn Glu Leu Glu Ser Ile Ala Phe Arg Ser Glu Asp Ile
450                 455                 460

Thr Gly Gln Leu Gly Asn Asn Asp Asp Leu Ile Leu Ser Cys Cys Leu
465                 470                 475                 480

His Tyr Cys Lys Asp Lys Ala Lys Asp Phe Met Pro Ala Ser Lys Glu
                485                 490                 495

Glu Pro Ile Arg Leu Leu Arg Glu Val Val Leu Leu Thr Asp Asp Arg
            500                 505                 510

Asn Leu Arg Val Lys Ala Leu Thr Arg Asn Val Pro Val Arg Asp Ile
        515                 520                 525

Pro Ala Phe Leu Thr Trp Ala Gln Val Gly
530                 535
```

-continued

```
<210> SEQ ID NO 8
<211> LENGTH: 538
<212> TYPE: PRT
<213> ORGANISM: Artificial
<220> FEATURE:
<223> OTHER INFORMATION: Artificial sequence-specific RNA endonuclease
      (ASRE) sequence

<400> SEQUENCE: 8
```

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
            20                  25                  30

Gln His Gly Ser Arg Phe Ile Glu Leu Lys Leu Glu Arg Ala Thr Pro
        35                  40                  45

Ala Glu Arg Gln Leu Val Phe Asn Glu Ile Leu Gln Ala Ala Tyr Gln
    50                  55                  60

Leu Met Val Asp Val Phe Gly Asn Tyr Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Cys Arg Val Ile Gln
            100                 105                 110

Lys Ala Leu Glu Phe Ile Pro Ser Asp Gln Gln Asn Glu Met Val Arg
        115                 120                 125

Glu Leu Asp Gly His Val Leu Lys Cys Val Lys Asp Gln Asn Gly Asn
130                 135                 140

His Val Val Gln Lys Cys Ile Glu Cys Val Gln Pro Gln Ser Leu Gln
145                 150                 155                 160

Phe Ile Ile Asp Ala Phe Lys Gly Gln Val Phe Ala Leu Ser Thr His
                165                 170                 175

Pro Tyr Gly Cys Arg Val Ile Gln Arg Ile Leu Glu His Cys Leu Pro
            180                 185                 190

Asp Gln Thr Leu Pro Ile Leu Glu Glu Leu His Gln His Thr Glu Gln
        195                 200                 205

Leu Val Gln Asp Gln Tyr Gly Ser Tyr Val Ile Glu His Val Leu Glu
    210                 215                 220

His Gly Arg Pro Glu Asp Lys Ser Lys Ile Val Ala Glu Ile Arg Gly
225                 230                 235                 240

Asn Val Leu Val Leu Ser Gln His Lys Phe Ala Asn Asn Val Val Gln
                245                 250                 255

Lys Cys Val Thr His Ala Ser Arg Thr Glu Arg Ala Val Leu Ile Asp
            260                 265                 270

Glu Val Cys Thr Met Asn Asp Gly Pro His Ser Ala Leu Tyr Thr Met
        275                 280                 285

Met Lys Asp Gln Tyr Ala Asn Tyr Val Val Gln Lys Met Ile Asp Val
    290                 295                 300

Ala Glu Pro Gly Gln Arg Lys Ile Val Met His Lys Ile Arg Pro His
305                 310                 315                 320

Ile Ala Thr Leu Arg Lys Tyr Thr Tyr Gly Lys His Ile Leu Ala Lys
                325                 330                 335

Leu Glu Lys Tyr Tyr Met Lys Asn Gly Val Asp Leu Gly Val Asp Thr
            340                 345                 350

Gly Asn Gly Ser Gln Met Glu Leu Glu Ile Arg Pro Leu Phe Leu Val
        355                 360                 365

```
Pro Asp Thr Asn Gly Phe Ile Asp His Leu Ala Ser Leu Ala Arg Leu
    370                 375                 380

Leu Glu Ser Arg Lys Tyr Ile Leu Val Val Pro Leu Ile Val Ile Asn
385                 390                 395                 400

Glu Leu Asp Gly Leu Ala Lys Gly Gln Glu Thr Asp His Arg Ala Gly
                405                 410                 415

Gly Tyr Ala Arg Val Val Gln Glu Lys Ala Arg Lys Ser Ile Glu Phe
            420                 425                 430

Leu Glu Gln Arg Phe Glu Ser Arg Asp Ser Cys Leu Arg Ala Leu Thr
                435                 440                 445

Ser Arg Gly Asn Glu Leu Glu Ser Ile Ala Phe Arg Ser Glu Asp Ile
450                 455                 460

Thr Gly Gln Leu Gly Asn Asn Asp Asp Leu Ile Leu Ser Cys Cys Leu
465                 470                 475                 480

His Tyr Cys Lys Asp Lys Ala Lys Asp Phe Met Pro Ala Ser Lys Glu
                485                 490                 495

Glu Pro Ile Arg Leu Leu Arg Glu Val Val Leu Leu Thr Asp Asp Arg
                500                 505                 510

Asn Leu Arg Val Lys Ala Leu Thr Arg Asn Val Pro Val Arg Asp Ile
                515                 520                 525

Pro Ala Phe Leu Thr Trp Ala Gln Val Gly
                530                 535

<210> SEQ ID NO 9
<211> LENGTH: 538
<212> TYPE: PRT
<213> ORGANISM: Artificial
<220> FEATURE:
<223> OTHER INFORMATION: Artificial sequence-specific RNA endonuclease
      (ASRE) sequence

<400> SEQUENCE: 9

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
                20                  25                  30

Gln His Gly Ser Arg Phe Ile Glu Leu Lys Leu Glu Arg Ala Thr Pro
            35                  40                  45

Ala Glu Arg Gln Leu Val Phe Asn Glu Ile Leu Gln Ala Ala Tyr Gln
        50                  55                  60

Leu Met Val Asp Val Phe Gly Asn Tyr Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Ser Arg Val Ile Glu
                100                 105                 110

Lys Ala Leu Glu Phe Ile Pro Ser Asp Gln Gln Asn Glu Met Val Arg
            115                 120                 125

Glu Leu Asp Gly His Val Leu Lys Cys Val Lys Asp Gln Asn Gly Asn
        130                 135                 140

His Val Gln Lys Cys Ile Glu Cys Val Gln Pro Gln Ser Leu Gln
145                 150                 155                 160

Phe Ile Ile Asp Ala Phe Lys Gly Gln Val Phe Ala Leu Ser Thr His
                165                 170                 175

Pro Tyr Gly Ser Arg Val Ile Glu Arg Ile Leu Glu His Cys Leu Pro
            180                 185                 190
```

Asp Gln Thr Leu Pro Ile Leu Glu Glu Leu His Gln His Thr Glu Gln
            195                 200                 205

Leu Val Gln Asp Gln Tyr Gly Asn Tyr Val Ile Gln His Val Leu Glu
        210                 215                 220

His Gly Arg Pro Glu Asp Lys Ser Lys Ile Val Ala Glu Ile Arg Gly
225                 230                 235                 240

Asn Val Leu Val Leu Ser Gln His Lys Phe Ala Ser Asn Val Val Glu
                245                 250                 255

Lys Cys Val Thr His Ala Ser Arg Thr Glu Arg Ala Val Leu Ile Asp
            260                 265                 270

Glu Val Cys Thr Met Asn Asp Gly Pro His Ser Ala Leu Tyr Thr Met
        275                 280                 285

Met Lys Asp Gln Tyr Ala Asn Tyr Val Val Gln Lys Met Ile Asp Val
    290                 295                 300

Ala Glu Pro Gly Gln Arg Lys Ile Val Met His Lys Ile Arg Pro His
305                 310                 315                 320

Ile Ala Thr Leu Arg Lys Tyr Thr Tyr Gly Lys His Ile Leu Ala Lys
                325                 330                 335

Leu Glu Lys Tyr Tyr Met Lys Asn Gly Val Asp Leu Gly Val Asp Thr
            340                 345                 350

Gly Asn Gly Ser Gln Met Glu Leu Glu Ile Arg Pro Leu Phe Leu Val
        355                 360                 365

Pro Asp Thr Asn Gly Phe Ile Asp His Leu Ala Ser Leu Ala Arg Leu
    370                 375                 380

Leu Glu Ser Arg Lys Tyr Ile Leu Val Val Pro Leu Ile Val Ile Asn
385                 390                 395                 400

Glu Leu Asp Gly Leu Ala Lys Gly Gln Glu Thr Asp His Arg Ala Gly
                405                 410                 415

Gly Tyr Ala Arg Val Val Gln Glu Lys Ala Arg Lys Ser Ile Glu Phe
            420                 425                 430

Leu Glu Gln Arg Phe Glu Ser Arg Asp Ser Cys Leu Arg Ala Leu Thr
        435                 440                 445

Ser Arg Gly Asn Glu Leu Glu Ser Ile Ala Phe Arg Ser Glu Asp Ile
    450                 455                 460

Thr Gly Gln Leu Gly Asn Asn Asp Asp Leu Ile Leu Ser Cys Cys Leu
465                 470                 475                 480

His Tyr Cys Lys Asp Lys Ala Lys Asp Phe Met Pro Ala Ser Lys Glu
                485                 490                 495

Glu Pro Ile Arg Leu Leu Arg Glu Val Val Leu Leu Thr Asp Asp Arg
            500                 505                 510

Asn Leu Arg Val Lys Ala Leu Thr Arg Asn Val Pro Val Arg Asp Ile
        515                 520                 525

Pro Ala Phe Leu Thr Trp Ala Gln Val Gly
    530                 535

<210> SEQ ID NO 10
<211> LENGTH: 538
<212> TYPE: PRT
<213> ORGANISM: Artificial
<220> FEATURE:
<223> OTHER INFORMATION: Artificial sequence-specific RNA endonuclease
      (ASRE) sequence

<400> SEQUENCE: 10

Gly Arg Ser Arg Leu Leu Glu Asp Phe Arg Asn Asn Arg Tyr Pro Asn

-continued

```
1               5                   10                  15
Leu Gln Leu Arg Glu Ile Ala Gly His Ile Met Glu Phe Ser Gln Asp
                20                  25                  30

Gln His Gly Ser Arg Phe Ile Glu Leu Lys Leu Glu Arg Ala Thr Pro
                35                  40                  45

Ala Glu Arg Gln Leu Val Phe Asn Glu Ile Leu Gln Ala Ala Tyr Gln
            50                  55                  60

Leu Met Val Asp Val Phe Gly Cys Arg Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Cys Arg Val Ile Gln
                100                 105                 110

Lys Ala Leu Glu Phe Ile Pro Ser Asp Gln Gln Asn Glu Met Val Arg
                115                 120                 125

Glu Leu Asp Gly His Val Leu Lys Cys Val Lys Asp Gln Asn Gly Asn
                130                 135                 140

His Val Val Gln Lys Cys Ile Glu Cys Val Gln Pro Gln Ser Leu Gln
145                 150                 155                 160

Phe Ile Ile Asp Ala Phe Lys Gly Gln Val Phe Ala Leu Ser Thr His
                165                 170                 175

Pro Tyr Gly Cys Arg Val Ile Gln Arg Ile Leu Glu His Cys Leu Pro
                180                 185                 190

Asp Gln Thr Leu Pro Ile Leu Glu Glu Leu His Gln His Thr Glu Gln
                195                 200                 205

Leu Val Gln Asp Gln Tyr Gly Ser Tyr Val Ile Glu His Val Leu Glu
            210                 215                 220

His Gly Arg Pro Glu Asp Lys Ser Lys Ile Val Ala Glu Ile Arg Gly
225                 230                 235                 240

Asn Val Leu Val Leu Ser Gln His Lys Phe Ala Asn Asn Val Val Gln
                245                 250                 255

Lys Cys Val Thr His Ala Ser Arg Thr Glu Arg Ala Val Leu Ile Asp
                260                 265                 270

Glu Val Cys Thr Met Asn Asp Gly Pro His Ser Ala Leu Tyr Thr Met
                275                 280                 285

Met Lys Asp Gln Tyr Ala Ser Tyr Val Val Glu Lys Met Ile Asp Val
                290                 295                 300

Ala Glu Pro Gly Gln Arg Lys Ile Val Met His Lys Ile Arg Pro His
305                 310                 315                 320

Ile Ala Thr Leu Arg Lys Tyr Thr Tyr Gly Lys His Ile Leu Ala Lys
                325                 330                 335

Leu Glu Lys Tyr Tyr Met Lys Asn Gly Val Asp Leu Gly Val Asp Thr
                340                 345                 350

Gly Asn Gly Ser Gln Met Glu Leu Glu Ile Arg Pro Leu Phe Leu Val
                355                 360                 365

Pro Asp Thr Asn Gly Phe Ile Asp His Leu Ala Ser Leu Ala Arg Leu
            370                 375                 380

Leu Glu Ser Arg Lys Tyr Ile Leu Val Val Pro Leu Ile Val Ile Asn
385                 390                 395                 400

Glu Leu Asp Gly Leu Ala Lys Gly Gln Glu Thr Asp His Arg Ala Gly
                405                 410                 415

Gly Tyr Ala Arg Val Val Gln Glu Lys Ala Arg Lys Ser Ile Glu Phe
                420                 425                 430
```

```
Leu Glu Gln Arg Phe Glu Ser Arg Asp Ser Cys Leu Arg Ala Leu Thr
        435                 440                 445

Ser Arg Gly Asn Glu Leu Glu Ser Ile Ala Phe Arg Ser Glu Asp Ile
    450                 455                 460

Thr Gly Gln Leu Gly Asn Asn Asp Asp Leu Ile Leu Ser Cys Cys Leu
465                 470                 475                 480

His Tyr Cys Lys Asp Lys Ala Lys Asp Phe Met Pro Ala Ser Lys Glu
                485                 490                 495

Glu Pro Ile Arg Leu Leu Arg Glu Val Val Leu Leu Thr Asp Asp Arg
            500                 505                 510

Asn Leu Arg Val Lys Ala Leu Thr Arg Asn Val Pro Val Arg Asp Ile
        515                 520                 525

Pro Ala Phe Leu Thr Trp Ala Gln Val Gly
    530                 535

<210> SEQ ID NO 11
<211> LENGTH: 538
<212> TYPE: PRT
<213> ORGANISM: Artificial
<220> FEATURE:
<223> OTHER INFORMATION: Artificial sequence-specific RNA endonuclease
      (ASRE) sequence

<400> SEQUENCE: 11

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
            20                  25                  30

Gln His Gly Ser Arg Phe Ile Gln Leu Lys Leu Glu Arg Ala Thr Pro
        35                  40                  45

Ala Glu Arg Gln Leu Val Phe Asn Glu Ile Leu Gln Ala Ala Tyr Gln
    50                  55                  60

Leu Met Val Asp Val Phe Gly Cys Arg Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Ser Arg Val Ile Glu
            100                 105                 110

Lys Ala Leu Glu Phe Ile Pro Ser Asp Gln Gln Asn Glu Met Val Arg
        115                 120                 125

Glu Leu Asp Gly His Val Leu Lys Cys Val Lys Asp Gln Asn Gly Asn
    130                 135                 140

His Val Val Gln Lys Cys Ile Glu Cys Val Gln Pro Gln Ser Leu Gln
145                 150                 155                 160

Phe Ile Ile Asp Ala Phe Lys Gly Gln Val Phe Ala Leu Ser Thr His
                165                 170                 175

Pro Tyr Gly Cys Arg Val Ile Gln Arg Ile Leu Glu His Cys Leu Pro
            180                 185                 190

Asp Gln Thr Leu Pro Ile Leu Glu Glu Leu His Gln His Thr Glu Gln
        195                 200                 205

Leu Val Gln Asp Gln Tyr Gly Ser Tyr Val Ile Glu His Val Leu Glu
    210                 215                 220

His Gly Arg Pro Glu Asp Lys Ser Lys Ile Val Ala Glu Ile Arg Gly
225                 230                 235                 240

Asn Val Leu Val Leu Ser Gln His Lys Phe Ala Ser Asn Val Val Glu
```

```
            245                 250                 255
Lys Cys Val Thr His Ala Ser Arg Thr Glu Arg Ala Val Leu Ile Asp
            260                 265                 270

Glu Val Cys Thr Met Asn Asp Gly Pro His Ser Ala Leu Tyr Thr Met
        275                 280                 285

Met Lys Asp Gln Tyr Ala Asn Tyr Val Val Gln Lys Met Ile Asp Val
    290                 295                 300

Ala Glu Pro Gly Gln Arg Lys Ile Val Met His Lys Ile Arg Pro His
305                 310                 315                 320

Ile Ala Thr Leu Arg Lys Tyr Thr Tyr Gly Lys His Ile Leu Ala Lys
            325                 330                 335

Leu Glu Lys Tyr Tyr Met Lys Asn Gly Val Asp Leu Gly Val Asp Thr
        340                 345                 350

Gly Asn Gly Ser Gln Met Glu Leu Glu Ile Arg Pro Leu Phe Leu Val
    355                 360                 365

Pro Asp Thr Asn Gly Phe Ile Asp His Leu Ala Ser Leu Ala Arg Leu
370                 375                 380

Leu Glu Ser Arg Lys Tyr Ile Leu Val Pro Leu Ile Val Ile Asn
            385                 390                 395             400

Glu Leu Asp Gly Leu Ala Lys Gly Gln Glu Thr Asp His Arg Ala Gly
        405                 410                 415

Gly Tyr Ala Arg Val Val Gln Glu Lys Ala Arg Lys Ser Ile Glu Phe
    420                 425                 430

Leu Glu Gln Arg Phe Glu Ser Arg Asp Ser Cys Leu Arg Ala Leu Thr
435                 440                 445

Ser Arg Gly Asn Glu Leu Glu Ser Ile Ala Phe Arg Ser Glu Asp Ile
    450                 455                 460

Thr Gly Gln Leu Gly Asn Asn Asp Leu Ile Leu Ser Cys Cys Leu
465                 470                 475                 480

His Tyr Cys Lys Asp Lys Ala Lys Asp Phe Met Pro Ala Ser Lys Glu
            485                 490                 495

Glu Pro Ile Arg Leu Leu Arg Glu Val Val Leu Leu Thr Asp Asp Arg
        500                 505                 510

Asn Leu Arg Val Lys Ala Leu Thr Arg Asn Val Pro Val Arg Asp Ile
    515                 520                 525

Pro Ala Phe Leu Thr Trp Ala Gln Val Gly
    530                 535

<210> SEQ ID NO 12
<211> LENGTH: 538
<212> TYPE: PRT
<213> ORGANISM: Artificial
<220> FEATURE:
<223> OTHER INFORMATION: Artificial sequence-specific RNA endonuclease
      (ASRE) sequence

<400> SEQUENCE: 12

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
            20                  25                  30

Gln His Gly Ser Arg Phe Ile Gln Leu Lys Leu Glu Arg Ala Thr Pro
        35                  40                  45

Ala Glu Arg Gln Leu Val Phe Asn Glu Ile Leu Gln Ala Ala Tyr Gln
    50                  55                  60
```

```
Leu Met Val Asp Val Phe Gly Asn Tyr Val Ile Gln Lys Phe Phe Glu
 65                  70                  75                  80

Phe Gly Ser Leu Glu Gln Lys Leu Ala Leu Ala Glu Arg Ile Arg Gly
             85                   90                  95

His Val Leu Ser Leu Ala Leu Gln Met Tyr Gly Ser Arg Val Ile Glu
            100                 105                 110

Lys Ala Leu Glu Phe Ile Pro Ser Asp Gln Gln Asn Glu Met Val Arg
            115                 120                 125

Glu Leu Asp Gly His Val Leu Lys Cys Val Lys Asp Gln Asn Gly Asn
        130                 135                 140

His Val Val Gln Lys Cys Ile Glu Cys Val Gln Pro Gln Ser Leu Gln
145                 150                 155                 160

Phe Ile Ile Asp Ala Phe Lys Gly Gln Val Phe Ala Leu Ser Thr His
                165                 170                 175

Pro Tyr Gly Cys Arg Val Ile Gln Arg Ile Leu Glu His Cys Leu Pro
            180                 185                 190

Asp Gln Thr Leu Pro Ile Leu Glu Glu Leu His Gln His Thr Glu Gln
        195                 200                 205

Leu Val Gln Asp Gln Tyr Gly Asn Tyr Val Ile Gln His Val Leu Glu
210                 215                 220

His Gly Arg Pro Glu Asp Lys Ser Lys Ile Val Ala Glu Ile Arg Gly
225                 230                 235                 240

Asn Val Leu Val Leu Ser Gln His Lys Phe Ala Ser Asn Val Val Glu
                245                 250                 255

Lys Cys Val Thr His Ala Ser Arg Thr Glu Arg Ala Val Leu Ile Asp
            260                 265                 270

Glu Val Cys Thr Met Asn Asp Gly Pro His Ser Ala Leu Tyr Thr Met
        275                 280                 285

Met Lys Asp Gln Tyr Ala Asn Tyr Val Val Gln Lys Met Ile Asp Val
    290                 295                 300

Ala Glu Pro Gly Gln Arg Lys Ile Val Met His Lys Ile Arg Pro His
305                 310                 315                 320

Ile Ala Thr Leu Arg Lys Tyr Thr Tyr Gly Lys His Ile Leu Ala Lys
                325                 330                 335

Leu Glu Lys Tyr Tyr Met Lys Asn Gly Val Asp Leu Gly Val Asp Thr
            340                 345                 350

Gly Asn Gly Ser Gln Met Glu Leu Glu Ile Arg Pro Leu Phe Leu Val
        355                 360                 365

Pro Asp Thr Asn Gly Phe Ile Asp His Leu Ala Ser Leu Ala Arg Leu
370                 375                 380

Leu Glu Ser Arg Lys Tyr Ile Leu Val Val Pro Leu Ile Val Ile Asn
385                 390                 395                 400

Glu Leu Asp Gly Leu Ala Lys Gly Gln Glu Thr Asp His Arg Ala Gly
                405                 410                 415

Gly Tyr Ala Arg Val Val Gln Lys Ala Arg Lys Ser Ile Glu Phe
            420                 425                 430

Leu Glu Gln Arg Phe Glu Ser Arg Asp Ser Cys Leu Arg Ala Leu Thr
            435                 440                 445

Ser Arg Gly Asn Glu Leu Glu Ser Ile Ala Phe Arg Ser Glu Asp Ile
            450                 455                 460

Thr Gly Gln Leu Gly Asn Asn Asp Asp Leu Ile Leu Ser Cys Cys Leu
465                 470                 475                 480

His Tyr Cys Lys Asp Lys Ala Lys Asp Phe Met Pro Ala Ser Lys Glu
```

```
                    485                 490                 495
Glu Pro Ile Arg Leu Leu Arg Glu Val Val Leu Thr Asp Asp Arg
                500                 505                 510

Asn Leu Arg Val Lys Ala Leu Thr Arg Asn Val Pro Val Arg Asp Ile
            515                 520                 525

Pro Ala Phe Leu Thr Trp Ala Gln Val Gly
        530                 535

<210> SEQ ID NO 13
<211> LENGTH: 584
<212> TYPE: PRT
<213> ORGANISM: Artificial
<220> FEATURE:
<223> OTHER INFORMATION: Artificial sequence-specific RNA endonuclease
      (ASRE) sequence

<400> SEQUENCE: 13

Met Leu Phe Asn Leu Arg Ile Leu Leu Asn Asn Ala Ala Phe Arg Asn
1               5                   10                  15

Gly His Asn Phe Met Val Arg Asn Phe Arg Cys Gly Gln Pro Leu Gln
            20                  25                  30

Asn Lys Val Gln Asp Tyr Lys Asp Asp Asp Lys Glu Phe Gly Arg
        35                  40                  45

Ser Arg Leu Leu Glu Asp Phe Arg Asn Asn Arg Tyr Pro Asn Leu Gln
    50                  55                  60

Leu Arg Glu Ile Ala Gly His Ile Met Glu Phe Ser Gln Asp Gln His
65                  70                  75                  80

Gly Ser Arg Phe Ile Glu Leu Lys Leu Glu Arg Ala Thr Pro Ala Glu
                85                  90                  95

Arg Gln Leu Val Phe Asn Glu Ile Leu Gln Ala Ala Tyr Gln Leu Met
            100                 105                 110

Val Asp Val Phe Gly Asn Tyr Val Ile Gln Lys Phe Phe Glu Phe Gly
        115                 120                 125

Ser Leu Glu Gln Lys Leu Ala Leu Ala Glu Arg Ile Arg Gly His Val
    130                 135                 140

Leu Ser Leu Ala Leu Gln Met Tyr Gly Ser Arg Val Ile Glu Lys Ala
145                 150                 155                 160

Leu Glu Phe Ile Pro Ser Asp Gln Gln Asn Glu Met Val Arg Glu Leu
                165                 170                 175

Asp Gly His Val Leu Lys Cys Val Lys Asp Gln Asn Gly Asn His Val
            180                 185                 190

Val Gln Lys Cys Ile Glu Cys Val Gln Pro Gln Ser Leu Gln Phe Ile
        195                 200                 205

Ile Asp Ala Phe Lys Gly Gln Val Phe Ala Leu Ser Thr His Pro Tyr
    210                 215                 220

Gly Cys Arg Val Ile Gln Arg Ile Leu Glu His Cys Leu Pro Asp Gln
225                 230                 235                 240

Thr Leu Pro Ile Leu Glu Glu Leu His Gln His Thr Glu Gln Leu Val
                245                 250                 255

Gln Asp Gln Tyr Gly Asn Tyr Val Ile Gln His Val Leu Glu His Gly
            260                 265                 270

Arg Pro Glu Asp Lys Ser Lys Ile Val Ala Glu Ile Arg Gly Asn Val
        275                 280                 285

Leu Val Leu Ser Gln His Lys Phe Ala Asn Asn Val Val Gln Lys Cys
    290                 295                 300
```

```
Val Thr His Ala Ser Arg Thr Glu Arg Ala Val Leu Ile Asp Glu Val
305                 310                 315                 320

Cys Thr Met Asn Asp Gly Pro His Ser Ala Leu Tyr Thr Met Met Lys
            325                 330                 335

Asp Gln Tyr Ala Asn Tyr Val Val Gln Lys Met Ile Asp Val Ala Glu
        340                 345                 350

Pro Gly Gln Arg Lys Ile Val Met His Lys Ile Arg Pro His Ile Ala
    355                 360                 365

Thr Leu Arg Lys Tyr Thr Tyr Gly Lys His Ile Leu Ala Lys Leu Glu
    370                 375                 380

Lys Tyr Tyr Met Lys Asn Gly Val Asp Leu Gly Val Asp Thr Gly Asn
385                 390                 395                 400

Gly Ser Gln Met Glu Leu Glu Ile Arg Pro Leu Phe Leu Val Pro Asp
            405                 410                 415

Thr Asn Gly Phe Ile Asp His Leu Ala Ser Leu Ala Arg Leu Leu Glu
        420                 425                 430

Ser Arg Lys Tyr Ile Leu Val Val Pro Leu Ile Val Ile Asn Glu Leu
    435                 440                 445

Asp Gly Leu Ala Lys Gly Gln Glu Thr Asp His Arg Ala Gly Gly Tyr
450                 455                 460

Ala Arg Val Val Gln Glu Lys Ala Arg Lys Ser Ile Glu Phe Leu Glu
465                 470                 475                 480

Gln Arg Phe Glu Ser Arg Asp Ser Cys Leu Arg Ala Leu Thr Ser Arg
            485                 490                 495

Gly Asn Glu Leu Glu Ser Ile Ala Phe Arg Ser Glu Asp Ile Thr Gly
        500                 505                 510

Gln Leu Gly Asn Asn Asp Asp Leu Ile Leu Ser Cys Cys Leu His Tyr
    515                 520                 525

Cys Lys Asp Lys Ala Lys Asp Phe Met Pro Ala Ser Lys Glu Glu Pro
530                 535                 540

Ile Arg Leu Leu Arg Glu Val Val Leu Leu Thr Asp Asp Arg Asn Leu
545                 550                 555                 560

Arg Val Lys Ala Leu Thr Arg Asn Val Pro Val Arg Asp Ile Pro Ala
            565                 570                 575

Phe Leu Thr Trp Ala Gln Val Gly
            580

<210> SEQ ID NO 14
<211> LENGTH: 538
<212> TYPE: PRT
<213> ORGANISM: Artificial
<220> FEATURE:
<223> OTHER INFORMATION: Artificial sequence-specific RNA endonuclease
      (ASRE) sequence

<400> SEQUENCE: 14

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
            20                  25                  30

Gln His Gly Ser Arg Phe Ile Gln Leu Lys Leu Glu Arg Ala Thr Pro
        35                  40                  45

Ala Glu Arg Gln Leu Val Phe Asn Glu Ile Leu Gln Ala Ala Tyr Gln
    50                  55                  60

Leu Met Val Asp Val Phe Gly Asn Tyr Val Ile Gln Lys Phe Phe Glu
65                  70                  75                  80
```

```
Phe Gly Ser Leu Glu Gln Lys Leu Ala Leu Ala Glu Arg Ile Arg Gly
                85                  90                  95
His Val Leu Ser Leu Ala Leu Gln Met Tyr Gly Cys Arg Val Ile Gln
            100                 105                 110
Lys Ala Leu Glu Phe Ile Pro Ser Asp Gln Gln Asn Glu Met Val Arg
        115                 120                 125
Glu Leu Asp Gly His Val Leu Lys Cys Val Lys Asp Gln Asn Gly Asn
    130                 135                 140
His Val Val Gln Lys Cys Ile Glu Cys Val Gln Pro Gln Ser Leu Gln
145                 150                 155                 160
Phe Ile Ile Asp Ala Phe Lys Gly Gln Val Phe Ala Leu Ser Thr His
                165                 170                 175
Pro Tyr Gly Cys Arg Val Ile Gln Arg Ile Leu Glu His Cys Leu Pro
            180                 185                 190
Asp Gln Thr Leu Pro Ile Leu Glu Glu Leu His Gln His Thr Glu Gln
        195                 200                 205
Leu Val Gln Asp Gln Tyr Gly Ser Tyr Val Ile Glu His Val Leu Glu
    210                 215                 220
His Gly Arg Pro Glu Asp Lys Ser Lys Ile Val Ala Glu Ile Arg Gly
225                 230                 235                 240
Asn Val Leu Val Leu Ser Gln His Lys Phe Ala Asn Asn Val Val Gln
                245                 250                 255
Lys Cys Val Thr His Ala Ser Arg Thr Glu Arg Ala Val Leu Ile Asp
            260                 265                 270
Glu Val Cys Thr Met Asn Asp Gly Pro His Ser Ala Leu Tyr Thr Met
        275                 280                 285
Met Lys Asp Gln Tyr Ala Asn Tyr Val Val Gln Lys Met Ile Asp Val
    290                 295                 300
Ala Glu Pro Gly Gln Arg Lys Ile Val Met His Lys Ile Arg Pro His
305                 310                 315                 320
Ile Ala Thr Leu Arg Lys Tyr Thr Tyr Gly Lys His Ile Leu Ala Lys
                325                 330                 335
Leu Glu Lys Tyr Tyr Met Lys Asn Gly Val Asp Leu Gly Val Asp Thr
            340                 345                 350
Gly Asn Gly Ser Gln Met Glu Leu Glu Ile Arg Pro Leu Phe Leu Val
        355                 360                 365
Pro Asp Thr Asn Gly Phe Ile Asp His Leu Ala Ser Leu Ala Arg Leu
    370                 375                 380
Leu Glu Ser Arg Lys Tyr Ile Leu Val Val Pro Leu Ile Val Ile Asn
385                 390                 395                 400
Glu Leu Asp Gly Leu Ala Lys Gly Gln Glu Thr Asp His Arg Ala Gly
                405                 410                 415
Gly Tyr Ala Arg Val Val Gln Glu Lys Ala Arg Lys Ser Ile Glu Phe
            420                 425                 430
Leu Glu Gln Arg Phe Glu Ser Arg Asp Ser Cys Leu Arg Ala Leu Thr
        435                 440                 445
Ser Arg Gly Asn Glu Leu Glu Ser Ile Ala Phe Arg Ser Glu Asp Ile
    450                 455                 460
Thr Gly Gln Leu Gly Asn Asn Ala Asp Leu Ile Leu Ser Cys Cys Leu
465                 470                 475                 480
His Tyr Cys Lys Asp Lys Ala Lys Asp Phe Met Pro Ala Ser Lys Glu
                485                 490                 495
```

```
Glu Pro Ile Arg Leu Leu Arg Glu Val Val Leu Thr Asp Asp Arg
                500                 505                 510

Asn Leu Arg Val Lys Ala Leu Thr Arg Asn Val Pro Val Arg Asp Ile
            515                 520                 525

Pro Ala Phe Leu Thr Trp Ala Gln Val Gly
        530                 535

<210> SEQ ID NO 15
<211> LENGTH: 538
<212> TYPE: PRT
<213> ORGANISM: Artificial
<220> FEATURE:
<223> OTHER INFORMATION: Artificial sequence-specific RNA endonuclease
      (ASRE) sequence

<400> SEQUENCE: 15

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
            20                  25                  30

Gln His Gly Ser Arg Phe Ile Gln Leu Lys Leu Glu Arg Ala Thr Pro
        35                  40                  45

Ala Glu Arg Gln Leu Val Phe Asn Glu Ile Leu Gln Ala Ala Tyr Gln
    50                  55                  60

Leu Met Val Asp Val Phe Gly Cys Arg Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Ser Arg Val Ile Glu
            100                 105                 110

Lys Ala Leu Glu Phe Ile Pro Ser Asp Gln Gln Asn Glu Met Val Arg
        115                 120                 125

Glu Leu Asp Gly His Val Leu Lys Cys Val Lys Asp Gln Asn Gly Asn
    130                 135                 140

His Val Val Gln Lys Cys Ile Glu Cys Val Gln Pro Gln Ser Leu Gln
145                 150                 155                 160

Phe Ile Ile Asp Ala Phe Lys Gly Gln Val Phe Ala Leu Ser Thr His
                165                 170                 175

Pro Tyr Gly Cys Arg Val Ile Gln Arg Ile Leu Glu His Cys Leu Pro
            180                 185                 190

Asp Gln Thr Leu Pro Ile Leu Glu Glu Leu His Gln His Thr Glu Gln
        195                 200                 205

Leu Val Gln Asp Gln Tyr Gly Ser Tyr Val Ile Glu His Val Leu Glu
    210                 215                 220

His Gly Arg Pro Glu Asp Lys Ser Lys Ile Val Ala Glu Ile Arg Gly
225                 230                 235                 240

Asn Val Leu Val Leu Ser Gln His Lys Phe Ala Ser Asn Val Val Glu
                245                 250                 255

Lys Cys Val Thr His Ala Ser Arg Thr Glu Arg Ala Val Leu Ile Asp
            260                 265                 270

Glu Val Cys Thr Met Asn Asp Gly Pro His Ser Ala Leu Tyr Thr Met
        275                 280                 285

Met Lys Asp Gln Tyr Ala Asn Tyr Val Val Gln Lys Met Ile Asp Val
    290                 295                 300

Ala Glu Pro Gly Gln Arg Lys Ile Val Met His Lys Ile Arg Pro His
305                 310                 315                 320
```

```
Ile Ala Thr Leu Arg Lys Tyr Thr Tyr Gly Lys His Ile Leu Ala Lys
                325                 330                 335

Leu Glu Lys Tyr Tyr Met Lys Asn Gly Val Asp Leu Gly Val Asp Thr
            340                 345                 350

Gly Asn Gly Ser Gln Met Glu Leu Glu Ile Arg Pro Leu Phe Leu Val
        355                 360                 365

Pro Asp Thr Asn Gly Phe Ile Asp His Leu Ala Ser Leu Ala Arg Leu
    370                 375                 380

Leu Glu Ser Arg Lys Tyr Ile Leu Val Val Pro Leu Ile Val Ile Asn
385                 390                 395                 400

Glu Leu Asp Gly Leu Ala Lys Gly Gln Glu Thr Asp His Arg Ala Gly
                405                 410                 415

Gly Tyr Ala Arg Val Val Gln Glu Lys Ala Arg Lys Ser Ile Glu Phe
            420                 425                 430

Leu Glu Gln Arg Phe Glu Ser Arg Asp Ser Cys Leu Arg Ala Leu Thr
        435                 440                 445

Ser Arg Gly Asn Glu Leu Glu Ser Ile Ala Phe Arg Ser Glu Asp Ile
    450                 455                 460

Thr Gly Gln Leu Gly Asn Asn Ala Asp Leu Ile Leu Ser Cys Cys Leu
465                 470                 475                 480

His Tyr Cys Lys Asp Lys Ala Lys Asp Phe Met Pro Ala Ser Lys Glu
                485                 490                 495

Glu Pro Ile Arg Leu Leu Arg Glu Val Val Leu Leu Thr Asp Asp Arg
            500                 505                 510

Asn Leu Arg Val Lys Ala Leu Thr Arg Asn Val Pro Val Arg Asp Ile
        515                 520                 525

Pro Ala Phe Leu Thr Trp Ala Gln Val Gly
    530                 535
```

<210> SEQ ID NO 16
<211> LENGTH: 584
<212> TYPE: PRT
<213> ORGANISM: Artificial
<220> FEATURE:
<223> OTHER INFORMATION: Artificial sequence-specific RNA endonuclease
      (ASRE) sequence

<400> SEQUENCE: 16

```
Met Leu Phe Asn Leu Arg Ile Leu Leu Asn Asn Ala Ala Phe Arg Asn
1               5                   10                  15

Gly His Asn Phe Met Val Arg Asn Phe Arg Cys Gly Gln Pro Leu Gln
            20                  25                  30

Asn Lys Val Gln Asp Tyr Lys Asp Asp Asp Lys Glu Phe Gly Arg
        35                  40                  45

Ser Arg Leu Leu Glu Asp Phe Arg Asn Asn Arg Tyr Pro Asn Leu Gln
    50                  55                  60

Leu Arg Glu Ile Ala Gly His Ile Met Glu Phe Ser Gln Asp Gln His
65                  70                  75                  80

Gly Ser Arg Phe Ile Glu Leu Lys Leu Glu Arg Ala Thr Pro Ala Glu
                85                  90                  95

Arg Gln Leu Val Phe Asn Glu Ile Gln Ala Ala Tyr Gln Leu Met
            100                 105                 110

Val Asp Val Phe Gly Asn Tyr Val Ile Gln Lys Phe Phe Glu Phe Gly
        115                 120                 125

Ser Leu Glu Gln Lys Leu Ala Leu Ala Glu Arg Ile Arg Gly His Val
```

```
            130                 135                 140
Leu Ser Leu Ala Leu Gln Met Tyr Gly Ser Arg Val Ile Glu Lys Ala
145                 150                 155                 160

Leu Glu Phe Ile Pro Ser Asp Gln Gln Asn Glu Met Val Arg Glu Leu
                165                 170                 175

Asp Gly His Val Leu Lys Cys Val Lys Asp Gln Asn Gly Asn His Val
                180                 185                 190

Val Gln Lys Cys Ile Glu Cys Val Gln Pro Gln Ser Leu Gln Phe Ile
                195                 200                 205

Ile Asp Ala Phe Lys Gly Gln Val Phe Ala Leu Ser Thr His Pro Tyr
210                 215                 220

Gly Cys Arg Val Ile Gln Arg Ile Leu Glu His Cys Leu Pro Asp Gln
225                 230                 235                 240

Thr Leu Pro Ile Leu Glu Glu Leu His Gln His Thr Glu Gln Leu Val
                245                 250                 255

Gln Asp Gln Tyr Gly Asn Tyr Val Ile Gln His Val Leu Glu His Gly
                260                 265                 270

Arg Pro Glu Asp Lys Ser Lys Ile Val Ala Glu Ile Arg Gly Asn Val
                275                 280                 285

Leu Val Leu Ser Gln His Lys Phe Ala Asn Asn Val Val Gln Lys Cys
290                 295                 300

Val Thr His Ala Ser Arg Thr Glu Arg Ala Val Leu Ile Asp Glu Val
305                 310                 315                 320

Cys Thr Met Asn Asp Gly Pro His Ser Ala Leu Tyr Thr Met Met Lys
                325                 330                 335

Asp Gln Tyr Ala Asn Tyr Val Val Gln Lys Met Ile Asp Val Ala Glu
                340                 345                 350

Pro Gly Gln Arg Lys Ile Val Met His Lys Ile Arg Pro His Ile Ala
                355                 360                 365

Thr Leu Arg Lys Tyr Thr Tyr Gly Lys His Ile Leu Ala Lys Leu Glu
                370                 375                 380

Lys Tyr Tyr Met Lys Asn Gly Val Asp Leu Gly Val Asp Thr Gly Asn
385                 390                 395                 400

Gly Ser Gln Met Glu Leu Glu Ile Arg Pro Leu Phe Leu Val Pro Asp
                405                 410                 415

Thr Asn Gly Phe Ile Asp His Leu Ala Ser Leu Ala Arg Leu Leu Glu
                420                 425                 430

Ser Arg Lys Tyr Ile Leu Val Val Pro Leu Ile Val Ile Asn Glu Leu
                435                 440                 445

Asp Gly Leu Ala Lys Gly Gln Glu Thr Asp His Arg Ala Gly Gly Tyr
                450                 455                 460

Ala Arg Val Val Gln Glu Lys Ala Arg Lys Ser Ile Glu Phe Leu Glu
465                 470                 475                 480

Gln Arg Phe Glu Ser Arg Asp Ser Cys Leu Arg Ala Leu Thr Ser Arg
                485                 490                 495

Gly Asn Glu Leu Glu Ser Ile Ala Phe Arg Ser Glu Asp Ile Thr Gly
                500                 505                 510

Gln Leu Gly Asn Asn Ala Asp Leu Ile Leu Ser Cys Cys Leu His Tyr
                515                 520                 525

Cys Lys Asp Lys Ala Lys Asp Phe Met Pro Ala Ser Lys Glu Glu Pro
530                 535                 540

Ile Arg Leu Leu Arg Glu Val Val Leu Leu Thr Asp Asp Arg Asn Leu
545                 550                 555                 560
```

```
Arg Val Lys Ala Leu Thr Arg Asn Val Pro Val Arg Asp Ile Pro Ala
            565                 570                 575

Phe Leu Thr Trp Ala Gln Val Gly
            580

<210> SEQ ID NO 17
<211> LENGTH: 7
<212> TYPE: PRT
<213> ORGANISM: Artificial
<220> FEATURE:
<223> OTHER INFORMATION: Linker sequence

<400> SEQUENCE: 17

Val Asp Thr Gly Asn Trp Phe
1               5

<210> SEQ ID NO 18
<211> LENGTH: 7
<212> TYPE: PRT
<213> ORGANISM: Artificial
<220> FEATURE:
<223> OTHER INFORMATION: Linker sequence

<400> SEQUENCE: 18

Val Asp Thr Gly Asn Gly Ser
1               5

<210> SEQ ID NO 19
<211> LENGTH: 12
<212> TYPE: PRT
<213> ORGANISM: Artificial
<220> FEATURE:
<223> OTHER INFORMATION: Linker sequence

<400> SEQUENCE: 19

Val Asp Arg Arg Met Ala Arg Asp Gly Leu Val His
1               5                   10

<210> SEQ ID NO 20
<211> LENGTH: 16
<212> TYPE: PRT
<213> ORGANISM: Artificial
<220> FEATURE:
<223> OTHER INFORMATION: PCR primer

<400> SEQUENCE: 20

Val Asp Phe Val Gly Tyr Pro Arg Phe Pro Ala Pro Val Glu Phe Ile
1               5                   10                  15

<210> SEQ ID NO 21
<211> LENGTH: 7
<212> TYPE: PRT
<213> ORGANISM: Artificial
<220> FEATURE:
<223> OTHER INFORMATION: PCR primer

<400> SEQUENCE: 21

Val Asp Thr Gly Asn Gly Ser
1               5

<210> SEQ ID NO 22
<211> LENGTH: 11
<212> TYPE: PRT
<213> ORGANISM: Artificial
<220> FEATURE:
<223> OTHER INFORMATION: PCR primer
```

```
<400> SEQUENCE: 22

Val Asp Met Ala Leu His Ala Arg Asn Ile Ala
1               5                   10

<210> SEQ ID NO 23
<211> LENGTH: 13
<212> TYPE: PRT
<213> ORGANISM: Artificial
<220> FEATURE:
<223> OTHER INFORMATION: PCR primer

<400> SEQUENCE: 23

Val Asp Leu Leu Ala Leu Asp Arg Glu Val Gln Glu Leu
1               5                   10

<210> SEQ ID NO 24
<211> LENGTH: 10
<212> TYPE: PRT
<213> ORGANISM: Artificial
<220> FEATURE:
<223> OTHER INFORMATION: PCR primer

<400> SEQUENCE: 24

Leu Leu Ala Leu Asp Arg Glu Val Gln Glu
1               5                   10

<210> SEQ ID NO 25
<211> LENGTH: 9
<212> TYPE: PRT
<213> ORGANISM: Artificial
<220> FEATURE:
<223> OTHER INFORMATION: PCR primer

<400> SEQUENCE: 25

Leu Leu Ala Leu Asp Arg Glu Val Gln
1               5

<210> SEQ ID NO 26
<211> LENGTH: 8
<212> TYPE: PRT
<213> ORGANISM: Artificial
<220> FEATURE:
<223> OTHER INFORMATION: PCR primer

<400> SEQUENCE: 26

Leu Leu Ala Leu Asp Arg Glu Val
1               5

<210> SEQ ID NO 27
<211> LENGTH: 10
<212> TYPE: PRT
<213> ORGANISM: Artificial
<220> FEATURE:
<223> OTHER INFORMATION: PCR primer

<400> SEQUENCE: 27

Val Asp His Ile Gln Arg Gly Gly Ser Pro
1               5                   10

<210> SEQ ID NO 28
<211> LENGTH: 12
<212> TYPE: PRT
<213> ORGANISM: Artificial
<220> FEATURE:
<223> OTHER INFORMATION: PCR primer
```

```
<400> SEQUENCE: 28

Val Asp Arg Arg Met Ala Arg Asp Gly Leu Val His
1               5                   10

<210> SEQ ID NO 29
<211> LENGTH: 29
<212> TYPE: PRT
<213> ORGANISM: Artificial
<220> FEATURE:
<223> OTHER INFORMATION: PCR primer

<400> SEQUENCE: 29

Cys Ala Cys Gly Ala Ala Thr Thr Cys Ala Ala Gly Gly Cys Cys Gly
1               5                   10                  15
Cys Ala Gly Cys Cys Gly Cys Cys Thr Thr Thr Thr Gly
                20                  25

<210> SEQ ID NO 30
<211> LENGTH: 31
<212> TYPE: PRT
<213> ORGANISM: Artificial
<220> FEATURE:
<223> OTHER INFORMATION: PCR primer

<400> SEQUENCE: 30

Cys Ala Cys Gly Thr Cys Gly Ala Cys Cys Cys Cys Thr Ala Ala Gly
1               5                   10                  15
Thr Cys Ala Ala Cys Ala Cys Cys Gly Thr Thr Cys Thr Thr Cys
                20                  25                  30

<210> SEQ ID NO 31
<211> LENGTH: 47
<212> TYPE: PRT
<213> ORGANISM: Artificial
<220> FEATURE:
<223> OTHER INFORMATION: PCR primer

<400> SEQUENCE: 31

Cys Ala Cys Gly Thr Cys Gly Ala Cys Ala Cys Cys Gly Gly Cys Ala
1               5                   10                  15
Ala Cys Gly Gly Cys Thr Cys Thr Cys Ala Gly Ala Thr Gly Gly Ala
                20                  25                  30
Gly Cys Thr Cys Gly Ala Ala Ala Thr Cys Ala Gly Ala Cys Cys
            35                  40                  45

<210> SEQ ID NO 32
<211> LENGTH: 30
<212> TYPE: PRT
<213> ORGANISM: Artificial
<220> FEATURE:
<223> OTHER INFORMATION: PCR primer

<400> SEQUENCE: 32

Cys Ala Cys Gly Cys Gly Gly Cys Cys Gly Cys Thr Thr Ala Gly Cys
1               5                   10                  15
Cys Cys Ala Cys Cys Thr Gly Gly Gly Cys Cys Cys Ala Cys
                20                  25                  30

<210> SEQ ID NO 33
<211> LENGTH: 34
<212> TYPE: PRT
<213> ORGANISM: Artificial
<220> FEATURE:
<223> OTHER INFORMATION: PCR primer
```

```
<400> SEQUENCE: 33

Cys Ala Cys Gly Ala Ala Thr Thr Cys Ala Cys Ala Gly Ala Thr
1               5                   10                  15

Gly Gly Ala Gly Cys Thr Cys Gly Ala Ala Thr Cys Ala Gly Ala
            20                  25                  30

Cys Cys

<210> SEQ ID NO 34
<211> LENGTH: 30
<212> TYPE: PRT
<213> ORGANISM: Artificial
<220> FEATURE:
<223> OTHER INFORMATION: PCR primer

<400> SEQUENCE: 34

Cys Ala Cys Gly Thr Cys Gly Ala Cys Ala Cys Thr Cys Ala Gly Ala
1               5                   10                  15

Thr Gly Gly Ala Gly Cys Thr Cys Gly Ala Ala Thr Cys
            20                  25                  30

<210> SEQ ID NO 35
<211> LENGTH: 60
<212> TYPE: PRT
<213> ORGANISM: Artificial
<220> FEATURE:
<223> OTHER INFORMATION: PCR primer

<400> SEQUENCE: 35

Cys Ala Cys Gly Thr Cys Gly Ala Cys Cys Gly Thr Cys Gly Thr Ala
1               5                   10                  15

Thr Gly Gly Cys Thr Cys Gly Thr Gly Ala Thr Gly Gly Thr Cys Thr
            20                  25                  30

Thr Gly Thr Thr Cys Ala Thr Cys Ala Thr Cys Ala Gly Ala Thr Gly
        35                  40                  45

Gly Ala Gly Cys Thr Cys Gly Ala Ala Thr Cys
    50                  55                  60

<210> SEQ ID NO 36
<211> LENGTH: 29
<212> TYPE: PRT
<213> ORGANISM: Artificial
<220> FEATURE:
<223> OTHER INFORMATION: PCR primer

<400> SEQUENCE: 36

Cys Ala Cys Ala Ala Gly Cys Thr Thr Cys Cys Thr Cys Ala Thr
1               5                   10                  15

Thr Gly Ala Cys Thr Ala Gly Ala Gly Cys Thr Cys Cys
            20                  25

<210> SEQ ID NO 37
<211> LENGTH: 30
<212> TYPE: PRT
<213> ORGANISM: Artificial
<220> FEATURE:
<223> OTHER INFORMATION: PCR primer

<400> SEQUENCE: 37

Cys Ala Cys Thr Cys Thr Ala Gly Ala Thr Gly Cys Ala Thr Gly Cys
1               5                   10                  15

Thr Cys Gly Ala Cys Thr Thr Gly Gly Ala Ala Ala Ala Cys
```

```
                 20                  25                  30
```

<210> SEQ ID NO 38
<211> LENGTH: 28
<212> TYPE: PRT
<213> ORGANISM: Artificial
<220> FEATURE:
<223> OTHER INFORMATION: PCR primer

<400> SEQUENCE: 38

```
Gly Gly Thr Thr Cys Thr Cys Gly Ala Gly Ala Ala Thr Gly Thr Gly
1               5                   10                  15

Ala Thr Ala Ala Gly Thr Thr Cys Gly Gly Cys
            20                  25
```

<210> SEQ ID NO 39
<211> LENGTH: 30
<212> TYPE: PRT
<213> ORGANISM: Artificial
<220> FEATURE:
<223> OTHER INFORMATION: PCR primer

<400> SEQUENCE: 39

```
Gly Gly Thr Thr Cys Thr Cys Thr Cys Gly Ala Gly Ala Ala Thr Thr
1               5                   10                  15

Thr Gly Ala Thr Ala Thr Gly Thr Thr Cys Gly Gly Gly Cys
            20                  25                  30
```

<210> SEQ ID NO 40
<211> LENGTH: 28
<212> TYPE: PRT
<213> ORGANISM: Artificial
<220> FEATURE:
<223> OTHER INFORMATION: PCR primer

<400> SEQUENCE: 40

```
Cys Ala Cys Gly Ala Ala Thr Thr Cys Thr Gly Gly Cys Cys Gly Cys
1               5                   10                  15

Ala Gly Cys Cys Gly Cys Cys Thr Thr Thr Thr Gly
            20                  25
```

<210> SEQ ID NO 41
<211> LENGTH: 29
<212> TYPE: PRT
<213> ORGANISM: Artificial
<220> FEATURE:
<223> OTHER INFORMATION: PCR primer

<400> SEQUENCE: 41

```
Cys Ala Cys Thr Cys Thr Ala Gly Ala Cys Cys Cys Thr Cys Ala Cys
1               5                   10                  15

Cys Thr Thr Gly Ala Ala Thr Thr Gly Gly Gly Cys Cys
            20                  25
```

<210> SEQ ID NO 42
<211> LENGTH: 38
<212> TYPE: PRT
<213> ORGANISM: Artificial
<220> FEATURE:
<223> OTHER INFORMATION: PCR primer

<400> SEQUENCE: 42

```
Ala Cys Cys Cys Ala Ala Gly Cys Thr Thr Gly Gly Thr Ala Cys Cys
1               5                   10                  15
```

Gly Ala Gly Cys Thr Thr Thr Thr Thr Thr Thr Thr Thr Thr
            20                  25                  30

Thr Thr Thr Thr Thr Thr
        35

<210> SEQ ID NO 43
<211> LENGTH: 20
<212> TYPE: PRT
<213> ORGANISM: Artificial
<220> FEATURE:
<223> OTHER INFORMATION: PCR primer

<400> SEQUENCE: 43

Ala Cys Cys Cys Ala Ala Gly Cys Thr Thr Gly Gly Thr Ala Cys Cys
1               5                   10                  15

Gly Ala Gly Cys
            20

<210> SEQ ID NO 44
<211> LENGTH: 29
<212> TYPE: PRT
<213> ORGANISM: Artificial
<220> FEATURE:
<223> OTHER INFORMATION: PCR primer

<400> SEQUENCE: 44

Cys Ala Cys Gly Gly Ala Thr Cys Cys Gly Cys Ala Thr Ala Thr Thr
1               5                   10                  15

Ala Gly Ala Thr Thr Gly Cys Ala Cys Cys Ala Cys Cys
            20                  25

<210> SEQ ID NO 45
<211> LENGTH: 19
<212> TYPE: PRT
<213> ORGANISM: Artificial
<220> FEATURE:
<223> OTHER INFORMATION: PCR primer

<400> SEQUENCE: 45

Gly Gly Ala Gly Thr Gly Thr Thr Gly Thr Gly Gly Thr Gly Thr Ala
1               5                   10                  15

Gly Thr Cys

<210> SEQ ID NO 46
<211> LENGTH: 20
<212> TYPE: PRT
<213> ORGANISM: Artificial
<220> FEATURE:
<223> OTHER INFORMATION: PCR primer

<400> SEQUENCE: 46

Gly Gly Ala Cys Cys Cys Ala Cys Thr Thr Cys Thr Gly Cys Cys Ala
1               5                   10                  15

Cys Cys Ala Cys
            20

<210> SEQ ID NO 47
<211> LENGTH: 23
<212> TYPE: PRT
<213> ORGANISM: Artificial
<220> FEATURE:
<223> OTHER INFORMATION: PCR primer

<400> SEQUENCE: 47

-continued

```
Cys Cys Thr Gly Cys Thr Gly Ala Thr Gly Ala Ala Gly Cys Ala Gly
1               5                   10                  15

Cys Ala Gly Ala Ala Cys Ala
            20

<210> SEQ ID NO 48
<211> LENGTH: 20
<212> TYPE: PRT
<213> ORGANISM: Artificial
<220> FEATURE:
<223> OTHER INFORMATION: PCR primer

<400> SEQUENCE: 48

Ala Gly Ala Cys Gly Ala Thr Thr Cys Ala Thr Thr Gly Gly Cys Ala
1               5                   10                  15

Cys Cys Ala Thr
            20

<210> SEQ ID NO 49
<211> LENGTH: 19
<212> TYPE: PRT
<213> ORGANISM: Artificial
<220> FEATURE:
<223> OTHER INFORMATION: PCR primer

<400> SEQUENCE: 49

Gly Ala Gly Gly Ala Thr Cys Gly Cys Gly Ala Thr Gly Cys Ala Thr
1               5                   10                  15

Thr Gly Cys

<210> SEQ ID NO 50
<211> LENGTH: 19
<212> TYPE: PRT
<213> ORGANISM: Artificial
<220> FEATURE:
<223> OTHER INFORMATION: PCR primer

<400> SEQUENCE: 50

Cys Thr Thr Cys Ala Gly Cys Gly Ala Cys Gly Ala Cys Thr Gly Gly
1               5                   10                  15

Thr Gly Cys

<210> SEQ ID NO 51
<211> LENGTH: 33
<212> TYPE: PRT
<213> ORGANISM: Artificial
<220> FEATURE:
<223> OTHER INFORMATION: PCR primer

<400> SEQUENCE: 51

Cys Ala Cys Gly Gly Ala Thr Cys Gly Ala Ala Thr Thr Cys Ala Thr
1               5                   10                  15

Gly Gly Ala Gly Cys Thr Cys Gly Ala Ala Ala Thr Cys Ala Gly Ala
            20                  25                  30

Cys

<210> SEQ ID NO 52
<211> LENGTH: 25
<212> TYPE: PRT
<213> ORGANISM: Artificial
<220> FEATURE:
<223> OTHER INFORMATION: PCR primer

<400> SEQUENCE: 52
```

Cys Ala Cys Gly Cys Thr Ala Gly Cys Gly Cys Cys Ala Cys Cys
1               5                   10                  15

Thr Gly Gly Gly Cys Cys Cys Ala Cys
            20              25

<210> SEQ ID NO 53
<211> LENGTH: 41
<212> TYPE: PRT
<213> ORGANISM: Artificial
<220> FEATURE:
<223> OTHER INFORMATION: PCR primer

<400> SEQUENCE: 53

Cys Ala Cys Gly Cys Thr Ala Gly Cys Ala Cys Cys Gly Gly Cys Ala
1               5                   10                  15

Ala Cys Gly Gly Cys Thr Cys Thr Gly Gly Cys Cys Gly Cys Ala Gly
            20                  25                  30

Cys Cys Gly Cys Thr Thr Thr Thr Gly
        35                  40

<210> SEQ ID NO 54
<211> LENGTH: 36
<212> TYPE: PRT
<213> ORGANISM: Artificial
<220> FEATURE:
<223> OTHER INFORMATION: PCR primer

<400> SEQUENCE: 54

Cys Ala Cys Gly Cys Gly Gly Cys Cys Gly Cys Thr Thr Ala Cys Cys
1               5                   10                  15

Cys Thr Ala Ala Gly Thr Cys Ala Ala Cys Ala Cys Cys Gly Thr Thr
            20                  25                  30

Cys Thr Thr Cys
        35

<210> SEQ ID NO 55
<211> LENGTH: 351
<212> TYPE: PRT
<213> ORGANISM: Homo sapiens

<400> SEQUENCE: 55

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
            20                  25                  30

Gln His Gly Ser Arg Phe Ile Gln Leu Lys Leu Glu Arg Ala Thr Pro
        35                  40                  45

Ala Glu Arg Gln Leu Val Phe Asn Glu Ile Leu Gln Ala Ala Tyr Gln
    50                  55                  60

Leu Met Val Asp Val Phe Gly Asn Tyr Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Cys Arg Val Ile Gln
            100                 105                 110

Lys Ala Leu Glu Phe Ile Pro Ser Asp Gln Gln Val Ile Asn Glu Met
        115                 120                 125

Val Arg Glu Leu Asp Gly His Val Leu Lys Cys Val Lys Asp Gln Asn
    130                 135                 140

-continued

```
Gly Asn His Val Val Gln Lys Cys Ile Glu Cys Val Gln Pro Gln Ser
145                 150                 155                 160

Leu Gln Phe Ile Ile Asp Ala Phe Lys Gly Gln Val Phe Ala Leu Ser
            165                 170                 175

Thr His Pro Tyr Gly Cys Arg Val Ile Gln Arg Ile Leu Glu His Cys
        180                 185                 190

Leu Pro Asp Gln Thr Leu Pro Ile Leu Glu Glu Leu His Gln His Thr
    195                 200                 205

Glu Gln Leu Val Gln Asp Gln Tyr Gly Asn Tyr Val Ile Gln His Val
210                 215                 220

Leu Glu His Gly Arg Pro Glu Asp Lys Ser Lys Ile Val Ala Glu Ile
225                 230                 235                 240

Arg Gly Asn Val Leu Val Leu Ser Gln His Lys Phe Ala Ser Asn Val
                245                 250                 255

Val Glu Lys Cys Val Thr His Ala Ser Arg Thr Glu Arg Ala Val Leu
            260                 265                 270

Ile Asp Glu Val Cys Thr Met Asn Asp Gly Pro His Ser Ala Leu Tyr
        275                 280                 285

Thr Met Met Lys Asp Gln Tyr Ala Asn Tyr Val Val Gln Lys Met Ile
    290                 295                 300

Asp Val Ala Glu Pro Gly Gln Arg Lys Ile Val Met His Lys Ile Arg
305                 310                 315                 320

Pro His Ile Ala Thr Leu Arg Lys Tyr Thr Tyr Gly Lys His Ile Leu
                325                 330                 335

Ala Lys Leu Glu Lys Tyr Tyr Met Lys Asn Gly Val Asp Leu Gly
            340                 345                 350
```

<210> SEQ ID NO 56
<211> LENGTH: 361
<212> TYPE: PRT
<213> ORGANISM: Mus musculus

<400> SEQUENCE: 56

```
Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
            20                  25                  30

Gln His Gly Ser Arg Phe Ile Gln Leu Lys Leu Glu Arg Ala Thr Ala
        35                  40                  45

Ala Glu Arg Gln Leu Val Phe Asn Glu Ile Leu Gln Ala Ala Tyr Gln
    50                  55                  60

Leu Met Val Asp Val Phe Gly Asn Tyr Val Ile Gln Lys Phe Phe Glu
65                  70                  75                  80

Phe Gly Ser His Glu Gln Lys Leu Ala Leu Ala Glu Arg Ile Arg Gly
                85                  90                  95

His Val Leu Ser Leu Ala Leu Gln Met Tyr Gly Cys Arg Val Ile Gln
            100                 105                 110

Lys Ala Leu Glu Phe Ile Pro Ser Asp Gln Gln Val Ile Asn Glu Met
        115                 120                 125

Val Arg Glu Leu Asp Gly His Val Leu Lys Cys Val Lys Asp Gln Asn
    130                 135                 140

Gly Asn His Val Val Gln Lys Cys Ile Glu Cys Val Gln Pro Gln Ser
145                 150                 155                 160

Leu Gln Phe Ile Ile Asp Ala Phe Lys Gly Gln Val Phe Ala Leu Ser
```

```
            165                 170                 175
Thr His Pro Tyr Gly Cys Arg Val Ile Gln Arg Ile Leu Glu His Cys
            180                 185                 190

Leu Pro Asp Gln Thr Leu Pro Ile Leu Glu Glu Leu His Gln His Thr
            195                 200                 205

Glu Gln Leu Val Gln Asp Gln Tyr Gly Asn Tyr Val Ile Gln His Val
            210                 215                 220

Leu Glu His Gly Arg Pro Glu Asp Lys Ser Lys Ile Val Ala Glu Ile
225                 230                 235                 240

Arg Gly Asn Val Leu Val Leu Ser Gln His Lys Phe Ala Ser Asn Val
                245                 250                 255

Val Glu Lys Cys Val Thr His Ala Ser Arg Thr Glu Arg Ala Val Leu
            260                 265                 270

Ile Asp Glu Val Cys Thr Met Asn Asp Gly Pro His Ser Ala Leu Tyr
            275                 280                 285

Thr Met Met Lys Asp Gln Tyr Ala Asn Tyr Val Val Gln Lys Met Ile
            290                 295                 300

Asp Val Ala Glu Pro Gly Gln Arg Lys Ile Val Met His Lys Ile Arg
305                 310                 315                 320

Pro His Ile Ala Thr Leu Arg Lys Tyr Thr Tyr Gly Lys His Ile Leu
                325                 330                 335

Ala Lys Leu Glu Lys Tyr Tyr Met Lys Asn Gly Val Asp Leu Gly Pro
            340                 345                 350

Ile Cys Gly Pro Pro Asn Gly Ile Ile
            355                 360

<210> SEQ ID NO 57
<211> LENGTH: 361
<212> TYPE: PRT
<213> ORGANISM: Rattus norvegicus

<400> SEQUENCE: 57

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
                20                  25                  30

Gln His Gly Ser Arg Phe Ile Gln Leu Lys Leu Glu Arg Ala Thr Ala
            35                  40                  45

Ala Glu Arg Gln Leu Val Phe Asn Glu Ile Leu Gln Ala Ala Tyr Gln
        50                  55                  60

Leu Met Val Asp Val Phe Gly Asn Tyr Val Ile Gln Lys Phe Phe Glu
65                  70                  75                  80

Phe Gly Ser His Glu Gln Lys Leu Ala Leu Ala Glu Arg Ile Arg Gly
                85                  90                  95

His Val Leu Ser Leu Ala Leu Gln Met Tyr Gly Cys Arg Val Ile Gln
            100                 105                 110

Lys Ala Leu Glu Phe Ile Pro Ser Asp Gln Val Ile Asn Glu Met
            115                 120                 125

Val Arg Glu Leu Asp Gly His Val Leu Lys Cys Val Lys Asp Gln Asn
        130                 135                 140

Gly Asn His Val Val Gln Lys Cys Ile Glu Cys Val Gln Pro Gln Ser
145                 150                 155                 160

Leu Gln Phe Ile Ile Asp Ala Phe Lys Gly Gln Val Phe Ala Leu Ser
                165                 170                 175
```

```
Thr His Pro Tyr Gly Cys Arg Val Ile Gln Arg Ile Leu Glu His Cys
            180                 185                 190

Leu Pro Asp Gln Thr Leu Pro Ile Leu Glu Glu Leu His Gln His Thr
        195                 200                 205

Glu Gln Leu Val Gln Asp Gln Tyr Gly Asn Tyr Val Ile Gln His Val
    210                 215                 220

Leu Glu His Gly Arg Pro Glu Asp Lys Ser Lys Ile Val Ala Glu Ile
225                 230                 235                 240

Arg Gly Asn Val Leu Val Leu Ser Gln His Lys Phe Ala Ser Asn Val
                245                 250                 255

Val Glu Lys Cys Val Thr His Ala Ser Arg Thr Glu Arg Ala Val Leu
            260                 265                 270

Ile Asp Glu Val Cys Thr Met Asn Asp Gly Pro His Ser Ala Leu Tyr
        275                 280                 285

Thr Met Met Lys Asp Gln Tyr Ala Asn Tyr Val Val Gln Lys Met Ile
    290                 295                 300

Asp Val Ala Glu Pro Gly Gln Arg Lys Ile Val Met His Lys Ile Arg
305                 310                 315                 320

Pro His Ile Ala Thr Leu Arg Lys Tyr Thr Tyr Gly Lys His Ile Leu
                325                 330                 335

Ala Lys Leu Glu Lys Tyr Tyr Met Lys Asn Gly Val Asp Leu Gly Pro
            340                 345                 350

Ile Cys Gly Pro Pro Asn Gly Ile Ile
            355                 360

<210> SEQ ID NO 58
<211> LENGTH: 359
<212> TYPE: PRT
<213> ORGANISM: Homo sapiens

<400> SEQUENCE: 58

Gly Arg Ser Arg Leu Leu Glu Asp Phe Arg Asn Asn Arg Phe Pro Asn
1               5                   10                  15

Leu Gln Leu Arg Asp Leu Ile Gly His Ile Val Glu Phe Ser Gln Asp
            20                  25                  30

Gln His Gly Ser Arg Phe Ile Gln Gln Lys Leu Glu Arg Ala Thr Pro
        35                  40                  45

Ala Glu Arg Gln Met Val Phe Asn Glu Ile Leu Gln Ala Ala Tyr Gln
    50                  55                  60

Leu Met Thr Asp Val Phe Gly Asn Tyr Val Ile Gln Lys Phe Phe Glu
65                  70                  75                  80

Phe Gly Ser Leu Asp Gln Lys Leu Ala Leu Ala Thr Arg Ile Arg Gly
                85                  90                  95

His Val Leu Pro Leu Ala Leu Gln Met Tyr Gly Cys Arg Val Ile Gln
            100                 105                 110

Lys Ala Leu Glu Ser Ile Ser Ser Asp Gln Gln Ser Glu Met Val Lys
        115                 120                 125

Glu Leu Asp Gly His Val Leu Lys Cys Val Lys Asp Gln Asn Gly Asn
    130                 135                 140

His Val Val Gln Lys Cys Ile Glu Cys Val Gln Pro Gln Ser Leu Gln
145                 150                 155                 160

Phe Ile Ile Asp Ala Phe Lys Gly Gln Val Phe Val Leu Ser Thr His
                165                 170                 175

Pro Tyr Gly Cys Arg Val Ile Gln Arg Ile Leu Glu His Cys Thr Ala
            180                 185                 190
```

Glu Gln Thr Leu Pro Ile Leu Glu Glu Leu His Gln His Thr Glu Gln
    195                 200                 205

Leu Val Gln Asp Gln Tyr Gly Asn Tyr Val Ile Gln His Val Leu Glu
    210                 215                 220

His Gly Arg Pro Glu Asp Lys Ser Lys Ile Val Ser Glu Ile Arg Gly
225                 230                 235                 240

Lys Val Leu Ala Leu Ser Gln His Lys Phe Ala Ser Asn Val Val Glu
                245                 250                 255

Lys Cys Val Thr His Ala Ser Arg Ala Glu Arg Ala Leu Leu Ile Asp
                260                 265                 270

Glu Val Cys Cys Gln Asn Asp Gly Pro His Ser Ala Leu Tyr Thr Met
                275                 280                 285

Met Lys Asp Gln Tyr Ala Asn Tyr Val Val Gln Lys Met Ile Asp Met
    290                 295                 300

Ala Glu Pro Ala Gln Arg Lys Ile Ile Met His Lys Ile Arg Pro His
305                 310                 315                 320

Ile Thr Thr Leu Arg Lys Tyr Thr Tyr Gly Lys His Ile Leu Ala Lys
                325                 330                 335

Leu Glu Lys Tyr Tyr Leu Lys Asn Ser Pro Asp Leu Gly Pro Ile Gly
                340                 345                 350

Gly Pro Pro Asn Gly Met Leu
            355

<210> SEQ ID NO 59
<211> LENGTH: 361
<212> TYPE: PRT
<213> ORGANISM: Mus musculus

<400> SEQUENCE: 59

Gly Arg Ser Arg Leu Leu Glu Asp Phe Arg Asn Asn Arg Phe Pro Asn
1               5                   10                  15

Leu Gln Leu Arg Asp Leu Ile Gly His Ile Val Glu Phe Ser Gln Asp
                20                  25                  30

Gln His Gly Ser Arg Phe Ile Gln Gln Lys Leu Glu Arg Ala Thr Pro
            35                  40                  45

Ala Glu Arg Gln Ile Val Phe Asn Glu Ile Leu Gln Ala Ala Tyr Gln
    50                  55                  60

Leu Met Thr Asp Val Phe Gly Asn Tyr Val Ile Gln Lys Phe Phe Glu
65                  70                  75                  80

Phe Gly Ser Leu Asp Gln Lys Leu Ala Leu Ala Thr Arg Ile Arg Gly
                85                  90                  95

His Val Leu Pro Leu Ala Leu Gln Met Tyr Gly Cys Arg Val Ile Gln
                100                 105                 110

Lys Ala Leu Glu Ser Ile Ser Ser Asp Gln Gln Val Ile Ser Glu Met
            115                 120                 125

Val Lys Glu Leu Asp Gly His Val Leu Lys Cys Val Lys Asp Gln Asn
    130                 135                 140

Gly Asn His Val Val Gln Lys Cys Ile Glu Cys Val Gln Pro Gln Ser
145                 150                 155                 160

Leu Gln Phe Ile Ile Asp Ala Phe Lys Gly Gln Val Phe Val Leu Ser
                165                 170                 175

Thr His Pro Tyr Gly Cys Arg Val Ile Gln Arg Ile Leu Glu His Cys
                180                 185                 190

Thr Ala Glu Gln Thr Leu Pro Ile Leu Glu Glu Leu His Gln His Thr

```
                    195                 200                 205
Glu Gln Leu Val Gln Asp Gln Tyr Gly Asn Tyr Val Ile Gln His Val
    210                 215                 220
Leu Glu His Gly Arg Pro Glu Asp Lys Ser Lys Ile Val Ser Glu Ile
225                 230                 235                 240
Arg Gly Lys Val Leu Ala Leu Ser Gln His Lys Phe Ala Ser Asn Val
                245                 250                 255
Val Glu Lys Cys Val Thr His Ala Ser Arg Ala Glu Arg Ala Leu Leu
            260                 265                 270
Ile Asp Glu Val Cys Cys Gln Asn Asp Gly Pro His Ser Ala Leu Tyr
        275                 280                 285
Thr Met Met Lys Asp Gln Tyr Ala Asn Tyr Val Val Gln Lys Met Ile
    290                 295                 300
Asp Met Ala Glu Pro Ala Gln Arg Lys Ile Ile Met His Lys Ile Arg
305                 310                 315                 320
Pro His Ile Thr Thr Leu Arg Lys Tyr Thr Tyr Gly Lys His Ile Leu
                325                 330                 335
Ala Lys Leu Glu Lys Tyr Tyr Leu Lys Asn Ser Pro Asp Leu Gly Pro
            340                 345                 350
Ile Gly Gly Pro Pro Asn Gly Met Leu
        355                 360

<210> SEQ ID NO 60
<211> LENGTH: 441
<212> TYPE: PRT
<213> ORGANISM: Drosophila melanogaster

<400> SEQUENCE: 60

Gly Arg Ser Arg Leu Leu Glu Asp Phe Arg Asn Gln Arg Tyr Pro Asn
1               5                   10                  15
Leu Gln Leu Arg Asp Leu Ala Asn His Ile Val Glu Phe Ser Gln Asp
            20                  25                  30
Gln His Gly Ser Arg Phe Ile Gln Gln Lys Leu Glu Arg Ala Thr Ala
        35                  40                  45
Ala Glu Lys Gln Met Val Phe Ser Glu Ile Leu Ala Ala Ala Tyr Ser
    50                  55                  60
Leu Met Thr Asp Val Phe Gly Asn Tyr Val Ile Gln Lys Phe Phe Glu
65                  70                  75                  80
Phe Gly Thr Pro Glu Gln Lys Asn Thr Leu Gly Met Gln Val Lys Gly
                85                  90                  95
His Val Leu Gln Leu Ala Leu Gln Met Tyr Gly Cys Arg Val Ile Gln
            100                 105                 110
Lys Ala Leu Glu Ser Ile Ser Pro Glu Gln Gln Gln Glu Ile Val His
        115                 120                 125
Glu Leu Asp Gly His Val Leu Lys Cys Val Lys Asp Gln Asn Gly Asn
    130                 135                 140
His Val Val Gln Lys Cys Ile Glu Cys Val Asp Pro Val Ala Leu Gln
145                 150                 155                 160
Phe Ile Ile Asn Ala Phe Lys Gly Gln Val Tyr Ser Leu Ser Thr His
                165                 170                 175
Pro Tyr Gly Cys Arg Val Ile Gln Arg Ile Leu Glu His Cys Thr Ala
            180                 185                 190
Glu Gln Thr Thr Pro Ile Leu Asp Glu Leu His Glu His Thr Glu Gln
        195                 200                 205
```

```
Leu Ile Gln Asp Gln Tyr Gly Asn Tyr Val Ile Gln His Val Leu Glu
        210                 215                 220

His Gly Lys Gln Glu Asp Lys Ser Ile Leu Ile Asn Ser Val Arg Gly
225                 230                 235                 240

Lys Val Leu Val Leu Ser Gln His Lys Phe Ala Ser Asn Val Val Glu
                245                 250                 255

Lys Cys Val Thr His Ala Thr Arg Gly Glu Arg Thr Gly Leu Ile Asp
                260                 265                 270

Glu Val Cys Thr Phe Asn Asp Asn Ala Leu His Val Met Met Lys Asp
                275                 280                 285

Gln Tyr Ala Asn Tyr Val Val Gln Lys Met Ile Asp Val Ser Glu Pro
                290                 295                 300

Thr Gln Leu Lys Lys Leu Met Thr Lys Ile Arg Lys Asn Met Ala Ala
305                 310                 315                 320

Leu Arg Lys Tyr Thr Tyr Gly Lys His Ile Asn Ala Lys Leu Glu Lys
                325                 330                 335

Tyr Tyr Met Lys Ile Thr Asn Pro Ile Thr Val Gly Thr Gly Ala Gly
                340                 345                 350

Gly Val Pro Ala Ala Ser Ser Ala Ala Val Ser Ser Gly Ala Thr
                355                 360                 365

Ser Ala Ser Val Thr Ala Cys Thr Ser Gly Ser Ser Thr Thr Thr Thr
370                 375                 380

Ser Thr Thr Asn Ser Leu Ala Ser Pro Thr Ile Cys Ser Val Gln Glu
385                 390                 395                 400

Asn Gly Ser Ala Met Val Val Glu Pro Ser Pro Asp Ala Ser Glu
                405                 410                 415

Ser Ser Ser Ser Val Val Ser Gly Ala Val Asn Ser Ser Leu Gly Pro
                420                 425                 430

Ile Gly Pro Pro Thr Asn Gly Asn Val
                435                 440

<210> SEQ ID NO 61
<211> LENGTH: 397
<212> TYPE: PRT
<213> ORGANISM: Homo sapiens

<400> SEQUENCE: 61

Glu Ala Lys Tyr Arg Ser Ala Ser Ser Ala Ser Ser Leu Phe Ser Pro
1               5                   10                  15

Ser Ser Thr Leu Phe Ser Ser Ser Arg Leu Arg Tyr Gly Met Ser Asp
                20                  25                  30

Val Met Pro Ser Gly Arg Ser Arg Leu Leu Glu Asp Phe Arg Asn Asn
                35                  40                  45

Arg Tyr Pro Asn Leu Gln Leu Arg Glu Ile Ala Gly His Ile Met Glu
        50                  55                  60

Phe Ser Gln Asp Gln His Gly Ser Arg Phe Ile Gln Leu Lys Leu Glu
65                  70                  75                  80

Arg Ala Thr Pro Ala Glu Arg Gln Leu Val Phe Asn Glu Ile Leu Gln
                85                  90                  95

Ala Ala Tyr Gln Leu Met Val Asp Val Phe Gly Asn Tyr Val Ile Gln
                100                 105                 110

Lys Phe Phe Glu Phe Gly Ser Leu Glu Gln Lys Leu Ala Leu Ala Glu
                115                 120                 125

Arg Ile Arg Gly His Val Leu Ser Leu Ala Leu Gln Met Tyr Gly Cys
        130                 135                 140
```

```
Arg Val Ile Gln Lys Ala Leu Glu Phe Ile Pro Ser Asp Gln Gln Val
145                 150                 155                 160

Ile Asn Glu Met Val Arg Glu Leu Asp Gly His Val Leu Lys Cys Val
                165                 170                 175

Lys Asp Gln Asn Gly Asn His Val Val Gln Lys Cys Ile Glu Cys Val
            180                 185                 190

Gln Pro Gln Ser Leu Gln Phe Ile Ile Asp Ala Phe Lys Gly Gln Val
        195                 200                 205

Phe Ala Leu Ser Thr His Pro Tyr Gly Cys Arg Val Ile Gln Arg Ile
210                 215                 220

Leu Glu His Cys Leu Pro Asp Gln Thr Leu Pro Ile Leu Glu Glu Leu
225                 230                 235                 240

His Gln His Thr Glu Gln Leu Val Gln Asp Gln Tyr Gly Asn Tyr Val
                245                 250                 255

Ile Gln His Val Leu Glu His Gly Arg Pro Glu Asp Lys Ser Lys Ile
            260                 265                 270

Val Ala Glu Ile Arg Gly Asn Val Leu Val Leu Ser Gln His Lys Phe
        275                 280                 285

Ala Ser Asn Val Val Glu Lys Cys Val Thr His Ala Ser Arg Thr Glu
290                 295                 300

Arg Ala Val Leu Ile Asp Glu Val Cys Thr Met Asn Asp Gly Pro His
305                 310                 315                 320

Ser Ala Leu Tyr Thr Met Met Lys Asp Gln Tyr Ala Asn Tyr Val Val
                325                 330                 335

Gln Lys Met Ile Asp Val Ala Glu Pro Gly Gln Arg Lys Ile Val Met
            340                 345                 350

His Lys Ile Arg Pro His Ile Ala Thr Leu Arg Lys Tyr Thr Tyr Gly
        355                 360                 365

Lys His Ile Leu Ala Lys Leu Glu Lys Tyr Tyr Met Lys Asn Gly Val
370                 375                 380

Asp Leu Gly Pro Ile Cys Gly Pro Pro Asn Gly Ile Ile
385                 390                 395

<210> SEQ ID NO 62
<211> LENGTH: 395
<212> TYPE: PRT
<213> ORGANISM: Homo sapiens

<400> SEQUENCE: 62

Glu Ala Lys Tyr Arg Ser Ala Ser Ser Thr Ser Ser Leu Phe Ser Ser
1               5                   10                  15

Ser Ser Gln Leu Phe Pro Pro Ser Arg Leu Arg Tyr Asn Arg Ser Asp
            20                  25                  30

Ile Met Pro Ser Gly Arg Ser Arg Leu Leu Glu Asp Phe Arg Asn Asn
        35                  40                  45

Arg Phe Pro Asn Leu Gln Leu Arg Asp Leu Ile Gly His Ile Val Glu
50                  55                  60

Phe Ser Gln Asp Gln His Gly Ser Arg Phe Ile Gln Gln Lys Leu Glu
65                  70                  75                  80

Arg Ala Thr Pro Ala Glu Arg Gln Met Val Phe Asn Glu Ile Leu Gln
                85                  90                  95

Ala Ala Tyr Gln Leu Met Thr Asp Val Phe Gly Asn Tyr Val Ile Gln
            100                 105                 110

Lys Phe Phe Glu Phe Gly Ser Leu Asp Gln Lys Leu Ala Leu Ala Thr
```

```
                 115                 120                 125
Arg Ile Arg Gly His Val Leu Pro Leu Ala Leu Gln Met Tyr Gly Cys
        130                 135                 140

Arg Val Ile Gln Lys Ala Leu Glu Ser Ile Ser Ser Asp Gln Gln Ser
145                 150                 155                 160

Glu Met Val Lys Glu Leu Asp Gly His Val Leu Lys Cys Val Lys Asp
                165                 170                 175

Gln Asn Gly Asn His Val Val Gln Lys Cys Ile Glu Cys Val Gln Pro
            180                 185                 190

Gln Ser Leu Gln Phe Ile Ile Asp Ala Phe Lys Gly Gln Val Phe Val
        195                 200                 205

Leu Ser Thr His Pro Tyr Gly Cys Arg Val Ile Gln Arg Ile Leu Glu
    210                 215                 220

His Cys Thr Ala Glu Gln Thr Leu Pro Ile Leu Glu Glu Leu His Gln
225                 230                 235                 240

His Thr Glu Gln Leu Val Gln Asp Gln Tyr Gly Asn Tyr Val Ile Gln
                245                 250                 255

His Val Leu Glu His Gly Arg Pro Glu Asp Lys Ser Lys Ile Val Ser
            260                 265                 270

Glu Ile Arg Gly Lys Val Leu Ala Leu Ser Gln His Lys Phe Ala Ser
        275                 280                 285

Asn Val Val Glu Lys Cys Val Thr His Ala Ser Arg Ala Glu Arg Ala
    290                 295                 300

Leu Leu Ile Asp Glu Val Cys Cys Gln Asn Asp Gly Pro His Ser Ala
305                 310                 315                 320

Leu Tyr Thr Met Met Lys Asp Gln Tyr Ala Asn Tyr Val Val Gln Lys
                325                 330                 335

Met Ile Asp Met Ala Glu Pro Ala Gln Arg Lys Ile Ile Met His Lys
            340                 345                 350

Ile Arg Pro His Ile Thr Thr Leu Arg Lys Tyr Thr Tyr Gly Lys His
        355                 360                 365

Ile Leu Ala Lys Leu Glu Lys Tyr Tyr Leu Lys Asn Ser Pro Asp Leu
    370                 375                 380

Gly Pro Ile Gly Gly Pro Asn Gly Met Leu
385                 390                 395

<210> SEQ ID NO 63
<211> LENGTH: 479
<212> TYPE: PRT
<213> ORGANISM: Drosophila melanogaster

<400> SEQUENCE: 63

Ala Ala Ala Ala Ala Ala Ala Asn Ser Arg Gln Val Ala Ala Thr
1               5                   10                  15

Ala Ala Ala Ala Ala Val Ala Ala Ala Gly Gly Val Gly Gly
            20                  25                  30

Ala Pro Gln Pro Gly Arg Ser Arg Leu Leu Glu Asp Phe Arg Asn Gln
        35                  40                  45

Arg Tyr Pro Asn Leu Gln Leu Arg Asp Leu Ala Asn His Ile Val Glu
    50                  55                  60

Phe Ser Gln Asp Gln His Gly Ser Arg Phe Ile Gln Gln Lys Leu Glu
65                  70                  75                  80

Arg Ala Thr Ala Ala Glu Lys Gln Met Val Phe Ser Glu Ile Leu Ala
                85                  90                  95
```

```
Ala Ala Tyr Ser Leu Met Thr Asp Val Phe Gly Asn Tyr Val Ile Gln
            100                 105                 110

Lys Phe Phe Glu Phe Gly Thr Pro Glu Gln Lys Asn Thr Leu Gly Met
        115                 120                 125

Gln Val Lys Gly His Val Leu Gln Leu Ala Leu Gln Met Tyr Gly Cys
    130                 135                 140

Arg Val Ile Gln Lys Ala Leu Glu Ser Ile Ser Pro Glu Gln Gln Gln
145                 150                 155                 160

Glu Ile Val His Glu Leu Asp Gly His Val Leu Lys Cys Val Lys Asp
                165                 170                 175

Gln Asn Gly Asn His Val Val Gln Lys Cys Ile Glu Cys Val Asp Pro
            180                 185                 190

Val Ala Leu Gln Phe Ile Ile Asn Ala Phe Lys Gly Gln Val Tyr Ser
        195                 200                 205

Leu Ser Thr His Pro Tyr Gly Cys Arg Val Ile Gln Arg Ile Leu Glu
    210                 215                 220

His Cys Thr Ala Glu Gln Thr Pro Ile Leu Asp Glu Leu His Glu
225                 230                 235                 240

His Thr Glu Gln Leu Ile Gln Asp Gln Tyr Gly Asn Tyr Val Ile Gln
                245                 250                 255

His Val Leu Glu His Gly Lys Gln Glu Asp Lys Ser Ile Leu Ile Asn
            260                 265                 270

Ser Val Arg Gly Lys Val Leu Val Leu Ser Gln His Lys Phe Ala Ser
        275                 280                 285

Asn Val Val Glu Lys Cys Val Thr His Ala Thr Arg Gly Glu Arg Thr
    290                 295                 300

Gly Leu Ile Asp Glu Val Cys Thr Phe Asn Asp Asn Ala Leu His Val
305                 310                 315                 320

Met Met Lys Asp Gln Tyr Ala Asn Tyr Val Val Gln Lys Met Ile Asp
                325                 330                 335

Val Ser Glu Pro Thr Gln Leu Lys Lys Leu Met Thr Lys Ile Arg Lys
            340                 345                 350

Asn Met Ala Ala Leu Arg Lys Tyr Thr Tyr Gly Lys His Ile Asn Ala
        355                 360                 365

Lys Leu Glu Lys Tyr Tyr Met Lys Ile Thr Asn Pro Ile Thr Val Gly
    370                 375                 380

Thr Gly Ala Gly Gly Val Pro Ala Ala Ser Ala Ala Ala Val Ser
385                 390                 395                 400

Ser Gly Ala Thr Ser Ala Ser Val Thr Ala Cys Thr Ser Gly Ser Ser
                405                 410                 415

Thr Thr Thr Thr Ser Thr Thr Asn Ser Leu Ala Ser Pro Thr Ile Cys
            420                 425                 430

Ser Val Gln Glu Asn Gly Ser Ala Met Val Val Glu Pro Ser Ser Pro
        435                 440                 445

Asp Ala Ser Glu Ser Ser Ser Val Val Ser Gly Ala Val Asn Ser
450                 455                 460

Ser Leu Gly Pro Ile Gly Pro Pro Thr Asn Gly Asn Val Val Leu
465                 470                 475

<210> SEQ ID NO 64
<211> LENGTH: 5
<212> TYPE: PRT
<213> ORGANISM: Artificial
<220> FEATURE:
<223> OTHER INFORMATION: PUF domain RNA recognition code
```

-continued

```
<220> FEATURE:
<221> NAME/KEY: misc_feature
<222> LOCATION: (2)..(4)
<223> OTHER INFORMATION: Xaa can be any naturally occurring amino acid

<400> SEQUENCE: 64

Asn Xaa Xaa Xaa Gln
1               5

<210> SEQ ID NO 65
<211> LENGTH: 5
<212> TYPE: PRT
<213> ORGANISM: Artificial
<220> FEATURE:
<223> OTHER INFORMATION: PUF domain RNA recognition code
<220> FEATURE:
<221> NAME/KEY: misc_feature
<222> LOCATION: (2)..(4)
<223> OTHER INFORMATION: Xaa can be any naturally occurring amino acid

<400> SEQUENCE: 65

Ser Xaa Xaa Xaa Glu
1               5

<210> SEQ ID NO 66
<211> LENGTH: 5
<212> TYPE: PRT
<213> ORGANISM: Artificial
<220> FEATURE:
<223> OTHER INFORMATION: PUF domain RNA recognition code
<220> FEATURE:
<221> NAME/KEY: MISC_FEATURE
<222> LOCATION: (1)..(1)
<223> OTHER INFORMATION: Xaa can be C or S
<220> FEATURE:
<221> NAME/KEY: misc_feature
<222> LOCATION: (2)..(4)
<223> OTHER INFORMATION: Xaa can be any naturally occurring amino acid

<400> SEQUENCE: 66

Xaa Xaa Xaa Xaa Gln
1               5

<210> SEQ ID NO 67
<211> LENGTH: 182
<212> TYPE: PRT
<213> ORGANISM: Homo sapiens

<400> SEQUENCE: 67

Gln Met Glu Leu Glu Ile Arg Pro Leu Phe Leu Val Pro Asp Thr Asn
1               5                   10                  15

Gly Phe Ile Asp His Leu Ala Ser Leu Ala Arg Leu Leu Glu Ser Arg
                20                  25                  30

Lys Tyr Ile Leu Val Val Pro Leu Ile Val Ile Asn Glu Leu Asp Gly
            35                  40                  45

Leu Ala Lys Gly Gln Glu Thr Asp His Arg Ala Gly Gly Tyr Ala Arg
        50                  55                  60

Val Val Gln Glu Lys Ala Arg Lys Ser Ile Glu Phe Leu Glu Gln Arg
65                  70                  75                  80

Phe Glu Ser Arg Asp Ser Cys Leu Arg Ala Leu Thr Ser Arg Gly Asn
                85                  90                  95

Glu Leu Glu Ser Ile Ala Phe Arg Ser Glu Asp Ile Thr Gly Gln Leu
            100                 105                 110

Gly Asn Asn Asp Asp Leu Ile Leu Ser Cys Cys Leu His Tyr Cys Lys
        115                 120                 125
```

```
Asp Lys Ala Lys Asp Phe Met Pro Ala Ser Lys Glu Glu Pro Ile Arg
            130                 135                 140
Leu Leu Arg Glu Val Val Leu Leu Thr Asp Asp Arg Asn Leu Arg Val
145                 150                 155                 160
Lys Ala Leu Thr Arg Asn Val Pro Val Arg Asp Ile Pro Ala Phe Leu
                165                 170                 175
Thr Trp Ala Gln Val Gly
            180

<210> SEQ ID NO 68
<211> LENGTH: 182
<212> TYPE: PRT
<213> ORGANISM: Mus musculus

<400> SEQUENCE: 68

Gln Met Glu Leu Glu Ile Arg Pro Leu Phe Leu Val Pro Asp Thr Asn
1               5                   10                  15
Gly Phe Ile Asp His Leu Ala Ser Leu Ala Arg Leu Leu Glu Ser Arg
            20                  25                  30
Lys Tyr Ile Leu Val Val Pro Leu Ile Val Ile Asn Glu Leu Asp Gly
        35                  40                  45
Leu Ala Lys Gly Gln Glu Thr Asp His Arg Ala Gly Gly Tyr Ala Arg
    50                  55                  60
Val Val Gln Glu Lys Ala Arg Lys Ser Ile Glu Phe Leu Glu Arg Arg
65                  70                  75                  80
Phe Glu Ser Arg Asp Ser Cys Leu Arg Ala Leu Thr Ser Arg Gly Asn
                85                  90                  95
Glu Leu Glu Ser Ile Ala Phe Arg Ser Glu Asp Ile Thr Gly Gln Leu
            100                 105                 110
Gly Asn Asn Asp Asp Leu Ile Leu Ser Cys Cys Leu His Tyr Cys Lys
        115                 120                 125
Asp Lys Ala Lys Asp Tyr Met Pro Thr Ser Lys Glu Glu Pro Ile Arg
    130                 135                 140
Leu Leu Arg Glu Val Val Leu Leu Thr Asp Asp Arg Asn Leu Arg Val
145                 150                 155                 160
Lys Ala Leu Thr Arg Asn Val Pro Val Arg Asp Ile Pro Ala Phe Leu
                165                 170                 175
Thr Trp Ala Gln Val Gly
            180

<210> SEQ ID NO 69
<211> LENGTH: 184
<212> TYPE: PRT
<213> ORGANISM: Drosophila melanogaster

<400> SEQUENCE: 69

Ile Tyr Ile Glu Val Arg Pro Arg Tyr Leu Leu Pro Asp Thr Asn Cys
1               5                   10                  15
Phe Ile Asp Cys Leu Glu Asp Phe Glu Lys Leu Ser Thr Glu Phe Lys
            20                  25                  30
Arg Tyr Thr Leu Ile Ile Pro Leu Thr Val Val Lys Glu Leu Asp Gly
        35                  40                  45
Leu Ser Lys Gly Val Lys Leu Asp Ser Tyr Arg Ser Ser Lys Gln Thr
    50                  55                  60
Gln Arg Ile His His Phe Asp Glu Val Ser Ser Arg Ala Lys Lys Ser
65                  70                  75                  80
```

```
Leu Glu Phe Ile Lys Ser Ala Lys Gly Asn Val Lys Cys Ala Thr Thr
                85                  90                  95

Lys Gly Ser Phe Val Asn Ala Ser Val Phe Ala Leu Val Glu Glu Glu
            100                 105                 110

Tyr Leu Ser Asn Asp Asp Lys Ile Leu Ala Thr Ala Met Ala Val Ser
            115                 120                 125

Lys Thr Ala Lys Thr Glu Gln Cys Thr Asp Gly Lys Cys Phe Ile Gln
            130                 135                 140

Thr Glu Leu Val Leu Ile Thr Thr Asp Arg Asn Leu Arg Val Lys Ala
145                 150                 155                 160

Leu Ser Arg Asn Leu Ala Val Ser Ala Leu Asp Glu Phe Leu Gln Trp
                165                 170                 175

Ala Lys Asp Cys Arg Glu Ser Thr
            180

<210> SEQ ID NO 70
<211> LENGTH: 184
<212> TYPE: PRT
<213> ORGANISM: Caenorhabditis elegans

<400> SEQUENCE: 70

Thr Thr Ile Val Ile His Pro Glu Tyr Leu Ile Pro Asp Thr Asn Val
1               5                   10                  15

Leu Ile Gly Asp Leu Gln Leu Met Lys Asn Leu Leu Glu Thr Ala Gln
                20                  25                  30

Lys Asn Lys Lys Phe Gln Ile Leu Val Pro Thr Thr Val Leu Asp Glu
            35                  40                  45

Leu Gln Tyr Ile Ala Lys Leu Ser Pro Leu Asp Ser Lys Ser Asn Ser
    50                  55                  60

Glu Ala His Asp Pro Glu Arg Ile Ser Lys Ala Lys Ile Ala Val Ala
65                  70                  75                  80

Trp Leu Lys Glu Gln Ala Lys Gln Lys Thr Gly His Leu Tyr Thr Leu
                85                  90                  95

Thr Thr Thr Gly Lys Arg Leu Pro Thr Leu Ser Ile Val Ser Glu Asp
            100                 105                 110

Leu Glu Gly His Glu Met Thr Thr Asn Asp Asp Met Ile Leu Asn Ser
            115                 120                 125

Ala Leu Arg Trp Ser Glu Ser Leu Pro Gly Ser Thr Ala Pro Ser Ala
            130                 135                 140

Thr Glu Ile Ser Gln Lys Cys Val Leu Ile Thr Gly Asp Arg Gly Leu
145                 150                 155                 160

Thr Ile Lys Ala Ile Gly Asn Asn Phe Pro Cys Arg Gly Ile Ser Asn
                165                 170                 175

Phe Thr Lys Trp Ile Ile Asn Val
            180

<210> SEQ ID NO 71
<211> LENGTH: 32
<212> TYPE: PRT
<213> ORGANISM: Artificial
<220> FEATURE:
<223> OTHER INFORMATION: Ornithine transcarbamylase leader peptide

<400> SEQUENCE: 71

Met Leu Phe Asn Leu Arg Ile Leu Leu Asn Asn Ala Ala Phe Arg Asn
1               5                   10                  15
```

```
Gly His Asn Phe Met Val Arg Asn Phe Arg Cys Gly Gln Pro Leu Gln
            20                  25                  30
```

<210> SEQ ID NO 72
<211> LENGTH: 7
<212> TYPE: PRT
<213> ORGANISM: Artificial
<220> FEATURE:
<223> OTHER INFORMATION: SV40 nuclear localization signal

<400> SEQUENCE: 72

```
Pro Lys Lys Lys Arg Lys Val
1               5
```

<210> SEQ ID NO 73
<211> LENGTH: 5
<212> TYPE: PRT
<213> ORGANISM: Artificial
<220> FEATURE:
<223> OTHER INFORMATION: PUF domain RNA recognition code
<220> FEATURE:
<221> NAME/KEY: misc_feature
<222> LOCATION: (3)..(4)
<223> OTHER INFORMATION: Xaa can be any naturally occurring amino acid

<400> SEQUENCE: 73

```
Ser Tyr Xaa Xaa Arg
1               5
```

<210> SEQ ID NO 74
<211> LENGTH: 29
<212> TYPE: DNA
<213> ORGANISM: Artificial
<220> FEATURE:
<223> OTHER INFORMATION: PCR primer

<400> SEQUENCE: 74
ggatccgagg ccgcagccgc cttttggaa                                      29

<210> SEQ ID NO 75
<211> LENGTH: 33
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (10)..(12)
<223> OTHER INFORMATION: n is a, c, g, or t

<400> SEQUENCE: 75
gattacatan nntccatatt gatcctgtac cag                                 33

<210> SEQ ID NO 76
<211> LENGTH: 32
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (10)..(12)
<223> OTHER INFORMATION: n is a, c, g, or t

<400> SEQUENCE: 76
tatgtaatcn nncatgtact ggagcacggt cg                                  32

<210> SEQ ID NO 77

<211> LENGTH: 29
<212> TYPE: DNA
<213> ORGANISM: Artificial
<220> FEATURE:
<223> OTHER INFORMATION: PCR primer

<400> SEQUENCE: 77
ctcgagcccc taagtcaaca ccgttcttc                                29

<210> SEQ ID NO 78
<211> LENGTH: 6
<212> TYPE: PRT
<213> ORGANISM: Artificial
<220> FEATURE:
<223> OTHER INFORMATION: PUF domain RNA recognition code
<220> FEATURE:
<221> NAME/KEY: MISC_FEATURE
<222> LOCATION: (1)..(1)
<223> OTHER INFORMATION: Xaa can be G, A, S, T or C
<220> FEATURE:
<221> NAME/KEY: misc_feature
<222> LOCATION: (3)..(5)
<223> OTHER INFORMATION: Xaa can be any naturally occurring amino acid

<400> SEQUENCE: 78

Xaa Cys Xaa Xaa Xaa Arg
1               5

<210> SEQ ID NO 79
<211> LENGTH: 5
<212> TYPE: PRT
<213> ORGANISM: Artificial
<220> FEATURE:
<223> OTHER INFORMATION: PUF domain RNA recognition code
<220> FEATURE:
<221> NAME/KEY: misc_feature
<222> LOCATION: (3)..(4)
<223> OTHER INFORMATION: Xaa can be any naturally occurring amino acid

<400> SEQUENCE: 79

Ser Arg Xaa Xaa Arg
1               5

<210> SEQ ID NO 80
<211> LENGTH: 5
<212> TYPE: PRT
<213> ORGANISM: Artificial
<220> FEATURE:
<223> OTHER INFORMATION: PUF domain RNA recognition code
<220> FEATURE:
<221> NAME/KEY: misc_feature
<222> LOCATION: (3)..(4)
<223> OTHER INFORMATION: Xaa can be any naturally occurring amino acid

<400> SEQUENCE: 80

Asn Tyr Xaa Xaa Gln
1               5

<210> SEQ ID NO 81
<211> LENGTH: 5
<212> TYPE: PRT
<213> ORGANISM: Artificial
<220> FEATURE:
<223> OTHER INFORMATION: PUF domain RNA recognition code
<220> FEATURE:
<221> NAME/KEY: misc_feature
<222> LOCATION: (3)..(4)
<223> OTHER INFORMATION: Xaa can be any naturally occurring amino acid

<400> SEQUENCE: 81

```
Ser His Xaa Xaa Arg
1               5

<210> SEQ ID NO 82
<211> LENGTH: 5
<212> TYPE: PRT
<213> ORGANISM: Artificial
<220> FEATURE:
<223> OTHER INFORMATION: PUF domain RNA recognition code
<220> FEATURE:
<221> NAME/KEY: misc_feature
<222> LOCATION: (3)..(4)
<223> OTHER INFORMATION: Xaa can be any naturally occurring amino acid

<400> SEQUENCE: 82

Ser Asn Xaa Xaa Glu
1               5

<210> SEQ ID NO 83
<211> LENGTH: 5
<212> TYPE: PRT
<213> ORGANISM: Artificial
<220> FEATURE:
<223> OTHER INFORMATION: PUF domain RNA recognition code
<220> FEATURE:
<221> NAME/KEY: misc_feature
<222> LOCATION: (3)..(4)
<223> OTHER INFORMATION: Xaa can be any naturally occurring amino acid

<400> SEQUENCE: 83

Ser Arg Xaa Xaa Glu
1               5

<210> SEQ ID NO 84
<211> LENGTH: 5
<212> TYPE: PRT
<213> ORGANISM: Artificial
<220> FEATURE:
<223> OTHER INFORMATION: PUF domain RNA recognition code
<220> FEATURE:
<221> NAME/KEY: misc_feature
<222> LOCATION: (3)..(4)
<223> OTHER INFORMATION: Xaa can be any naturally occurring amino acid

<400> SEQUENCE: 84

Ser Tyr Xaa Xaa Glu
1               5

<210> SEQ ID NO 85
<211> LENGTH: 5
<212> TYPE: PRT
<213> ORGANISM: Artificial
<220> FEATURE:
<223> OTHER INFORMATION: PUF domain RNA recognition code
<220> FEATURE:
<221> NAME/KEY: misc_feature
<222> LOCATION: (3)..(4)
<223> OTHER INFORMATION: Xaa can be any naturally occurring amino acid

<400> SEQUENCE: 85

Asn Arg Xaa Xaa Gln
1               5

<210> SEQ ID NO 86
<211> LENGTH: 24
<212> TYPE: RNA
<213> ORGANISM: Artificial
<220> FEATURE:
<223> OTHER INFORMATION: GU/UG RNA substrate sequence
```

```
<400> SEQUENCE: 86
ucgagaauuu gauauauucg ggcc                                              24

<210> SEQ ID NO 87
<211> LENGTH: 11
<212> TYPE: RNA
<213> ORGANISM: Artificial
<220> FEATURE:
<223> OTHER INFORMATION: 5' ASRE cleavage product

<400> SEQUENCE: 87
ucgagaauuu g                                                            11

<210> SEQ ID NO 88
<211> LENGTH: 20
<212> TYPE: RNA
<213> ORGANISM: Artificial
<220> FEATURE:
<223> OTHER INFORMATION: 5' ASRE cleavage product

<400> SEQUENCE: 88
ucgagaauuu gauauauucg                                                   20

<210> SEQ ID NO 89
<211> LENGTH: 19
<212> TYPE: RNA
<213> ORGANISM: Artificial
<220> FEATURE:
<223> OTHER INFORMATION: 3' ASRE cleavage product

<400> SEQUENCE: 89
gauauauucg ggcccagca                                                    19

<210> SEQ ID NO 90
<211> LENGTH: 10
<212> TYPE: RNA
<213> ORGANISM: Artificial
<220> FEATURE:
<223> OTHER INFORMATION: 3' ASRE cleavage product

<400> SEQUENCE: 90
gggcccagca                                                              10

<210> SEQ ID NO 91
<211> LENGTH: 39
<212> TYPE: RNA
<213> ORGANISM: Artificial
<220> FEATURE:
<223> OTHER INFORMATION: 3' UTR RNA repeat sequence

<400> SEQUENCE: 91
cugcugcugc ugcugcugcu gcugcugcug cugcugcug                              39

<210> SEQ ID NO 92
<211> LENGTH: 29
<212> TYPE: DNA
<213> ORGANISM: Artificial
<220> FEATURE:
<223> OTHER INFORMATION: Randomized library sequence for residue 16 and
      20 in PUF repeat 6
<220> FEATURE:
<221> NAME/KEY: misc_feature
<222> LOCATION: (7)..(9)
<223> OTHER INFORMATION: n is a, c, g, or t
<220> FEATURE:
<221> NAME/KEY: misc_feature
<222> LOCATION: (19)..(21)
```

<223> OTHER INFORMATION: n is a, c, g, or t

<400> SEQUENCE: 92
tatggannnt atgtaatcnn ncatgtact                                29

<210> SEQ ID NO 93
<211> LENGTH: 33
<212> TYPE: DNA
<213> ORGANISM: Artificial
<220> FEATURE:
<223> OTHER INFORMATION: 5' VEGF-A pre-mRNA splice site sequence

<400> SEQUENCE: 93
tcagatgtga caagccgagg cggtgagccg ggc                           33

<210> SEQ ID NO 94
<211> LENGTH: 31
<212> TYPE: DNA
<213> ORGANISM: Artificial
<220> FEATURE:
<223> OTHER INFORMATION: 3' VEGF-A pre-mRNA splice site sequence

<400> SEQUENCE: 94
accagatctc tcaccaggaa agactgatac a                             31

<210> SEQ ID NO 95
<211> LENGTH: 6
<212> TYPE: PRT
<213> ORGANISM: Artificial
<220> FEATURE:
<223> OTHER INFORMATION: 5' VEGF-A splice site protein sequence

<400> SEQUENCE: 95

Cys Asp Lys Pro Arg Arg
1               5

<210> SEQ ID NO 96
<211> LENGTH: 6
<212> TYPE: PRT
<213> ORGANISM: Artificial
<220> FEATURE:
<223> OTHER INFORMATION: 3' VEGF-A splice site protein sequence

<400> SEQUENCE: 96

Ser Leu Thr Arg Lys Asp
1               5

<210> SEQ ID NO 97
<211> LENGTH: 36
<212> TYPE: PRT
<213> ORGANISM: Chlamydomonas reinhardtii

<400> SEQUENCE: 97

Ala Ile Cys Pro His Leu Tyr Asp Tyr Ala Thr Asp Arg Phe Ala Thr
1               5                   10                  15

His Val Val Arg Arg Leu Leu Cys Leu Ala Ala Gly Arg Asn Val Leu
            20                  25                  30

Pro Pro Ala Gly
        35

<210> SEQ ID NO 98
<211> LENGTH: 36
<212> TYPE: PRT
<213> ORGANISM: Volvox carteri

```
<400> SEQUENCE: 98

Ser Ile Cys Pro His Leu Tyr Asp Tyr Val Thr Asp Arg Phe Ala Thr
1               5                   10                  15

His Val Val Arg Arg Leu Leu Cys Leu Leu Thr Gly Arg Asn Asn Val
                20                  25                  30

Leu Pro Pro Gly
            35

<210> SEQ ID NO 99
<211> LENGTH: 36
<212> TYPE: PRT
<213> ORGANISM: Sordaria macrospora

<400> SEQUENCE: 99

Glu Leu Glu Glu His Leu Gly Tyr Leu Leu Thr Asp Arg Phe Gly Ser
1               5                   10                  15

His Ala Ile Arg Ala Leu Leu Val Ile Leu Ser Gly Arg Pro Leu Asp
                20                  25                  30

Gln Ala Gly Thr
            35

<210> SEQ ID NO 100
<211> LENGTH: 36
<212> TYPE: PRT
<213> ORGANISM: Gibberella zeae

<400> SEQUENCE: 100

Glu Leu Glu Gly Ala Leu Ser Tyr Leu Val Thr Asp Arg Phe Ala Ser
1               5                   10                  15

His Thr Leu Arg Val Leu Leu Leu Val Leu Ala Gly Arg Pro Leu Glu
                20                  25                  30

Asp Ala Ser Val
            35

<210> SEQ ID NO 101
<211> LENGTH: 36
<212> TYPE: PRT
<213> ORGANISM: Nectria haematococca

<400> SEQUENCE: 101

Glu Leu Glu Gly Ser Leu Ser Tyr Leu Ile Thr Asp Arg Phe Ala Ser
1               5                   10                  15

His Thr Leu Arg Val Leu Leu Leu Val Leu Ser Gly Arg Pro Leu Glu
                20                  25                  30

Asp Ser Ser Arg
            35

<210> SEQ ID NO 102
<211> LENGTH: 36
<212> TYPE: PRT
<213> ORGANISM: Arthroderma otae

<400> SEQUENCE: 102

Glu Leu Gln Gly Asn Trp Gly Tyr Leu Leu Thr Glu Pro Phe Ala Ser
1               5                   10                  15

His Thr Ile Arg Leu Leu Leu Leu Ile Leu Ala Gly Glu Pro Leu Ala
                20                  25                  30

Asp Gln Ser Asn
            35
```

<210> SEQ ID NO 103
<211> LENGTH: 36
<212> TYPE: PRT
<213> ORGANISM: Penicillium chrysogenum

<400> SEQUENCE: 103

Glu Leu Lys Glu Asn Trp Gly Tyr Leu Leu Thr Glu Arg Phe Ala Ser
1               5                   10                  15

His Thr Ile Arg Val Leu Leu Leu Val Leu Ala Gly Glu Pro Val Asp
            20                  25                  30

Val Thr Ser Asn
        35

<210> SEQ ID NO 104
<211> LENGTH: 36
<212> TYPE: PRT
<213> ORGANISM: Aspergillus flavus

<400> SEQUENCE: 104

Glu Leu Glu Gly Asn Trp Gly Tyr Leu Leu Thr Glu Arg Phe Ala Ser
1               5                   10                  15

His Thr Ile Arg Val Leu Leu Leu Val Leu Ala Gly Glu Pro Val Asp
            20                  25                  30

Val Ser Ala Asn
        35

<210> SEQ ID NO 105
<211> LENGTH: 36
<212> TYPE: PRT
<213> ORGANISM: Neosartorya fischeri

<400> SEQUENCE: 105

Glu Leu Glu Gly Asn Trp Gly Tyr Leu Leu Thr Glu Arg Phe Ala Ser
1               5                   10                  15

His Thr Ile Arg Val Leu Leu Leu Val Leu Ala Gly Glu Pro Val Asp
            20                  25                  30

Leu Ser Ser Thr
        35

<210> SEQ ID NO 106
<211> LENGTH: 36
<212> TYPE: PRT
<213> ORGANISM: Talaromyces stipitatus

<400> SEQUENCE: 106

Glu Leu Glu Ser Asn Trp Gly Tyr Leu Met Thr Glu Arg Phe Ala Ser
1               5                   10                  15

His Thr Ile Arg Val Leu Leu Leu Val Leu Ala Gly Glu Pro Val Asp
            20                  25                  30

Leu Ser Ser His
        35

<210> SEQ ID NO 107
<211> LENGTH: 36
<212> TYPE: PRT
<213> ORGANISM: Coccidioides posadasii

<400> SEQUENCE: 107

```
Glu Leu Glu Gly Asn Trp Gly Tyr Leu Leu Thr Glu Ser Phe Ala Ser
1               5                   10                  15
```

-continued

His Thr Ile Arg Val Leu Leu Leu Ile Leu Ala Gly Lys Ser Leu Asp
            20                  25                  30

Asn Ser Ser Asn
        35

<210> SEQ ID NO 108
<211> LENGTH: 36
<212> TYPE: PRT
<213> ORGANISM: Paracoccidioides brasiliensis

<400> SEQUENCE: 108

Glu Leu Glu Gly Asn Trp Gly Tyr Leu Leu Thr Glu Arg Phe Ala Ser
1               5                   10                  15

His Thr Ile Arg Val Leu Leu Leu Val Leu Ala Gly Lys Pro Leu Arg
            20                  25                  30

Asn Pro Ser Thr
        35

<210> SEQ ID NO 109
<211> LENGTH: 36
<212> TYPE: PRT
<213> ORGANISM: Ajellomyces capsulatus

<400> SEQUENCE: 109

Glu Leu Glu Gly Asn Trp Gly Tyr Leu Leu Thr Asp Arg Phe Ala Ser
1               5                   10                  15

His Thr Ile Arg Val Leu Leu Leu Ile Leu Ala Gly Glu Gln Leu Asp
            20                  25                  30

Ser Pro Ser Lys
        35

<210> SEQ ID NO 110
<211> LENGTH: 36
<212> TYPE: PRT
<213> ORGANISM: Physcomitrella patens

<400> SEQUENCE: 110

Gly Glu Gly Tyr Thr Gly Ser Asp Leu Met Asn Asn Arg Tyr Gly Ser
1               5                   10                  15

His Val Leu Arg Gln Leu Leu Ser Leu Cys Ser Gly Ile Pro Ile Glu
            20                  25                  30

Thr Leu Cys Lys
        35

<210> SEQ ID NO 111
<211> LENGTH: 36
<212> TYPE: PRT
<213> ORGANISM: Sorghum bicolor

<400> SEQUENCE: 111

Val Ile Ala Ala Asp Ala Ala Asn Val Met Ser Ser Cys Tyr Gly Ser
1               5                   10                  15

His Val Leu Arg Thr Leu Leu Cys Leu Cys Lys Gly Val Pro Ser Glu
            20                  25                  30

Cys Leu Gln Asp
        35

<210> SEQ ID NO 112
<211> LENGTH: 36
<212> TYPE: PRT
<213> ORGANISM: Oryza sativa

```
<400> SEQUENCE: 112

Val Ile Ala Gly Asp Ala Ala Asn Val Met Ser Ser Cys Tyr Gly Ser
1               5                   10                  15

His Val Leu Arg Thr Leu Leu Cys Leu Cys Lys Gly Val Pro Leu Gln
            20                  25                  30

Ser Leu Gln Asp
        35

<210> SEQ ID NO 113
<211> LENGTH: 36
<212> TYPE: PRT
<213> ORGANISM: Arabidopsis thaliana

<400> SEQUENCE: 113

Val Ile Val Asp Asn Pro Leu Asp Met Met Cys Asn Cys Tyr Gly Ser
1               5                   10                  15

His Val Leu Arg Arg Leu Leu Cys Leu Cys Lys Gly Val Ser Leu Asp
            20                  25                  30

Ser Pro Glu Leu
        35

<210> SEQ ID NO 114
<211> LENGTH: 36
<212> TYPE: PRT
<213> ORGANISM: Vitis vinifera

<400> SEQUENCE: 114

Val Ile Val Val Asn Pro Val Asp Val Met Cys Asn Cys Tyr Gly Ser
1               5                   10                  15

His Val Ile Arg Ser Leu Leu Cys Leu Cys Lys Gly Val Pro Leu Asp
            20                  25                  30

Ser Pro Glu Pro
        35

<210> SEQ ID NO 115
<211> LENGTH: 36
<212> TYPE: PRT
<213> ORGANISM: Populus trichocarpa

<400> SEQUENCE: 115

Val Ile Val Ala Ser Pro Val Asp Met Met Cys Asn Cys Tyr Gly Ser
1               5                   10                  15

His Val Phe Arg Ser Leu Leu Cys Leu Cys Gly Gly Val Pro Leu Asp
            20                  25                  30

Ser Pro Val Phe
        35

<210> SEQ ID NO 116
<211> LENGTH: 36
<212> TYPE: PRT
<213> ORGANISM: Ricinus communis

<400> SEQUENCE: 116

Val Ile Val Ala Asn Pro Val Asp Met Met Cys Asn Arg Tyr Gly Ser
1               5                   10                  15

His Val Phe Arg Ser Leu Leu Cys Leu Cys Gly Gly Val Pro Leu Asp
            20                  25                  30

Ser Gln Glu Phe
        35
```

<210> SEQ ID NO 117
<211> LENGTH: 36
<212> TYPE: PRT
<213> ORGANISM: Trichomonas vaginalis

<400> SEQUENCE: 117

Glu Leu Lys Ser Tyr Ala Pro Asp Leu Ser Glu Asp Arg Tyr Gly Ser
1               5                   10                  15

His Val Ile Arg Ser Leu Ile Thr His Tyr Gly Gly Phe Lys Ser Met
            20                  25                  30

Asn Gln His Ile
        35

<210> SEQ ID NO 118
<211> LENGTH: 36
<212> TYPE: PRT
<213> ORGANISM: Thalassiosira pseudonana

<400> SEQUENCE: 118

Glu Leu Lys Pro Tyr Ala Ser Glu Leu Ala Val His Val Cys Gly Thr
1               5                   10                  15

His Val Leu Arg Thr Gly Ile Cys Ile Leu Ser Gly Val Glu Phe Ile
            20                  25                  30

Asp Ala Tyr Ala
        35

<210> SEQ ID NO 119
<211> LENGTH: 36
<212> TYPE: PRT
<213> ORGANISM: Phaeodactylum tricornutum

<400> SEQUENCE: 119

Glu Ile Val Pro Phe Thr Asp Asp Leu Ala Ile His Ile Cys Gly Ser
1               5                   10                  15

His Val Leu Arg Ser Leu Val Cys Ile Leu Gly Gly Val Lys Val Val
            20                  25                  30

Gln Gln Pro Gly
        35

<210> SEQ ID NO 120
<211> LENGTH: 36
<212> TYPE: PRT
<213> ORGANISM: Nematostella vectensis

<400> SEQUENCE: 120

Val Ile Ser Glu Asp Leu Glu Glu Leu Met Ser Ser Thr Tyr Gly Ser
1               5                   10                  15

His Val Val Arg Ala Val Phe Glu Val Leu Gly Gly Val Lys Val Ala
            20                  25                  30

Ala Ser Val Gln
        35

<210> SEQ ID NO 121
<211> LENGTH: 36
<212> TYPE: PRT
<213> ORGANISM: Strongylocentrotus purpuratus

<400> SEQUENCE: 121

Glu Met Ser Glu Asn Phe Lys Glu Val Ile Leu Asp Thr Tyr Ala Ser
1               5                   10                  15

-continued

His Val Leu Arg Thr Leu Ile Ala Ser Leu Ala Gly Ile Gln Ala Pro
                20                  25                  30

Glu Asn Val Ser
        35

<210> SEQ ID NO 122
<211> LENGTH: 36
<212> TYPE: PRT
<213> ORGANISM: Monosiga brevicollis

<400> SEQUENCE: 122

His Leu Met Glu Asn Leu Gln Gln Thr Trp Glu Asp Thr Tyr Ala Ala
1               5                   10                  15

His Val Phe Arg Ser His Val Cys Cys Leu Ser Gly Met Glu Leu Pro
                20                  25                  30

Lys Lys Leu Arg
        35

<210> SEQ ID NO 123
<211> LENGTH: 36
<212> TYPE: PRT
<213> ORGANISM: Ashbya gossypii

<400> SEQUENCE: 123

Glu Leu Lys Pro His Met Lys Met Met Ile Asn His Gln Tyr Ala Ser
1               5                   10                  15

His Val Phe Arg Leu Leu Ile Leu Val Leu Ser Ala Lys Lys Leu Pro
                20                  25                  30

Lys Ser Thr Gln
        35

<210> SEQ ID NO 124
<211> LENGTH: 36
<212> TYPE: PRT
<213> ORGANISM: Candida glabrata

<400> SEQUENCE: 124

Glu Ile Lys Pro His Leu Lys Ser Met Ile Asn His Gln Tyr Ala Ser
1               5                   10                  15

His Val Leu Arg Leu Ile Ile Leu Ile Leu Ser Ser Lys Thr Leu Pro
                20                  25                  30

Ser Thr Thr Gln
        35

<210> SEQ ID NO 125
<211> LENGTH: 36
<212> TYPE: PRT
<213> ORGANISM: Saccharomyces cerevisiae

<400> SEQUENCE: 125

Glu Leu Lys Pro His Leu Lys Thr Met Met Asn His Gln Tyr Ala Ser
1               5                   10                  15

His Val Leu Arg Leu Leu Ile Leu Ile Leu Ser Ser Lys Thr Leu Pro
                20                  25                  30

Asn Ser Thr Lys
        35

<210> SEQ ID NO 126
<211> LENGTH: 36
<212> TYPE: PRT

<213> ORGANISM: Giardia intestinalis

<400> SEQUENCE: 126

Lys Ile Ile Pro Glu Ile Ser Asp Leu Ile Thr His Lys Phe Thr Asn
1               5                   10                  15

His Val Leu Arg Thr Leu Leu Arg Val Glu Gly Gly Ser Pro Pro Glu
            20                  25                  30

Asp Glu Gly Arg
        35

<210> SEQ ID NO 127
<211> LENGTH: 37
<212> TYPE: PRT
<213> ORGANISM: Homo sapiens

<400> SEQUENCE: 127

Glu Val Cys Asp Asp Phe Leu Val Tyr Cys Gly Asp Thr His Gly Ser
1               5                   10                  15

Phe Val Val Arg Thr Leu Leu Gln Val Leu Gly Gly Thr Ile Leu Glu
            20                  25                  30

Ser Glu Arg Ala Arg
        35

<210> SEQ ID NO 128
<211> LENGTH: 37
<212> TYPE: PRT
<213> ORGANISM: Pan troglodytes

<400> SEQUENCE: 128

Glu Val Cys Asp Asp Phe Leu Val Tyr Cys Gly Asp Thr His Gly Ser
1               5                   10                  15

Phe Val Val Arg Thr Leu Leu Gln Val Leu Gly Gly Thr Ile Leu Glu
            20                  25                  30

Ser Glu Arg Ala Arg
        35

<210> SEQ ID NO 129
<211> LENGTH: 37
<212> TYPE: PRT
<213> ORGANISM: Canis familiaris

<400> SEQUENCE: 129

Glu Val Cys Asp Asp Phe Leu Val Tyr Cys Gly Asp Thr His Gly Ser
1               5                   10                  15

Phe Val Val Arg Thr Leu Leu Gln Val Leu Gly Gly Thr Leu Leu Glu
            20                  25                  30

Ser Glu Arg Ala Arg
        35

<210> SEQ ID NO 130
<211> LENGTH: 37
<212> TYPE: PRT
<213> ORGANISM: Bos taurus

<400> SEQUENCE: 130

Glu Val Cys Asp Asp Phe Leu Phe Tyr Cys Gly Asp Thr His Gly Ser
1               5                   10                  15

Phe Val Val Arg Thr Leu Leu Gln Val Leu Gly Gly Thr Leu Leu Glu
            20                  25                  30

Ser Glu Arg Ala Arg

-continued

```
<210> SEQ ID NO 131
<211> LENGTH: 37
<212> TYPE: PRT
<213> ORGANISM: Mus musculus

<400> SEQUENCE: 131

Glu Val Cys Asp Asp Phe Leu Phe Phe Cys Gly Asp Thr His Gly Ser
1               5                   10                  15

Phe Val Val Arg Thr Leu Leu Gln Val Leu Gly Gly Thr Leu Leu Glu
            20                  25                  30

Ser Glu Arg Gly Lys
            35

<210> SEQ ID NO 132
<211> LENGTH: 37
<212> TYPE: PRT
<213> ORGANISM: Rattus norvegicus

<400> SEQUENCE: 132

Glu Val Cys Asp Asp Phe Leu Phe Phe Cys Gly Asp Thr His Gly Ser
1               5                   10                  15

Phe Val Val Arg Thr Leu Leu Gln Val Leu Gly Gly Thr Leu Leu Glu
            20                  25                  30

Ser Glu Arg Val Lys
            35

<210> SEQ ID NO 133
<211> LENGTH: 37
<212> TYPE: PRT
<213> ORGANISM: Danio rerio

<400> SEQUENCE: 133

Ala Val Arg Glu Lys Ile Thr Glu Phe Cys Thr Asp Pro Tyr Gly Ser
1               5                   10                  15

His Val Leu Arg Thr Leu Ile His Val Leu Ser Gly Cys Arg Ser Val
            20                  25                  30

Glu Thr Thr Ala Pro
            35

<210> SEQ ID NO 134
<211> LENGTH: 37
<212> TYPE: PRT
<213> ORGANISM: Arabidopsis thaliana

<400> SEQUENCE: 134

Val Ile Val Asp Asn Pro Leu Asp Met Met Cys Asn Cys Tyr Gly Ser
1               5                   10                  15

His Val Leu Arg Arg Leu Leu Cys Leu Cys Lys Gly Val Ser Leu Asp
            20                  25                  30

Ser Pro Glu Leu Tyr
            35

<210> SEQ ID NO 135
<211> LENGTH: 37
<212> TYPE: PRT
<213> ORGANISM: Oryza sativa

<400> SEQUENCE: 135

Val Ile Ala Gly Asp Ala Ala Asn Val Met Ser Ser Cys Tyr Gly Ser
```

```
                1               5                  10                 15
His Val Leu Arg Thr Leu Leu Cys Leu Cys Lys Gly Val Pro Leu Gln
                20                  25                 30

Ser Leu Gln Asp Phe
        35

<210> SEQ ID NO 136
<211> LENGTH: 36
<212> TYPE: PRT
<213> ORGANISM: Saccharomyces cerevisiae

<400> SEQUENCE: 136

Glu Leu Lys Pro His Leu Lys Thr Met Met Asn His Gln Tyr Ala Ser
1               5                   10                  15

His Val Leu Arg Leu Leu Ile Leu Ile Leu Ser Ser Lys Thr Leu Pro
                20                  25                  30

Asn Ser Thr Lys
        35

<210> SEQ ID NO 137
<211> LENGTH: 36
<212> TYPE: PRT
<213> ORGANISM: Ashbya gossypii

<400> SEQUENCE: 137

Glu Leu Lys Pro His Met Lys Met Met Ile Asn His Gln Tyr Ala Ser
1               5                   10                  15

His Val Phe Arg Leu Leu Ile Leu Val Leu Ser Ala Lys Lys Leu Pro
                20                  25                  30

Lys Ser Thr Gln
        35

<210> SEQ ID NO 138
<211> LENGTH: 36
<212> TYPE: PRT
<213> ORGANISM: Kluyveromyces lactis

<400> SEQUENCE: 138

Glu Leu Gln Pro Asn Leu Arg Phe Met Val Ser His Gln Tyr Ala Ser
1               5                   10                  15

His Val Leu Arg Ile Leu Ile Leu Val Leu Ser Ser Lys Thr Leu Pro
                20                  25                  30

Ser Thr Val Gln
        35

<210> SEQ ID NO 139
<211> LENGTH: 36
<212> TYPE: PRT
<213> ORGANISM: Schizosaccharomyces pombe

<400> SEQUENCE: 139

Glu Ile Arg Pro Glu Val Ser Met Leu Met Ser His Lys Leu Ala Val
1               5                   10                  15

His Val Leu Gly Lys Ile Phe Leu Leu Leu Asp Gly Tyr Arg Phe Val
                20                  25                  30

Tyr His Asp Gly
        35

<210> SEQ ID NO 140
<211> LENGTH: 37
```

```
<212> TYPE: PRT
<213> ORGANISM: Drosophila melanogaster

<400> SEQUENCE: 140

Phe Met Leu Asn Asn Leu Glu Asp Phe Val Trp Asp Ala Cys Ala Ser
1               5                   10                  15

His Ile Met Arg Thr Ala Ile Leu Cys Leu Val Gly Met His Val Pro
            20                  25                  30

Lys Ile Ala Phe Glu
        35

<210> SEQ ID NO 141
<211> LENGTH: 37
<212> TYPE: PRT
<213> ORGANISM: Anopheles gambiae

<400> SEQUENCE: 141

Ala Glu Arg Gly Asp Arg Ser Glu Phe Val Trp Glu Ala Thr Ala Gly
1               5                   10                  15

Tyr Val Ile Arg Gln Cys Val Leu Asn Leu Gly Gly Ile Thr Glu Lys
            20                  25                  30

Lys Ala Thr Asn Asp
        35

<210> SEQ ID NO 142
<211> LENGTH: 37
<212> TYPE: PRT
<213> ORGANISM: Volvox carteri

<400> SEQUENCE: 142

Ser Ile Cys Pro His Leu Tyr Asp Tyr Val Thr Asp Arg Phe Ala Thr
1               5                   10                  15

His Val Val Arg Arg Leu Leu Cys Leu Leu Thr Gly Arg Asn Val Leu
            20                  25                  30

Pro Pro Pro Gly Lys
        35

<210> SEQ ID NO 143
<211> LENGTH: 5
<212> TYPE: PRT
<213> ORGANISM: Artificial
<220> FEATURE:
<223> OTHER INFORMATION: PUF domain RNA recognition code
<220> FEATURE:
<221> NAME/KEY: misc_feature
<222> LOCATION: (2)..(4)
<223> OTHER INFORMATION: Xaa can be any naturally occurring amino acid

<400> SEQUENCE: 143

Ser Xaa Xaa Xaa Arg
1               5

<210> SEQ ID NO 144
<211> LENGTH: 12
<212> TYPE: RNA
<213> ORGANISM: Artificial
<220> FEATURE:
<223> OTHER INFORMATION: CUG repeat sequence

<400> SEQUENCE: 144
cugcugcugc ug                                                         12

<210> SEQ ID NO 145
```

```
<211> LENGTH: 14
<212> TYPE: PRT
<213> ORGANISM: Artificial
<220> FEATURE:
<223> OTHER INFORMATION: 1al04_1 inter-domain linker sequence

<400> SEQUENCE: 145

Phe Val Gly Tyr Pro Arg Phe Pro Ala Pro Val Glu Phe Ile
1               5                   10

<210> SEQ ID NO 146
<211> LENGTH: 11
<212> TYPE: PRT
<213> ORGANISM: Artificial
<220> FEATURE:
<223> OTHER INFORMATION: 1sesA_1 inter-domain linker sequence

<400> SEQUENCE: 146

Leu Leu Ala Leu Asp Arg Glu Val Gln Glu Leu
1               5                   10

<210> SEQ ID NO 147
<211> LENGTH: 9
<212> TYPE: PRT
<213> ORGANISM: Artificial
<220> FEATURE:
<223> OTHER INFORMATION: 1qaxA_3 inter-domain linker sequence

<400> SEQUENCE: 147

Met Ala Leu His Ala Arg Asn Ile Ala
1               5

<210> SEQ ID NO 148
<211> LENGTH: 10
<212> TYPE: PRT
<213> ORGANISM: Artificial
<220> FEATURE:
<223> OTHER INFORMATION: 1pfkA_2 inter-domain linker sequence

<400> SEQUENCE: 148

Leu Gly His Ile Gln Arg Gly Gly Ser Pro
1               5                   10

<210> SEQ ID NO 149
<211> LENGTH: 1186
<212> TYPE: PRT
<213> ORGANISM: Homo sapiens

<400> SEQUENCE: 149

Met Ser Val Ala Cys Val Leu Lys Arg Lys Ala Val Leu Trp Gln Asp
1               5                   10                  15

Ser Phe Ser Pro His Leu Lys His Pro Gln Glu Pro Ala Asn Pro
            20                  25                  30

Asn Met Pro Val Val Leu Thr Ser Gly Thr Gly Ser Gln Ala Gln Pro
        35                  40                  45

Gln Pro Ala Ala Asn Gln Ala Leu Ala Ala Gly Thr His Ser Ser Pro
    50                  55                  60

Val Pro Gly Ser Ile Gly Val Ala Gly Arg Ser Gln Asp Asp Ala Met
65                  70                  75                  80

Val Asp Tyr Phe Phe Gln Arg Gln His Gly Glu Gln Leu Gly Gly Gly
                85                  90                  95

Gly Ser Gly Gly Gly Gly Tyr Asn Asn Ser Lys His Arg Trp Pro Thr
            100                 105                 110
```

```
Gly Asp Asn Ile His Ala Glu His Gln Val Arg Ser Met Asp Glu Leu
            115                 120                 125

Asn His Asp Phe Gln Ala Leu Ala Leu Glu Gly Arg Ala Met Gly Glu
130                 135                 140

Gln Leu Leu Pro Gly Lys Lys Phe Trp Glu Thr Asp Glu Ser Ser Lys
145                 150                 155                 160

Asp Gly Pro Lys Gly Ile Phe Leu Gly Asp Gln Trp Arg Asp Ser Ala
                165                 170                 175

Trp Gly Thr Ser Asp His Ser Val Ser Gln Pro Ile Met Val Gln Arg
            180                 185                 190

Arg Pro Gly Gln Ser Phe His Val Asn Ser Glu Val Asn Ser Val Leu
        195                 200                 205

Ser Pro Arg Ser Glu Ser Gly Gly Leu Gly Val Ser Met Val Glu Tyr
    210                 215                 220

Val Leu Ser Ser Ser Pro Gly Asp Ser Cys Leu Arg Lys Gly Gly Phe
225                 230                 235                 240

Gly Pro Arg Asp Ala Asp Ser Asp Glu Asn Asp Lys Gly Glu Lys Lys
                245                 250                 255

Asn Lys Gly Thr Phe Asp Gly Asp Lys Leu Gly Asp Leu Lys Glu Glu
            260                 265                 270

Gly Asp Val Met Asp Lys Thr Asn Gly Leu Pro Val Gln Asn Gly Ile
        275                 280                 285

Asp Ala Asp Val Lys Asp Phe Ser Arg Thr Pro Gly Asn Cys Gln Asn
    290                 295                 300

Ser Ala Asn Glu Val Asp Leu Leu Gly Pro Asn Gln Asn Gly Ser Glu
305                 310                 315                 320

Gly Leu Ala Gln Leu Thr Ser Thr Asn Gly Ala Lys Pro Val Glu Asp
                325                 330                 335

Phe Ser Asn Met Glu Ser Gln Ser Val Pro Leu Asp Pro Met Glu His
            340                 345                 350

Val Gly Met Glu Pro Leu Gln Phe Asp Tyr Ser Gly Thr Gln Val Pro
        355                 360                 365

Val Asp Ser Ala Ala Thr Val Gly Leu Phe Asp Tyr Asn Ser Gln
    370                 375                 380

Gln Gln Leu Phe Gln Arg Pro Asn Ala Leu Ala Val Gln Gln Leu Thr
385                 390                 395                 400

Ala Ala Gln Gln Gln Tyr Ala Leu Ala Ala Ala His Gln Pro His
                405                 410                 415

Ile Gly Leu Ala Pro Ala Ala Phe Val Pro Asn Pro Tyr Ile Ile Ser
            420                 425                 430

Ala Ala Pro Pro Gly Thr Asp Pro Tyr Thr Ala Gly Leu Ala Ala Ala
        435                 440                 445

Ala Thr Leu Gly Pro Ala Val Val Pro His Gln Tyr Tyr Gly Val Thr
    450                 455                 460

Pro Trp Gly Val Tyr Pro Ala Ser Leu Phe Gln Gln Ala Ala Ala
465                 470                 475                 480

Ala Ala Ala Ala Thr Asn Ser Ala Asn Gln Gln Thr Thr Pro Gln Ala
                485                 490                 495

Gln Gln Gly Gln Gln Val Leu Arg Gly Gly Ala Ser Gln Arg Pro
            500                 505                 510

Leu Thr Pro Asn Gln Asn Gln Gln Gly Gln Gln Thr Asp Pro Leu Val
        515                 520                 525
```

```
Ala Ala Ala Ala Val Asn Ser Ala Leu Ala Phe Gly Gln Gly Leu Ala
        530                 535                 540

Ala Gly Met Pro Gly Tyr Pro Val Leu Ala Pro Ala Ala Tyr Tyr Asp
545                 550                 555                 560

Gln Thr Gly Ala Leu Val Val Asn Ala Gly Arg Asn Gly Leu Gly
                565                 570                 575

Ala Pro Val Arg Leu Val Ala Pro Ala Pro Val Ile Ile Ser Ser Ser
            580                 585                 590

Ala Ala Gln Ala Ala Val Ala Ala Ala Ala Ser Ala Asn Gly Ala
        595                 600                 605

Ala Gly Gly Leu Ala Gly Thr Thr Asn Gly Pro Phe Arg Pro Leu Gly
        610                 615                 620

Thr Gln Gln Pro Gln Pro Gln Pro Gln Gln Pro Asn Asn Asn Leu
625                 630                 635                 640

Ala Ser Ser Ser Phe Tyr Gly Asn Asn Ser Leu Asn Ser Asn Ser Gln
                645                 650                 655

Ser Ser Ser Leu Phe Ser Gln Gly Ser Ala Gln Pro Ala Asn Thr Ser
            660                 665                 670

Leu Gly Phe Gly Ser Ser Ser Leu Gly Ala Thr Leu Gly Ser Ala
        675                 680                 685

Leu Gly Gly Phe Gly Thr Ala Val Ala Asn Ser Asn Thr Gly Ser Gly
        690                 695                 700

Ser Arg Arg Asp Ser Leu Thr Gly Ser Ser Asp Leu Tyr Lys Arg Thr
705                 710                 715                 720

Ser Ser Ser Leu Thr Pro Ile Gly His Ser Phe Tyr Asn Gly Leu Ser
                725                 730                 735

Phe Ser Ser Ser Pro Gly Pro Val Gly Met Pro Leu Pro Ser Gln Gly
            740                 745                 750

Pro Gly His Ser Gln Thr Pro Pro Ser Leu Ser Ser His Gly Ser
        755                 760                 765

Ser Ser Ser Leu Asn Leu Gly Gly Leu Thr Asn Gly Ser Gly Arg Tyr
770                 775                 780

Ile Ser Ala Ala Pro Gly Ala Glu Ala Lys Tyr Arg Ser Ala Ser Ser
785                 790                 795                 800

Ala Ser Ser Leu Phe Ser Pro Ser Ser Thr Leu Phe Ser Ser Ser Arg
            805                 810                 815

Leu Arg Tyr Gly Met Ser Asp Val Met Pro Ser Gly Arg Ser Arg Leu
        820                 825                 830

Leu Glu Asp Phe Arg Asn Asn Arg Tyr Pro Asn Leu Gln Leu Arg Glu
        835                 840                 845

Ile Ala Gly His Ile Met Glu Phe Ser Gln Asp Gln His Gly Ser Arg
        850                 855                 860

Phe Ile Gln Leu Lys Leu Glu Arg Ala Thr Pro Ala Glu Arg Gln Leu
865                 870                 875                 880

Val Phe Asn Glu Ile Leu Gln Ala Ala Tyr Gln Leu Met Val Asp Val
                885                 890                 895

Phe Gly Asn Tyr Val Ile Gln Lys Phe Phe Glu Phe Gly Ser Leu Glu
            900                 905                 910

Gln Lys Leu Ala Leu Ala Glu Arg Ile Arg Gly His Val Leu Ser Leu
        915                 920                 925

Ala Leu Gln Met Tyr Gly Cys Arg Val Ile Gln Lys Ala Leu Glu Phe
        930                 935                 940
```

-continued

```
Ile Pro Ser Asp Gln Gln Asn Glu Met Val Arg Glu Leu Asp Gly His
945                 950                 955                 960

Val Leu Lys Cys Val Lys Asp Gln Asn Gly Asn His Val Val Gln Lys
                965                 970                 975

Cys Ile Glu Cys Val Gln Pro Gln Ser Leu Gln Phe Ile Ile Asp Ala
                980                 985                 990

Phe Lys Gly Gln Val Phe Ala Leu Ser Thr His Pro Tyr Gly Cys Arg
            995                 1000                1005

Val Ile Gln Arg Ile Leu Glu His Cys Leu Pro Asp Gln Thr Leu
    1010                1015                1020

Pro Ile Leu Glu Glu Leu His Gln His Thr Glu Gln Leu Val Gln
    1025                1030                1035

Asp Gln Tyr Gly Asn Tyr Val Ile Gln His Val Leu Glu His Gly
    1040                1045                1050

Arg Pro Glu Asp Lys Ser Lys Ile Val Ala Glu Ile Arg Gly Asn
    1055                1060                1065

Val Leu Val Leu Ser Gln His Lys Phe Ala Ser Asn Val Val Glu
    1070                1075                1080

Lys Cys Val Thr His Ala Ser Arg Thr Glu Arg Ala Val Leu Ile
    1085                1090                1095

Asp Glu Val Cys Thr Met Asn Asp Gly Pro His Ser Ala Leu Tyr
    1100                1105                1110

Thr Met Met Lys Asp Gln Tyr Ala Asn Tyr Val Val Gln Lys Met
    1115                1120                1125

Ile Asp Val Ala Glu Pro Gly Gln Arg Lys Ile Val Met His Lys
    1130                1135                1140

Ile Arg Pro His Ile Ala Thr Leu Arg Lys Tyr Thr Tyr Gly Lys
    1145                1150                1155

His Ile Leu Ala Lys Leu Glu Lys Tyr Tyr Met Lys Asn Gly Val
    1160                1165                1170

Asp Leu Gly Pro Ile Cys Gly Pro Pro Asn Gly Ile Ile
    1175                1180                1185
```

METHODS AND COMPOSITIONS FOR SYNTHETIC RNA ENDONUCLEASES

STATEMENT OF PRIORITY

This application is a continuation application of, and claims priority to, U.S. application Ser. No. 15/602,546, filed May 23, 2017 (abandoned), which is a continuation application of U.S. application Ser. No. 15/353,485, filed Nov. 16, 2016 (abandoned), which is a divisional application of, and claims priority to, U.S. application Ser. No. 13/805,240, filed Jan. 31, 2013, and issued on Nov. 22, 2016 as U.S. Pat. No. 9,499,805, which is a 35 U.S.C. § 371 national phase application of Application Serial No. PCT/US2011/040933, filed Jun. 17, 2011, which claims the benefit, under 35 U.S.C. § 119(e), of U.S. Provisional Application Ser. No. 61/356,340, filed Jun. 18, 2010, the entire contents of each of which are incorporated herein by reference.

STATEMENT REGARDING ELECTRONIC FILING OF A SEQUENCE LISTING

A Sequence Listing in ASCII text format, submitted under 37 C.F.R. § 1.821, entitled 5470-561TSDVCT2 updated ST25.txt, 139,810 bytes in size, generated on Oct. 29, 2019 and filed via EFS-Web, is provided in lieu of a paper copy. This Sequence Listing is hereby incorporated by reference into the specification for its disclosures.

FIELD OF THE INVENTION

The present invention is directed to sequence specific restriction enzymes for site-specific cleavage of RNA, as well as methods of their use.

BACKGROUND OF THE INVENTION

Ribonucleases play important roles in various pathways of nucleic acid metabolism, including control of gene expression, mRNA surveillance and degradation and host defense mechanism against RNA viruses (1-3). Since the first ribonuclease was discovered as a heat stable enzyme from pancreas capable of digesting yeast RNA, a diverse panel of RNases has been characterized. However, unlike DNA restriction enzymes, a protein enzyme that cleaves RNA in a sequence-specific manner has not been found in nature. The known RNA endonucleases either specifically cleave their target through recognition of certain structures (e.g., RNase III family, RNase H or most ribozymes) (4-6), or have essentially no sequence specificity (e.g., RNase A cleaves after pyrimidine residues and RNase T1 cleaves after G residues) (7). The sequence specific cleavage of RNA can be achieved by a large multi-component complex such as the spliceosome or the RISC complex in RNAi pathway, each of which require guide RNA to recognize their targets (8, 9) and involve large protein/RNA assemblies, limiting their application in probing structured RNA or manipulating recombinant RNA in vitro.

Sequence specific cleavage of RNA has been achieved using engineered hammerhead ribozymes or RNA-cleaving DNAzymes (10). Both types of enzyme recognize their substrates through Watson-Crick binding arms of 6-12 nt, and therefore can achieve high target selectivity. However, these nucleic acid enzymes generally have low turnover rate (with $k_{cat}$ around 1 $min^{-1}$) compared to protein enzymes, possibly due to tight binding to their substrates. In addition, the in vitro application of such nucleic acid enzymes is compromised by the high production cost and low stability of RNA, as well as the difficulty in controlling the folding of single stranded RNA or DNA.

The present invention overcomes previous shortcoming in the art by providing site specific RNA endonucleases and methods of their use.

SUMMARY OF THE INVENTION

In one aspect, the present invention provides a synthetic RNA endonuclease comprising the formula: A-B-C, wherein: A is an RNA binding domain, B is a linker peptide, and C is a cleavage domain.

In addition, the present invention provides a method of detecting a target RNA in a sample, comprising: a) contacting the sample with the RNA endonuclease of this invention under conditions whereby cleavage of RNA occurs if the target RNA is present in the sample and wherein the RNA binding domain of the RNA endonuclease is modified to bind the target RNA; and b) detecting a cleavage product of the target RNA, thereby detecting the target RNA in the sample.

Furthermore, the present invention provides a method of cleaving a target mRNA in a sample, comprising contacting the sample with the RNA endonuclease of this invention under conditions whereby cleavage of the target mRNA occurs and wherein the RNA binding domain of the RNA endonuclease is modified to bind the target mRNA, thereby cleaving the target mRNA in the sample.

In yet further aspects of this invention, a method is provided of cleaving a target mRNA in a cell, comprising introducing into the cell the RNA endonuclease of this invention, wherein the RNA binding domain of the RNA endonuclease is modified to bind the target mRNA, under conditions whereby cleavage of the mRNA occurs, thereby cleaving the target mRNA in the cell.

Also provided herein is a method of inhibiting expression of a target gene in a cell, comprising introducing into the cell the RNA endonuclease this invention, wherein the RNA binding domain of the RNA endonuclease is modified to bind mRNA encoding a gene product of the target gene, under conditions whereby cleavage of the mRNA occurs, thereby inhibiting expression of the target gene in the cell.

The present invention additionally provides a method of cleaving a target mRNA in a mitochondrion in a cell, comprising introducing into the cell the RNA endonuclease of this invention, wherein the RNA binding domain of the RNA endonuclease is modified to bind the target mRNA in the mitochondrion and wherein the RNA endonuclease comprises a mitochondrial targeting signal sequence, under conditions whereby cleavage of the target mRNA in the mitochondrion occurs, thereby cleaving the target mRNA in the mitochondrion in the cell.

Further provided herein is a method of inhibiting expression of a target mitochondrial gene in a cell, comprising introducing into the cell the RNA endonuclease of this invention, wherein the RNA binding domain of the RNA endonuclease is modified to bind mRNA encoding a gene product of the target mitochondrial gene and wherein the RNA endonuclease comprises a mitochondrial targeting signal sequence, under conditions whereby cleavage of the target mRNA in the mitochondrion occurs, thereby inhibiting expression of the target mitochondrial gene in the cell.

Additional aspects of this invention include a method of treating dystrophia myotonica (DM) in a subject, comprising administering to the subject an effective amount of the RNA endonuclease of this invention, wherein the RNA binding domain of the RNA endonuclease is modified to bind mRNA encoding (CUG)n repeats in the 3' UTR of DMPK to treat DM1 and/or mRNA encoding (CCUG)n repeats in intron 1 of ZNF9 to treat DM2 and wherein the RNA endonuclease comprises a mitochondrial targeting signal sequence, thereby treating DM in the subject.

The present invention also provides a method of detecting an RNA virus in a sample, comprising: a) contacting the sample with the RNA endonuclease of this invention under conditions whereby cleavage of RNA occurs if RNA of the RNA virus is present in the sample and wherein the RNA binding domain of the RNA endonuclease is modified to bind a target RNA of the RNA virus; and b) detecting a cleavage product of the target RNA, thereby detecting the RNA virus in the sample.

A method is also provided herein of diagnosing a viral infection in a subject, comprising: a) contacting the sample from the subject with the RNA endonuclease of this invention under conditions whereby cleavage of RNA occurs if viral RNA is present in the sample and wherein the RNA binding domain of the RNA endonuclease is modified to bind viral RNA; and b) detecting a cleavage product of the target RNA, thereby detecting viral RNA in the sample and thereby diagnosing a viral infection in the subject.

Furthermore, the present invention provides a method of identifying a strain of an RNA virus in a sample, comprising: a) contacting the sample with the RNA endonuclease of this invention under conditions whereby cleavage of RNA occurs if the RNA of the strain of the RNA virus is present in the sample and wherein the RNA binding domain of the RNA endonuclease is modified to bind a target RNA specific to the strain of the RNA virus; and b) detecting a cleavage product of the target RNA, thereby identifying the strain of the RNA virus in the sample.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

DESCRIPTION OF THE FIGURES

FIG. 1. Design and activity validation of artificial sequence specific RNA endonucleases (ASREs). (Panel A) Structures of the PUF domain of pumiliol with NRE-19 RNA (1M8W) and the PIN domain of Smg6 (2HWW). The PUF domain contains eight repeats, each recognizing a single RNA base. Three amino acids from each repeat interact with the Watson-Crick edge of an RNA base and determine the binding specificity of the repeat (left panel). The PIN domain has an RNase H like active site with three Asp residues and co-ordinates one divalent metal cation (right panel). (Panel B) ASRE with N-terminal PUF, C-terminal PIN and a heptapeptide linker was incubated with a cognate RNA substrate for 30 min. Site-specific cleavage of RNA was obtained with the ASRE containing a wild type PIN domain (lane 2) but not with ASRE containing a mutated PIN domain (lane 3). (Panel C) Inverted ASRE (PIN-PUF fusion protein from N to C terminus) caused complete, non-specific cleavage of an RNA substrate. The ASRE in PUF-PIN orientation was included as control (lane 1).

FIG. 2. Biochemical characterization of ASREs. (Panel A) The linker length affects the activity of ASRE. ASRE with a tripeptide linker showed limited activity whereas efficient cleavage activity was achieved with medium (heptapeptide) and long linkers (dodecapeptide). At longer reaction time, non-specific digestion products (indicated by asterisks in lane 5) were observed with ASRE containing a dodecapeptide linker. (Panel B) Digestion time course of 7u6g RNA by ASRE(6-2/7-2). Digestion was followed in the standard reaction condition substituted with 3 mM $Mn^{2+}$. (Panel C) RNA substrates containing either an NRE site (UGUAUAUA) or 7u6g site (UugAUAUA) were incubated with ASRE(Wt) or ASRE(6-2/7-2). Lanes 1 and 4 are controls without enzyme. (Panel D) ASRE shows divalent metal ion selectivity, with $Mn^{2+}$ yielding highest activity and $Mg^{2+}$ and $Co^{2+}$ giving lower activity. The concentrations of divalent metal ions were 3 mM in all lanes. (Panel E) Semilog plots were used to determine the pseudo first-order reaction rates of ASRE catalyzed RNA cleavage in the presence of 2.5 mM (♦), 5 mM (■) and 7.5 mM (▲) $Mn^{2+}$. Non-specific digestion occurred with $Mn^{2+}$ concentration greater than 7.5 mM (data not shown).

FIG. 3. Kinetic parameters and cleavage sites of ASREs. (Panel A) Plot of initial reaction rates vs. substrate concentration for ASRE(wt). The enzyme was incubated with various concentration of cognate substrate for 5 min and the initial reaction rates were measured as the amount of RNA cleaved per minute. Kinetics constants were determined by fitting the curve to a Michaelis-Menton kinetic model. (Panel B) Plot of initial reaction rates vs. substrate concentration for ASRE(6-2/7-2). Reaction conditions and data analysis were the same as panel A. (Panel C) The cleavage site was mapped by 5' or 3' DSS-RACE from gel purified RNA products. The positions of two cleavage sites are indicated with arrows and the relative frequencies are plotted. The 8-nt binding sequence of PUF is shown in bold. (Panel D) The "curve back" model of ASRE best explains the cleavage positions mapped in panel C.

FIG. 5. Sequence alignment of human, mouse, rat *Pumilio* 1 (hpum1, Mpum1, Ratpum1, SEQ ID NOS:55-57) human and mouse *Pumilio*2 (hpum2, Mpum2, SEQ ID NOS:58 and 59) and *Drosophila Pumilio* (Dspum, SEQ ID NO:60).

FIG. 6. Sequence alignment and comparison of the *Drosophila Pumilio* (PumDr, SEQ ID NO:61) and human PUM1 (SEQ ID NO:62) and PUM2 (SEQ ID NO:63) proteins.

FIG. 7. Unique RNA binding mode of PUF domain. (Panel A) Crystal structure of a PUF domain that binds to RNA. (Panel B) Schematic diagram of modular recognition code of each PUF repeat and the RNA base. The 8 PUF repeats bind RNA in an anti-parallel fashion, with each repeat recognizing a single base. Each base was stacked between two PUF repeats by the Tyr, His or Arg residue, and the side chains of two amino acid residues in each repeat determine which RNA base to recognize. The U will be recognized by NxxxQ (SEQ ID NO:64) residues in a PUF repeat, the G will be recognized by SxxxE (SEQ ID NO:65), and the A will be recognized by (C/S)xxxQ (SEQ ID NO:66). By mutating each repeat, a PUF domain can be generated that specifically recognizes an 8-nt with high affinity.

FIG. 8. Sequence alignment of the PIN domains of EST1A family proteins from *Homo sapiens* (hu_pin, SEQ ID NO:67), *Mus musculus* (Ms_pin, SEQ ID NO:68), *Drosophila melanogaster* (Dm_pin, SEQ ID NO:69), and *Caenorhabditis elegans* (Ce_pin, SEQ ID NO:70) (upper alignment).

FIG. 9. Structure of the potential functional residues of the smg6 PIN domain and archael PIN-domain proteins.

FIG. 13. (Panel A) Expression and purification of ASRE proteins. The proteins were purified from soluble bacterial fraction using Ni-NTA column chromatography. The purification yields milligram levels of homogeneous preparation as shown in the figures. The approximate molecular weight of the protein is 63 KDa. (Panel B) ASRE activity with varying pH.

FIG. 15. Measurement of initial rate of ASRE catalyzed cleavage. (Panel A) A representative example of urea-PAGE gel used for determination of kinetic parameters of ASRE (6-2/7-2). Different amounts of RNA substrates were incubated with ASRE or buffer for only 5 mins, equal volumes of digested products and undigested controls in adjacent lanes of PAGE. (Panel B). The plot of RNA band intensity vs. the input RNA amount of undigested control samples, suggesting the linear range of quantification.

FIG. 20. Proposed models for the non-specific cleavage of the PIN-PUF fusion protein. (Panel A) The ASRE with PUF-PIN orientation from N- to C-terminus. The PIN domain is probably curved back with the active site facing the PIN domain and RNA substrate. (Panel B) ProPanel posed model of fusion protein in PIN-PUF orientation. The active site of the PIN domain may face away from PUF, therefore it can non-specifically cleave RNA. (Panel C) An alternative proposed model of fusion protein in PIN-PUF orientation. The C-terminal residue/linker of the PUF domain is very flexible, therefore allowing RNA to access the PIN active site and be cleaved non-specifically.

FIG. 21. (Panel A) Diagram of human mitochondrial genome. The 13 protein coding genes are shown and the tRNA genes are represented with a black or grey bar. (Panel B) Diagram of three ASREs used in experiments. (Panel C) Subcellular localization of mitoASRE and control ASREs. HeLa cells were transiently transfected with expression vectors and the ASREs were detected with anti-flag antibody. Mitotrackers were used to mark the mitochondria. (Panel D) The decrease of ND5 mRNA as judged by real time RT-PCR. (Panel E) The change of ND5 protein level measured by western blots. Samples are assayed 24 hours after tetracycline (tet) induction.

FIG. 27. Identification of a cytosine-recognition code by yeast three-hybrid screen. (Panel A) Schematic representation of the interaction between wild-type PUF and its RNA target sequence (5'-UGUAUAUA). Protein repeats are indicated by squares and RNA bases by ovals (dashed lines, hydrogen bonds; parentheses, van der Waals contacts). For library screening, the third RNA base was mutated to cytosine (C3) and served as a new target. Nucleotides encoding positions 1043 and 1047 of the PUF were randomized in the screened library. (Panel B) Illustration of the yeast three-hybrid assay used to screen the PUF library for binding to C3 RNA (5'-ugCauaua-3') and to measure PUF-RNA interaction. The interaction between Gal4-PUF and target RNA fused with MS2 binding sequence can trigger the expression of both reporter genes, LacZ and HIS3. (Panel C) Sequences of the PUF library (SEQ ID NO:92) with randomized coding sequences at positions 1043 and 1047. (Panel D) Validation of the yeast three-hybrid system. The expression of the reporter genes, LacZ (left panel) and HIS3 (right panel), was measured for yeast expressing wild-type PUF and the wild type RNA (U3) or the mutated RNA C3. Positive binding was found only when wild-type PUF and U3 RNA were expressed. (Panel E) Measurement of specific interactions between PUF domains and RNAs with base substitutions at position 3. Positions of the mutated amino acids and RNA bases are indicated in the left panel. Protein-RNA binding was measured with the yeast three-hybrid system using liquid β-galactosidase assays. For each sample, 12 colonies were picked and the experiments were performed in triplicate. The β-galactosidase activity relative to that of the wild-type PUF-U3 RNA pair was plotted to reflect the strength of protein-RNA interaction (right). The fold increase in binding of the mutant protein to the cognate base vs. the non-cognate base in the wild-type RNA is indicated above the bars.

FIG. 28. The cytosine-recognition code can be transferred to other PUM repeats. (Panel A) Mutation of PUM repeat 2 to convert its binding specificity to recognize C7 RNA. Indicated mutations were introduced in repeat 2 (left). Protein-RNA binding measured with the yeast three-hybrid system using β-galactosidase activity is shown (right). Wild-type PUF and its cognate target RNA were included in all experiments as controls and its relative activity set to 1. (Panel B) Mutation of PUM repeat 5 to convert its binding specificity to recognize C4 RNA. Indicated mutations were introduced in repeat 5. (Panel C) Mutation of PUM repeat 6 to convert its binding specificity to recognize C3 RNA. Indicated mutations, including two different stacking residues, were introduced. (Panel D) Mutation of PUM repeat 7 to convert its binding specificity to recognize C2 RNA. Indicated mutations, including two different stacking residues, were introduced. For panels A-D, the fold increase in binding of the mutant protein to the cognate base vs. the non-cognate base in the wild-type RNA is indicated above the bars. (Panel E) Mutation of PUM repeat 3 to convert its binding specificity to recognize C6 RNA. Indicated mutations, including mutation of the base stacking residue of repeat 4, were introduced. For all panels, the experimental conditions and data analyses are similar to that in panel A.

The gene (SEQ ID NOS:93 and 94) and protein sequences (SEQ ID NOS:95 and 96) of VEGF-A in the region near the alternative splice sites are shown with two PUFs recognizing different cytosine-containing sequences. To shift the splicing towards anti-angiogenic VEGF-A isoforms, the cultured MDA-MB-231 cells were transfected with 1 µg expression vectors of Gly-PUF #1 or RS-PUF #2. Total RNA was purified 24 hours after transfection to detect VEGF-A splicing by RT-PCR. The percentages of b isoforms were quantified and are plotted below the gel.

Figure 32:
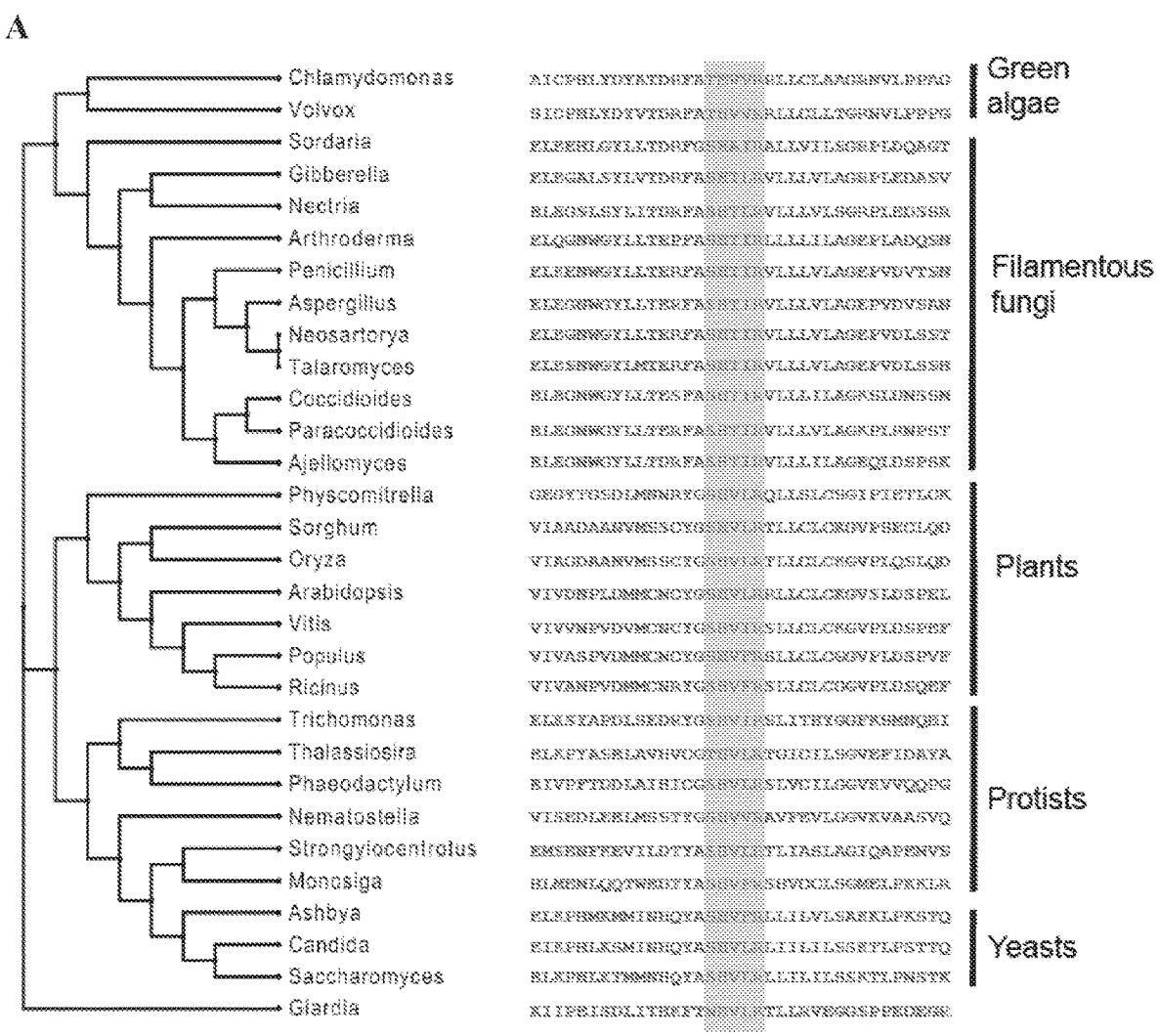
Figure 32:
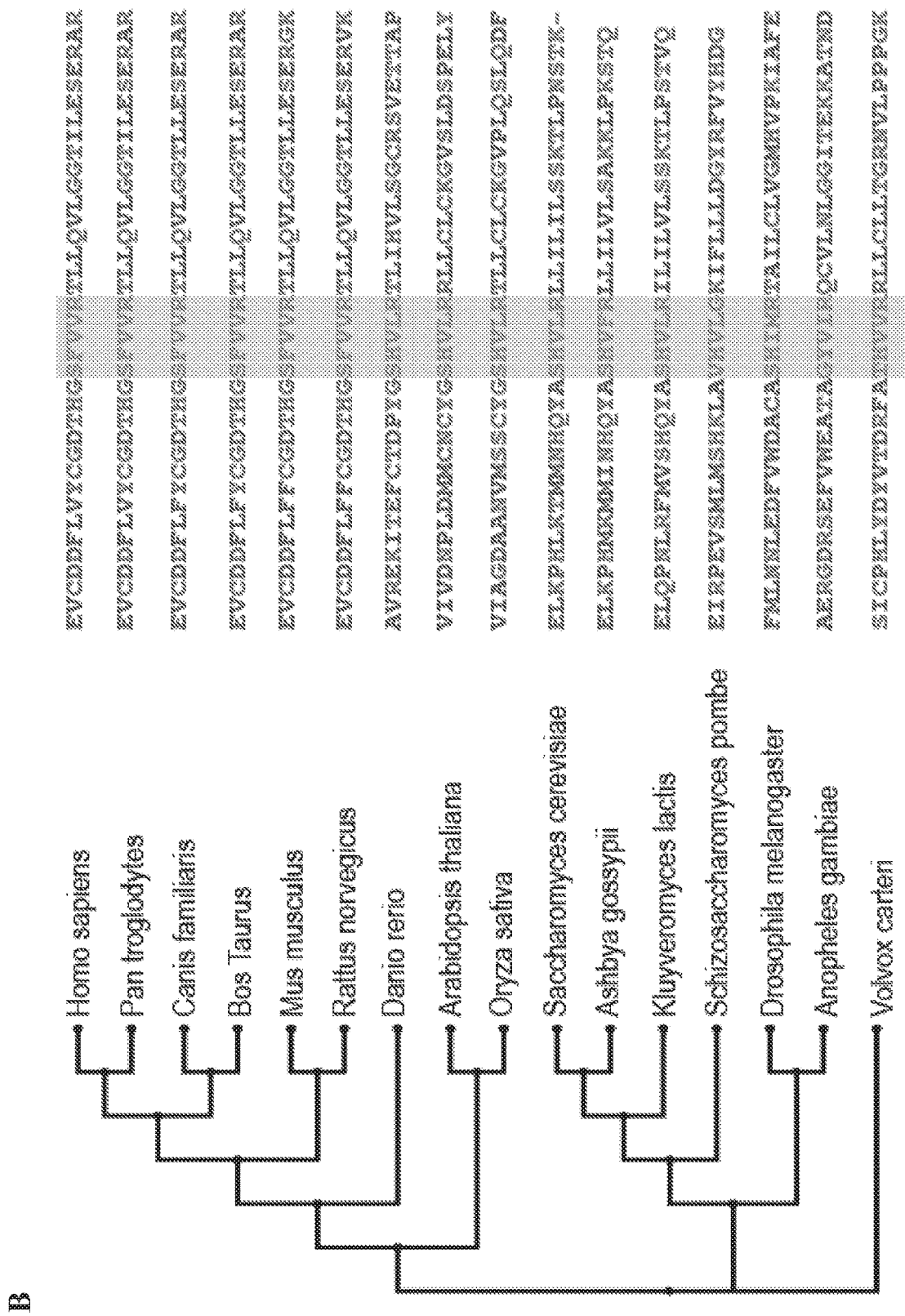

FIG. 32. Natural PUF proteins with putative cytosine-recognition code. (Panel A) Alignment and phylogenetic tree of the putative C-recognition PUM repeat in Nop9p homologs from yeast, plants, filamentous fungi and protists (SEQ ID NOS:97-126). The query sequences were selected to maximize the divergence of the species, but are otherwise arbitrary. The Giardia protein EES98274 was chosen as the outgroup in the phylogenetic tree. (Panel B) Alignment of the putative C-recognition PUM repeat in Nop9p homologs from the HomoloGene database (SEQ ID NOS:127-142). The homologous Volvox carteri protein (Accession No. XP_002952190) was included in the alignment as the outgroup in the phylogenetic tree. The conserved positions for cytosine recognition are highlighted.

DETAILED DESCRIPTION OF THE INVENTION

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate, if the specification states that a complex comprises components A, B and C, it is specifically intended that any of A, B or C, or a combination thereof, can be omitted and disclaimed singularly or in any combination.

As used herein, the transitional phrase "consisting essentially of" (and grammatical variants) is to be interpreted as encompassing the recited materials or steps "and those that do not materially affect the basic and novel characteristic(s)" of the claimed invention. See, *In re Herz*, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "about," as used herein when referring to a measurable value such as an amount or concentration (e.g., the signal-to-background ratio) and the like, is meant to encompass variations of 20%, 10%, 5%, 1%, 0.5%, or even 0.1% of the specified amount.

The present invention provides a new class of synthetic RNA endonucleases that are analogous to DNA restriction enzymes. These artificial site-specific RNA endonucleases (ASREs) were created by combining an RNA endonuclease (e.g., the PIN domain of human SMG6, with a series of modified PUF domains specifically recognizing an 8-nt region of RNA as an RNA substrate. The ASRE binds this RNA substrate with high affinity and efficiently makes a single cleavage near the binding site. ASREs containing different PUF domains can recognize and cleave distinct substrates without detectable activity between non-cognate ASRE/RNA pairs. Such cleavage requires manganese (II) ions, and a mutation at the active site of PIN domain abolishes the endonuclease activity. Since a PUF domain can be designed to recognize almost any 8-nt RNA, a large panel of ASREs can be designed to recognize and cleave various RNA targets. Expression of an ASRE of this invention that recognizes an endogenous mRNA in bacterial cells can silence the target gene by inducing mRNA cleavage. This new class of RNA endonucleases provides a useful tool to manipulate RNA in vitro, and for silencing gene expression in organisms where interfering RNA (RNAi) machinery is not available.

Thus, in one embodiment, the present invention provides a synthetic RNA endonuclease comprising the formula: A-B-C, wherein: A is an RNA binding domain, B is a linker peptide, and C is a cleavage domain.

RNA Binding Domain

In various embodiments, the RNA binding domain can be a *Pumilio* homology domain (PU-HUD) and in particular embodiments, the PU-HUD can be a human *Pumilio* 1 (PUF) domain. However, it is to be understood that the RNA binding domain can be any protein or peptide that binds RNA in s sequence specific manner. In particular, the RNA binding domain can be any protein or peptide that contains modular armadillo repeats (ARM repeats) and in particular can be any such modular protein that binds RNA in a sequence specific manner wherein the RNA specificity can be changed by modifying the amino acid side chain(s) of the protein. Thus, the RNA binding domain can be, for example any PUF protein family member with a Pum-HD domain. Nonlimiting examples of a PUF family member include FBF in *C. elegans*, Ds pum in *Drosophila* and PUF proteins in plants such as *Arabidopsis* and rice (the genes are yet to be named. A phylogenetic tree of the PUM-HDs of *Arabidop-* sis, rice and other plant and non-plant species is provided in Tam et al. ("The Puf family of RNA-binding proteins in plants: phylogeny, structural modeling, activity and subcellular localization" BMC Plant Biol. 10:44, 2010, the entire contents of which are incorporated by reference herein). PUF family members are highly conserved from yeast to human and all members of the family bind to RNA in a sequence specific manner with a predictable code. The accession number for the domain is PS50302 in the Prosite database (Swiss Institute of Bioinformatics) and a sequence alignment of some of the members of this family is shown in FIG. 5 (ClustalW multiple sequence alignment of human, mouse, rat *Pumilio* 1 (hpum1, Mpum1, Ratpum1) and human and mouse *Pumilio*2 (hpum2, Mpum2), respectively, is shown. The *Drosophila* pum1 is very different in length from other mammalian *Pumilio*1 homologues. The C-terminal PUF HUD domain is only shown in the sequence alignment.

Figure 6:
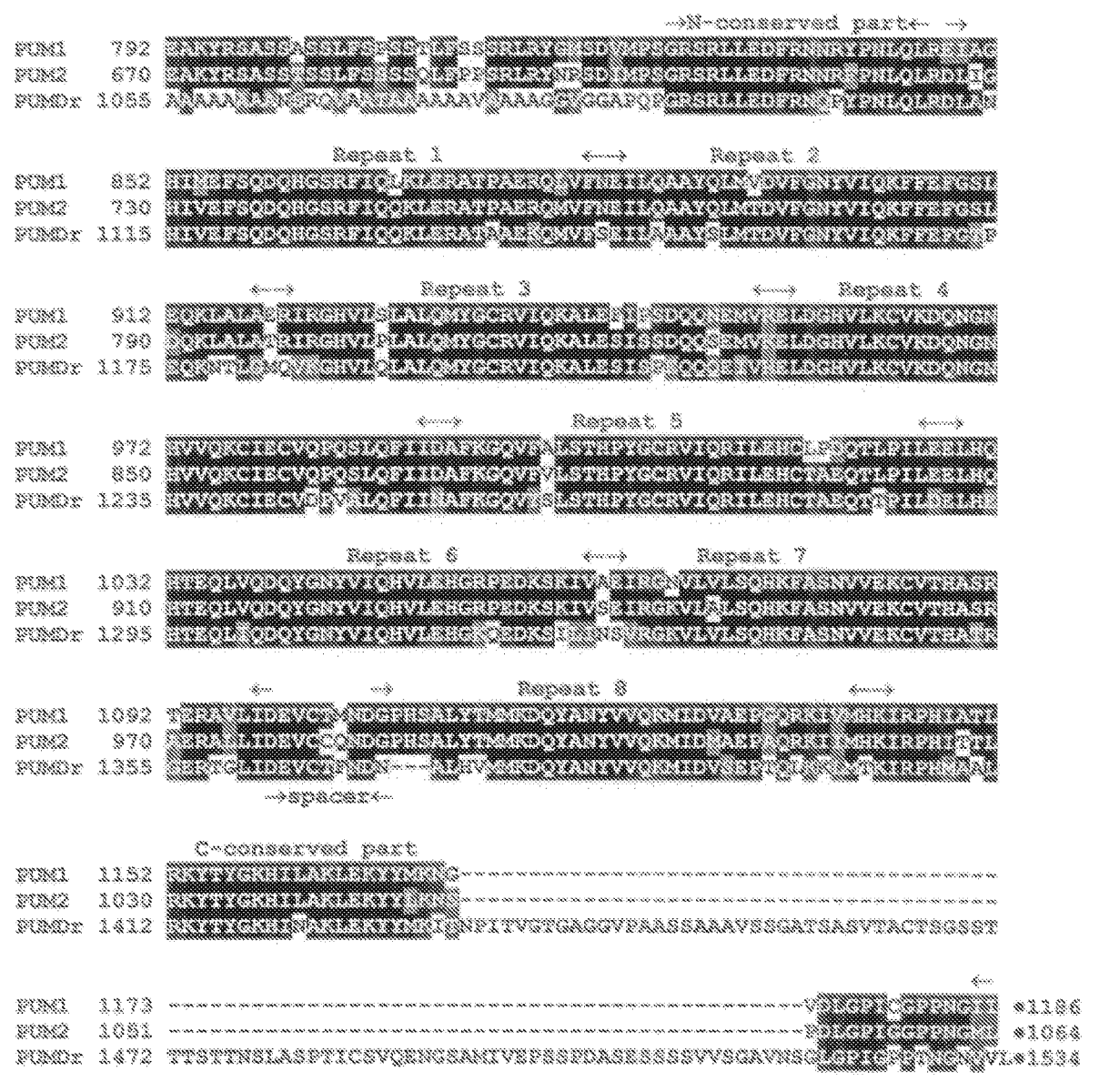

FIG. 6 shows the ClustalW amino acid sequence alignment and comparison of the *Drosophila Pumilio* (PumDr) and human PUM1 and PUM2 proteins. The N-terminal part of human and fly Pum proteins shows weak homology (40% similarity) and differs significantly in size and protein sequence. The C-terminal part shows a very high degree of homology and evolutionary conservation (78% identity, 86% similarity for PUM1 and 79% identity, 88% similarity for PUM2), with highly conserved protein sequence and structure of the Pum RNA-binding domain. In all three proteins PUM-HD is composed of the N-terminal conserved part of 20 amino acids, eight Pum repeats of 36 amino acids each, and the C-terminal conserved region. In human *Pumilio* proteins the C-conserved part is 44 amino acids long, whereas *Drosophila* protein has an insert of additional 85 amino acids in the C-conserved region. The nucleotide and amino acid sequences can be found in the DDBJ/EMBL/ GenBank® databases under accession nos. AF315592 (PUM1: SEQ ID NO:149) and AF315591 (PUM2) (Spassov & Jurecic, "Cloning and comparative sequence analysis of PUM1 and PUM2 genes, human members of the *Pumilio* family of RNA-binding proteins" Gene, 299:195-204, October 2002, the entire contents of each of which (publication and sequences) are incorporated by reference herein).

In some embodiments, the PUF domain of this invention can be made up of eight 36 mers, in which 33 of the amino acids are conserved and the 34$^{th}$, 35$^{th}$ and 36$^{th}$ amino acids can vary, imparting specificity for a particular base in an RNA sequence. In particular embodiments, the RNA binding domain is about 300 (e.g., 310, 309, 308, 307, 306, 305, 304, 303, 302, 301, 300, 299, 298, 297, 296, 295, 294, 293, 292, 291, 290, etc.) amino acids in length. In particular embodiments, the RNA cleavage domain is about 120 amino acids in length. In some embodiments, the RNA endonuclease of this invention is designed to bind to a specific RNA sequence of about 8 nucleotides (e.g., 8-16 contiguous RNA bases) to position the cleavage domain to cut the RNA at a specific site. In some embodiments, the RNA can be cut between any of the 8 contiguous RNA bases as well as at any site upstream and/or downstream of the 8-nt sequence bound by the RNA binding domain (e.g., 1, 2, 3, 4, 5, 6, 7, 8, 9, 10 or more nucleotides upstream or downstream of the 8-nt RNA sequence). In particular embodiments, the fifth nucleotide of the 8-nt sequence is a U or C, while the other 7 nucleotides can vary.

One aspect of this invention is the ability to modify the RNA binding domain of the ASRE of this invention to target a specific RNA sequence. Thus, in some embodiments, the RNA endonuclease of this invention comprises an RNA binding domain (e.g., Puf-HUD) that is modified to bind an RNA sequence that is different than the RNA sequence bound by an unmodified (e.g., wild type) RNA binding domain. The RNA sequence can be about an 8mer (e.g., an 8mer, 9mer, 10mer, 11mer, 12mer, 13mer, 14mer, 15mer, 16mer, etc.). The ability to introduce modifications into the amino acid sequence of the RNA binding domain to alter its specificity for a target RNA sequence is based on the known interactions of bases with the different amino acid side chains of the RNA binding domain (e.g., Puf protein) (FIG. 1A). FIG. 7 shows the RNA recognition code of the PUF domain. Thus, the recognition code can be generally written as:

SerXXXGlu→ G (guanine, SEQ ID NO: 1),
CysArgXXXGln→A (adenine, SEQ ID NO: 2),
AsnXXXGln→U (uracil, SEQ ID NO: 3), and
SerTyrXXArg (cytosine, SEQ ID NO: 4), where X is any amino acid. In some embodiments, the recognition code for A (adenine) can be SerArgXXXGln (SEQ ID NO:5).

Other RNA binding domains that can be employed in the RNA endonuclease of this invention include RNA binding domains (RBDs), such as in most splicing proteins, including heteronuclear ribonuclear proteins (HNRNP) and the K homology group of proteins (KH loop proteins); any of which can be used as the RNA binding module of the ASREs of this invention.

Linker Peptide

Figure 26:
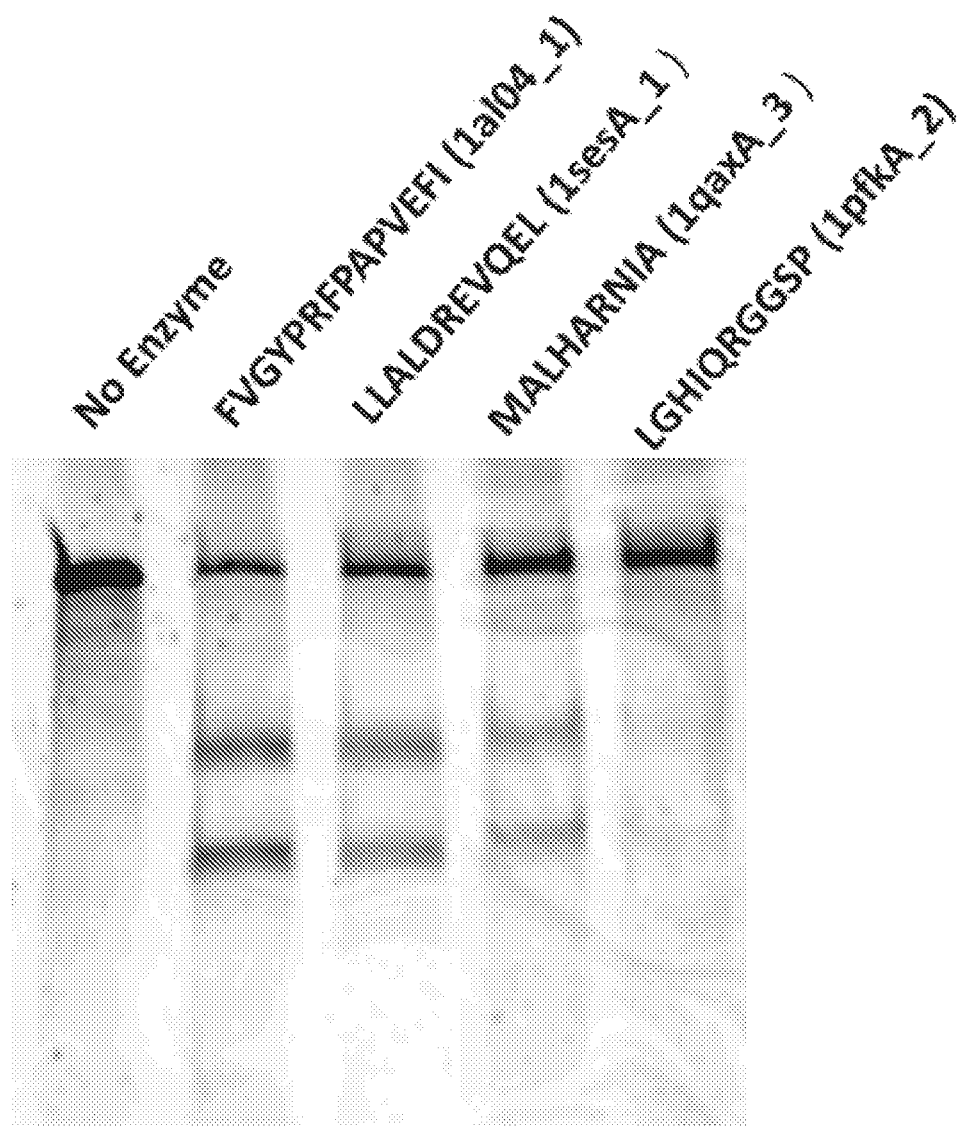
FIG. 26. Effects of linker sequence and structure on ASRE activity. The ASRE(6-2/7-2) containing different linker sequences (SEQ ID NOS: 145-148) was incubated with its cognate substrate and the cleavage of the RNA was detected with urea-PAGE gel. The different linkers were chosen from the protein inter-domain linker database. Both the sequence and the PDB code were shown. The secondary structures of the linkers are: 1a104_1 (SEQ ID NO:145): HHHHTTC-CCCCCCHHHH; 1sesA_1 SEQ ID NO:146): HHHHHH-HHHHH; 1qaxA_3 SEQ ID NO:147): HHHHTTTHHH; 1pfkA_2 SEQ ID NO:148): CGGGGGCSCC. The structure of inter-domain linkers was determined in the natural context of respective proteins. The notation of secondary structure follows the standard DSSP code (H, α helix; T, hydrogen bonded turn; C, coil; G, $3_{10}$ helix; S, bend). See Table 2 for details.

The ASREs of this invention comprise a linker peptide, which can be from about three amino acids to about 20 amino acids in length (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, etc.) amino acids). In some embodiments, a particular linker peptide of this invention is VDTGNGS (SEQ ID NO:18). However it is to be understood that any suitable linker peptide can be used in the ASRE of this invention. Basic structural guidelines for selection of a linker peptide sequence are that the linker sequence is ideally rich in neutral to polar amino acids that have a slight helical propensity. In some embodiments, the linker peptide forms an alpha helical structure. Proline (Pro) and aromatic amino acids (Phe, Tyr, Trp) are typically not used in the linker peptide sequence. Thus, in some embodiments, a linker peptide of this invention does not comprise a proline, a phenylalanine, a tyrosine and/or a tryptophan. Table 2 and FIG. 26 show various nonlimiting examples of linker peptides of this invention.

Cleavage Domain

In various embodiments of the RNA endonuclease of this invention, the cleavage domain can be the PilT N-terminus (PIN) domain of SMG6. However, it is to be understood that any suitable cleavage domain can be used in the ASREs of this invention. In general, a cleavage domain of this invention typically would not exceed 30 KDa and it would have independent activity in trans. The cleavage domain may also have a RNAse H/A-like fold at the active site lined by acidic residues (Asp/Glu) or His, which acts via a metal ion (divalent or tetravalent) and can cleave the phosphodiester bond in the nucleic acid backbone.

In particular embodiments, the PIN domain of hsMG6 (EST1A; GenBank® Database Accession No. NM_017575, incorporated by reference herein; synonyms include C17orf31, KIAA0732 and SMG-6)) can be used in the ASREs of this invention. (see FIG. 1A for PIN domain structure). FIG. 8 shows a sequence alignment of the PIN domains of EST1A family proteins from *Homo sapiens* (hu_pin), *Mus musculus* (Ms_pin), *Drosophila melanogaster* (Dm_pin), and *Caenorhabditis elegans* (Ce_pin) (upper alignment). Conserved residues are shown by asterisk. The PIN domain has an RnaseH like active site fold and is also very similar in active site architecture to an Archaebacterial PIN domain.

FIG. 9 shows the structure of the potential functional residues of the smg6 PIN domain and archaeal PIN-domain proteins. A stereoview of the residues at the putative active sites of the smg6 PIN domain is shown. Molecules A and B in the asymmetric unit are superimposed. Residues D1251, E1282, D1353, T1390, and D1392 are shown as stick models, and the four water molecules are shown as spheres. The hydrogen bonds are shown as dashed lines.

Figure 10:
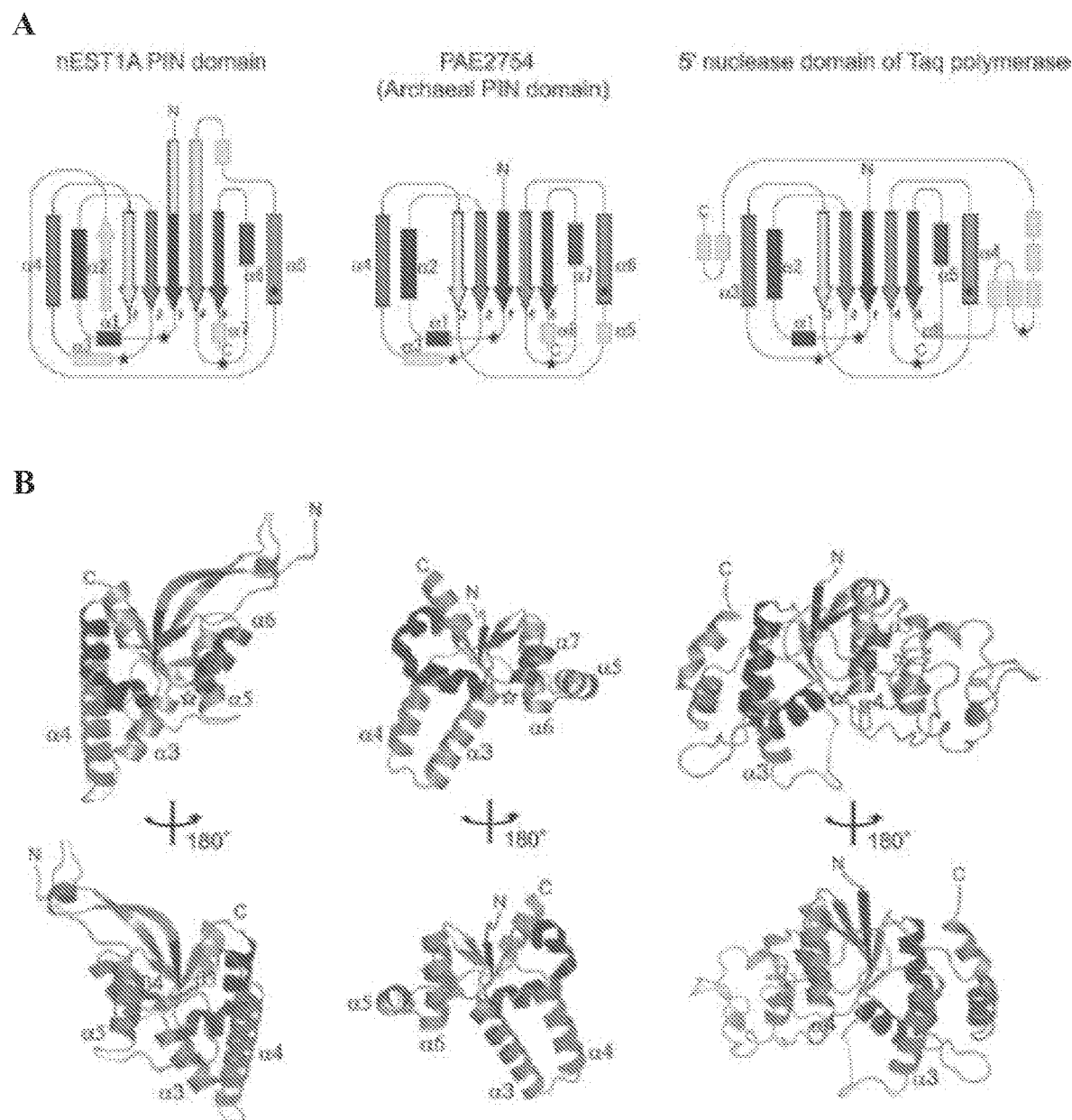
FIG. 10. Structurally similar proteins.

FIG. 10 shows structurally similar proteins. (Panel A) Topology diagrams of the PIN domain of hEST1A, archaeal PIN-domain protein PAE2754, and the 50 nuclease domain of Taq polymerase. Strands are represented by arrows and helices by rectangles. The core structures of these proteins consist of a parallel β-sheet with strand order 32145. The structurally similar elements are shown in different grey shades. Asterisks indicate the residue positions at the active site of Taq polymerase and at the putative active sites of the hEST1A PIN domain and PAE2754. (Panel B) Ribbon representations of the PIN domain of hEST1A, PAE2754, and the 50 nuclease domain of Taq polymerase. The three structures are shown in a similar orientation. The secondary structure elements of the 50 nuclease fold are shown in grey shades [same as in (Panel A)]. Stars indicate the active site of the 50 nuclease domain of Taq polymerase and the putative active sites of the hEST1A PIN domain and PAE2754 (Takeshita et al. "Crystal structure of the PIN domain of human telomerase-associated protein EST1A" *Proteins* 68:980-989, 2007, the entire contents of which are incorporated by reference herein.

Figure 11:
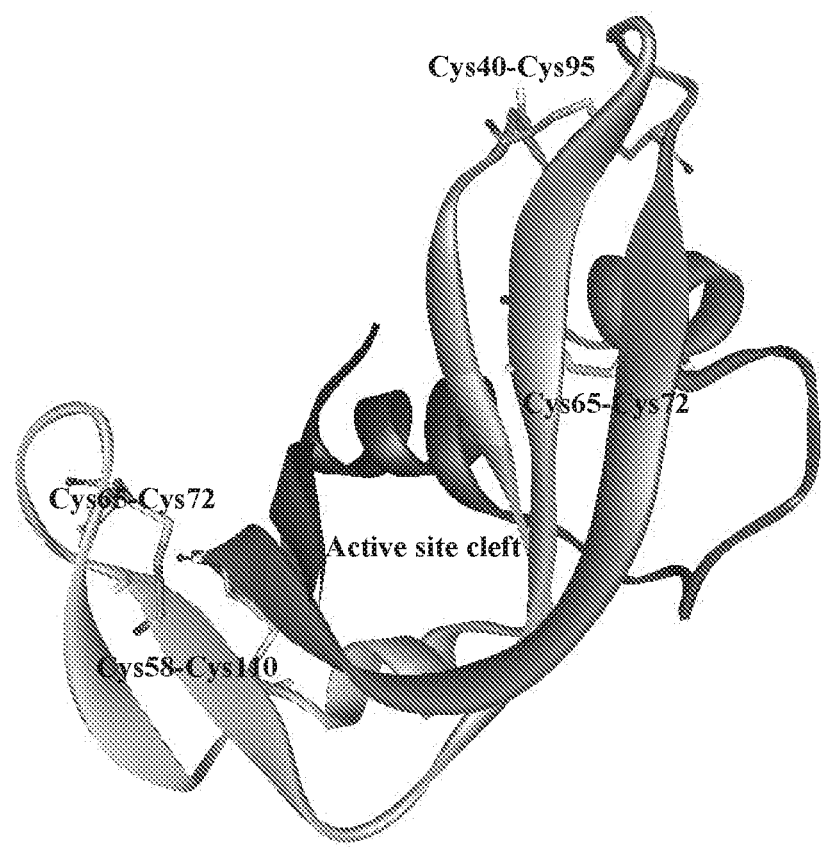
FIG. 11. Structure of RNAse A-like fold.
Figure 12:
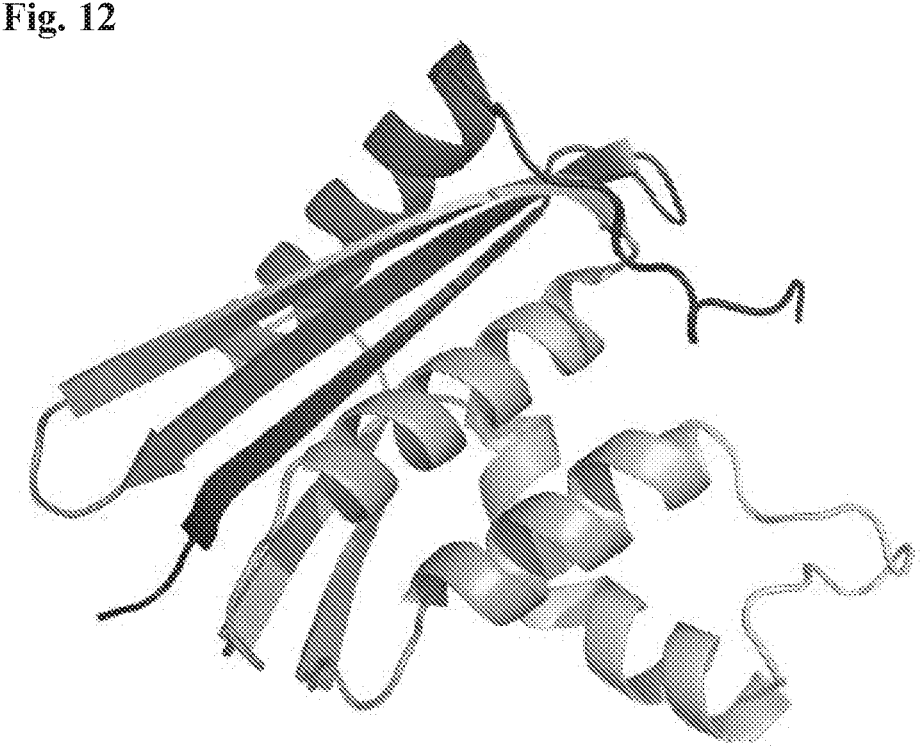
FIG. 12. Structure of RNAse H-like fold.

In some embodiments of this invention, the RNA cleavage domain can include an RNAse A-like fold (FIG. 11) and/or an RNAse H-like fold (FIG. 12).

RNAse A is a relatively small protein (124 residues, ~13.7 kDa). It can be characterized as a two-layer α+β protein that is folded in half, with a deep cleft for binding the RNA substrate. The first layer is composed of three alpha helices (residues 3-13, 24-34 and 50-60) from the N-terminal half of the protein. The second layer consists of three β-hairpins (residues 61-74, 79-104 and 105-124 from the C-terminal half) arranged in two β-sheets. The hairpins 61-74 and 105-124 form a four-stranded, antiparallel β-sheet that lays on helix 3 (residues 50-60). The longest β-hairpin 79-104 mates with a short β-strand (residues 42-45) to form a three-stranded, antiparallel β-sheet that lays on helix 2 (residues 24-34).

RNase A has four disulfide bonds in its native state: Cys26-Cys84, Cys58-110, Cys40-95 and Cys65-72. The first two (26-84 and 58-110) are essential for conformational folding; each joins an alpha helix of the first layer to a beta sheet of the second layer, forming a small hydrophobic core in its vicinity. The latter two disulfide bonds (40-95 and 65-72) are less essential for folding; either one can be reduced (but not both) without affecting the native structure under physiological conditions. These disulfide bonds connect loop segments and are relatively exposed to solvent. The 65-72 disulfide bond has an extraordinarily high propensity to form, significantly more than would be expected from its loop entropy, both as a peptide and in the full-length protein. This suggests that the 61-74 β-hairpin has a high propensity to fold conformationally. The active site is lined by His 119, Lys 66, Lys 41, His 12 and His 12 (PDB ID 2aas).

The RNase H domain is responsible for hydrolysis of the RNA portion of RNA-DNA hybrids, and this activity requires the presence of divalent cations ($Mg^{2+}$ or $Mn^{2+}$) that bind its active site. This domain is a part of a large family of homologous RNase H enzymes of which the RNase HI protein from *Escherichia coli* is the best characterized Secondary structure predictions for the enzymes from *E. coli*, yeast, human liver and diverse retroviruses (such as Rous sarcoma virus and the Foamy viruses) supported, in every case, the five beta-strands (1 to 5) and four or five alpha-helices (A, B/C, D, E) that have been identified by crystallography in the RNase H domain of human immunodeficiency virus 1 (HIV-1) reverse transcriptase and in *E. coli* RNase H.

In some embodiments of the RNA endonuclease of this invention, the RNA binding domain can be at the amino terminus of the endonuclease and the cleavage domain can be at the carboxy terminus of the endonuclease. In this orientation, sequence specific cleavage can be achieved. In other embodiments, the cleavage domain can be at the amino terminus of the endonuclease and the RNA binding domain can be at the carboxy terminus of the endonuclease. In this orientation, nonspecific cleavage of RNA can be achieved (see FIG. 1, Panels B and C and Examples section below).

In some embodiments of this invention, the RNA endonuclease can comprise, consist of, or consist essentially the following amino acid sequences, designated ASRE(WT), ASRE(6-2/7-2), ASRE(6-2/7-2/1-1), ASRE(531), ASRE (87621), ASRE(LacZ), ASRE(3-2) and mitoASRE(ND5), which are provided as nonlimiting examples of the ESRAs of this invention, as it is readily apparent to the skilled artisan that numerous other ESRAs can be designed according to the teachings of this invention to target any RNA sequence for cleavage. The nomenclature of the exemplary ASREs and their respective targets are provided in Table 5.

ASRE(6-2/7-2)

(SEQ ID NO: 6)

GRSRLLEDFRNNRYPNLQLREIAGHIMEFSQDQHGSRFIQLKLERATPAERQLVFNEIL

QAAYQLMVDVFGNYVIQKFFEFGSLEQKLALAERIRGHVLSLALQMYGCRVIQKAL

EFIPSDQQNEMVRELDGHVLKCVKDQNGNHVVQKCIECVQPQSLQFIIDAFKGQVFA

LSTHPYGCRVIQRILEHCLPDQTLPILEELHQHTEQLVQDQYGSYVIEHVLEHGRPED

KSKIVAEIRGNVLVLSQHKFANNVVQKCVTHASRTERAVLIDEVCTMNDGPHSALY

TMMKDQYANYVVQKMIDVAEPGQRKIVMHKIRPHIATLRKYTYGKHILAKLEKYY

```
MKNGVDLGVDTGNGSQMELEIRPLFLVPDTNGFIDHLASLARLLESRKYILVVPLIVI

NELDGLAKGQETDHRAGGYARVVQEKARKSIEFLEQRFESRDSCLRALTSRGNELES

IAFRSEDITGQLGNNDDLILSCCLHYCKDKAKDFMPASKEEPIRLLREVVLLTDDRNL

RVKALTRNVPVRDIPAFLTWAQVG

ASRE(WT)
                                                      (SEQ ID NO: 7)
GRSRLLEDFRNNRYPNLQLREIAGHIMEFSQDQHGSRFIQLKLERATPAERQLVFNEIL

QAAYQLMVDVFGNYVIQKFFEFGSLEQKLALAERIRGHVLSLALQMYGCRVIQKAL

EFIPSDQQNEMVRELDGHVLKCVKDQNGNHVVQKCIECVQPQSLQFIIDAFKGQVFA

LSTHPYGCRVIQRILEHCLPDQTLPILEELHQHTEQLVQDQYGNYVIQHVLEHGRPED

KSKIVAEIRGNVLVLSQHKFASNVVEKCVTHASRTERAVLIDEVCTMNDGPHSALYT

MMKDQYANYVVQKMIDVAEPGQRKIVMHKIRPHIATLRKYTYGKHELAKLEKYYM

KNGVDLGVDTGNGSQMELEIRPLFLVPDTNGFIDHLASLARLLESRKYILVVPLIVINE

LDGLAKGQETDHRAGGYARVVQEKARKSIEFLEQRFESRDSCLRALTSRGNELESIA

FRSEDITGQLGNNDDLILSCCLHYCKDKAKDFMPASKEEPIRLLREVVLLTDDRNLRV

KALTRNVPVRDIPAFLTWAQVG

ASRE(6-2/7-2/14)
                                                      (SEQ ID NO: 8)
GRSRLLEDFRNNRYPNLQLREIAGHIMEFSQDQHGSRFIELKLERATPAERQLVFNEIL

QAAYQLMVDVFGNYVIQKFFEFGSLEQKLALAERIRGHVLSLALQMYGCRVIQKAL

EFIPSDQQNEMVRELDGHVLKCVKDQNGNHVVQKCIECVQPQSLQFIIDAFKGQVFA

LSTHPYGCRVIQRILEHCLPDQTLPILEELHQHTEQLVQDQYGSYVIEHVLEHGRPED

KSKIVAEIRGNVLVLSQHKFANNVVQKCVTHASRTERAVLIDEVCTMNDGPHSALY

TMMKDQYANYVVQKMIDVAEPGQRKIVMHKIRPHIATLRKYTYGKHILAKLEKYY

MKNGVDLGVDTGNGSQMELEIRPLFLVPDTNGFIDHLASLARLLESRKYILVVPLIVI

NELDGLAKGQETDITRAGGYARVVQEKARKSIEFLEQRFESRDSCLRALTSRGNELES

IAFRSEDITGQLGNNDDLILSCCLHYCKDKAKDFMPASKEEPIRLLREVVLLTDDRNL

RVKALTRNVPVRDIPAFLTWAQVG

ASRE(5-3-1)
                                                      (SEQ ID NO: 9)
GRSRLLEDFRNNRYPNLQLREIAGHIMEFSQDQHGSRFIELKLERATPAERQLVFNEIL

QAAYQLMVDVFGNYVIQKFFEFGSLEQKLALAERIRGHVLSLALQMYGSRVIEKALE

FIPSDQQNEMVRELDGHVLKCVKDQNGNHVVQKCIECVQPQSLQFIIDAFKGQVFAL

STHPYGSRVIERILEHCLPDQTLPILEELHQHTEQLVQDQYGNYVIQHVLEHGRPEDK

SKIVAEIRGNVLVLSQHKFASNVVEKCVTHASRTERAVLIDEVCTMNDGPHSALYTM

MKDQYANYVVQKMIDVAEPGQRKIVMHKIRPHIATLRKYTYGKHILAKLEKYYMK

NGVDLGVDTGNGSQMELEIRPLFLVPDTNGFIDHLASLARLLESRKYILVVPLIVINEL

DGLAKGQETDHRAGGYARVVQEKARKSIEFLEQRFESRDSCLRALTSRGNELESIAF

RSEDITGQLGNNDDLILSCCLHYCKDKAKDFMPASKEEPIRLLREVVLLTDDRNLRV

KALTRNVPVRDIPAFLTWAQVG

ASRE(87621)
                                                      (SEQ ID NO: 10)
GRSRLLEDFRNNRYPNLQLREIAGHIMEFSQDQHGSRFIELKLERATPAERQLVFNEIL

QAAYQLMVDVFGCRVIQKFFEFGSLEQKLALAERIRGHVLSLALQMYGCRVIQKAL

EFIPSDQQNEMVRELDGHVLKCVKDQNGNHVVQKCIECVQPQSLQFIIDAFKGQVFA
```

LSTHPYGCRVIQRILEHCLPDQTLPILEELHQTEQLVQDQYGSYVIEHVLEHGRPED

KSKIVAEIRGNVLVLSQHKFANNVVQKCVTHASRTERAVLIDEVCTMNDGPHSALY

TMMKDQYASYVVEKMIDVAEPGQRKIVMHKIRPHIATLRKYTYGKHILAKLEKYY

MKNGVDLG<u>VDTGNGS</u>QMELEIRPLFLVPDTNGFIDHLASLARLLESRKYILVVPLIVI

NELDGLAKGQETDHRAGGYARVVQEKARKSIEFLEQRFESRDSCLRALTSRGNELES

IAFRSEDITGQLGNNDDLILSCCLHYCKDKAKDFMPASKEEPIRLLREVVLLTDDRNL

RVKALTRNVPVRDIPAFLTWAQVG

ASRE(LacZ) (SEQ ID NO: 11)
GRSRLLEDFRNNRYPNLQLREIAGHIMEFSQDQHGSRFIQLKLERATPAERQLVFNEIL

QAAYQLMVDVFGCRVIQKFFEFGSLEQKLALAERIRGHVLSLALQMYGSRVIEKALE

FIPSDQQNEMVRELDGHVLKCVKDQNGNHVVQKCIECVQPQSLQFIIDAFKGQVFAL

STHPYGCRVIQRILEHCLPDQTLPILEELHQTEQLVQDQYGSYVIEHVLEHGRPEDK

SKIVAEIRGNVLVLSQHKFASNVVEKCVTHASRTERAVLIDEVCTMNDGPHSALYTM

MKDQYANYVVQKMIDVAEPGQRKIVMHKIRPHIATLRKYTYGKHILAKLEKYYMK

NGVDLG<u>VDTGNGS</u>QMELEIRPLFLVPDTNGFIDHLASLARLLESRKYILVVPLIVINEL

DGLAKGQETDHRAGGYARVVQEKARKSIEFLEQRFESRDSCLRALTSRGNELESIAF

RSEDITGQLGNNDDLILSCCLHYCKDKAKDFMPASKEEPIRLLREVVLLTDDRNLRV

KALTRNVPVRDIPAFLTWAQVG

ASRE (3-2) (SEQ ID NO: 12)
GRSRLLEDFRNNRYPNLQLREIAGHIMEFSQDQHGSRFIQLKLERATPAERQLVFNEIL

QAAYQLMVDVFGNYVIQKFFEFGSLEQKLALAERIRGHVLSLALQMYGSRVIEKALE

FIPSDQQNEMVRELDGHVLKCVKDQNGNHVVQKCIECVQPQSLQFIIDAFKGQVFAL

STHPYGCRVIQRILEHCLPDQTLPILEELHQTEQLVQDQYGNYVIQHVLEHGRPEDK

SKIVAEIRGNVLVLSQHKFASNVVEKCVTHASRTERAVLIDEVCTMNDGPHSALYTM

MKDQYANYVVQKMIDVAEPGQRKIVMHKIRPHIATLRKYTYGKHILAKLEKYYMK

NGVDLG<u>VDTGNGS</u>QMELEIRPLFLVPDTNGFIDHLASLARLLESRKYILVVPLIVINEL

DGLAKGQETDHRAGGYARVVQEKARKSIEFLEQRFESRDSCLRALTSRGNELESIAF

RSEDITGQLGNNDDLILSCCLHYCKDKAKDFMPASKEEPIRLLREVVLLTDDRNLRV

KALTRNVPVRDIPAFLTWAQVG mitoASRE(ND5) (SEQ ID NO: 13)
MLFNLRILLNNAAFRNGHNFMVRNFRCGQPLQNKVQDYKDDDDKEFGRSRLLEDF

RNNRYPNLQLREIAGHIMEFSQDQHGSRFIELKLERATPAERQLVFNEILQAAYQLM

VDVFGNYVIQKFFEFGSLEQKLALAERIRGHVLSLALQMYGSRVIEKALEFIPSDQQN

EMVRELDGHVLKCVKDQNGNHVVQKCIECVQPQSLQFIIDAFKGQVFALSTHPYGC

RVIQRILEHCLPDQTLPILEELHQTEQLVQDQYGNYVIQHVLEHGRPEDKSKIVAEIR

GNVLVLSQHKFANNVVQKCVTHASRTERAVLIDEVCTMNDGPHSALYTMMKDQY

ANYVVQKMIDVAEPGQRKIVMHKIRPHIATLRKYTYGKHILAKLEKYYMKNGVDLG

<u>VDTGNGS</u>QMELEIRPLFLVPDTNGFIDHLASLARLLESRKYILVVPLIVINELDGLAKG

QETDHRAGGYARVVQEKARKSIEFLEQRFESRDSCLRALTSRGNELESIAFRSEDITG

QLGNNDDLILSCCLHYCKDKAKDFMPASKEEPIRLLREVVLLTDDRNLRVKALTRNV

PVRDIPAFLTWAQVG

ASREs with mutations and used as controls in the studies described herein are provided below.

ASRE(6-2/7-2) with D→A mutation
(SEQ ID NO: 14)
GRSRLLEDFRNNRYPNLQLREIAGHIMEFSQDQHGSRFIQLKLERATPAERQLVFNEIL

QAAYQLMVDVFGNYVIQKFFEFGSLEQKLALAERIRGHVLSLALQMYGCRVIQKAL

EFIPSDQQNEMVRELDGHVLKCVKDQNGNHVVQKCIECVQPQSLQFIIDAFKGQVFA

LSTHPYGCRVIQRILEHCLPDQTLPILEELHQHTEQLVQDQYGSYVIEHVLEHGRPED

KSKIVAEIRGNVLVLSQHKFANNVVQKCVTHASRTERAVLIDEVCTMNDGPHSALY

TMMKDQYANYVVQKMEDVAEPGQRKIVMHKIRPHIATLRKYTYGKHILAKLEKYY

MKNGVDLGVDTGNGSQMELEIRPLFLVPDTNGFIDHLASLARLLESRKYILVVPLIVI

NELDGLAKGQETDFIRAGGYARVVQEKARKSIEFLEQRFESRDSCLRALTSRGNELES

IAFRSEDITGQLGNNADLILSCCLHYCKDKAKDFMPASKEEPIRLLREVVLLTDDRNL

RVKALTRNVPVRDIPAFLTWAQVG

ASRE(LacZ) with D→A mutation
(SEQ ID NO: 15)
GRSRLLEDFRNNRYPNLQLREIAGHIMEFSQDQHGSRFIQLKLERATPAERQLVFNEIL

QAAYQLMVDVFGCRVIQKFFEFGSLEQKLALAERIRGHVLSLALQMYGSRVIEKALE

FIPSDQQNEMVRELDGHVLKCVKDQNGNHVVQKCIECVQPQSLQFIIDAFKGQVFAL

STHPYGCRVIQRILEHCLPDQTLPILEELHQHTEQLVQDQYGSYVIEHVLEHGRPEDK

SKIVAEIRGNVLVLSQHKFASNVVEKCVTHASRTERAVLIDEVCTMNDGPHSALYTM

MKDQYANYVVQKMIDVAEPGQRKIVMHKIRPHIATLRKYTYGKHILAKLEKYYMK

NGVDLGVDTGNGSQMELEIRPLFLVPDTNGFIDHLASLARLLESRKYILVVPLIVINEL

DGLAKGQETDEMAGGYARVVQEKARKSIEFLEQRFESRDSCLRALTSRGNELESIAF

RSEDITGQLGNNADLILSCCLHYCKDKAKDFMPASKEEPIRLLREVVLLTDDRNLRV

KALTRNVPVRDIPAFLTWAQVG mitoASRE(ND5) with D→A mutation
(SEQ ID NO: 16)
MLFNLRILLNNAAFRNGHNFMVRNFRCGQPLQNKVQDYKDDDDKEFGRSRLLEDF

RNNRYPNLQLREIAGHIIVIEFSQDQHGSRFIELKLERATPAERQLVFNEILQAAYQLM

VDVFGNYVIQKFFEFGSLEQKLALAERIRGHVLSLALQMYGSRVIEKALEFIPSDQQN

EMVRELDGHVLKCVKDQNGNHVVQKCIECVQPQSLQFIIDAFKGQVFALSTHPYGC

RVIQRILEHCLPDQTLPILEELHQHTEQLVQDQYGNYVIQHVLEHGRPEDKSKIVAEIR

GNVLVLSQHKFANNVVQKCVTHASRTERAVLIDEVCTMNDGPHSALYTMMKDQY

ANYVVQKMIDVAEPGQRKIVMHKIRPHIATLRKYTYGKHILAKLEKYYMKNGVDLG

VDTGNGSQMELEIRPLFLVPDTNGFIDHLASLARLLESRKYILVVPLIVINELDGLAKG

QETDBRAGGYARVVQEKARKSIEFLEQRFESRDSCLRALTSRGNELESIAFRSEDITG

QLGNNADLILSCCLHYCKDKAKDFMPASKEEPIRLLREVVLLTDDRNLRVKALTRNV

PVRDIPAFLTWAQVG

It would be well understood by the ordinary artisan that the RNA endonucleases of this invention can be employed in various methods, both in vitro and in vivo. Thus, in one embodiment, the present invention provides a method of detecting a target RNA in a sample, comprising: a) contacting the sample with an RNA endonuclease of this invention under conditions whereby cleavage of RNA occurs if the target RNA is present in the sample and wherein the RNA binding domain of the RNA endonuclease is modified to bind the target RNA; and b) detecting a cleavage product of the target RNA, thereby detecting the target RNA in the sample. As a nonlimiting example, the RNA endonuclease of this invention can function at about pH 7.5 (e.g., in a range of about pH 7.0 to about pH 8.0) in the presence of divalent metal cation. Activity is observed in the presence of manganese, magnesium and cobalt, with enzyme activity in the order of $Mn^{2+}>Mg^{2+}, >Co^{2+}$. The cleavage product can be visualized on urea-polyacrylamide or denatured formaldehyde agarose gels by staining with ethidium bromide or by SYBR green dyes. The RNA digestion product can also be detected by radioactive methods as well as non-radioactive methods, including, e.g., DIG and cyanine dye labeled probes.

In addition, the present invention provides a method of cleaving a target mRNA in a sample, comprising contacting the sample with the RNA endonuclease of this invention under conditions whereby cleavage of the target mRNA occurs and wherein the RNA binding domain of the RNA endonuclease is modified to bind the target mRNA, thereby cleaving the target mRNA in the sample.

In yet further embodiments, the present invention provides a method of cleaving a target mRNA in a cell, comprising introducing into the cell the RNA endonuclease of this invention, wherein the RNA binding domain of the RNA endonuclease is modified to bind the target mRNA, under conditions whereby cleavage of the target mRNA occur, thereby cleaving the target mRNA in the cell. The amount of cleavage of the target mRNA can be, for example, 1%, 2%, 3%, 5%, 10%, 15%, 20%, 25%, 30%, 40%, 50%, 60%, 70%, 80%, 90% 95%, 98% or 100% as compared with a suitable control.

As nonlimiting examples, the following methods can be used to introduce expression vectors that encode ASRE in various cell types:
1. A nucleic acid vector (e.g., a plasmid vector) encoding the RNA endonuclease can be delivered directly to bacterial cells or cultured cells (e g, mammalian cells) by electroporation.
2. A nucleic acid vector (e.g., a plasmid vector) encoding the RNA endonuclease can be delivered directly to bacterial cells by chemical transformation.
3. A viral vector (e.g., a retroviral vector, adenoviral vector, an adeno associated viral vector, an alphavirus vector, a vaccinia viral vector, a herpesviral vector, etc., as are known in the art) comprising a nucleotide sequence encoding the RNA endonuclease can be used to deliver the RNA endonuclease to cells (e.g., mammalian cells).
4. A baculovirus expression system can be used to deliver the RNA endonuclease to insect cells.
5. *Agrobacterium* mediated delivery can be employed in plants.
6. Lipid mediated delivery (e.g., lipofectamine, oligofectamine) can also be employed for mammalian cells.

In some embodiments, the RNA endonuclease of this invention can be directly introduced in various cell types using membrane penetrating peptide (aka, cell penetrating peptide). This can involve fusing the RNA endonuclease with the membrane penetrating peptide.

In various embodiments, the nucleotide sequence encoding the RNA endonuclease of this invention can be present in a cell transiently and/or can be stably integrated into the genome of the cell and/or the genome of the cell. The nucleotide sequence can also be stably expressed in the cell even without being integrated into the genome, via a plasmid or other nucleic acid construct as would be well known in the art.

In some embodiments, a systemic delivery of RNA endonuclease expression vectors into animals can be achieved by nanoparticles or viral vectors such as those commonly used in gene therapy and as are well known in the art.

The present invention provides a nucleic acid molecule comprising a nucleotide sequence encoding an RNA endonuclease of this invention, as well as a nucleic acid construct (e.g., vector, plasmid, etc. comprising such a nucleic acid molecule and a cell comprising such a nucleic acid molecule and/or nucleic acid construct. A cell comprising a nucleic acid molecule, nucleic acid construct, vector and/or polypeptide of this invention is also provided herein. A composition comprising such a cell, nucleic acid molecule, nucleic acid construct, vector and/or polypeptide of this invention in a carrier, such as a pharmaceutically acceptable carrier is further provided herein.

Also provided herein is a method of inhibiting (e.g., silencing) expression of a target gene in a cell, comprising introducing into the cell the RNA endonuclease of this invention, wherein the RNA binding domain of the RNA endonuclease is modified to bind mRNA encoding a gene product of the target gene, under conditions whereby cleavage of the mRNA occurs, thereby inhibiting (either partially or totally) expression of the target gene in the cell. Expression of the target gene can be inhibited, for example, by 1%, 2%, 3%, 5%, 10%, 15%, 20%, 25%, 30%, 40%, 50%, 60%, 70%, 80%, 90% 95%, 98% or 100% as compared with a suitable control.

In some embodiments of the methods of inhibiting gene expression as described herein, the cell can be a bacterium (e.g., a pathogenic strain of a bacterium) or the cell can be in an organism, such as a parasite.

Nonlimiting examples of a bacterium of this invention include *Escherichia coli, Bacillus anthracis, Bordatella pertussis, Borrelia burgdorferi, Brucella canis, Brucella melitensis, Brucella suis, Chlamydia pneumoniae, Chlamydia trachomatis, Clostridium botulinum, Clostridium difficile, Pseudomembranous colitis, Clostridium perfringens, Enterococcus faecalis, Enterococcus faecium, Legionella pneumophila, Neisseria gonorrhoea* and *Yersinia pestis*.

Nonlimiting examples of a parasite of this invention include *Plasmodium falciparum, Toxoplasma gondii, Leishmania donovan* and *Trypanosoma cruzi*.

The present invention further provides a method of cleaving a target mRNA in a mitochondrion in a cell, comprising introducing into the cell the RNA endonuclease of this invention, wherein the RNA binding domain of the RNA endonuclease is modified to bind the target mRNA in the mitochondrion and wherein the RNA endonuclease comprises a mitochondrial targeting signal sequence, under conditions whereby cleavage of the target mRNA in the mitochondrion occurs, thereby cleaving the target mRNA in the mitochondrion in the cell. This method can also be employed to target an RNA in the nucleus of a cell, as well as an RNA in a chloroplast of a plant, according to the methods described herein.

Additionally provided herein is a method of inhibiting expression of a target mitochondrial gene in a cell, comprising introducing into the cell the RNA endonuclease of this invention, wherein the RNA binding domain of the RNA endonuclease is modified to bind mRNA encoding a gene product of the target mitochondrial gene and wherein the RNA endonuclease comprises a mitochondrial targeting signal sequence, under conditions whereby cleavage of the target mRNA in the mitochondrion occurs, thereby inhibiting expression of the target mitochondrial gene in the cell. Nonlimiting examples of mitochondrial genes that can be targeted according to methods of this invention include NADH dehydrogenase (complex 1) genes (e.g., MN-ND1, MT-ND2, MT-ND3, MT-ND4, MT-ND4L, MT-ND5, MY-ND6), Coenzyme Q-cytochrome c reductase/Cytochrome b (complex III) (e.g., MT-CYB), cytochrome c oxidase (complex IV) (e.g., MT-COL MT-CO2, MT-CO3) and ATP synthase (e.g., MT-ATP6, MT-ATPS). The RNA endonuclease can be introduced into the cell via a viral vector comprising a nucleotide sequence encoding the RNA endonuclease and in some embodiments, the viral vector can be an adeno associated viral vector. Furthermore the cell of these methods can be in an organism, which can be a mammal and in some embodiments, is a human subject.

Additional embodiments of this invention include a method of treating dystrophia myotonica (DM) in a subject, comprising administering to the subject an effective amount of the RNA endonuclease of this invention, wherein the RNA binding domain of the RNA endonuclease is modified to bind mRNA encoding (CUG)n repeats in the 3' UTR of DMPK to treat DM1 and/or mRNA encoding (CCUG)n repeats in intron 1 of the ZNF9 gene to treat DM2 and wherein the RNA endonuclease comprises a nuclear targeting signal sequence, thereby treating DM in the subject. Such a method can be expanded to encompass treating various trinucleotide repeat disorders (e.g., Alzheimer's disease) as are known in the art, by employing the teachings of this invention.

The methods of the present invention can also be employed for treating infection by an RNA virus in a subject according to the teachings set forth herein.

Also as used herein, the terms "treat," "treating" or "treatment" refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, prevention or delay of the onset of the disease, disorder, or illness, and/or change in clinical parameters of the condition, disorder, disease or illness, etc., as would be well known in the art.

As used herein "effective response" or "responding effectively" means a positive or beneficial response to a particular treatment in contrast to a "lack of an effective response" which can be an ineffectual, negative or detrimental response as well as the lack of a positive or beneficial response. An effective response or lack of effective response (i.e., ineffective response) is detected by evaluation, according to known protocols, of various immune functions (e.g., cell-mediated immunity, humoral immune response, etc.) and pharmacological and biological functions as would be known in the art.

"Effective amount" refers to an amount of a compound or composition of this invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation. (See, for example, Remington, *The Science And Practice of Pharmacy* (20th ed. 2000)).

An exemplary dosage range for the administration to a subject of a nucleic acid molecule comprising a nucleotide sequence of this invention in the form of a viral vector can be, for example, from about $5 \times 10^{12}$ viral genomes per kg to about $5 \times 10^{15}$ viral genomes per kg. One of skill in the art would be able to determine the optimal dose for a given subject and a given condition.

A method is also provided herein of detecting an RNA virus in a sample, comprising: a) contacting the sample with the RNA endonuclease this invention under conditions whereby cleavage of RNA occurs if RNA of the RNA virus is present in the sample and wherein the RNA binding domain of the RNA endonuclease is modified to bind a target RNA of the RNA virus; and b) detecting a cleavage product of the target RNA, thereby detecting the RNA virus in the sample.

Additionally provided is a method of diagnosing infection by an RNA virus in a subject, comprising: a) contacting the sample from the subject with the RNA endonuclease of this invention under conditions whereby cleavage of RNA occurs if viral RNA (e.g., of the RNA virus) is present in the sample and wherein the RNA binding domain of the RNA endonuclease is modified to bind target viral RNA; and b) detecting a cleavage product of the target viral RNA, thereby detecting viral RNA in the sample and thereby diagnosing infection by an RNA virus in the subject. Nonlimiting examples of an RNA virus include retroviruses, alphaviruses, flaviruses, etc., as are well known in the art.

Furthermore, the present invention provides a method of identifying a strain of an RNA virus (e.g., a particular strain of an RNA virus) in a sample, comprising: a) contacting the sample with the RNA endonuclease of this invention under conditions whereby cleavage of RNA occurs if RNA of the strain of the RNA virus is present in the sample and wherein the RNA binding domain of the RNA endonuclease is modified to bind a target RNA specific to the strain of the RNA virus; and b) detecting a cleavage product of the target RNA, thereby identifying the strain of the RNA virus in the sample.

Various methods described herein can be used, for example, to probe an RNA structure (e.g., characterize an unknown or partially identified RNA structure), as well as to detect and/or identify an RNA virus in a sample by detecting an RNA cleavage pattern that detects and/or identifies the RNA virus. The design of such methods, employing the ASREs of this invention, would be well known to those of skill in the art. As one example, the cleavage will provide a unique tool to fractionate single stranded RNA into small pieces prior to deep sequencing of RNA. The ASRE-mediated cleavage of this invention can also be used, for example, to distinguish single stranded RNA from double stranded RNA, and/or be used to probe the structure or RNA.

EXAMPLES

Example 1

The present invention provides a protein "restriction enzyme" of RNAs, which specifically recognizes an 8-nt RNA sequence and makes a single cleavage in the target. As the data shown below demonstrate, these enzymes efficiently and specifically cleave diverse RNA targets not only in vitro, but also in bacterial cells in mitochondria—any cells these data-reporter protein with target sequence. Mitochondrial target is endogenous gene. Thus, this invention provides new methods for in vitro detection or manipulation of RNA (e.g. generating an RNA digestion map) and for modulating (e.g., inhibiting) gene expression in organisms where interfering RNA (RNAi) machinery is not available.

Construction and Expression of ASREs

The PUF domain of human Pum1 (residue 828-1176) (SwissProt Accession No. Q14671 Pum1-human; incorporated by reference herein) and the PIN domain of human Smg6 (residue 1238-1421) (SwissProt Accession No. Q86US8; incorporated by reference herein) were amplified with PCR and joined to sequences encoding different peptide linkers designed according to amino acid propensity of known protein linkers. The resulting fusion proteins were cloned in expression vector pT7HTb or pET43.1b, both of which encode an N-terminal Hisx6 tag; the latter also included a soluble Nus tag that can be removed by enterokinase digestion. To produce recombinant ASREs, the expression constructs were introduced into BL21(DE3) E. coli cells and expression was induced with 0.3 mM IPTG. The bacterial cells were disrupted by sonication in lysis buffer and the recombinant proteins were purified with a Ni-NTA column (His-Gravy Trap, GE Health Care). Protein purity was assessed with SDS-PAGE and the proteins were further concentrated in 20 mM HEPES pH 7.0, 150 mM NaCl, 1 mM DTT, and stored at −20° C. in aliquots supplemented with 50% glycerol. Preparations were stable for 2-3 months under these conditions.

Nomenclature of ASREs

The ASREs were named according to the identity of their PUF domains, since most ASREs all had the same PIN domain. Each PUF domain recognizes its 8-nt target sequence in an anti-parallel fashion, with the first repeat recognizing the $8^{th}$ base and so on.

WT PUF repeat: C terminus-8 7 6 5 4 3 2 1-N terminus

RNA target (5' to 3' ends): 5'-U G U A U A U A-3'

The targets of a modified PUF were named in a reverse order (from C to N terminus) with the number of the mutated PUF repeat and the base recognized by the corresponding repeat. For example, RNA target 7u6g represents UugAUAUA sequence, with the mutated base shown in lower case. The PUF domains were named by the mutated repeats and the number of the mutated amino acid in each repeat. For example, ASRE(6-2/7-2) has two mutated amino acids in each of the $6^{th}$ and $7^{th}$ repeat, causing it to recognize the 7u6g RNA. See Table 5 for more examples.

Substrate Preparation and Digestion Reaction

DNA fragments containing single PUF domain binding sites were amplified by PCR and inserted between the HindIII and XbaI sites of pcDNA3. The resulting plasmids were linearized by overnight XbaI digestion, purified, and used as templates in an in vitro transcription reaction with T7 RNA polymerase (NEB). The reaction mixtures were treated further with RNase-free DNAse I (Promega) to remove template and the RNA products were purified. All ASRE digestion reactions were performed in buffers containing 20 mM HEPES (pH 8.0), 150 mM NaCl, and 10% glycerol supplemented with respective divalent metal ions. Reactions were carried out at 37° C. for various times, and stopped by adding Ficoll-UREA RNA-loading buffer and heating at 70° C. The resulting products were separated on 10% urea-PAGE gels, stained with ethidium bromide, scanned on a Typhoon Trio+ scanner, and quantified with Image-Quant software (GE Health Care).

Determination of the RNA Cleavage Site by DSS-RACE

Figure 17:
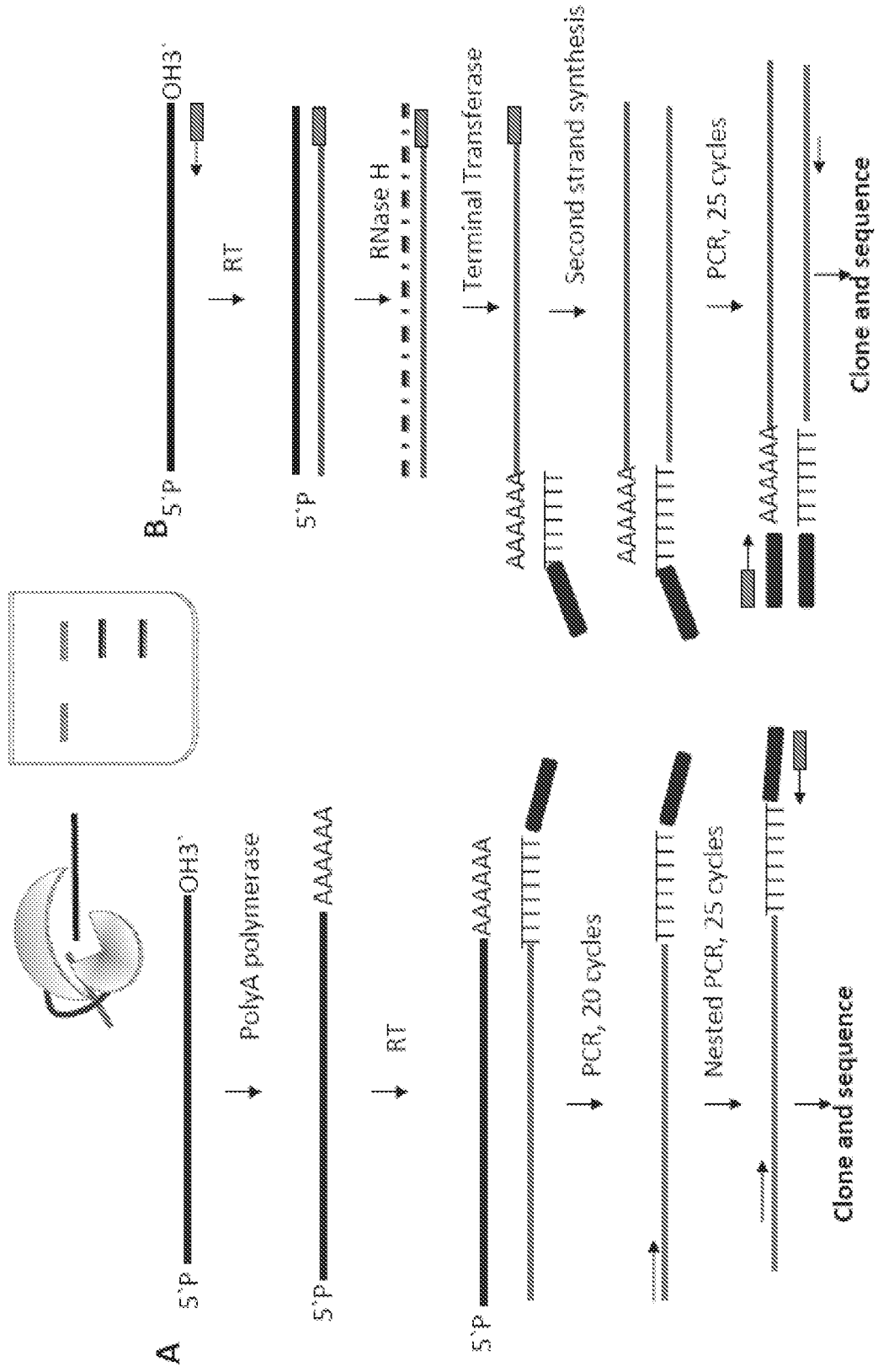
FIG. 17. Schematic diagram of DSS-RACE. Top panel shows digestion of RNA substrate by ASRE-the 5' portion of the product is shown in grey and the 3' end in black. The cut site is either mapped by 3'RACE (Panel A) or 5'RACE (Panel B). A number of clones (~40) were sequenced for determination of cleavage sites.

To determine the cleavage sites of ASREs, the 5' and 3' digestion products were extracted from denaturing urea-PAGE gels, and RACE was used to map both ends of the cleavage products. To map the 3' end of the 5' fragment, polyA polymerase was used to add a 10-30 nt poly-A tail at the end of the 5' fragment, and the resulting RNA was reverse transcribed with a poly-T containing primer. The resulting cDNA was amplified by nested PCR, cloned in pcDNA3, and sequenced (FIG. 17, Panel A). To map the 5' end of the 3' cleavage fragment (FIG. 17, Panel B), the gel extracted RNA was first reverse transcribed with a specific primer. The resulting cDNA was purified and elongated with terminal transferase in the presence of dATP. Second strand synthesis was carried out using a poly-T-containing primer and Klenow fragment (NEB). The resulting product was PCR amplified, cloned and sequenced.

Gene Silencing by ASRE in Bacterial Cells

E coli BL21(DE3) was transformed with either empty vector pET43.1b, or the vector encoding ASRE(lacZ) or control ASREs not targeting lacZ mRNA. Multiple colonies were selected in each sample to circumvent clonal variation. Protein expression of each clone was induced with 0.3 mM IPTG for 6 h at 37° C. To measure β-galactosidase activity, cells were lysed with two rounds of sonication in cold buffer and the standard β-galactosidase activity assay for all lysates was carried out in a 96 well plate format as described previously[27]. Total protein concentrations of each sample were measured using the Bradford method (Pierce) to ensure that equal amounts of total protein were used in the activity assays.

To measure mRNA levels, total cellular RNA was purified with a Qiagen RNeasy kit and treated with DNase I. Equal amounts of total RNA (300-500 ng) from each sample were used to make first strand cDNA by random priming (High capacity cDNA reverse transcription kit from Applied Biosystem), and the lacZ mRNA was measured with q-PCR using a SYBR green kit of Applied Biosystem Immunoblotting with a monoclonal 3-galactosidase antibody (Santa Cruz cat # sc-56394) was used to measure β-galactosidase protein levels.

Construction and Expression of ASREs

The PUF domain of human Pum1 (residue 828-1176) (SwissProt Accession No. Q14671 Pum1-human; incorporated by reference herein) and the PIN domain of human Smg6 (residue 1238-1421) (SwissProt Accession No. Q86US8; incorporated by reference herein) were amplified with PCR primer pairs 1,2 and 3,4 (Table 4) using Roche Hi-fidelity Taq DNA polymerase. DNA fragments encoding the two domains were joined with sequences encoding different peptide linkers designed according to amino acid propensity of known protein linkers. To change the linker length, different forward primers of the PIN domain were used that contained extra sequences encoding the linkers at their 5' ends. The resultant products were cloned in expression vector pT7HTb or pET43.1b, both of which have an N-terminal 6×His tag that can be removed by enterokinase digestion. To produce recombinant ASRE, the expression constructs were introduced into BL21(DE3) E coli cells and grown overnight in liquid LB medium with appropriate antibiotics. The saturated culture was freshly inoculated in LB medium and protein expression was induced with 0.3 mM IPTG at an $OD_{600}$ of 0.4-0.6. Cells were grown at ambient temperature with shaking speed not exceeding 170 rpm overnight. The cells were then harvested and disrupted by sonication in lysis buffer (20 mM sodium phosphate pH 7.4, 500 mM NaCl, 20 mM imidazole, 1 mM 2-mercaptoethanol, 1 mM PMSF). Lysates were loaded onto a Ni-NTA column (His-Gravy Trap, GE Health Care) and washed with the same buffer. Elution was obtained with a linear step gradient of imidazole from 50-300 mM and protein purity was assessed by SDS-PAGE. Imidazole was removed using a Millipore Amicon ultra centrifugal concentrator. The proteins were further treated with TEV (Promega) or enterokinase (NEB) to remove the His-tag or Nus-tag as per manufacturer's instructions and the fragments containing His-tag were removed by Ni-NTA. Proteins were further concentrated in 20 mM HEPES pH 7.0, 150 mM NaCl, 1 mM DTT and stored at −20° C. in aliquots supplemented with 50% glycerol. Preparations were stable over 2-3 months at −20° C.

Design of Linker Using Linker Database

ASRE peptide linkers were designed according to amino acid propensity of known protein inter-domain linkers distinct from intra-domain loops. Residues Pro, Gly, Asp, Asn, His, Ser and Thr are preferred in intra-domain loop regions and, thus, were avoided. Thus, in some embodiments, a peptide linker of this invention can exclude Pro, Gly, Asp, Asn, His, Ser and/or Thr in any combination. A proline residue is highly likely in both loops and linkers; within loops, proline is usually involved in tight turns, whereas few proline turns are found in linkers. Most residues in known linkers adopt an α-helical structure, although a significant fraction of non-helical residues have a coil structure. Therefore linkers with slight helical propensity were chosen. The first two amino acids of the linkers came from the restriction site SalI used for construction of fusion proteins. A natural linker with known 3D structure was chosen from the linker database (fumarate reductase flavoprotein subunit; PDB 1q1aB_1, VDTGNWF, SEQ ID NO:17). The last two aromatic amino acids in the 12 Å linker were changed to glycine and serine (VDTGNGS, SEQ ID NO:18), thus changing the helical propensity to EECHHCC (see Table 2).

Substrate Preparation and Reaction Conditions

DNA fragments from plasmid pGZ3 containing various single PUF domain binding sites (25) were amplified with SmSubHF1/GUXbR1 primer pairs and cloned between HindIII and XbaI site of pcDNA3. The resulting plasmid DNA was linearized with overnight XbaI digestion and purified. The linearized DNA (0.2 µg) was used as template in a 50 µl in vitro transcription reaction containing T7 RNA polymerase (NEB) supplemented with 1 unit of Murine RNase inhibitor (NEB). The reactions were further treated with RNase free DNAse I (Promega) for 1 h at 37° C. and RNA products were isolated by ethanol precipitation.

All ASRE digestion reactions were performed in buffers containing 20 mM HEPES (pH 8.0), 150 mM NaCl, and 10% glycerol supplemented with respective divalent metal ions. A typical reaction contained 2 µg RNA substrate and 0.2-0.5 µg purified ASRE. Reactions were carried out at 37° C. for various times, and stopped by adding Ficoll-UREA RNA-loading buffer and heated at 70° C. The resulting products were separated on 10% UREA-PAGE gels, stained with ethidium bromide, scanned on Typhoon Trio+ scanner, and quantified with Image-Quant software (GE Health Care).

Kinetic Analysis

To measure the kinetic parameters of ASREs, various amounts of substrates (0.14 to 6 µM) were incubated with either 0.5 µg enzyme or buffer only (as undigested control) for 5 mM, and equal volumes of digested products and undigested controls were separated in adjacent lanes of a denaturing PAGE gel. After scanning each gel, the undigested RNA bands were first quantified to ensure that their intensities were directly proportional to the RNA loaded (FIG. 16), which was achieved by adjusting the volume of samples loaded for each concentration pair (thus to avoid saturation). Then substrates consumed at each input concentration were calculated using the relative ratio of remaining substrate to undigested controls. The resulting data were plotted with SigmaPlot (SYSTAT) and fitted to a Michaelis-Menten model using the enzyme kinetics module of SigmaPlot.

Determination of the RNA Cleavage Site by DSS RACE

To determine the cleavage sites of ASRE, the 5' and 3' digestion products were extracted from denaturing PAGE gels, and RACE (rapid amplification of cDNA ends) was used to map both ends of the cleavage products. To map the 3' end of the 5' cleavage fragment, a poly-A tail was first added to purified RNA by incubating 100-300 ng RNA with polyA polymerase (NEB) and 2 mM ATP for 30 min following manufacturer's instructions (FIG. 17, Panel A). An average of 10-30 nt was added at the end of the RNA. Products were subsequently used in the RT reaction with a poly-T containing primer (GUHIF1, Table 4), and the complementary DNA was used for nested PCR. The first PCR step involved SmSubHF1 and an anchor primer (GUHIF2), and the PCR product was again amplified using a nested primer (3'RACE BamF1) downstream of the transcription start site. The resulting product was cloned between the BamHI and HindIII sites in pcDNA3 and sequenced (FIG. 17, Panel A).

To map the 5' end of the 3' cleavage fragment (FIG. 17, Panel B), the gel extracted RNA (~75 nt) was reverse transcribed using a known reverse primer GuXbR1 Table 4). The complementary DNA product was further purified with ethanol precipitation, and elongated with terminal transferase (3 units) in a 50 µl reaction supplemented with dATP for 30 min at 37° C. according to the manufacturer's instructions. The reaction was stopped by heating at 80° C. for 20 min and further diluted in EB buffer (Qiagen) to 0.5 ml. Second strand synthesis was carried out using a poly-T containing primer (GUHIF1) and Klenow fragment (NEB). The resulting product was further PCR amplified using a 3' nested primer (GUnestedXbRl) and 5' anchor primer (GUHIF2) harboring XbaI and HindIII site. The resulting product was cloned in pcDNA3 and sequenced (FIG. 17, Panel B).

In Vivo Activity of ASRE

E coli BL21(DE3) was transformed with either empty vector pET43.1b or vector encoding ASRE(lacZ). E. coli was also transformed with ASRE(87621) to serve as non-specific control and with ASRE(lacZ) having a D1353A mutation as an inactive control. Multiple colonies were selected in each sample to circumvent clonal variation. Each clone was grown in liquid LB medium overnight, and the saturated culture was freshly inoculated (diluted 1:1000) in LB with an appropriate antibiotic and grown up to $OD_{600}$ of 0.25-0.3 for induction. Protein expression was induced with 0.3 mM IPTG, and 5 mM $Mn^{2+}$ was also added at this point. Bacterial cells were harvested 6 h after induction at 37° C. for the measurement of β-galactosidase activity. Two aliquots of each sample were snap frozen in an alcohol-dry ice mixture and stored at −80° C. for further analyses of RNA and protein levels.

To measure the β-galactosidase activity, the cells were lysed with two rounds of sonication in cold buffer (100 mM $KPO_4$ buffer pH 7.4, 2 mM 2-mercaptoethanol and 1 mM PMSF). Total protein concentrations of each sample were measured using the Bradford method (Pierce) to ensure that equal amounts of total protein were used in the activity assay. Standard β-galactosidase activity assays were performed for all samples in a 96 well plate format as described previously (27). Briefly, a total of 1-2 µg total protein was added in 300 ul assay reaction mixtures and incubated at 37° C. for 30 min, whereupon reactions were quenched by addition of $Na_2CO_3$ to 1 M. The amount of ONPG (ortho-Nitrophenyl-β-galactoside) hydrolysis was determined spectrophotometrically in a POLARstar Omega plate reader (BMG Labtech, GmBH, Germany), and activity units were calculated according to the formula: Miller units=1000×[($A_{420}$−(1.75×$A_{550}$))]/(T×V), where T is the time of the reaction before quenching with 1M $Na_2CO_3$ and V=volume of culture used in the assay. The units were normalized to total protein amount.

To measure RNA levels, frozen cells were thawed on ice and resuspended in 500 μl TE buffer (pH 7.9) with 1 mg/ml of lysozyme, and incubated at room temperature for 15 min. Two rounds of sonication were then used to lyse the cell membrane efficiently. Cell debris was pelleted by 5 min centrifugation at 15000 rpm in a microcentrifuge, and the supernatants were used for RNA purification with a Qiagen RNeasy mini kit. RNA eluted from the columns was treated with 2 U of DNase I at 37° C. for 30 min (Promega), followed by heat inactivation of DNase. For real time RT-PCR analyses, equal amounts of total RNA (300-500 ng) were used to make first strand cDNA by random priming (High capacity cDNA reverse transcription kit form Applied Biosystem cat. no. 4368814). Q-PCR was performed using lacZ specific primers (Table 4) and a SYBR green kit (Applied Biosystems), and the results were calibrated to the expression level of ftsZ using gene specific primers (FtsZF1, FtsZR1 in Table 4). The data analysis was performed using ABI-prism q-RT PCR software.

To determine the β-galactosidase protein level by immunoblotting, total bacterial protein was extracted by sonication in 100 mM $KPO_4$ buffer pH 7.4, 2 mM 2-mercaptoethanol and 1 mM PMSF. Protein concentrations were measured by Bradford assay (Pierce) and equal amounts of total protein were loaded in each well of SDS-PAGE gels. The blots were probed using a monoclonal β-galactosidase antibody (1:1000; Santa Cruz cat. no. sc-56394) and detected using ECL-Western Blot reagent (GE Heath Care). Blots were stripped using Restore Plus western blot stripping buffer (Pierce) and re-probed with anti-GroEL antibody (1:2000; Sigma cat. no. G6532) as loading control.

Design Principle of Artificial Sequence-Specific RNA Endonucleases (ASREs)

To engineer ASREs, a modular design was adopted by combining a target recognition domain and a catalytic domain. For the target recognition domain, the unique RNA recognition domain of PUF proteins (named for *Drosophila Pumilio* and *C. elegans* fem-3 binding factor)[11] was chosen. Although most sequence-specific RNA-binding proteins recognize their targets through RRM or K homology (KH) domains that bind to short RNA elements with moderate affinities, it is impractical to engineer an RNA recognition module using these domains due to their weak RNA binding affinity and the absence of a predictive RNA recognition code[12]. On the other hand, the RNA-binding domain of human *Pumilio*1 (PUF domain) contains eight repeats that recognize eight consecutive RNA bases, with each repeat recognizing a single base[13] (FIG. 1, Panel A, left). Moreover, two amino acid side chains in each PUF repeat recognize the Watson-Crick edge of the corresponding base and determine the specificity of that repeat[13,14]. Using this recognition code, a PUF domain can be designed to specifically bind most 8-mer RNA sequences[13,14].

For the RNA cleavage module, a small endonuclease domain with limited exonuclease activity was used. One good candidate is the PIN domain (PilT N-terminus) of SMG6, a key factor involved in nonsense-mediated decay (NMD). This domain has well-defined molecular architecture and requires only a divalent metal cation for sequence-independent RNA cleavage (FIG. 1, Panel A, right).

Joining the target recognition module and the RNA cleavage module by a short peptide linker flexible enough to give both domains easy access to RNA but rigid enough to prevent non-specific RNA cleavage was the next objective. To define the linker sequence and length, a rational design based on the amino acid propensity model of natural linkers in multi-domain proteins[15] was initiated. In addition, aromatic amino acids were excluded due to their potential to interact with base pairs by stacking, and proline was excluded because it can potentially form turns or cis-trans isomers that negatively affect domain independence. Based on these criteria, a hepta peptide linker (VDTGNGS; 12 Å, SEQ ID NO:18) was selected initially.

Using the selected target recognition domain, catalytic domain, and initial linker sequence, the architecture of this design was first tested by placing the PUF domain at the N-terminus and the PIN domain at the C-terminus and vice versa. An ASRE was constructed by fusing an N-terminal modified PUF(6-2/7-2) containing mutations N1043S/Q1047E in repeat 6 and S1079N/E1083Q in repeat 7 to specifically bind UugAUAUA (7u6g)[14] to a C-terminal wild type PIN or a mutated PIN (D1353A mutation in PIN active site). The recombinant ASREs (PUF-PIN fusion proteins) were expressed in *E. coli* and purified to homogeneity (FIG. 13, Panel A, lanes 2 and 3). As shown in FIG. 1, Panel B, incubation of the ASRE(6-2/7-2) with an in vitro transcribed RNA substrate (191-nt in length) containing a single 8-nt recognition site 7u6g led to the rapid cleavage of the substrate into two fragments (lane 2), whereas the mutated ASRE(6-2/7-2) containing an inactive PIN domain had no detectable activity (lane 3). These observations indicated that the cleavage was catalyzed by the PIN domain rather than contaminating nucleases. An inverted ASRE that contains N-terminal PIN and C-terminal PUF domains was also expressed and purified. However, when incubated with the same substrate under identical conditions, this enzyme caused nonspecific cleavage of RNA, resulting in total digestion of the entire RNA substrate (FIG. 1, Panel C). Therefore, the N-terminal PUF-C-terminal PIN orientation was chosen for the rest of this study.

Effect of ASRE Linker Length on its Activity

Studies were carried out to determine how different linkers affected the activities of ASRE. A suitable linker is important for the high catalytic activity of ASRE. A glycine or Gly/Ser rich linker may be too flexible and unstable and, thus, could act as an energetic, structural, or activity-interfering nuisance, especially when it is longer than necessary to connect two domains[16]. On the other hand, a short linker may generate a structural barrier that prevents simultaneous contact of the two domains with an RNA. A database of known linkers revealed that both short (less than 6 amino acids) and long linkers (more than 14 amino acids) are very rare in natural linkers and average linker length varies from 8-10 amino acids[15]. To optimize the ASRE linker length, a tri peptide (VDT; 7.3 Å), hepta peptide (VDTGNGS; 12 Å, SEQ ID NO:18) and do-deca peptide (VDRRMARDGLVH; 20.5 Å, SEQ ID NO:19) linker was designed and each was inserted between PUF(6-2/7-2) and wild type PIN. These peptides have mixed helical propensity and should provide limited flexibility to prevent non-native interactions between domains.

As shown in FIG. 2, Panel A, the purified ASRE with the tri-peptide linker had very low activity compared to the other two enzymes (lane 2). The enzymes had considerably higher activities with linker lengths of 7 aa or 12 aa (lanes 3 and 4). However, non-specific cleavage products were observed at longer incubation time with the 12-aa linker (FIG. 2, Panel A, lane 5). Thus the ASRE with hepta peptide linker was used in further studies described herein. Furthermore, the ASRE containing the heptapeptide linker completed RNA cleavage within two hours (FIG. 2, Panel B), and displayed strict pH selectivity with reduced reaction rate below pH 7.5 and no detectable cleavage at pH 6.0.

Sequence Specificity and the Ion Requirement of ASREs

Figure 14:
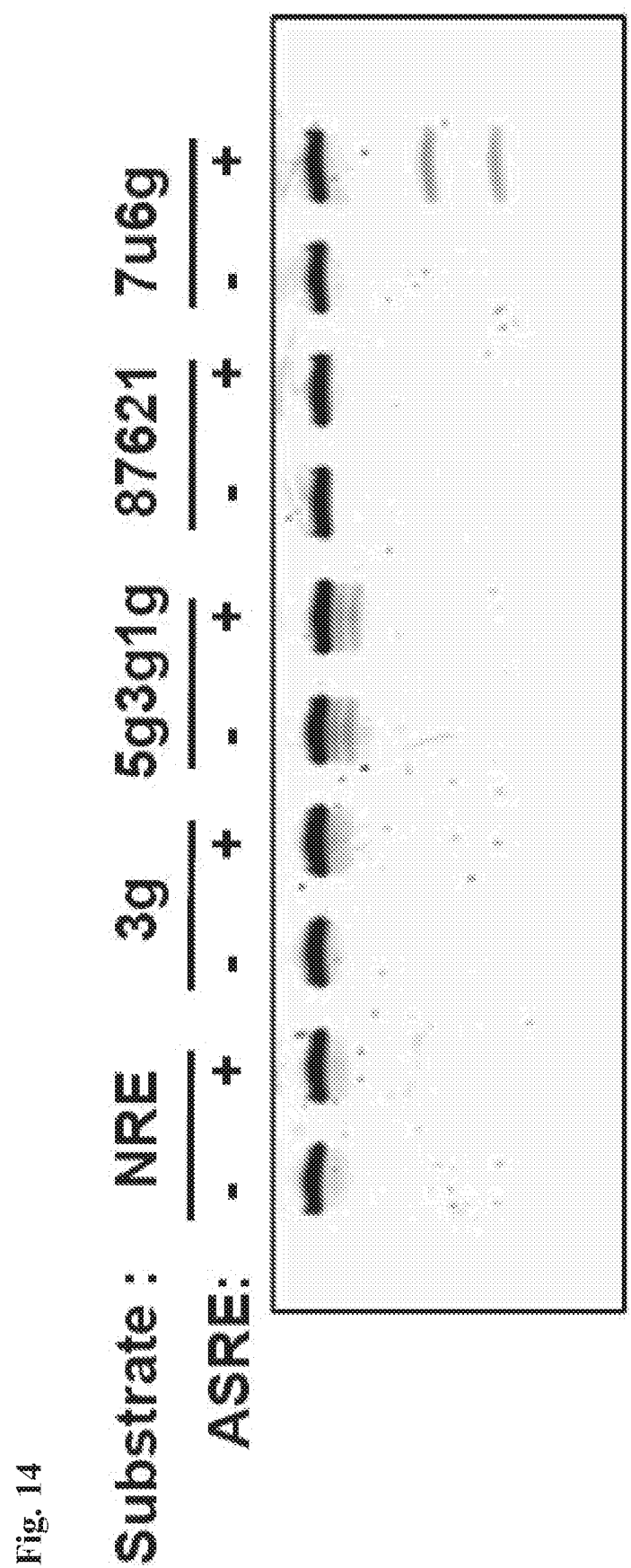
FIG. 14. Hi-fidelity cleavage of ASRE. ASRE(6-2/7-2) is used to test the activity in cleaving different substrates including NRE (UGUAUAUA), 3g (UGUAUgUA), 5g3g1g (UGUgUgUg), 87621 (gugAUAag, also named as 8g7u6g2a1g) and its cognate substrate, 7u6g in standard digestion assay. No digestion is obtained with non-specific substrates in the reaction conditions tested.

To confirm that the engineered ASREs mediate sequence specific RNA cleavage, an ASRE containing the wild type PUF domain that recognizes a different 8-nt target, the nanos response element (NRE: UGUAUAUA), was created. The NRE differs from the PUF(6-2/7-2) target by two nucleotides[14]. As shown in FIG. 2, Panel C, this ASRE(wt) cleaved only the substrate containing its cognate target NRE (lane 3) but not the closely related RNA 7u6g (lane 2). Conversely, the ASRE(6-2/7-2) specifically cleaved its cognate target (7u6g) but not the substrate containing NRE (FIG. 2, Panel C, lanes 6 and 5, respectively). In addition, the ASRE(6-2/7-2) failed to cleave other closely related RNAs, including UGUAUgUA (3g), UGUgUgUg (5g3g1g) and gugAUAag (8g7u6g2a1g, or 87621 in short) that vary by 3 or 6 nucleotides from the ASRE(6-2/7-2) substrate 7u6g (FIG. 14). These data indicated that the activities of ASREs are highly sequence specific.

The active site of the PIN domain is lined by three conserved aspartate residues (D1251, D1353, D1392) that coordinate one divalent metal cation to activate a water molecule for nucleophilic attack of the 3'-5' phosphodiester bonds[17,18]. To determine the metal ion preference of ASRE, the reaction was carried out in the presence of different divalent metal ions including $Mn^{2+}$, $Co^{2+}$, $Ca^{2+}$ and $Mg^{2+}$. Consistent with the metal ion selectivity of the wild-type PIN domain[17], optimal activity of ASRE was detected in the presence of $Mn^{2+}$ and suboptimal activity was detected in the presence of $Mg^{2+}$[17]. ASRE also had limited activity in presence of $Co^{2+}$ (FIG. 2, Panel D, lane 5), suggesting that the PIN domain may be able to use $Co^{2+}$ as a low activity substitute. In addition, an increase in the concentration of $Mn^{2+}$ led to higher ASRE RNA cleavage activity, as judged by the apparent rate constants calculated with a pseudo-first order reaction model (FIG. 2, Panel E).

Enzyme Kinetics of ASREs

The reactions catalyzed by ASREs in these assay conditions followed Michaelis-Menten-like kinetics. As shown in FIG. 3, Panels A and B, the initial cleavage rates in 5-minute reactions using different concentrations of cognate substrates were best fitted to a Michaelis-Menten model (a representative gel is shown in FIG. 15). Furthermore, the kinetic parameters of four related ASREs (Table 1) indicate that ASRE-catalyzed cleavage was fairly efficient ($k_{cat}/K_m$ in the $10^7$ $M^{-1}$ $min^{-1}$ range; this number is likely an underestimation as 100% of enzymes were assumed active). Most of the ASREs showed very little to no activity with non-cognate RNA substrates, with the exception of ASRE(671) toward non-cognate 7u6g RNA (UugAUAUA). This non-cognate activity, however, displayed more than a five-fold decrease in $V_{max}$ compared to ASRE(671)'s cognate substrate (UugAUAUg), which has a single base difference at the end of the 8-nt target. This non-cognate activity may be explained by the fact that the evolutionary plasticity of PUF domain allows recognition of suboptimal target sequences.

Figure 16:
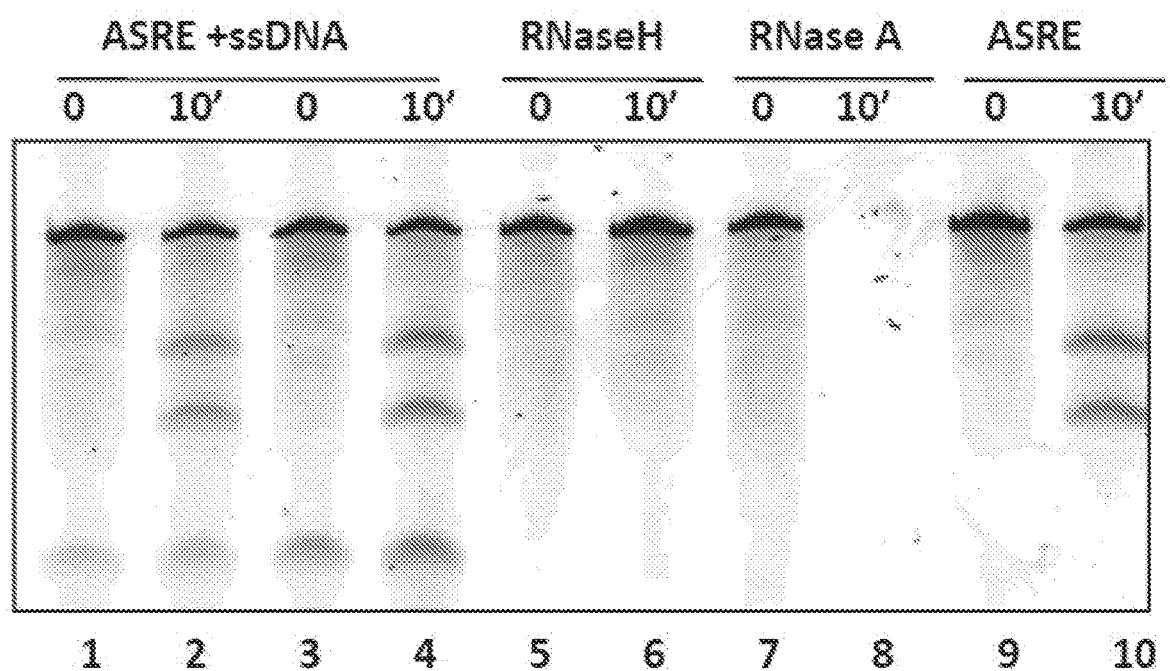
FIG. 16. Single stranded DNA does not interfere with ASRE activity. Addition of single stranded 60 nt DNA in the reaction mixture does not inhibit ASRE activity. RNA substrate (7u6g) is digested with ASRE in a 10 min reaction in the presence of ss DNA (the molar ratio of RNA:DNA is 1:1 in lanes-2 and 1:10 in lanes 3-4). Experimental controls (RNaseA and RNaseH) are also shown.

In addition, consistent with the inability of Pumilio1 to bind DNA[13], it was found that the presence of excess single-stranded DNA in the reaction mixture did not interfere with RNA cleavage (FIG. 16). These data further validate the specificity of ASREs as sequence-specific RNA enzymes.

Determining Cleavage Site of ASREs

Figure 18:
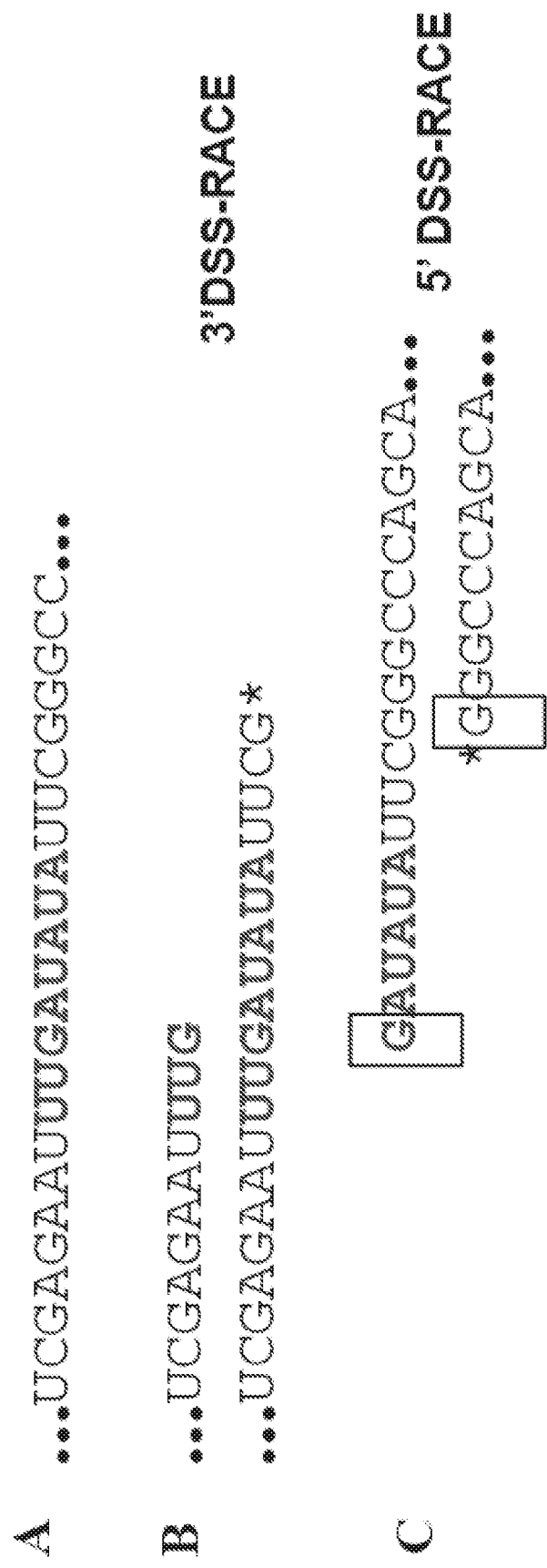
FIG. 18. Sequence at the cleavage sites as mapped by DSS-RACE. (Panel A) Part of the sequence near the recognition site of GU/UG RNA substrate SEQ ID NO:86) is shown with the PUF recognition site marked in bold. (Panel B) The 3' end sequence of 5' cleavage product (SEQ ID NOS:87 and 88). The major cut site is marked with an asterisk. (Panel C) The 5' end sequence of the 3' cleavage product (SEQ ID NOS:89 and 90). The major cut site is marked with an asterisk. An extra "G" residue (boxes) was usually added due to the terminal deoxynucleotide transferase activity of reverse transcriptase.

These data indicate that ASRE-mediated RNA cleavage occurs near the cognate binding site, generating two products whose lengths roughly add up to the length of input RNA. To determine the exact site of ASRE cleavage, both the 5' and 3' digestion products (FIG. 17, Panels A and B) of ASRE were purified and cloned using 5' and 3' DSS-RACE (digestion size selection and rapid amplification of cDNA ends). The 5' and 3' digestion products were purified from the same gel, amplified by RACE, cloned into a plasmid vector and sequenced. Forty clones in total were sequenced to determine the 5' and 3' sites, and only sites that were mapped by multiple clones were considered, since singly identified sites could be an artifact of the amplification process. Due to the limited terminal transferase (TdT) activity of the reverse transcriptase[19], an extra residue (mostly a G or A) was added in many of the 5' RACE products (FIG. 18).

As shown in FIG. 3, Panel C and 18, two cleavage sites were identified from both 5' and 3' RACE which are labeled as sites 1 and 2 according to their positions in substrate. The two cleavage products can be matched to the same site, suggesting that an ASRE makes only a single, distinct cleavage rather than several random cleavages. 'The digested RNA products can be cloned with the DSS-RACE protocol (FIG. 17), indicating that RNA cleavage catalyzed by ASRE generates a 5' fragment with 3' hydroxyl group and a 3' fragment with 5' phosphate.

The major digestion site (site 2) lies 4 bases downstream from the PUF binding site and accounts for ~80% of digestion products, whereas the minor cleavage site lies in the third position of the PUF binding 8-nt. Since PUF binds RNA in an anti-parallel fashion with the first repeat at N-terminus recognizing the $8^{th}$ position of RNA and the PIN domain is at the C-terminus of the ASRE, such a cleavage pattern is somewhat surprising. This result indicated that ASREs might form a foldback structure with the RNA substrate being bound by the one arm (PUF domain) and the PIN catalytic domain folded back to cleave the phosphodiester backbone at downstream sites (FIG. 3, Panel D). However, the fact that RNA can also form secondary and tertiary structure in solution adds complexity to this model. Minor cleavage sites were also determined near the PUF binding sequence that were mapped by single clones; such sites could be accounted for by experimental artifact of RNA amplification with RACE, by incomplete ASRE digestion, or by flexibility of the ASRE-RNA complex.

Silencing Gene Expression with ASRE in Living Cells

The in vitro sequence-specific RNA cleavage activity of ASREs raised the possibility that these enzymes could specifically cleave a target RNA, e.g., mRNA, in cells, thereby silencing gene expression. Such an application would be especially useful in organisms where interfering RNA (RNAi) machinery does not exist. As a proof of concept, the bacterial lacZ transcript was targeted. Bacteria were selected because: (1) bacteria do not express endogenous Pumilio-like protein homologues, and thus are cleaner systems to start with, (2) lacZ gene expression and regulation is very well understood in E. coli, and (3) ASREs are expressed as active forms in bacterial cells.

Figure 4:
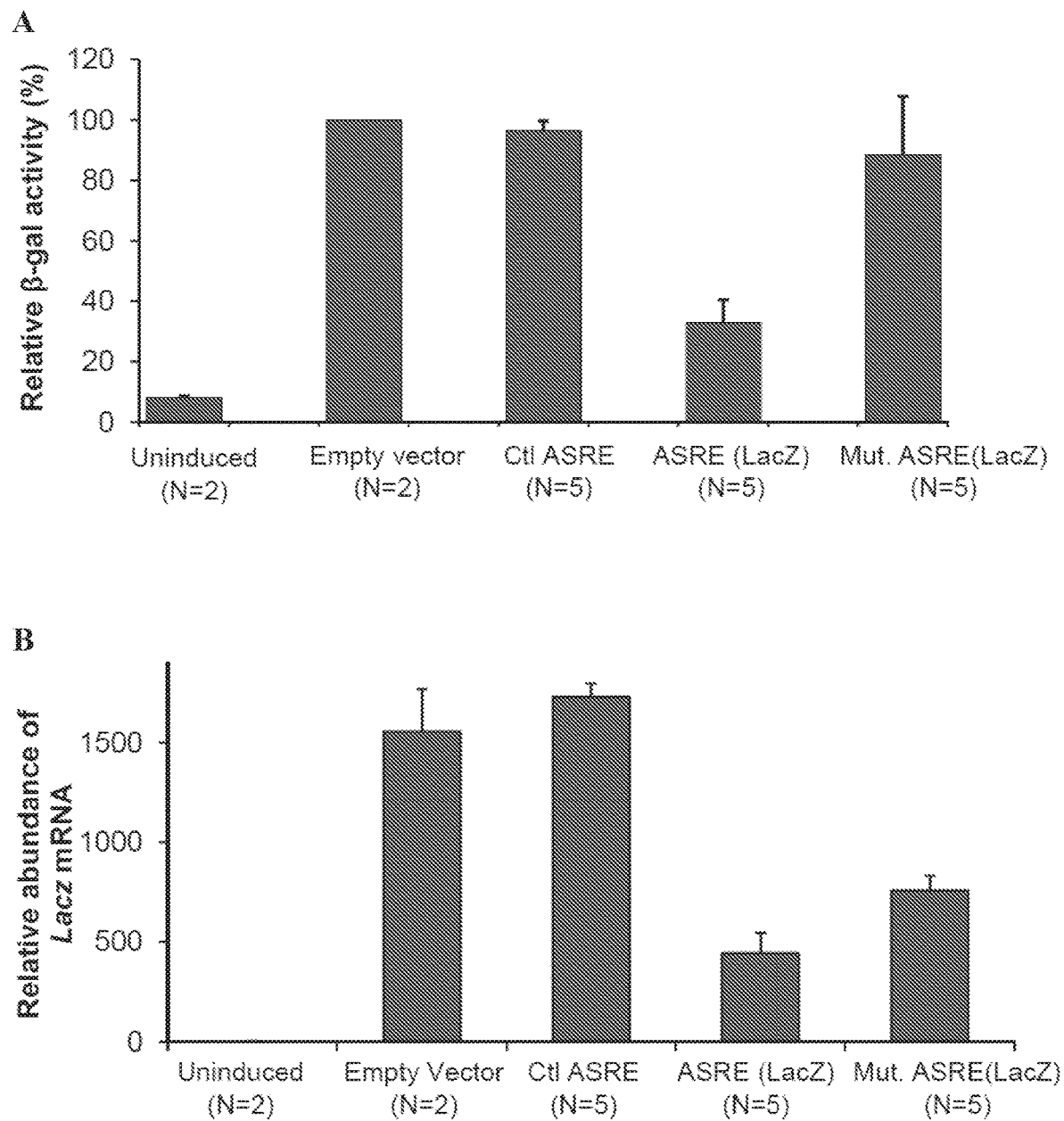
FIG. 4. Using ASRE to silence gene expression in bacterial cells. (Panel A) The activity of β-galactosidase in *E coli* strains transformed with expression plasmids of ASRE (lacZ) and control ASREs. Expression of ASRE and endogenous lacZ gene was induced with IPTG. For each ASRE strain, lacZ expression for five independent clones (N=5) over three experiments (in triplicates) was measured to circumvent clonal variation. The percent of β-galactosidase activity was normalized to clones transformed with the empty vector (N=2) and induced with the same condition. The β-galactosidase activity was also measured for uninduced clones containing empty vector as the baseline activity. Control ASREs include the non-specific ASRE(87621) that targets a different sequence and the mutated ASRE (LacZ) containing a D1353A mutation in the PIN domain active site. (Panel B) The levels of lacZ mRNA were measured by real time RT-PCR. The cell samples were the same as in panel A. LacZ mRNA levels were normalized to ftsZ mRNA and the relative RNA abundances compared to uninduced controls are plotted. In all figures, error bars represent the standard error across all clones. The lacZ mRNA was partially degraded in D1353A mutated ASRE (LacZ), consistent with previous finding that the PUF with a single mutation at D1353 still had partial activity in vivo[17].

To target the lacZ transcript, a modified ASRE, ASRE (LacZ) (or ASRE(6g3g2a) in the nomenclature used herein), was engineered with a mutant PUF domain (repeats 2,3,6) that specifically recognizes the target sequence UGGAUGAA, which occurs twice (position 1232-1239 and 1520-1527) in the lacZ mRNA. BL21(DE3) cells, in which expression of the LacZ is under the control of IPTG, were transformed with the expression vectors for either ASRE (LacZ) or control ASREs. As shown in FIG. 4, Panel A, after IPTG induction, the clones expressing ASRE(LacZ) had significantly decreased β-galactosidase activity compared to empty vector controls or non-specific ASRE controls. Consistent with the in vitro results (FIG. 1, Panel B), the D1353A mutation in the PIN domain of ASRE(LacZ) significantly relieved the gene silencing effect of ASRE(LacZ), suggesting that the decrease in β-galactosidase activity was most likely due to mRNA degradation rather than translational inhibition.

Figure 19:
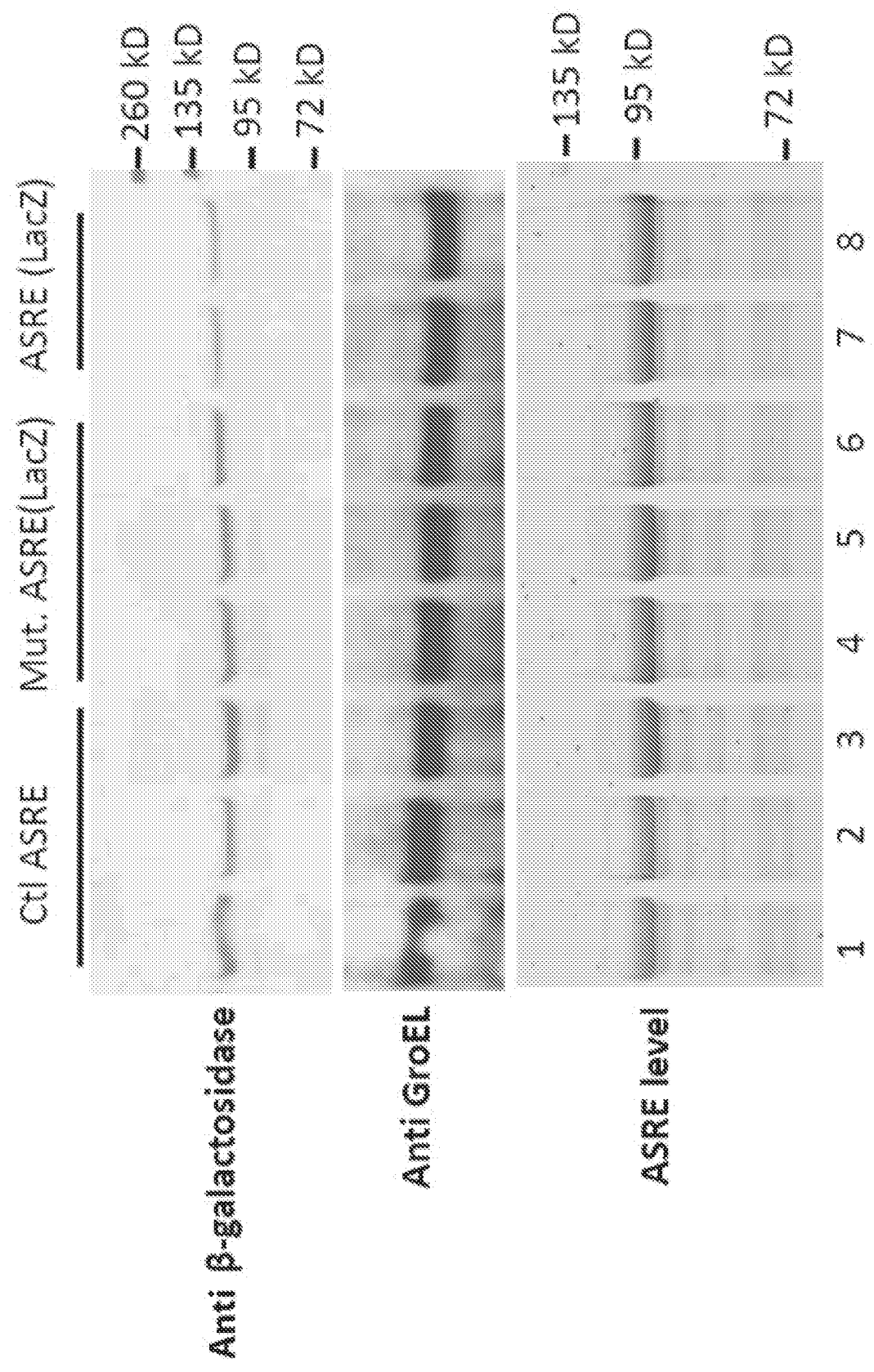
FIG. 19. Decrease in β-galactosidase protein level in ASRE(LacZ) treated cells. The cell lysates from independent clones of bacteria expressing control ASRE (lanes 1-3), D1353A mutated ASRE(LacZ) (lanes 4-6, and ASRE(LacZ) were separated with SDS-PAGE by western blots with antibody against β-galactosidase (top panel) or GroEL (middle panel). The expression level of ASREs was determined by Comassie staining in bottom panel.

To investigate whether the ASRE decreases the β-galactosidase activity by cleaving mRNA, the steady state level of LacZ mRNA was measured by real-time RT-PCR. As shown in FIG. 4, Panel B, the expression of ASRE(LacZ) resulted in a significant decrease in LacZ mRNA compared to strains containing an empty vector or control ASRE. In line with the mRNA levels and the β-galactosidase activity assays, the protein levels of β-galactosidase were significantly decreased in clones expressing ASRE(LacZ) as judged by western blots (FIG. 19). This effect is not due to differential expression of ASREs (FIG. 19, bottom panel) as the ASRE levels in all clones were roughly equal.

The discovery of type II DNA restriction enzymes 40 years ago marked the birth of the "recombinant DNA" era of modern biology[20,21] In addition to native DNA restriction enzymes, artificial enzymes (aka zinc-finger nucleases, ZFNs) that combine a zinc finger DNA-binding domain and a DNA-cleavage domain[22] have also been designed to target unique sequences within complex genomes[23]. However, restriction enzymes of RNA have not been discovered in nature and the creation of artificial enzymes resembling ZFNs has been proven difficult, primarily due to limited understanding of an RNA recognition code between RNA and protein[12]. In the present invention, an RNA "restriction enzyme" (ASRE) was created. The generation of this novel enzyme and other sequence-specific derivatives enables efficient and specific cleavage of diverse RNA targets both in vitro and in vivo.

The keys for successful generation of ASREs include the choice of a sequence-specific RNA binding domain, a suitable endonuclease domain, an optimal linker, and a correct orientation of these elements. These data indicate that the unique RNA recognition mode of the PUF domain renders ASREs the ability to specifically recognize a diverse panel of RNA targets without detectable cross activity between non-cognate ASRE/RNA pairs. These data also demonstrate that the PIN domain of human SMG6 cleaves RNA at specific sites only when fused to the C-terminus of the PUF domain, not vice versa (FIG. 1, Panel C). One possible explanation is that the PIN in PUF-PIN orientation can "fold back" so that the active site faces PUF domain to specifically cleave RNA (FIG. 3, Panel D and FIG. 20, Panel A), whereas in PIN-PUF orientation, the PIN active site faces away from PUF to cleave any nearby RNA (FIG. 20, Panel B). Alternatively, the C-terminal residues of PIN could be very flexible when fused with the peptide linker[17], probably allowing non-specific RNA sequences to become accessible to the PIN active site when ASRE is constructed in a PIN-PUF orientation (FIG. 20, Panel C). Medium-sized linkers (7-12 amino acids) rich in slightly polar hydrophilic amino acid are best suited for the design. In addition, linkers with helical or helix-coil-helix structures produced the most active ASREs, whereas linkers with helix-turn-helix or 3-10 helix structures reduced the activity of ASREs. Furthermore, the linker length also affects the specificity of the enzyme: non-specific cleavage became apparent with linkers approaching ~20 Å in length, probably due to excess flexibility that allowed the PIN endonuclease domain to recognize and cleave any RNA.

Several lines of evidence confirm that the RNA cleavage reaction of ASREs is indeed catalyzed by the PIN domain of SMG6: (1) ASRE has the same cation preference as that of PIN, both requiring $Mn^{2+}$ for maximum activity[17]; (2) a mutation in the active site of the PIN domain abolished ASRE activity; and (3) non-specific RNA cleavage was observed when the PIN domain had too much flexibility to recognize any RNA (either with a long linker or a reverse PIN-PUF orientation). The reaction catalyzed by ASREs was fairly efficient as judged by the $k_{cat}/K_m$ value ($>10^7$ $min^{-1}M^{-1}$). The Michaelis constants ($K_m$) of the ASREs were significantly higher than the dissociation constant of a typical PUF with its cognate sequence[14], suggesting that the ASRE $K_m$ is determined mainly by the interaction of PIN with RNA and the catalytic rate of PIN. In fact, a tight RNA-protein interaction may lead to slow turnover of the enzyme and affect its reaction rate. Therefore, the activity of ASREs may be improved by using a catalytic domain more efficient than PIN domain.

For ASRE mediated mRNA degradation in *E. coli* cells, the expression of both ASRE, driven by the T7 promoter, and chromosomal lacZ, driven by lacZ promoter/operator, was induced simultaneously with IPTG. Since T7 RNA polymerase is almost 8 times faster than *E coli* RNA polymerase[24], ASRE should have been synthesized faster than lacZ, providing a time window for the ASRE to cleave lacZ mRNA. Due to the absence of nuclear membrane, *E. coli* mRNAs undergo co-transcriptional translation, resulting in bacterial mRNA being constantly bound and protected by ribosomes. The observation that ASRE(lacZ) could specifically silence lacZ mRNA indicates that the ASRE can recognize its target in vivo with sufficiently high efficiency and affinity to overcome the protective effect of ribosomes. As an added benefit, the co-transcriptional binding of mRNA by ribosomes in bacteria may limit low affinity off-target effects of ASREs, as only the specific ASRE with high binding affinity will compete efficiently with ribosomes. The silencing effect was most likely due to mRNA degradation rather than a translational block, as an ASRE with a mutation in the PIN domain active site did not affect the β-galactosidase activity. In addition, mRNA degradation was also confirmed by q-RT-PCR analysis. Using a similar strategy, other gene product(s) may also be targeted in organisms where RNAi does not exist.

The present invention also includes various ways to optimize and expand ASRE usage. First, although the PUF domain can specifically recognize an 8-nt sequence, it may be desirable to create ASREs that recognize a substrate having a target sequence of different length. For example, the in vivo use of ASRE to silence gene expression would presumably benefit from a longer ASRE binding site that can minimize off-target effects, whereas the in vitro use of ASRE to probe RNA structure or sequence may require a shorter targeting site to produce multiple cleavages in a single substrate. It should be possible to increase the length of recognition site by adding more PUF repeats, or by using multiple PUFs in a single fusion protein. Conversely, it may be possible to decrease the length of the recognition site by relaxing the specificity of some PUF repeats (i.e., making some repeats to bind all four bases equally well). In addition, the catalytic activity of ASRE may also be improved by using riboendonuclease domains other than PIN, or by optimizing the PIN domain active site to increase activity. Finally, the relative positions of the cleavage site may be affected by the conformation of the linker region; thus, testing peptide linkers with different sequences and structures will likely reduce the "star activity" of ASREs so that cleavage occurs at only a single, predictable site.

References for Example 1

1. O. Takeuchi and S. Akira, Immunol Rev 227 (1), 75 (2009).
2. D. P. Bartel, Cell 136 (2), 215 (2009).
3. S. J. Baker, J. L. Morris, and I. L. Gibbins, Brain Res Mol Brain Res 111 (1-2), 136 (2003).
4. I. J. MacRae and J. A. Doudna, Curr Opin Struct Biol 17 (1), 138 (2007).
5. J. J. Champoux and S. J. Schultz, FEBS J 276 (6), 1506 (2009).
6. W. G. Scott, Curr Opin Struct Biol 17 (3), 280 (2007).
7. H. Yoshida, Methods Enzymol 341, 28 (2001).
8. Y. Tomari and P. D. Zamore, Genes Dev 19 (5), 517 (2005).
9. T. W. Nilsen, Bioessays 25 (12), 1147 (2003).
10. S. K. Silverman, Nucleic Acids Res 33 (19), 6151 (2005).
11. M. Wickens, D. S. Bernstein, J. Kimble et al., Trends Genet 18 (3), 150 (2002).
12. S. D. Auweter, F. C. Oberstrass, and F. H. Allain, Nucleic Acids Res 34 (17), 4943 (2006).
13. X. Wang, J. McLachlan, P. D. Zamore et al., Cell 110 (4), 501 (2002).
14. C. G. Cheong and T. M. Hall, Proc Natl Acad Sci USA 103 (37), 13635 (2006).
15. R. A. George and J. Heringa, Protein Eng 15 (11), 871 (2002).
16. P. Argos, J Mol Biol 211 (4), 943 (1990).
17. F. Glavan, I. Behm-Ansmant, E. Izaurralde et al., EMBO J 25 (21), 5117 (2006).
18. E. Huntzinger, I. Kashima, M. Fauser et al., RNA 14 (12), 2609 (2008).
19. D. Chen and J. T. Patton, Biotechniques 30 (3), 574 (2001).
20. H. O. Smith and K. W. Wilcox, J Mol Biol 51 (2), 379 (1970).
21. T. J. Kelly, Jr. and H. O. Smith, J Mol Biol 51 (2), 393 (1970).
22. T. Cathomen and J. K. Joung, Mol Ther 16 (7), 1200 (2008).
23. V. K. Shukla, Y. Doyon, J. C. Miller et al., Nature 459 (7245), 437 (2009).
24. I. Iost and M. Dreyfus, EMBO J 14 (13), 3252 (1995).
25. Y. Wang, C. G. Cheong, T. M. Hall et al., Nat Methods 6 (11), 825 (2009).
26. J. Tilsner, O. Linnik, N. M. Christensen et al., Plant J 57 (4), 758 (2009).
27. K. L. Griffith and R. E. Wolf, Jr., Biochem Biophys Res Commun 290 (1), 397 (2002).

Example 2

In addition to being the organelle in energy production for eukaryotic cells, the mitochondrion plays a critical role in myriad cellular processes such as control of apoptosis and ROS (reactive oxygen species) signaling. Thus mitochondria dysfunction is linked to various diseases such as cancer, autism and age-associated neurodegenerative diseases. Most mitochondrial proteins are coded by nuclear DNA and imported into mitochondria after translation. Mitochondria have a distinct genome, and the human mitochondrial genome contains 13 protein-coding, 2 rRNA, and 22 tRNA genes (FIG. 21, Panel A). Although mitochondrial gene mutations are closely linked to various diseases, the functions of these genes are hard to study because there are limited research tools to manipulate mitochondrial gene expression. A new ASRE with a mitochondrial targeting signal has been generated that can be used to specifically silence mitochondrial gene expression by cleaving mitochondrial RNA, making it possible to determine the function of each gene in the mitochondrial genome.

An 8-nt target sequence (TTTATGTG) in subunit 5 of the respiratory complex I (mtND5) gene was selected for these studies (FIG. 21, Panel A). The sequence is a unique hit in the 16.5 kb mitochondrial genome thus ensuring minimal off target effect. To facilitate the translocation of ASRE into mitochondria, the N-terminal mitochondrial targeting peptides from ornithine transcarbamylase (OTC) enzyme were used, which are cleaved by mitochondrial protease after protein translocation (FIG. 21, Panel B). The resulting enzyme, mitochondrial ASRE (mitoASRE), is translocated into mitochondia by natural cellular machinery and specifically induce gene silencing. As a control, ASRE(ND5) was engineered, which lacks mitochondrial targeting signals, as well a mutated ASRE(ND5) that contains a mutation in the active site of the PIN domain. To confirm the design, the initial study was to transiently transfect HELA and HEK293 cells with N-terminal flag tagged ASREs. It was found that the mitoASRE and mutated ASRE(ND5) could be successfully translocated to the mitochondrial matrix, and the control ASRE(ND5) that lacks mitochondrial targeting sequence is mainly located in the cytoplasm. Real time PCR showed 30% decrease of mtND5 transcript compared to control or cells expressing inactive DA control. A concomitant decrease in protein level was also noticed as depicted by western blot analysis. Cells also showed a slow growth phenotype on expression of mtND5 ASRE.

Because human cells typically contain from about 10 to several hundred copies of mitochondria and the transient transfection of expression vector has different efficiency among various cell types, mitochondrial gene inhibition by ASRE is better achieved through stable expression of ASRE. To homogeneously express equal amounts of ASRE in cells, tetracycline inducible stable cells lines were generated using the Flpin system. After 24 hours of tetracycline induction, robust expression of mitoASRE(ND5) was observed in mitochondria (FIG. 21, Panel C). The transcript level of mtND5 gene has decreased by 70% as determined by real time RT-PCR, compared to un-induced cells (FIG. 21, Panel D). As a control, cells expressing DA mutant mitoASRE (ND5) showed slightly increased amounts of mtND5 mRNA, likely because the inactive mitoASRE(ND5) can protect its target from natural mRNA turnover when binding to the target. Examination of ND5 protein level by western blot also showed that the mtND5 protein was decreased in cells expressing mitoASRE(ND5) but not mutated mitoASRE(ND5) (FIG. 21, Panel E). Induction of mitoASRE(ND5) reduced growth rate of cells.

Because mutation of mitochondrial genes is closely associated with many human diseases, the engineering of mitochondrial ASRE to specifically manipulate expression of mitochondria encoded genes has opened new doors to assess their role in such mitochondria associated diseases. Moreover, the capability to selectively probe and perturb this organelle within a living cell provides a novel means to examine mitochondrial function that is relevant to biology and physiology. This was not possible with conventional gene silencing tools like RNA interference (RNAi). To the inventors' knowledge, this is the first report to selectively probe organelle specific gene knock down. The fact that ASRE can be targeted to any compartment of a cell makes it a useful tool that is complementary to conventional gene silencing methods using RNAi.

A 32 aa mitochondrial targeting signal from ornithine transcarbamylase leader peptide (MLFNLRILLNNAAF-RNGHNFMVRNFRCGQPLQ, SEQ ID NO:71) was used as a mitochondrial targeting signal for ASRE (FIG. 21, Panel B). Tetracycline inducible stable lines were produced that expressed mitoASRE(ND5) or a catalytically inactive version cloned between Hinc1111 and Nod sites in a pCDNA5/FRT/TO construct. This construct was co-transfected with pOG44 plasmid to facilitate integration into an FRT locus of Flp-In T-Rex 293 cells (Cat no. K6500-01, Invitrogen). Stably integrated cells were selected using DMEM medium with 10% FBS and 100 ug/ml of hygromycin B. Cells were then passed for 8 generations on 60 mm dishes for stability and creation of isogenic lines. To induce mitoASRE expression, cells were re-plated in fresh DMEM medium with 10% FBS without any drug and induced with tetracycline (6-10 ug/ml). Twenty-four hour post induction expression of ASRE was checked on western blot using anti-flag antibody (M2 F1804, Sigma). Growth curves and viability assays were performed at different time points post induction. Briefly, cells were dislodged with trypsin after different growth times, mixed with 0.4% trypan blue (1:1) and counted. The proliferation assays were performed using a WST-1 assay kit (Roche, Cat. no. 11 644 807 001).

To purify RNA, the mitochondria were lysed in lysis buffer by sonication for 15 mins and then total RNA was purified using a PureLink RNA mini kit (Ambion Cat. no. 12183-018A). First strand cDNA synthesis was performed using a high capacity reverse transcription kit (Applied Biosystem Cat. no. 4368814). RNA levels were measured by real time quantitative PCR using QPCR SYBR Green Low Rox mix (Thermo Scientific, Cat. no. AB-4322/A) using gene specific primers and normalized against GAPDH gene expression. For western blot analysis, cells were lysed in RIPA buffer and further sonicated for 15 sec on ice. Protein was measured using Bradford reagent (Pierce). A total of 30-40 ug protein was loaded for each sample and blotted. Western blot was performed using anti human rabbit ND5 specific antibody (1:100 Ab Cam, Cat. No. ab92624) overnight in cold and detected using HRP linked secondary antibody (1:5000 Cell Signaling, Cat. no. 7074). The total protein was normalized against α-tubulin (Ab Cam, Cat. no. ab40742) which serves as loading control. ASRE expression was confirmed by anti flag mouse antibody.

Example 3

Myotonic dystrophy (dystrophia myotonica, DM) is the most common form of muscular dystrophy in adults that affects 1 in 8500 individuals worldwide. The genetic mutations responsible for DM were identified as the expanding $(CUG)_n$ repeats in the 3' UTR of DMPK mRNA (for DM1) or the $(CCUG)_n$ expansion in the intron of ZNF9 (for DM2). Such non-coding RNA repeats bind and sequester muscleblind proteins or increase the level of the CUG binding proteins that regulate alternative splicing of multiple endogenous genes critical to muscle and heart functions (1). Currently there is no cure for DM, although complications of the disease can be treated and alleviated.

The present study provides a novel approach to target and cleave the toxic RNA repeat with the artificial site-specific RNA nucleases (ASREs) as described herein. Such enzymes were constructed with an RNA binding module (PUF domain) that is specifically designed to recognize any 8-nt sequence and an endoribonuclease domain (PIN domain of SMG6) that efficiently cleave RNA. ASREs that can specifically bind and cleave expanding RNA repeats in the cell nucleus where the toxic RNAs are accumulated are described herein. The present study focuses on DM1, which is the most common and severe form of DM, while it is understood that similar strategies can be developed to treat DM2.

Engineering PUF domains to recognize the $(CUG)_n$ repeats with high affinity and specificity.

The native PUF domain contains 8 PUF repeats, each specifically recognizing one RNA nucleotide through hydrogen bonding with the base A, U or G. In addition, the modular "binding code" of the PUF repeat to C nucleotide has been identified, using a yeast-3-hybrid screen, making it possible to engineer a PUF domain that specifically recognizes any 8-nt RNA. PUF domains will be designed and engineered that specifically recognize all three possible 8-nt sequences in a $(CUG)_n$ repeat. The affinity and specificity of RNA-protein interaction will be determined with various assays to select for a modified PUF domain that binds a $(CUG)_n$ repeat with high affinity. Such PUF domains will be used either as the RNA binding modules of ASREs, or as competitors of the toxic RNA repeats that sequester endogenous RNA binding proteins in DM1 patients.

Cleavage of the toxic $(CUG)_n$ repeat in DM1 cells with artificial site-specific RNA endonucleases. PUF domains that specifically recognize $(CUG)_n$ will be used to generate novel ASREs. A nuclear localization sequence will also be included in the ASRE to direct the enzyme into the nucleus where the RNA repeats accumulate. The specific cleavage of $(CUG)_n$ repeats will be analyzed in vitro and in cultured DM1 cells. Experiments will be done to determine if expression of ASRE can reduce the number of ribonuclear aggregates caused by $(CUG)_n$, and to further determine if the normal expression level and localization of muscleblind-like 1 (MBNL1) and CUG-binding protein 1 (CUGBP1) can be restored by ASRE. ASREs will also be tested for the ability to reverse the mis-splicing of genes affected in patients, using cultured DM1 cells (such as CIC-1, cTnT and SERCA1). In addition, mRNA-seq will be used to determine (i) if normal gene expression and alternative splicing pattern can be restored at a genomic scale by the designer ASRE in DM1 cells, and (ii) the off-target effect of ASRE treatment.

Determination of the in vivo efficacy of designer ASREs using DM1 mouse model.

Adeno-associated virus (AAV) vectors will be used as a gene delivery tool to express ASRE in a DM1 mouse model ($HSA^{LR}$ mice), and to further test if ASRE can relief the DM1 phenotype in muscle and heart. The expression of ASRE will be analyzed in different muscle tissues and studies will be carried out to determine if the nuclear MBNL1 sequestration can be released. The splicing and the function of key DM1 marker genes (such as CIC-1, cTnT and SERCA1) will be examined to determine if they can be restored in muscles, and if the myopathy phenotype of DM1 mice can be reduced.

Unique RNA pathogenesis of myotonic dystrophy makes it difficult to develop targeted therapy.

Myotonic dystrophy (DM) is an autosomal dominant disease with multisystemic symptoms including myotonia, muscle wasting, cardiac conduction defects, insulin resistance, cataracts and cognitive dysfunction (1-3). Two forms of DM are caused by microsatellite expansions in different genes. The more severe form, DM1, is caused by $(CTG)_n$ expansion in the 3' UTR of the dystrophia myotonica-protein kinase gene (DMPK) (4,5); whereas DM2 is caused by $(CCTG)_n$ expansion in the intron of Zinc finger protein 9 (ZNF9) (6). These non-coding mutations have a profound effect on the function of many genes in a trans-dominant fashion, suggesting that the gain-of-function of toxic RNA causes the clinical features (1,3). Consistent with the RNA pathogenesis model, the transgenic mouse with $(CUG)_{250}$ in an untranslated region of a different mRNA was sufficient to generate DM1 phenotype (7).

Figure 22:
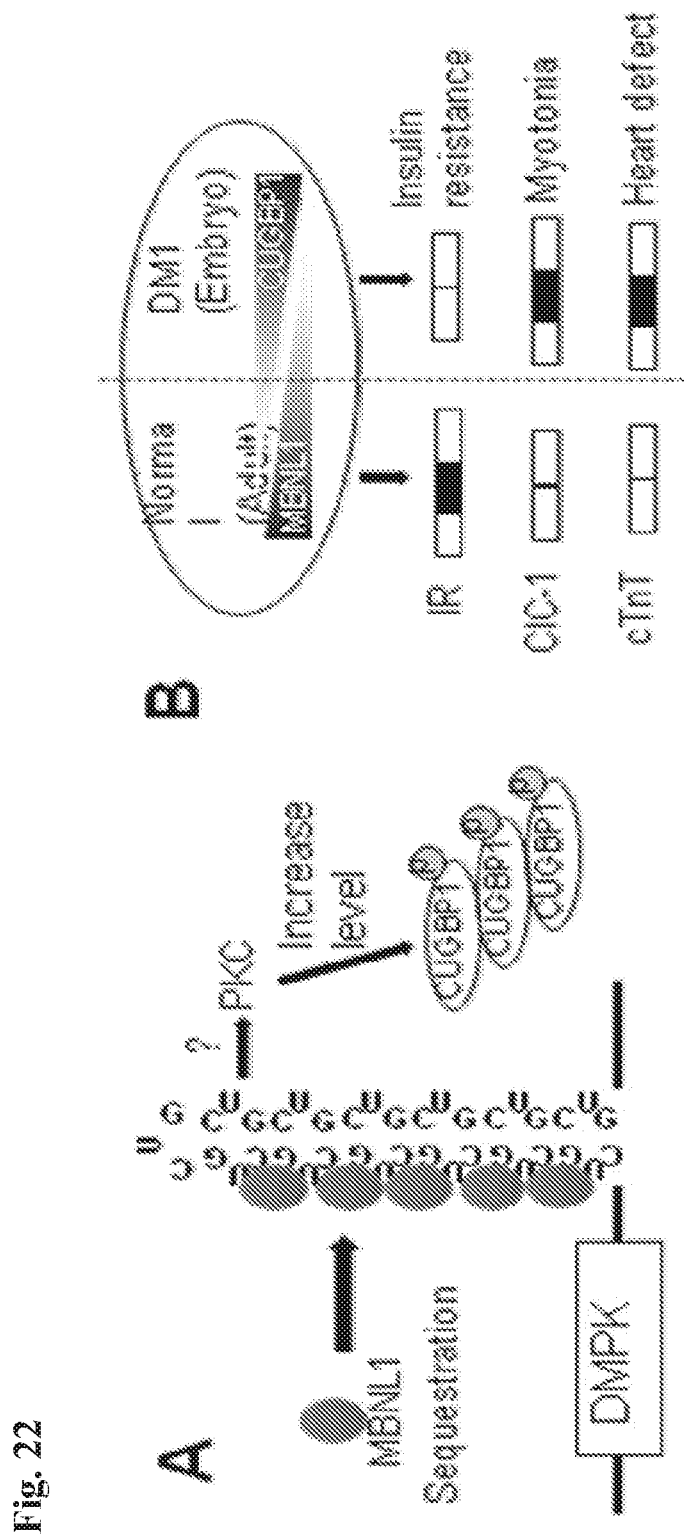
FIG. 22. RNA pathogenesis model of DM1. (Panel A) The RNA repeats in the 3'UTR of DMPK (SEQ ID NO:91) form a hairpin structure that sequesters MBNL1 and increases CUGBP1 level. (Panel B) Changes of balance for splicing factor level cause many genes to shift to embryonic splicing pattern in DM1 adults, and such splicing shifts cause various symptoms of DM1.

In DM1 cells, $(CUG)_n$ repeats specifically bind to splicing regulatory proteins, forming RNA-protein complexes that accumulate within the nucleus. Two classes of splicing factors are known to be affected by $(CUG)_n$ (FIG. 22; Ref. 1): (i) The members of muscleblind-like family (e.g., MBNL1) are sequestered in the nuclear foci, resulting in nuclear depletion and loss of function (8-10); (ii) The CUG binding proteins (e.g., CUGBP1) are up-regulated in DM1 cells through a PKC-mediated phosphorylation event that stabilizes the protein (11,12). Changes of these splicing factors cause splicing dysregulation in a large number of genes (13) including ClC-1 (14,15), insulin receptor (16), cTnT (11) and SERCA1 (17,18). Generally the embryonic isoforms of these gene are mis-spliced in adult DM tissues, leading to multisystemic defects in DM1 patients (19). Because the toxic RNA repeats affect two classes of splicing factors that sequentially cause mis-splicing of ~100 proteins (13), it is a complicated task to develop specific therapies targeting the molecular cause of DM1.

Several strategies have been used to develop specific therapy against DM1. One approach uses gene therapy to restore a normal level of the splicing factors affected by toxic RNA. For example, expression of muscleblind protein with adeno-associated virus (AAV) vector restored normal adult-splicing patterns of several pre-mRNAs in muscles of DM1 mice (20). Because AAV vectors can effectively deliver genes in muscle and heart (21) and the loss of MBNL1 is a primary pathogenic event in DM1, this method produced encouraging results in a mice model (20). The strength of such protein-based approaches is to use gene therapy tools (like AAV) to achieve efficient delivery. However, because multiple muscleblind like proteins are sequestered and CUGBP1 is increased in DM1 patients, conventional gene therapy approaches cannot restore the normal levels of all splicing factors affected in DM1.

Another approach is to use an antisense oligonucleotide (AON) based method to cleave $(CUG)_n$ repeats using RNAi (22), short antisense oligos (23) or ribozymes (24). This strategy has produced promising results in cultured cells, but systematic delivery of AON in muscle and heart has been a major challenge. In addition, the existence of nuclear RNAi is still under debate as dsRNA usually induces transcriptional gene silencing rather than RNA degradation. Another AON based method is to use a morpholino oligonucleotide that blocks the $(CUG)_n$ from binding to proteins. This short AON (i.e., CAG25) led to efficient reversal of RNA dominance and correction of many splicing defects in DM1 mice containing $(CUG)_n$ repeats (25). Given the encouraging results of CAG25, the main challenge becomes the delivery of morpholino AON to patients. Although it was delivered to mice by intramuscular injection followed by in vivo electroporation, this delivery route is not practical for human use. Some progress has been made in identifying small molecules that inhibit the binding of $(CUG)_n$ to MBNL1 and release the sequestered MBNL1 (26-28). These small molecules are fairly toxic as they all bind to structured RNAs. Additional work is needed to minimize the toxicity and increase their specificity to the $(CUG)_n$ repeats.

Unique RNA binding mode of PUF proteins provides new hope to target $(CUG)_n$ repeats.

The present study employs a new therapeutic strategy using an artificial site-specific RNA endonuclease (ASRE) to specifically cleave $(CUG)_n$ repeats. Engineering of such a novel enzyme takes advantage of the unique RNA recognition mode of PUF proteins, whose functions involve mediating mRNA stability and translation (29). The PUF domain of human *pumilio* 1 contains 8 repeats that bind consecutive bases in an anti-parallel fashion, with each repeat recognizing a single base (30) (FIG. 7). Each PUF repeat uses two amino acids to recognize the edge of the corresponding base and a third amino acid (Tyr, His or Arg) to stack between adjacent bases, causing a very specific binding between a PUF domain and an RNA. By changing two amino acids in each repeat, a PUF domain can be modified to bind most 8-nt RNA (30,31). This unique binding mode makes PUF a programmable RNA-binding domain that can be used in various artificial factors for specific splicing modulation or RNA detection (32,33). ASREs have been designed and engineered to specifically cleave RNA with an 8-nt PUF target, and in the present study, ASREs will be generated that recognize $(CUG)_n$ with high affinity and efficiently cleave the RNA repeats.

Novel RNA restriction enzymes will be engineered to specifically cleave RNAs. The simple protein enzyme that cleaves RNA in a sequence-specific manner has not been found in nature, and the known RNases either cleave their targets through recognition of certain structures (e.g., RNase III family, RNase H or most ribozymes) (34-36) or have essentially no cleavage specificity (e.g., RNase A or RNase T1) (37). Development of ASREs will have broad applications for in vitro RNA manipulations, and will make gene silencing possible in organisms lacking RNAi and/or in cellular compartments where RNAi machinery does not function (such as in mitochondria).

ASREs combine the strength of current DM1 therapies and overcome some of their limitations. The approaches under investigation are gene therapy and antisense oligonucleotide (AON) based methods. While gene delivery with AAV is quite efficient in muscle and heart, gene therapy does not allow for the targeting of toxic RNA but rather restores some but not all genes affected in DM patients. On the other hand, AON methods can target toxic RNA directly but have delivery problems. Thus, the present study provides a new approach using ASREs that target RNA directly and can be delivered into muscle and heart, for example, with AAV vectors. The designer ASREs can directly recognize and cleave $(CUG)_n$ repeats like AON does, and can be delivered to the muscle and heart of DM1 patient with vectors such as AAV vectors.

ASREs will be directed into the nucleus with NLS to specifically cleave $(CUG)_n$ repeats. The $(CUG)_n$ repeats accumulated in the nucleus are known to be the pathogenic molecules of DM1. As there may be a possibility that a small amount of cytoplasmic DMPK with $(CUG)_n$ is needed for normal function of DMPK, targeting only the $(CUG)_n$ in nuclear foci may be more specific and beneficial.

AAV vectors are proven to be efficient in delivering genes to muscle and heart, and are currently tested in human trails. Therefore this approach can be readily transferred to an animal DM1 model and human patients.

Engineering ASREs that Specifically Bind and Cleave RNAs.

Figure 23:
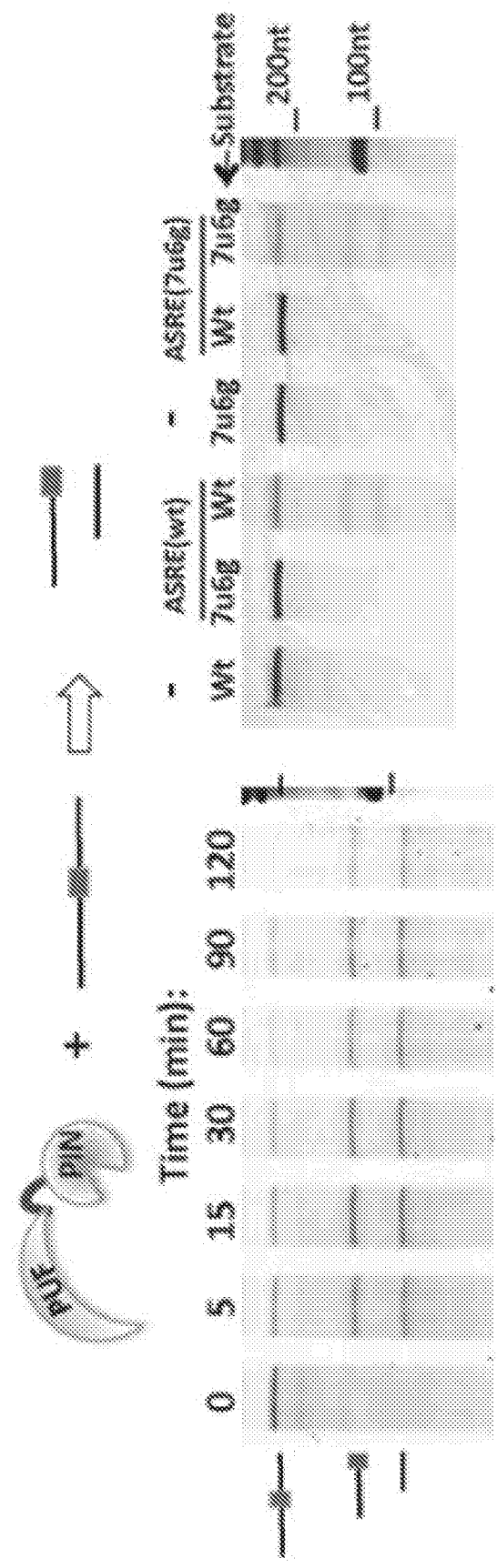
FIG. 23. Engineering ASRE for specific RNA cleavage. The ASRE was constructed by fusing N-terminal PUF and C-terminal PIN domains with a 7 aa linker. RNA substrates containing a PUF binding site (grey box) were incubated with the purified ASRE at 37° C. Left panel: time course of ASRE catalyzed RNA cleavage. Right panel: two ASREs, each recognizing Wt or 7u6g targets that differ by 2-nt. ASREs specifically cleave their cognate substrate.

The ability to specifically cleave RNA has important applications in control of gene expression, mRNA surveillance and turnover. However, an "RNA restriction enzyme" that cleaves RNA in a sequence-specific manner has not been found in nature. To engineer such an enzyme a modular design was used by combining a target recognition domain and a catalytic domain. The unique RNA recognition domain of human PUM1 was used as it is possible to "reprogram" the binding specificity of the PUF domain to recognize most 8-nt RNA. A short peptide linker was used to link a designer PUF with a small endonuclease domain, the PIN domain of human SMG6 that has a well-defined molecular architecture and requires only a divalent metal cation for RNA cleavage (39,40). The resulting ASREs were expressed and purified from an E. coli expression system and incubated with RNA substrate containing the recognition sequences. ASREs were found to efficiently recognize and cleave RNA substrates with cognate binding sites (FIG. 23), and can distinguish between substrates differing by 2-nt at recognition site (FIG. 23, two ASREs with different recognition sites were used). By mapping the ASRE cleave site with 3'- and 5'-RACE of gel purified products, it was found that ASREs make a single cut of RNA near the PUF binding site to generate products with 5'-phosphate and 3'-hydroxyl groups (FIG. 3, Panel C). The cleavage happens mostly downstream of the PUF binding site, suggesting a curve-back configuration of ASRE (FIG. 23, Panel B). The specifically designed ASRE can be used to silence gene expression in organisms where RNAi may not be available or active (FIG. 4).

In addition to cleaving RNA substrate in vitro, the ASRE can be used to specifically silence gene expression by directly targeting the corresponding RNA. An ASRE was designed to target the LacZ gene in bacterial cells, and it was shown that ASRE(LacZ) can indeed induce specific mRNA degradation and gene silencing, whereas control ASRE or ASRE with a mutated PIN domain did not affect gene expression (FIG. 4). This method is particularly useful to specifically cleave RNA in cell compartments where RNAi is not functional (e.g., in the mitochondrion and/or nucleus), and it was found that a specifically designed ASRE can be used to selectively degrade the mRNA of a mitochondrial-encoded gene ND1.

Determination of the Modular Binding Code of PUF Domain for C Nucleotide.

Figure 24:
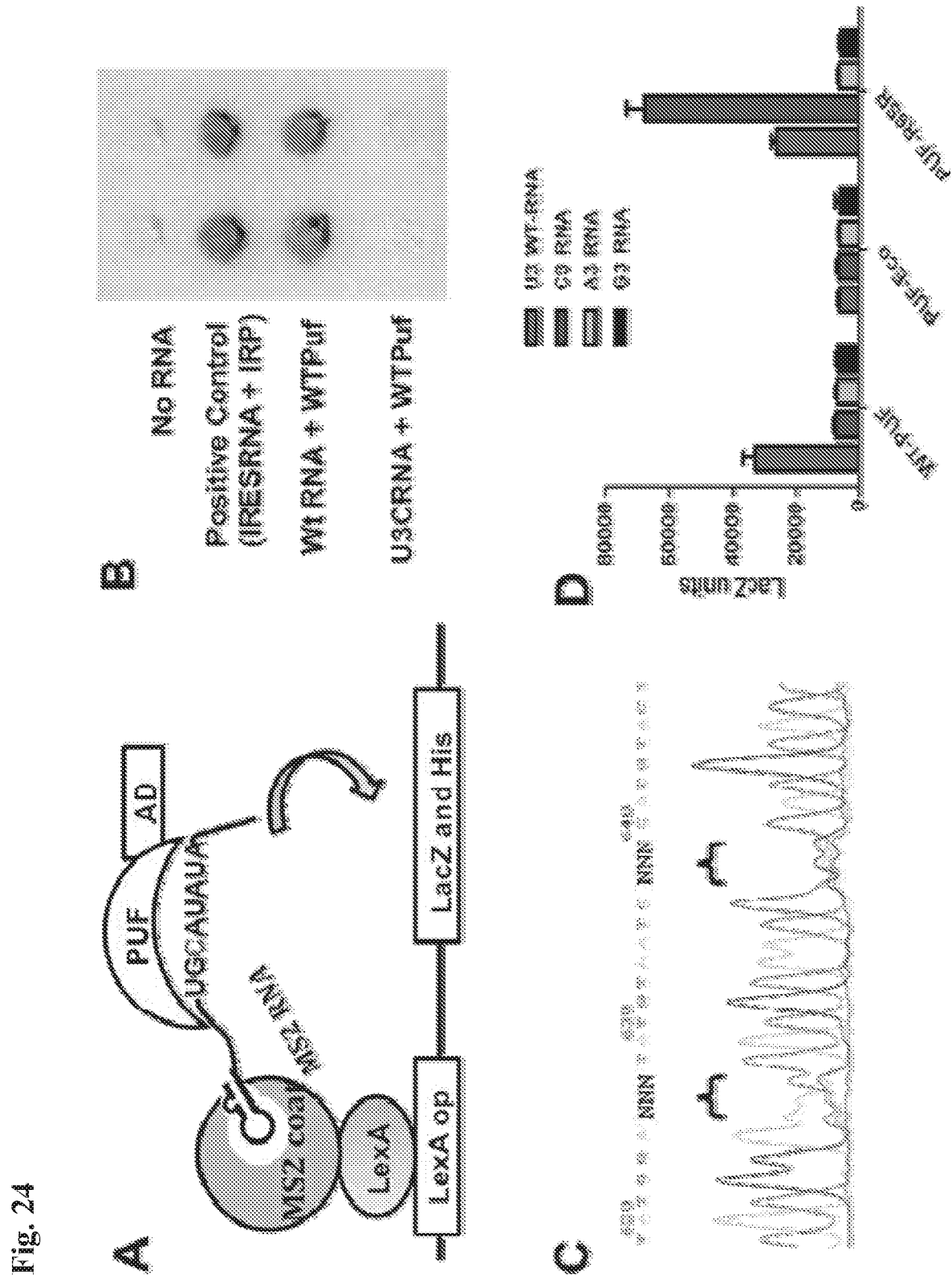
FIG. 24. Identification of PUF binding code for C residue. (Panel A) Diagram of yeast 3-hybrid (Y3H) screen to identify the C binding code of the PUF repeat. (Panel B) Measurement of the background of Y3H screen with positive and negative controls. Two independent yeast clones were assayed for β-gal activity, and the dark staining indicates the RNA-protein interaction. From top to bottom: no RNA control; a known RNA-protein interaction pair; Wt PUF and Wt RNA; and Wt PUF and U3C mutated RNA. (Panel C) Randomized library for residue 16 and 20 in PUF repeat 6 (SEQ ID NO:92). (Panel D) The SxxxR (SEQ ID NO:143) combination at PUF repeat 6 makes the PUF domain specifically recognize C at the position 3. PUF-Eco is a control PUF domain with an EcoRI site (equivalent of two amino acids) inserted between S and R residues. All RNA targets containing U, A, C and G in position 3 were tested for the specific binding of PUF:RNA, which was determined as the LacZ activity in the Y3H system. Higher LacZ activity reflects strong binding between RNA and protein.

Because the native PUF repeats can recognize A, U, or G residue in a modular fashion, the challenge of making an ASRE to cleave a $(CUG)_1$ repeat is to identify the C binding code of the PUF repeat to engineer specific PUF domains for $(CUG)_n$ sequence. The specificity of each PUF repeat is determined by the two residues at positions 16 and 20 in that repeat (31). To identify the C binding code of PUF repeat, a yeast three-hybrid (Y3H) screen was used to determine the specific amino acid combination that enables the PUF domain to recognize C (41). The design of the Y3H screen is similar to the Y2H screen except that an RNA molecule is used as an adaptor of molecular interaction (FIG. 24, Panel A). The specific binding of the PUF domain to the RNA adaptor can recruit the transcriptional activation domain and turn on the expression of reporter genes. The wild-type PUF specifically recognizes Wt RNA sequence (UGUAUAUA), and the third position of this target was changed to C (UGCAUAUA; U3C RNA) and amino acids responsible for base recognition in the PUF repeat 6 were randomized. As a positive control, the wild-type PUF can recognize WtRNA to activate LacZ gene (FIG. 24, Panel B), whereas the single mutation U3C completely abolished the binding of WT PUF and U3C RNA, giving a very low background for the screen.

The corresponding sequences coding for the repeat 6 of PUF domain (FIG. 24, Panel C) were randomized and cloned into the Y3H system to screen for yeast colonies that grew on His depleted plates. The positive clones were reconfirmed by the expression of the LacZ gene, and the plasmid DNAs were purified from the double positive clones and were further sequenced to identify the amino acid combination in PUF repeat 6. A total of 19 positive clones were sequenced and it was found that all have the same amino acid combinations (Ser in position 16 and Arg in position 20). In addition, all the triplet codes for Ser and Arg were found in the sequencing results, suggesting that the screen has good coverage for the random sequence space. Further testing was done to determine if the binding code of the C residue is selective using the RNAs with A, U and G at the third position and the PUF domains with SxxxR (SEQ ID NO:143) sequence in repeat 6 (R6SR). The modified PUF domain binds most strongly to RNA with a C in the third position (C3) as judged by the LacZ activity of yeast strain (FIG. 24, Panel D), whereas the binding between other bases was either not detectable (for A or G) or very weak (for U). As controls, the wild type PUF only binds to U3 RNA but not the other sequences, and a modified PUF with two amino acid inserted between Ser and Arg of repeat 6 (PUF-Eco) does not bind to any of the target RNAs (FIG. 24, Panel D).

Other PUF repeats were further changed into the SxxxR (SEQ ID NO:143) amino acid combination, and it was confirmed that such modification can generate new PUF domains that specifically recognize RNA with a C at the cognate position. The identification of the modular binding code for C residue enabled the generation of a PUF domain that recognizes any RNA sequence, making it possible to engineer artificial proteins to specifically manipulate any given RNA target.

Engineering of PUF domains to recognize $(CUG)_n$ repeats with high affinity and specificity.

Figure 25:
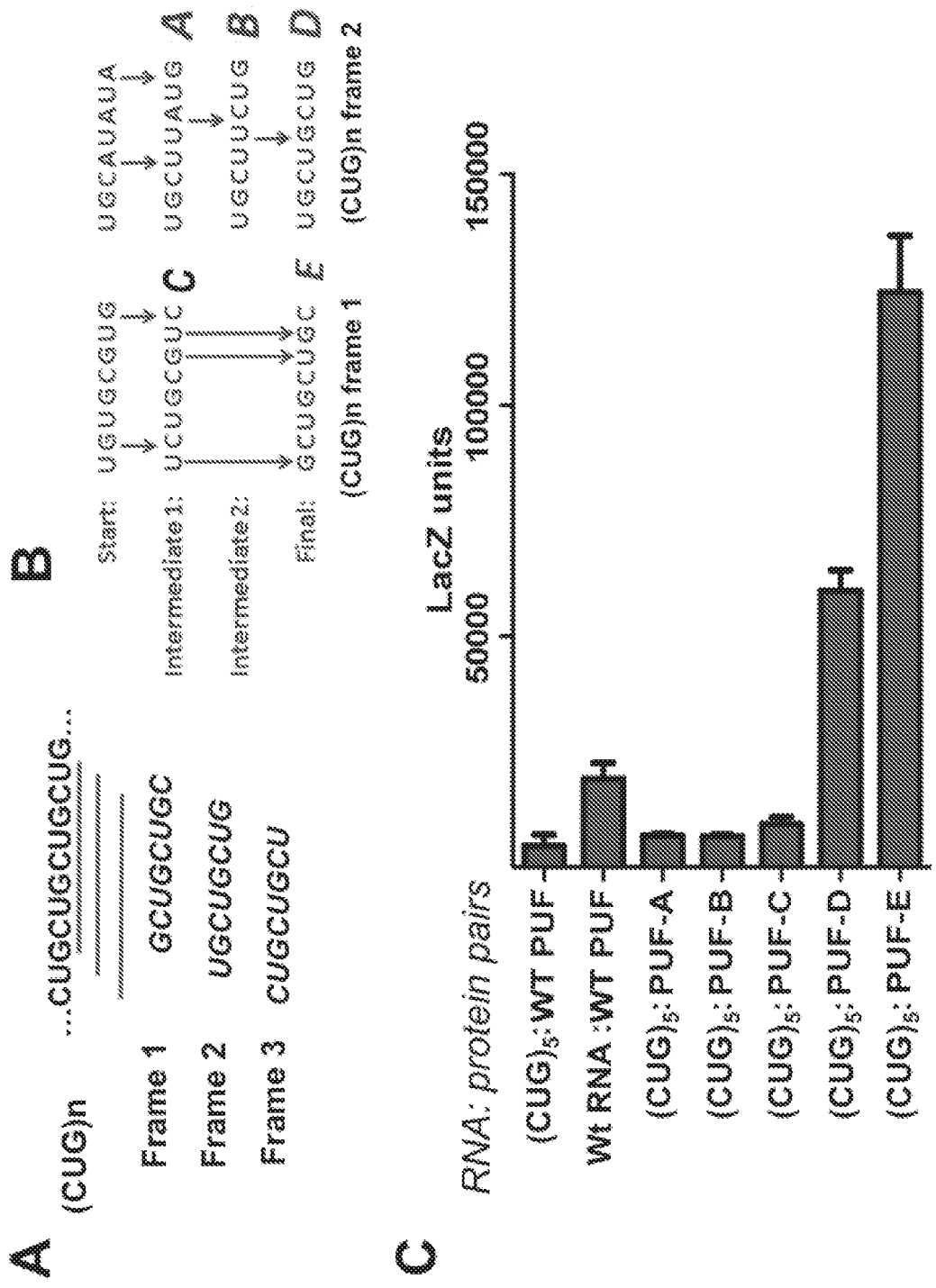
FIG. 25. Engineering PUF domains to specifically recognize $(CUG)_n$ repeats. (Panel A) The $(CUG)_n$ repeat (SEQ ID NO:144) can be recognized as 8-nt through three different frames, thus 3 possible PUF domains can be engineered. (Panel B) Step-wise mutating each PUF repeat to generate PUF domains that recognize different targets. The top row represents the starting sequences recognized by two modified PUF domains. Using site directed mutagenesis on each repeat, the PUF binding specificity was changed to recognize different intermediates, and the bottom sequences are $(CUG)_n$ frames 1 and 2 that were recognized by the PUF-D and PUF-E. (Panel C) Measurement of RNA:Protein interaction using Y3H system. The binding between wild type PUF and its cognate RNA was used as positive control.

The modular structure of the PUF domain enabled the programming of the specificity of each PUF repeat independently. After obtaining the "C binding code" with the Y3H screen of PUF repeat 6, other PUF repeats were changed into this modular code and it was confirmed that such modifications produced PUF domains that recognize RNAs with C at corresponding positions. This result suggested that the binding code is indeed "modular," which will enable the design of a PUF domain that specifically recognizes any 8-nt RNA in $(CUG)_n$ repeat. The $(CUG)_n$ repeat can generate three different RNA octamers (CUGCUGCU, UGCUGCUG and GCUGCUGC) according to different frames (FIG. 25, Panel A). Through step-wise mutagenesis on each PUF repeat, three PUF domains can be engineered, each recognizing one of the possible 8-nt in $(CUG)_n$. The binding affinity of PUF:$(CUG)_n$ will be assayed either with the Y3H assay (by measuring the β-gal activity (42)), or with a standard electrophoretic mobility shift assay (EMSA) using purified PUFs.

FIG. 25, Panel B shows two examples of PUF domains (PUF-D and PUF-E) that were step-wise mutated in each PUF repeat to recognize frame 1 and 2 of $(CUG)_n$. The starting PUF domains were generated for other reasons to recognize different sequence, and 1-3 PUF repeats were mutated in each step to change the binding specificity of that repeat (indicated with arrows in FIG. 25, Panel B). This process will generate several intermediate PUF domains (PUF-A to C) that recognize different 8-nt targets. The intermediate PUFs and final PUFs were co-transfected with $(CUG)_5$ RNA into the Y3H system, and assays were carried out to detect binding between different PUFs to the $(CUG)_5$ RNA which contains only a single copy of the 8-nt target. It was found that only the PUF-D and PUF-E, not the intermediate PUFs (PUF-A to C) or the wt-PUF, can bind $(CUG)_5$ to mediate LacZ expression (FIG. 25, Panel C). The binding between designer PUFs to the $(CUG)_5$ repeat is very specific, with much higher affinity than the binding between WT-PUF to its target as judged by LacZ expression (FIG. 25, Panel C). This experiment demonstrated that the newly identified "C code" could indeed be used to engineer PUFs.

PUF domains will be generated that bind to the third frame of $(CUG)_n$. The resulting PUFs for all three frames will be expressed and purified to measure the binding affinity to synthesized $(CUG)_n$ (n=10, 20 and 50, RNA will be chemically synthesized or transcribed in vitro). A determination will also be made of the PUF:$(CUG)_n$ binding stoichiometry, which may depend on RNA length. Studies will be conducted to examine if the designer PUF domains can bind to control sequences such as $(GUC)_n$ and $(CAG)_n$ that form similar structures but have different 8-nt sub-sequence. PUF domains will be generated that can be used either as the RNA binding modules of ASREs, or as competitors of the endogenous MBNL1 sequestered by the toxic RNA repeats.

Engineering and Optimizing ASREs that Recognize $(CUG)_n$ Repeats.

ASREs will be constructed with an N-terminal PUF domain and C-terminal PIN domain linked by a short linker (FIG. 23, Panel A). A nuclear localization signal (NLS) that directs the ASRE to the nucleus and a His-tag for detection/purification will be included. The NLS from SV40 large T-antigen (PKKKRKV, SEQ ID NO:72) will be used, which does not interfere with functions of PUF fusion proteins (33). At least three designer ASREs will be engineered with PUF domains recognizing all 8-nt sequences in $(CUG)_n$ repeats (FIG. 25, Panel A).

The ASREs will be expressed and purified, and their activities will be tested in vitro using $(CUG)_n$ substrates (n=10, 20 and 50). The RNA products will be separated with denatured PAGE gel to access the cleavage results. The catalytic efficiencies of new ASREs will be compared to the previous ones that have $k_{cat}/K_M$ in the range of $\sim 10^7 M^{-1} min^{-1}$. Since previous ASREs made a single cleavage in RNA substrate with one PUF binding site, studies will be conducted to examine how the new ASREs will cut $(CUG)_n$ containing multiple target sites.

The amino acid combination that can make the PUF repeat recognize C has been identified. Since the native PUF domains were never found to be able to recognize C, the Y3H screen makes it possible to engineer an RNA recognition domain for any 8-nt target. However, the binding selectivity against other bases may not be optimal, and it was found that the newly modified PUF can recognize a U residue in the third position with a low affinity (FIG. 24, Panel D). The binding specificity will be optimized by molecular modeling and mutagenesis. The PUF-RNA interface near the C nucleotide will be modeled using the PUF structure and Resetta software platform (43). The goal is to identify additional PUF mutations that decrease affinity to A, U and G while maintaining the affinity to C nucleotide.

The slight compromise of the binding affinity between designer PUFs and their target should not be very serious for the goal of recognizing $(CUG)_n$ repeats, as the long repeats contain many copies of the same sequence. The results of molecular modeling will be applied to mutate the base at position 17 of each repeat, which is responsible for the stacking of RNA base to the PUF repeat. Different amino acids will be tested in this position to increase the selectivity at the expense of decreasing binding affinity. The resulting PUFs will be optimized to recognize $(CUG)_n$, and have a balance between binding affinity and sequence selectivity.

Cleavage of Toxic (CUG)n Repeats in DM1 Cells with Artificial RNA Endonuclease.

Mammalian expression vectors of designer ASREs will be generated to test if they can cleave $(CUG)_n$ inside cultured cells. Cultured muscle cells from transgenic DM1 mouse ($HSA^{LR}$ mice; University of Rochester) and human DM1 fibroblasts (Coriell Cell Repositories) will be used. The cultured cells will be transfected with either transient or stable expression vectors containing designer ASRE genes, and assayed to determine (i) the expression and nuclear localization of ASREs, (ii) if the ASREs can disperse the nuclear foci of $(CUG)_n$, (iii) if the $(CUG)_n$ RNA is degraded, and (iv) if the MBNL1 are released from the nuclear foci by ASREs. Western blot will be used to examine if the level of CUGBP1 will be decreased in the ASRE transfected cells.

Further testing will be done to determine the level and localization of related splicing factors such as MBNL2, MBXL and CUGBP2, which may play partially overlapping roles with MBNL1 and CUGBP1 (10). In addition, RT-PCR will be used to examine the alternative splicing events in genes that are affected by $(CUG)_n$ in DM1 patients. Focus will be on splicing of ClC-1, insulin receptor, cTnT and SERCA1, all of which are known to undergo splicing shift in DM1 cells to produce embryonic isoforms. The reversal of the splicing by designer ASREs in cultured DM1 cells is the expected outcome.

Determination of how the designer ASREs affect alternative splicing in genomic scale.

Studies will be conducted to further examine how the designer ASREs will affect gene expression and alternative splicing in genomic scale. The high throughput (HTP) sequencing of total mRNA will be carried out using mRNAs from DM1 cells treated with designer ASREs, control ASRE and empty vector. Changes in both total gene expression and ratios of splicing isoforms will be determined. In other projects a reliable protocol was used to generate a directional cDNA library for HTP sequencing. It was possible to obtain >20 million reads of 75 nt in a single illumina sequencing lane, and the Bowtie-TopHat pipeline was used to analyze the alternative splicing events. The changes of each alternative splicing event between different samples can be scored using the fisher's exact test (44). The mRNA-seq data will be compared with the previous splicing microarray result in DM1 mice (13), and a determination will be made regarding whether the same set of alternative splicing events can be reversed by designer ASREs.

Because the mRNA-seq experiments can generate a large amount of data for the expression of all genes, such data can be used to assess the off-target effect of ASRE treatment. The $(CUG)_n$ repeat will be the best substrate of the designer ASRE as it contains many copies of ASRE targets. Other nuclear RNA may be cleaved to a lesser extent, and mRNA in the cytoplasm will largely evade cleavage. Therefore a large off-target effect is not expected. However, in case that other mRNAs containing the same 8-nt sequence are cleaved and such genes are critical to normal function of cells, a computer will be used to scan the mRNA for the ASRE target, and a combination of multiple ASREs that target different 8-nt in $(CUG)_n$ will be used to minimize the off-target effect. Using multiple ASREs at a lower level will decrease the off-target effects as only the (CUG)$_n$ can be targeted by all designer ASREs.

Determination of the in vivo efficacy of designer ASREs using DM1 mouse model.

In these studies, the in vivo efficacy of ASRE will be determined in a animal model of DM1. In particular, viral vectors will be used to deliver ASREs into DM1 mouse model (HSA$^{LR}$ mice) and tests will be done to determine if the ASREs can correct the alternative splicing of key genes and relieve the DM1 phenotype in muscle and heart.

Generation of AAV Virus Particles ASRE with AAV Vectors.

Because of the relatively small size of the ASRE gene (~1.5 kb), it can be packaged with an AAV vector that has been shown to efficiently deliver genes into skeletal muscles and heart (21,45,46).

ASREs that can effectively cleave (CUG)$_n$ repeat in vitro will be cloned into different AAV vectors. As controls, ASREs that recognize different RNA sequences and the ASRE with mutated active site in the PIN domain will be used. Two types of promoters will be tested to drive the expression of ASRE in AAV: the first is the CMV promoter that is commonly used in AAV systems for high level expression in all tissues, the second type are muscle-specific promoters such as inyogenin promoter and/or synthetic muscle promoters (47). The expression efficiency of the two types of promoters will be analyzed in cultured skeletal muscle cells, and the muscle-specific promoters will be selected if the expression level is comparable to CMV. The goal is to make ASRE expression more specific in muscles, therefore limiting the possible off-target effects. Upon confirming expression in muscle cells, AAV particles will be generated that contain ASREs.

Local Delivery of ASREs with AAV Vectors.

To test the efficiency of ASREs in the whole animal, experiments will be carried out using intra muscular injection of AAV particles into mouse vastus muscles. A DM1 mouse model (HSA$^{LR}$ mouse) that contains
  250 non-coding (CUG)$_n$ repeats and that can reproduce the DM phenotypes (7) will be used. AAV serotype 9 (AAV9), which can mediate high level gene expression in muscle and heart by either systematic injection or local injection (48, 49) will be used. It is expected that the muscle tissues near the injection region will stably express ASREs 1-2 weeks after injection, leading to the cleavage of (CUG)n repeats.

To determine the in vivo effects of ASREs, the muscle fibers will be dissected and assayed for the accumulation of (CUG)$_n$ repeat with fluorescence in situ hybridization (FISH). Assays will also be done to determine the distribution pattern of MBNL1 that is accumulated as nuclear foci in HSA$^{LR}$ mouse but has a dispersed nuclear localization pattern in normal mouse. The level of other proteins (such as CUGBP1) whose expressions have changed in DM1 patients by (CUG)$_n$ repeats will also be measured, and it will be determined if the ASRE can restore normal expression levels of these proteins. In addition, RNA will be purified from the muscle tissues in the injected region and RT-PCR will be used to assay for the alternative splicing pattern of key genes that were affected in HSA$^{LR}$ mouse (including ClC-1, cTnT and SERCA1). It is expected that the splicing pattern of these genes will be shifted towards the normal adult isoforms by ASREs compared to the controls. To determine whether AAV treatment can rescue the physiological deficits of DM1, the expression and function of muscle-specific chloride channel (ClC-1) will be examined. Finally, it will be determined whether the ASRE treatments can reduce the myotonia phenotype of muscles using electromyography (EMG) (7).

Systemic Delivery of ASREs with AAV9.

In the second stage of experiments, intravenous injection will be used to deliver ASRE expressing virus (AAV9) into HSA$^{LR}$ mice. Since AAV9 can facilitate robust gene expression in muscles and heart after systemic delivery (48, 49), it is expected that ASREs will be highly expressed in muscles and heart several days after IV injection. Similar experiments will be carried out to test the in vivo effects of ASREs on muscle tissues as described herein. Briefly, (i) assays for the accumulation of (CUG)$_n$ repeats will be carried out with FISH to determine if ASRE can disperse the nuclear foci; (2) assays for the distribution pattern of MBNL1 and the expression levels of CELF proteins will be carried out; (3) assays for alternative splicing patterns for key genes that were affected in HSA$^{LR}$ mouse (including ClC-1, cTnT and SERCA1) will be carried out; and (4) assays to determine whether AAV treatment can rescue the physiological deficits of DM1, including the electrophysiological properties of muscle-specific chloride channel (ClC-1) and the myotonia phenotype of muscles will be carried out.

Further studies will be conducted to examine if the ASRE treatment can reduce the histologically defined myopathy. In addition, the HSA$^{LR}$ mice had a mortality of 41% by 44 weeks after weaning (compared to <5% for non-transgenic mice) (7), thus studies will be conducted to determine if the ASRE treatment can reduce the mortality rate of DM1 mice.

References for Example 3

1. Lee J E, Cooper T A. Pathogenic mechanisms of myotonic dystrophy. Biochem Soc Trans. 2009; 37(Pt 6):1281-6.
2. Turner C, Hilton-Jones D. The myotonic dystrophies: diagnosis and management. J Neurol Neurosurg Psychiatry. 2010; 81 (4):358-67.
3. Wheeler T M, Thornton C A. Myotonic dystrophy: RNA-mediated muscle disease. Curr Opin Neurol. 2007; 20(5):572-6.
4. Mahadevan M, Tsilfidis C, Sabourin L, Shutler G, Amemiya C, Jansen G, et al. Myotonic dystrophy mutation: an unstable CTG repeat in the 3' untranslated region of the gene. Science. 1992; 255(5049):1253-5.
5. Brook J D, McCurrach M E, Harley H G, Buckler A J, Church D, Aburatani H, et al. Molecular basis of myotonic dystrophy: expansion of a trinucleotide (CTG) repeat at the 3' end of a transcript encoding a protein kinase family member. Cell. 1992; 68(4):799-808.
6. Liguori C L, Ricker K, Moseley M L, Jacobsen J F, Kress W, Naylor S L, et al. Myotonic dystrophy type 2 caused by a CCTG expansion in intron 1 of ZNF9. Science. 2001; 293(5531):864-7.
7. Mankodi A, Logigian E, Callahan L, McClain C, White R, Henderson D, et al. Myotonic dystrophy in transgenic mice expressing an expanded CUG repeat. Science. 2000; 289(5485): 1769-73.
8. Miller J W, Urbinati C R, Teng-Umnuay P, Stenberg M G, Byrne B J, Thornton C A, et al. Recruitment of human muscleblind proteins to (CUG)(n) expansions associated with myotonic dystrophy. EMBO J. 2000; 19(17):4439-48. PMCID: PMC302046.
9. Jiang H, Mankodi A, Swanson M S, Moxley R T, Thornton C A. Myotonic dystrophy type 1 is associated with nuclear foci of mutant RNA, sequestration of muscleblind proteins and deregulated alternative splicing in neurons. Hum Mol Genet. 2004; 13(24):3079-88.

10. Fardaei M, Rogers M T, Thorpe H M, Larkin K, Hamshere M G, Harper P S, et al. Three proteins, MBNL, MBLL and MBXL, co-localize in vivo with nuclear foci of expanded-repeat transcripts in DM1 and DM2 cells. Hum Mol Genet. 2002; 11(7):805-14.

11. Philips A V, Timchenko L T, Cooper T A. Disruption of splicing regulated by a CUG-binding protein in myotonic dystrophy. Science. 1998; 280(5364):737-41.

12. Kuyumcu-Martinez N M, Wang G S, Cooper T A. Increased steady-state levels of CUGBP1 in myotonic dystrophy 1 are due to PKC-mediated hyperphosphorylation. Mol Cell. 2007; 28(1):68-78. PMCID: PMC2083558.

13. Du H, Cline M S, Osborne R J, Tuttle D L, Clark T A, Donohue J P, et al. Aberrant alternative splicing and extracellular matrix gene expression in mouse models of myotonic dystrophy. Nat Struct Mol Biol. 2010; 17(2): 187-93. PMCID: PMC2852634.

14. Charlet B N, Savkur R S, Singh G, Philips A V, Grice E A, Cooper T A. Loss of the muscle-specific chloride channel in type 1 myotonic dystrophy due to misregulated alternative splicing. Mol Cell. 2002; 10(1):45-53.

15. Mankodi A, Takahashi M P, Jiang H, Beck C L, Bowers W J, Moxley R T, et al. Expanded CUG repeats trigger aberrant splicing of ClC-1 chloride channel pre-mRNA and hyperexcitability of skeletal muscle in myotonic dystrophy. Mol Cell. 2002; 10(1):35-44.

16. Savkur R S, Philips A V, Cooper T A. Aberrant regulation of insulin receptor alternative splicing is associated with insulin resistance in myotonic dystrophy. Nat Genet. 2001; 29(1):40-7.

17. Kimura T, Nakamori M, Lueck J D, Pouliquin P, Aoike F, Fujimura H, et al. Altered mRNA splicing of the skeletal muscle ryanodine receptor and sarcoplasmic/endoplasmic reticulum Ca2+-ATPase in myotonic dystrophy type 1. Hum Mol Genet. 2005; 14(15):2189-200.

18. Hino S, Kondo S, Sekiya H, Saito A, Kanemoto S, Murakami T, et al. Molecular mechanisms responsible for aberrant splicing of SERCA1 in myotonic dystrophy type 1. Hum Mol Genet. 2007; 16(23):2834-43.

19. Kalsotra A, Xiao X, Ward A J, Castle J C, Johnson J M, Burge C B, et al. A postnatal switch of CELF and MBNL proteins reprograms alternative splicing in the developing heart. Proc Natl Acad Sci USA. 2008; 105(51):20333-8. PMCID: PMC2629332.

20. Kanadia R N, Shin J, Yuan Y, Beattie S G, Wheeler T M, Thornton C A, et al. Reversal of RNA missplicing and myotonia after muscleblind overexpression in a mouse poly(CUG) model for myotonic dystrophy. Proc Natl Acad Sci USA. 2006; 103(31):11748-53. PMCID: PMC1544241.

21. Wang Z, Zhu T, Qiao C, Zhou L, Wang B, Zhang J, et al. Adeno-associated virus serotype 8 efficiently delivers genes to muscle and heart. Nat Biotechnol. 2005; 23(3): 321-8.

22. Langlois M A, Boniface C, Wang G, Alluin J, Salvaterra P M, Puymirat J, et al. Cytoplasmic and nuclear retained DMPK mRNAs are targets for RNA interference in myotonic dystrophy cells. J Biol Chem. 2005; 280(17):16949-54.

23. Mulders S A, van den Broek W J, Wheeler T M, Croes H J, van Kuik-Romeijn P, de Kimpe S J, et al. Triplet-repeat oligonucleotide-mediated reversal of RNA toxicity in myotonic dystrophy. Proc Natl Acad Sci USA. 2009; 106(33):13915-20. PMCID: PMC2728995.

24. Langlois M A, Lee N S, Rossi J J, Puymirat J Hammerhead ribozyme-mediated destruction of nuclear foci in myotonic dystrophy myoblasts. Mol Ther. 2003; 7(5 Pt 1):670-80.

25. Wheeler T M, Sobczak K, Lueck J D, Osborne R J, Lin X, Dirksen R T, et al. Reversal of RNA dominance by displacement of protein sequestered on triplet repeat RNA. Science. 2009; 325(5938):336-9.

26. Gareiss P C, Sobczak K, McNaughton B R, Palde P B, Thornton C A, Miller B L. Dynamic combinatorial selection of molecules capable of inhibiting the (CUG) repeat RNA-MBNL1 interaction in vitro: discovery of lead compounds targeting myotonic dystrophy (DM1). J Am Chem Soc. 2008; 130(48):16254-61. PMCID: PMC2645920.

27. Arambula J F, Ramisetty S R, Baranger A M, Zimmerman S C. A simple ligand that selectively targets CUG trinucleotide repeats and inhibits MBNL protein binding. Proc Natl Acad Sci USA. 2009; 106(38):16068-73. PMCID: PMC2752522.

28. Warf M B, Nakamori M, Matthys C M, Thornton C A, Berglund J A. Pentamidine reverses the splicing defects associated with myotonic dystrophy. Proc Natl Acad Sci USA. 2009; 106(44):18551-6. PMCID: PMC2774031.

29. Wickens M, Bernstein D S, Kimble J, Parker R. A PUF family portrait: 3'UTR regulation as a way of life. Trends Genet. 2002; 18(3):150-7.

30. Wang X, McLachlan J, Zamore P D, Hall T M. Modular recognition of RNA by a human *pumilio*-homology domain. Cell. 2002; 110(4): 501-12.

31. Cheong C G, Hall T M. Engineering RNA sequence specificity of *Pumilio* repeats. Proc Natl Acad Sci USA. 2006; 103(37):13635-9. PMCID: PMC1564246.

32. Ozawa T, Natori Y, Sato M, Umezawa Y. Imaging dynamics of endogenous mitochondrial RNA in single living cells. Nat Methods. 2007; 4(5):413-9.

33. Wang Y, Cheong C G, Hall T M, Wang Z. Engineering splicing factors with designed specificities. Nat Methods. 2009; 6(11):825-30.

34. MacRae I J, Doudna J A. Ribonuclease revisited: structural insights into ribonuclease III family enzymes. Curr Opin Struct Biol. 2007; 17(1):138-45.

35. Champoux J J, Schultz S J. Ribonuclease H: properties, substrate specificity and roles in retroviral reverse transcription. FEBS J. 2009; 276(6):1506-16.

36. Scott W G. Ribozymes. Curr Opin Struct Biol. 2007; 17(3):280-6.

37. Yoshida H. The ribonuclease T1 family. Methods Enzymol. 2001; 341:28-41.

38. Hammond S M, Wood M J. PRO-051, an antisense oligonucleotide for the potential treatment of Duchenne muscular dystrophy. Curr Opin Mol Ther. 2010; 12(4): 478-86.

39. Takeshita D, Zenno S, Lee W C, Saigo K, Tanokura M. Crystal structure of the PIN domain of human telomerase-associated protein EST1A. Proteins. 2007; 68(4):980-9.

40. Glavan F, Behm-Ansmant I, Izaurralde E, Conti E. Structures of the PIN domains of SMG6 and SMG5 reveal a nuclease within the mRNA surveillance complex. EMBO J. 2006; 25(21):5117-25.

41. Hook B, Bernstein D, Zhang B, Wickens M. RNA-protein interactions in the yeast three-hybrid system: affinity, sensitivity, and enhanced library screening. Rna. 2005; 11(2):227-33.

42. Stumpf C R, Opperman L, Wickens M. Chapter 14. Analysis of RNA-protein interactions using a yeast three-hybrid system. Methods Enzymol. 2008; 449:295-315.

43. Das R, Baker D. Macromolecular modeling with rosetta. Annu Rev Biochem. 2008; 77:363-82.
44. Wang E T, Sandberg R, Luo S, Khrebtukova I, Zhang L, Mayr C, et al. Alternative isoform regulation in human tissue transcriptomes. Nature. 2008; 456(7221):470-6. PMCID: PMC2593745.
45. Zhu T, Zhou L, Mori S, Wang Z, McTiernan C F, Qiao C, et al. Sustained whole-body functional rescue in congestive heart failure and muscular dystrophy hamsters by systemic gene transfer. Circulation. 2005; 112(17):2650-9.
46. Wang B, Li J, Fu F H, Xiao X. Systemic human minidystrophin gene transfer improves functions and life span of dystrophin and dystrophin/utrophin-deficient mice. J Orthop Res. 2009; 27(4):421-6.
47. Li X, Eastman E M, Schwartz R J, Draghia-Akli R. Synthetic muscle promoters: activities exceeding naturally occurring regulatory sequences. Nat Biotechnol. 1999; 17(3):241-5.
48. Kornegay J N, Li J, Bogan J R, Bogan D J, Chen C, Zheng H, et al. Widespread muscle expression of an AAV9 human mini-dystrophin vector after intravenous injection in neonatal dystrophin-deficient dogs. Mol Ther. 2010; 18(8):1501-8. PMCID: PMC2927072.
49. Inagaki K, Fuess S, Storm T A, Gibson G A, McTiernan C F, Kay M A, et al. Robust systemic transduction with AAV9 vectors in mice: efficient global cardiac gene transfer superior to that of AAV8. Mol Ther. 2006; 14(1): 45-53. PMCID: PMC1564441.

Example 4

PUF proteins possess a recognition code for bases A, U and G, allowing designed RNA sequence specificity of their modular *Pumilio* (PUM) repeats. However, recognition side chains in a PUM repeat for cytosine are unknown. Described herein is the identification of a cytosine-recognition code by screening random amino acid combinations at conserved RNA recognition positions using a yeast 3-hybrid system. This C-recognition code is specific and modular, as specificity can be transferred to different positions in the RNA recognition sequence. A crystal structure of a modified PUF domain reveals specific contacts between an arginine side chain and the cytosine base. The C-recognition code was applied to design PUF domains that recognize targets with multiple cytosines and to generate engineered splicing factors that modulate alternative splicing. A divergent yeast PUF protein, Nop9p, was also identified, that may recognize natural target RNAs with cytosine. This work furthers understanding of natural PUF protein target recognition and expands the ability to engineer PUF domains to recognize any RNA sequence.

The specific interaction of RNA and protein plays vital roles in RNA regulation including splicing, localization, translation and degradation. Such recognition may be directed toward unstructured RNA requiring discrimination of RNA sequences, folded RNA motifs, or some combination of sequence and structural specificity (1). Members of the PUF protein family (named after *Drosophila Pumilio* and *Caenorhabditis elegans* fem-3 mRNA binding factor [FBF]) are sequence-specific RNA-binding proteins that regulate networks of mRNAs encoding proteins of related function (2-7). PUF proteins generally recognize the 3'-UTR of their target mRNAs to control the mRNA stability and translation (2-7).

The RNA-binding domain of PUF proteins, known as the *Pumilio* homology domain (PUM-HD) or PUF domain, can bind to unstructured RNA sequences in a distinct fashion. The PUF domain of human *Pumilio* 1 contains eight PUM repeats, each containing three α-helices packed together in a curved structure (8-10). RNA is bound as an extended strand to the concave surface of the PUF domain with the bases contacted by protein side chains. In general, each PUM repeat recognizes a single RNA base through the second helix (a2) in an antiparallel arrangement, i.e., nucleotides 1-8 are recognized by PUF repeats 8-1, respectively. The a2 helices of PUM repeats contain a five-residue sequence, designated here as 12xx5, where the side chain at position 2 stacks with the recognized base and the side chains at positions 1 and 5 recognize the edge of the base (8,11) (FIG. 27, Panel A). Specific residues at these positions direct the base recognition properties of the repeat. This PUF-RNA recognition code makes it possible to modify a PUM repeat to bind a particular RNA base, producing a designed PUF domain that specifically recognizes a given 8-nt RNA target. Such de novo designed RNA binders have been used to track RNA localization in cells (12,13), study PUF protein function (14,15), and modulate alternative splicing (16) and continue to provide a useful tool for biomedical research with possible therapeutic applications.

One limitation to application of designed PUF proteins is that, although the modular code for recognition of RNA bases A, U and G has been deduced, a code for cytosine recognition by a PUM repeat is unknown. Thus recognition of a cytosine cannot be engineered in a repeat, although *Pumilio* 1 can accept any base including cytosine at the $5^{th}$ position of the target sequence and yeast Puf3p specifically recognizes a cytosine two bases upstream of the core PUF recognition sequence (17). Naturally occurring PUM repeats that specifically recognize a cytosine have not been identified, providing no clues to a cytosine-recognition code and uncertainty about whether such specific recognition exists or is possible. The identification of a combination of amino acid side chains in a PUM repeat that can recognize a cytosine is necessary to expand the use of designed PUF domains directed toward any RNA sequence.

Using a yeast 3-hybrid system, it was found that the five-residue RNA-interaction sequence SYxxR (SEQ ID NO:4) allows PUM repeats of human *Pumilio* 1 (hereafter referred to as PUF for simplicity) to specifically interact with cytosine. In a crystal structure of a complex between a mutant PUF(SYxxR) and cognate RNA, the arginine side chain interacts directly with the cytosine and the serine side chain helps to position the arginine residue. This recognition code is applied as described herein to design new PUF domains to recognize RNA targets with multiple cytosine residues such as CUG repeats that are responsible for the pathogenesis of myotonic dystrophy. The code is also used to engineer splicing factors that modulate alternative splicing of both a splicing reporter and an endogenous gene. Furthermore, a naturally occurring yeast PUF protein, Nop9p, appears to contain a repeat with a code for cytosine and is conserved in homologs from yeast to human, suggesting that the natural target sequences of these PUF proteins may contain cytosine (FIG. 32).

Generation of a Random Sequence Library.

A PUF mutant library was generated through three PCR amplifications using primers with randomized regions. In reaction 1, the 5' portion of the *Pumilio* 1 PUF domain was amplified from wild-type PUF with primers Bam-Puf-1F (5'-GGA TCC GAG GCC GCA GCC GCC TTT TGG AA, SEQ ID NO:74) and Puf-R6N-2R (5'-GAT TAC ATA NNN TCC ATA TTG ATC CTG TAC CAG, SEQ ID NO:75). In reaction 2, the 3' portion of the PUF domain was amplified with primers Puf-R6N-1F (5'-TAT GTA ATC NNN CAT GTA CTG GAG CAC GGT CG, SEQ ID NO:76) and Puf-Xho-2R (5'-CTC GAG CCC CTA AGT CAA CAC CGT TCT TC, SEQ ID NO:77). The Puf-R6N-2R contains 3 random nucleotides encoding the amino acid at position 1043 while Puf-R6N-1F contains random nucleotides encoding the residue at position 1047. The purified PCR products of reactions 1 and 2 were mixed as the template for reaction 3 with primers Bam-Puf1-1F and Puf-Xho-2R. The final PCR products encode the entire PUF domain and have the two randomized codons at positions 1043 and 1047.

Yeast expression plasmid encoding wild-type PUF fused at the N terminus to the Gal-4 AD was created by amplification of the coding sequence of the PUF domain from pTYB3-HsPUM1-HD (9) and subcloned into the pACT2 plasmid using BamHI and XhoI sites. Plasmids expressing target RNAs were made by annealing DNA oligonucleotides encoding the desired RNAs and subcloning into the pIIIA-MS2-2 plasmid using SmaI and SphI restriction sites.

Y3H assays were performed in yeast strain YBZ-1 as described previously (18,19). For the Y3H screen, instead of generating an *E. coli* plasmid library, a yeast library screening system was generated directly through gap-repair. First, the pIIIA-MS2-2 plasmid carrying UGCAUAUA RNA was transformed and expressed in yeast strain YBZ-1. Second, an EcoRI site was introduced by site-directed mutagenesis into wild-type pACT2-PUF between the nucleotides encoding positions 1043 and 1047. The pACT2-PUF-Eco DNA was linearized by EcoRI and co-transformed with the random PUF PCR library at a molar ratio of 6:1 into the yeast. About 50,000 yeast clones were generated, giving at least 10-fold coverage of the entire 6-nt sequence space ($4^6$=4096). Yeast transformants were screened on plates lacking histidine and containing 10 mM 3-AT. The transformants that survived HIS growth selection were confirmed with LacZ expression. Selected yeast plasmid DNAs were sequenced and reintroduced into the mother strain to confirm the interaction and specificity.

Plasmid Constructs.

Additional PUF site-directed mutants carried by pACT2 were generated using the QuikChange site-directed mutagenesis kit (Agilent). The pTYB3-PUF mutants for in vitro protein expression were created by PCR amplification from yeast expression plasmids and subcloning into the pTYB3 plasmid using NcoI and SapI restriction sites. To generate the ESFs that recognize C-containing target sequences, plasmids encoding the RS-PUF or Gly-PUF fusion proteins (16) were mutated.

Liquid β-Galactosidase Assays.

The activity of β-galactosidase was measured using 96-well plates using 12 clones from each sample (20). The yeast colonies were randomly picked and inoculated into 12 different wells with 100 µl culture media in a 96-well plate. After overnight growth in 24° C. with shaking, the culture density of each well was determined by reading $OD_{650}$ with a plate-type spectrophotometer (spectroMAX PLUS from Molecular Devices). In each clone, 25 µl of cell culture was removed and transferred into a new 96-well plate and mixed with 225 µl of assay buffer (60 mM $Na_2HPO_4$, 40 mM $NaH_2PO_4$, 1 mM $MgCl_2$, 0.2% (wt/vol) Sarkosyl and 0.4 mg/ml ONPG). The plate was incubated at 37° C. for 2 hours and 100 µl of 1M carbonate solution was added into each well to stop the reaction. The $OD_{405}$ was measured with a spectrophotometer to quantify the product (nitrophenol). The β-galactosidase units were calculated as the difference of $OD_{405}$ between the sample and the background calibrated by culture densities (20).

Protein Expression, Purification and Electrophoretic Mobility Shift Assay (EMSA).

All proteins were expressed in *E. coli* strain BL21 and purified as described previously (9,11). Protein purity was examined with SDS/PAGE gel electrophoresis. Protein concentration was determined by Bradford assay. RNAs were generated by in vitro transcription and purified on denaturing gels. 50 pmol of RNAs were labeled at the 3' end with biotinylated cytidine bisphosphate using T4 RNA ligase following manufacturer's directions (Thermo Scientific Pierce RNA 3' End Biotinylation Kit). In each sample, 20 fmol of labeled RNA (1 nM) and 4 pmol of proteins (0.2 µM) were incubated in binding buffer (10 mM HEPES, pH 7.3, 20 mM KCl, 1 mM $MgCl_2$, 1 mM DTT, and 0.1 g/L tRNA) for 1 hour at room temperature. The binding reactions were separated by electrophoresis on 6% nondenaturing PAGE run with 1×TBE at 4° C., transferred to nylon membranes, and crosslinked to the membrane by UV. Biotin-labeled RNA was detected by chemiluminescence using the Thermo Scientific LightShift Chemiluminescent RNA EMSA Kit following manufacturer's directions.

Crystallization, Structure Determination and Refinement.

Crystals of PUF-R6(SYxxR) mutant and C3 RNA (5'-AUUGCAUAUA-3', SEQ ID NO:73) were grown by sitting drop vapor diffusion. RNA oligonucleotide was obtained from Dharmacon (Lafayette, Colo.). The protein-RNA complex was prepared by mixing a 1:1.1 molar ratio of purified protein (3.5 mg/ml) and RNA in a buffer containing 20 mM Tris-HCl, pH 7.5; 100 mM NaCl; and 1 mM DTT. One ul of complex solution was added to 1 µl of a well solution containing 30% PEG 3350, 0.2M ammonium tartrate dibasic, and 0.1M bis-Tris, pH 5.5. Crystals were flash frozen after adding an equal volume of cryoprotectant solution (32% PEG 3350, 20% ethylene glycol) to the drop. Diffraction data were collected at the SER-CAT beamline ID-22, Advanced Photon Source at wavelength 1.0 Å and −180° C. All data sets were indexed, integrated, and scaled with the HKL2000 suite (21). The structure was determined by molecular replacement using the structure of human *Pumilio*1 (PDB ID: 1M8Y) as a search model with PHASER (22). Two complexes are present in the asymmetric unit. Iterative model building was performed with COOT (23), and the resulting models were refined with PHENIX (24). All Phi-Psi angles are within allowable regions of the Ramachandran plot. The atomic coordinates and structure factors have been deposited in the Protein Data Bank (PDB ID: 2yjy).

Cell Culture, Transfection, RNA Purification, and RT-PCR.

Human embryonic kidney 293T cells or breast cancer MDA-MB-231 cells were grown in Dulbecco's modified Eagle's medium supplemented with 10% fetal bovine serum. Cells were seeded onto 24-well plates and transfected with Lipofectamine 2000 following manufacturer's directions. The purification of total RNA and semi-quantitative RT-PCR were carried out as described previously (16).

Bioinformatic Analyses.

Two PUF proteins in budding yeast, Puf2p and Nop9p, were identified by searching the SMART database. The *Saccharomyces* Genome Database was also searched using the BLASTP with the following queries: (1) the two natural yeast PUF repeats containing a possible C-recognition code, and (2) all the yeast PUF repeats in which the native RNA recognition motifs were replaced with SxxxR (SEQ ID NO:143). Only the two PUF repeats from Puf2p and Nop9p were identified. The entire PUF domains of Puf2p and Nop9p were used as queries to search the non-redundant protein sequences using PSI-BLAST (Position-Specific Iterated BLAST), and the positive hits were manually inspected to filter out repeats. A subset of representative sequences with significant matches was selected to cover a diverse range of organisms. These sequences were aligned with ClustalW and a phylogenetic tree was generated with Phylowidget.

Random Library Screen for Cytosine Recognition.

To select a PUM repeat that specifically recognizes cytosine, a yeast 3-hybrid (Y3H) system was used that utilizes co-expression of the PUF domain fused with the Gal-4 activation domain (AD), an RNA target with an MS2 binding site, and an MS2-LexA fusion protein (FIG. 27, Panel B). This system can be used to reliably measure the relative binding affinity between RNA and protein (18,19). For this screening, a uridine-to-cytosine mutation was introduced at the $3^{rd}$ position of a wild-type PUF target sequence (FIG. 27, Panel A). A PUF domain library was generated with random sequences at the $1^{St}$ and $5^{th}$ positions of the RNA-interaction motif in repeat 6, which recognizes the third position of the RNA target sequence (FIG. 27, Panels A and C). In control experiments, co-expression of wild-type PUF and its cognate target sequence (U3) resulted in activation of HIS3 and LacZ reporter genes. In contrast, wild-type PUF cannot recognize the target RNA with a cytosine at the third position (C3), suggesting that the screen has a low false positive background (FIG. 27, Panel D). Yeast transformants were screened first for HIS3 expression, and 200 of the resulting positive clones were reconfirmed with a LacZ activity assay. Plasmids encoding functional PUFs were recovered from the doubly-positive yeast clones (178 clones), and a subset were sequenced to identify amino acid combinations directing cytosine recognition.

Of the 19 unambiguous sequences obtained, 18 coded for serine at amino acid position 1043 and arginine at amino acid position 1047, positions 1 and 5 in the 5-residue RNA-interaction motif (Table 3, FIG. 27, Panel A). The only exception, clone 15, contained a stop codon at position 1047, and therefore is likely a false positive. The 18 clones encoding S1043/R1047 contained four different serine codons and six arginine codons, suggesting that the screen adequately covered sequence space. Identification of a set of cytosine-specific RNA recognition side chains (G/A/S/T/CxxxR, SEQ ID NO:78) was published (25). The more stringent conditions used in the studies described herein (10 mM vs. 0.5 mM 3-AT) may have produced the dominance of the SYxxR (SEQ ID NO:4) sequence over other sets of side chains with arginine at the $5^{th}$ position as seen in this other study (25). The relative β-galactosidase activities for the different sets of side chains suggests that the SYxxR (SEQ ID NO:4) combination binds most tightly (18, 25).

To examine the specificity of the newly identified C-recognition code, the RNA-protein interaction between PUF domains and RNA targets containing each of the four bases at the $3^{rd}$ position (FIG. 27, Panel E) was measured. It was found using a Y3H assay that wild-type PUF bound only to the natural target sequence with a U at the $3^{rd}$ position (U3), and a mutant protein, PUF-Eco, with an EcoRI site inserted between positions 1043 and 1047 did not recognize any of the target RNAs (FIG. 27, Panel E). The PUF with S1043/R1047 mutations in repeat 6, PUF-R6(SYxxR), specifically bound to the C3-containing target with similar affinity as the PUF-WT protein and U3 RNA (18) and did not recognize targets with an A3 or G3. Residual binding of PUF-R6 (SYxxR) to the wild-type U3 sequence was measured, likely due to the lack of a stacking side chain (asparagine) in repeat 7.

To further confirm RNA binding, the recombinant PUF protein was purified and electrophoretic mobility shift assay (EMSA) was used to demonstrate direct binding of PUF-R6(SYxxR) to C3 RNA. Given the direct and specific interaction with this in vitro assay, it was concluded that the expression of LacZ was indeed caused by the direct RNA-protein binding.

The Cytosine-Recognition Code can be Transferred to Other PUM Repeats.

To examine the modularity of the C-binding code identified using PUM repeat 6, the code was applied to PUM repeats 2 and 5 that normally bind to U7 and A4, respectively. It was then tested if such changes specify cytosine recognition at the cognate positions (C7 for repeat 2 and C4 for repeat 5) using the Y3H assay. As expected, mutation of the conserved RNA-interacting positions in repeat 2 (positions 899-903 becoming SYxxR, SEQ ID NO:4) changed binding specificity from U7 to C7, while wild-type PUF did not recognize a C7 RNA target (FIG. 28, Panel A). Unlike PUF-R6(SYxxR), PUF-R2(SYxxR) did not recognize wild-type U7 RNA sequence.

Similarly, mutations in repeat 5 (C1007S/Q1011R or SRxxR, SEQ ID NO:79) are sufficient to change the binding specificity from A4 to C4, while wild-type PUF does not recognize a C4 target RNA. Repeat 5 of wild-type PUF has an arginine (R1008) in position to stack with the RNA base, and it was found that the two mutations in the edge-interacting side chains were sufficient for cytosine recognition. Therefore, arginine can serve as the stacking amino acid residue in the C-binding code. However, introduction of a third mutation in repeat 5 (SYxxR (SEQ ID NO:4) in positions 1007-1011) maintained C-binding specificity and may better prevent binding to A4-containing RNA (FIG. 28, Panel B).

Effect of the Stacking Residue on Cytosine Recognition.

Based on modifications of repeat 5, it was established that arginine can serve as a stacking side chain for cytosine (FIG. 28, Panel B). Studies were conducted to test the effects of the identity of the stacking side chain on cytosine specificity.

The effect of stacking side chain identity was examined using position 1044 in repeat 6 of *Pumilio* 1, which has wild-type RNA-interaction motif NYxxQ (SEQ ID NO:80) that recognizes U3. The interaction motif was mutated to SHxxR (SEQ ID NO:81) and binding of the mutant protein, PUF-R6(SYxxR), to wild-type U3 and mutant C3 RNA targets was measured (FIG. 28, Panel C). PUF-R6(SHxxR) binds well to RNA containing C3 and more weakly to U3. When the stacking side chain is changed to tyrosine, PUF-R6(SYxxR), similar effects are seen. It is concluded that specific binding of cytosine can be achieved with Y/H/R as stacking residue in the cognate repeat.

Another naturally, though uncommonly, occurring side chain at the stacking position is asparagine, as seen in repeat 7 of wild-type *Pumilio* 1. This repeat specifically recognizes a G base with an SNxxE (SEQ ID NO:82) RNA interaction motif, but the side chain of N1080 is not long enough to form a stacking interaction with G2 (8,11). In order to change the specificity of repeat 7 to cytosine, the base-interacting residues were mutated initially to S1079/R1083. However, it was found that PUF-R7(SNxxR) did not bind to target RNAs containing G2 or C2, as judged by Y3H measurement (FIG. 28, Panel D). When the stacking residue in repeat 7 was also changed to tyrosine (N1080Y), the resulting PUF-R7(SYxxR) bound strongly to C2 and more weakly to G2 (FIG. 28, Panel D). Thus, for cytosine recognition, a side chain forming a stacking interaction with the RNA base appears important for binding.

In addition to residues in the cognate repeat, it was found that the identity of the stacking residue in the following repeat, which also contacts the RNA base, can contribute to the binding affinity at some positions. Most wild-type repeats in *Pumilio* 1 have tyrosine or arginine as the stacking residue in the following repeat, the only exception being repeat 3 with a histidine in repeat 4. When an attempt was made to transfer the C-binding code to repeat 3, it was found that neither SRxxR (SEQ ID NO:79) nor SYxxR (SEQ ID NO:4) introduced recognition of the cognate C6 (FIG. 28, Panel E). However, mutation of the following stacking residue to tyrosine (H972Y) allowed recognition of the C6 target (FIG. 28, Panel E).

Designed PUF Domains Recognize Targets with Multiple Cytosines.

Figure 29:
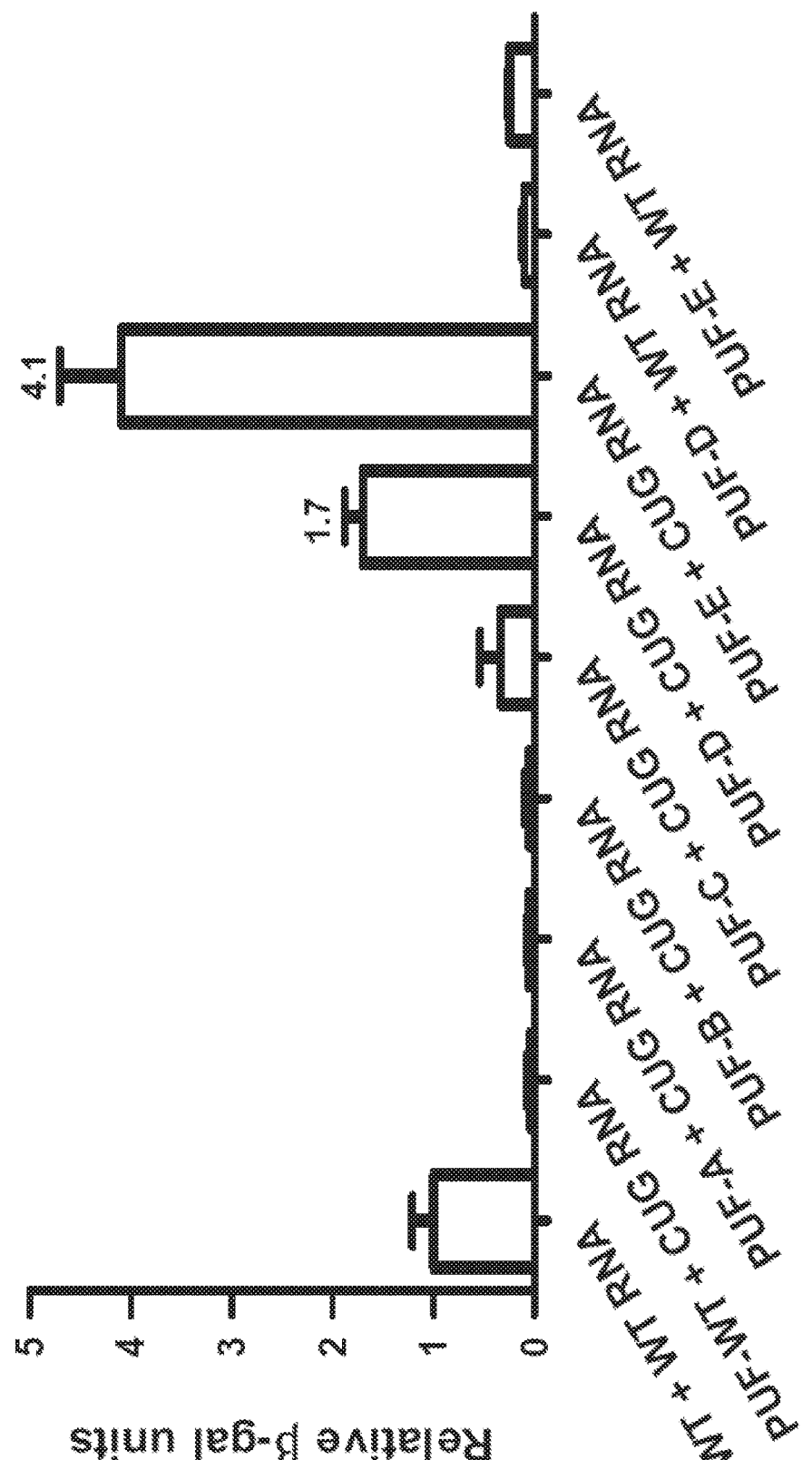
FIG. 29. Designed PUF domains that recognize targets with multiple cytosines. (Panel A) Diagram showing the mutations in PUM repeats 2 and 6 to recognize C3C7 RNA. Relative protein-RNA binding is shown as in FIG. 28. (Panel B) Stepwise generation of a PUF mutant (PUF-D) that can bind to $(CUG)_n$ repeat RNA. Diagrams showing the mutations in PUM repeats 1, 3, 4, 5 and 6 (PUF-D) or in PUM repeats 1, 2, 3, 5, 7 and 8 (PUF-E) to recognize $(CUG)_n$ repeat RNA. (Panel C) Relative protein-RNA binding to WT or $(CUG)_5$ RNA is shown as in FIG. 28.

To extend the studies of the modularity of the C-recognition code, it was sought to engineer new PUFs that can recognize multiple C residues in their target RNA sequences. A PUF was created to recognize the sequence UGCAUACA (C3C7) by combining previously studied modifications in repeats 2 and 6. It was found that only the PUF with both modified repeats, PUF-R6/R2(SYxxR), but neither the wild-type PUF nor PUFs with one modified repeat bound to the C3C7 sequence (FIG. 29, Panel A). This binding is specific because PUF-R6/R2(SYxxR) with two modified repeats did not bind to RNAs with one cytosine (C3U7) or no cytosines (wild type U3U7) at cognate positions (FIG. 29, Panel A).

Two PUFs were designed that recognize 8-nt signature sequences in $(CUG)_n$ RNA repeats. Expanded $(CUG)_n$ RNA repeats cause myotonic dystrophy type 1 (DM1). These toxic RNA repeats accumulate in the nucleus and sequester alternative splicing factors that normally regulate genes important for muscle and heart functions, thus leading to the pathogenesis observed in DM1 (27,28). Through stepwise mutagenesis two PUF domains were generated that recognize different frames of $(CUG)_n$ repeats. These proteins could be used to compete with the binding of splicing factors to pathogenic $(CUG)_n$ repeats. PUF-D was designed to recognize UGCUGCUG with five mutated repeats [R1 (SRxxE, SEQ ID NO:83), R3(SYxxR, SEQ ID NO:4), R4(SYxxE, SEQ ID NO:84), R5(NRxxQ, SEQ ID NO:85), and R6(SYxxR, SEQ ID NO:4)] and PUF-E was designed to recognize GCUGCUGC with mutations in six repeats [R1 (SYxxR, SEQ ID NO:4), R2(SYxxE, SEQ ID NO:84), R3(NRxxQ, SEQ ID NO:85), R5(SRxxE, SEQ ID NO:83), R7(SYxxR, SEQ ID NO:4), and R8(SYxxE, SEQ ID NO:84)] (FIG. 29, Panel B). It was found that PUF-D and PUF-E bound strongly to a $(CUG)_5$ target RNA but not to control RNA, whereas wild-type PUF and intermediate PUFs A to C essentially had no interaction with the $(CUG)_5$ target (FIG. 29, Panel B). The de novo design of $(CUG)_n$ binding PUFs demonstrates the potential to generate new RNA-binding scaffolds that may be used for therapeutic applications.

Crystal Structure of PUF-R6(SYxxR) and Cognate C3-Containing RNA.

Figure 30:
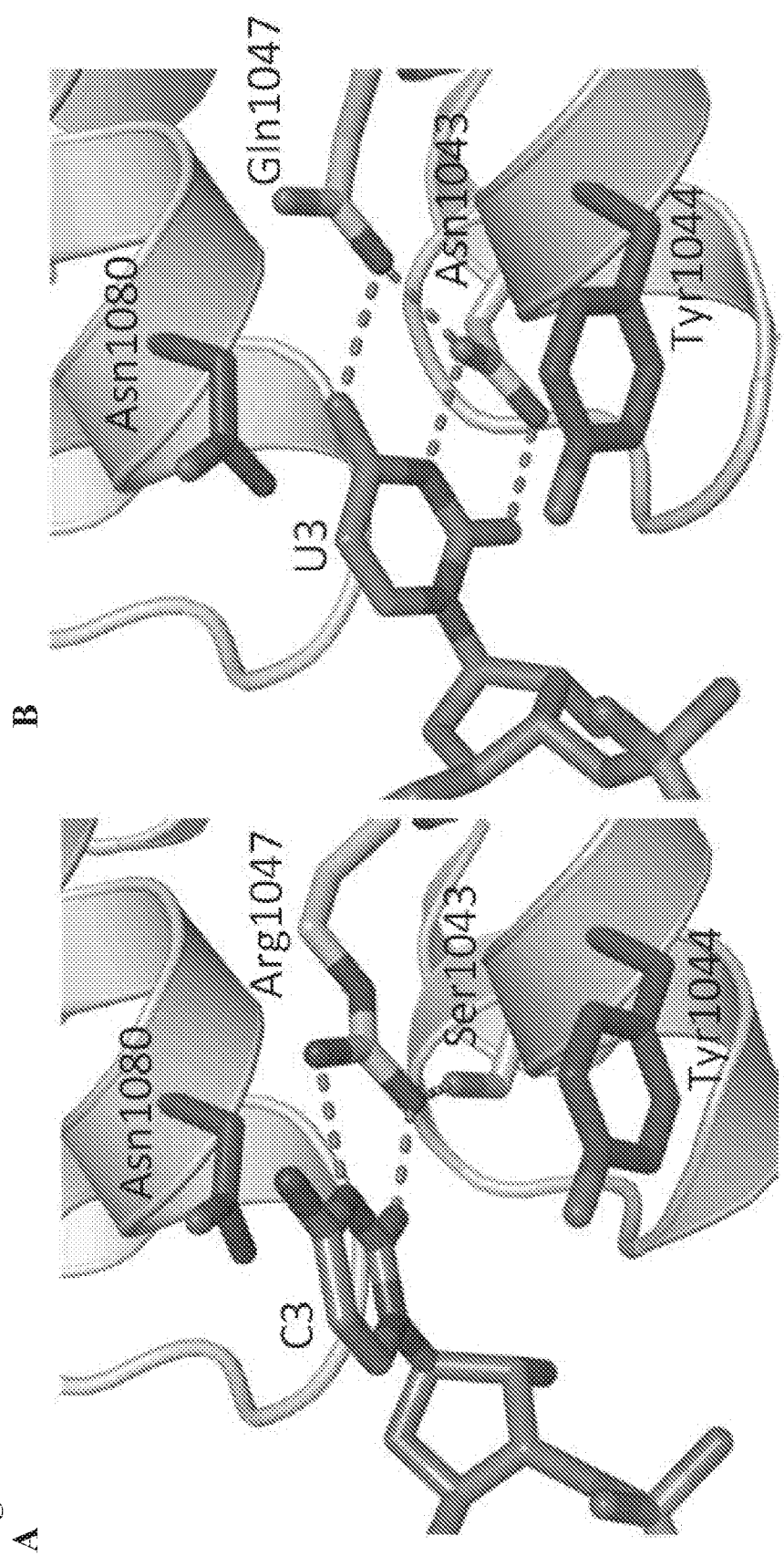
FIG. 30. Crystal structure of PUF-R6(SYxxR) in complex with C3 RNA. (Panel A) Interaction of PUF-R6(SYxxR) with C3 RNA. Ribbon diagram of interaction of repeat 6 with C3 base (complex 1 with chain A and C shown). (Panel B) Interaction of wild-type PUF(NYxxQ) with U3 RNA. Ribbon diagram of interaction of repeat 6 with U3 base. RNA and base-interacting side chains are shown as stick models. Hydrogen bonds are indicated with dashed lines. This figure was created with PyMol.

In order to examine how the side chains forming the C-recognition code are used to specifically recognize cytosine, a crystal structure of PUF-R6(SYxxR) in complex with a cognate C3 RNA (5'-AUUGCAUAUA-3', SEQ ID NO:73) was determined. In the structure, R1047 contacts the 02 and N3 positions of the cytosine (FIG. 30, Panel A). S1043 forms a hydrogen bond with an amino group of the arginine side chain, assisting in positioning R1047. This interaction is similar to the interaction of N1043 and Q1047 in the wild-type protein with the Watson-Crick edge of U3 (FIG. 30, Panel B), although the longer arginine side chain requires the cytosine base ring position to be shifted slightly away from the RNA-binding surface. Interaction with only the known base-interacting side chains is consistent with the ability to transfer C-recognition to other PUM repeats. The crystal structure also indicates that other small side chains could occupy the position of 51043 and alternate conformations of R1047 can recognize the cytosine, but the ability of the serine side chain to assist in positioning the arginine side chain may produce tighter binding (25).

Applying the Cytosine-Recognition Code to Designed Artificial Splicing Factors.

Engineered splicing factors (ESFs) have been developed by combining a designed PUF domain with different splicing modulation domains to specifically regulate different types of alternative splicing events (16).

Figure 31:
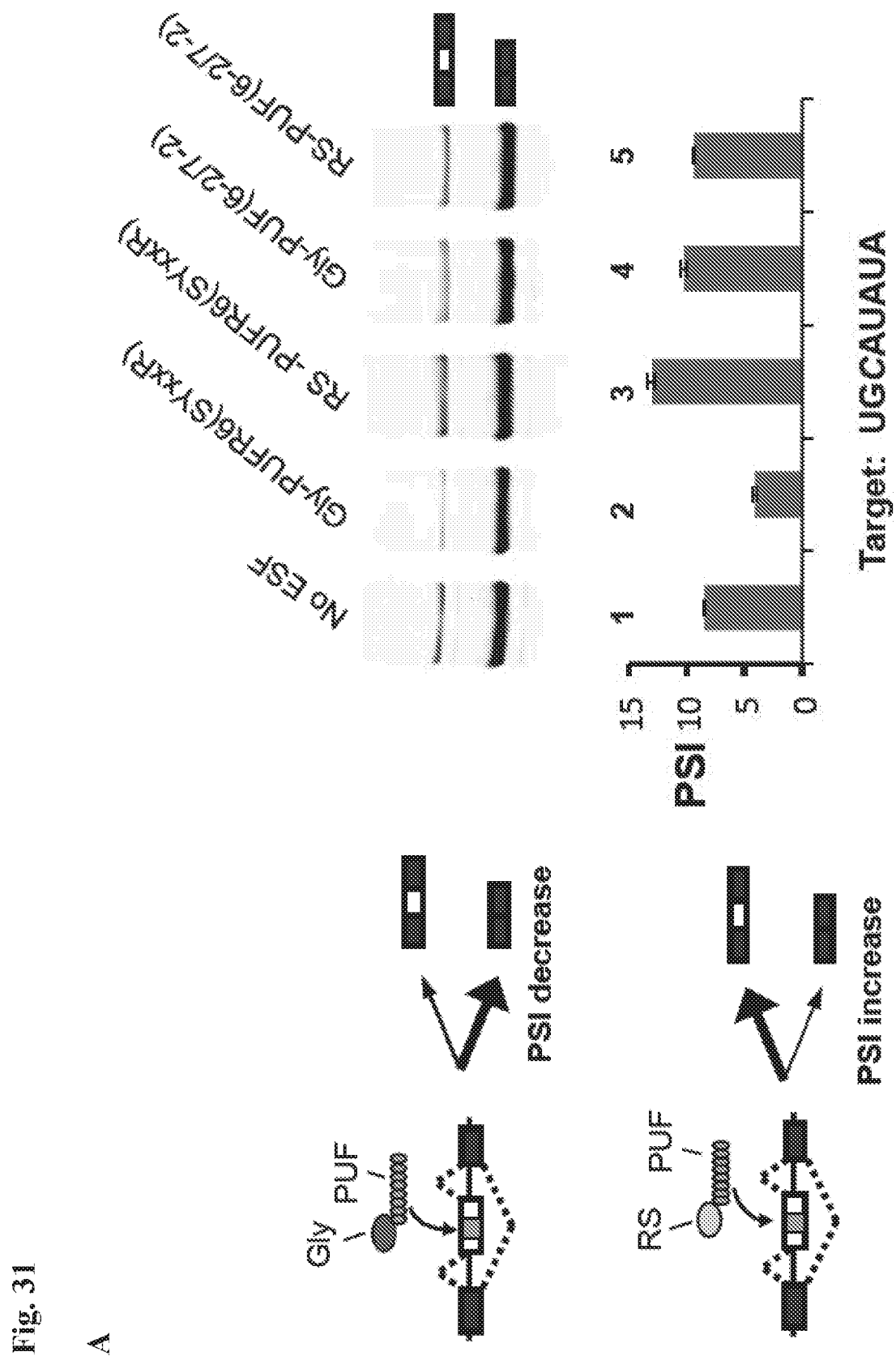
FIG. 31. Using the cytosine-recognition code to direct engineered splicing factors. (Panel A) Modulating alternative splicing of a cassette exon in a reporter RNA. Diagram of how the two types of ESFs can affect splicing of a cassette exon (left). Gly-PUF ESF directed to the exonic target can increase exon inclusion whereas the RS-PUF ESF can decrease exon inclusion. RT-PCR products of splicing reactions (top right) and quantification of splicing (bottom right). The splicing reporter gene and expression vectors for different ESFs were co-transfected at 1:2 ratio into 293T cells. Total RNA was purified 24 hours after transfection and splicing of test exon was detected with RT-PCR. The percentage of exon included isoform among all isoforms is represented with psi value (percent-spliced-in). The transfections were carried out in duplicate, and means of the value were plotted with error bar indicating the data range. Significant changes (p values are 0.04 and 0.01 for lanes 2 and 3 as judged by paired t-test) were observed for ESFs that recognize cognate C-containing target. (Panel B) Design of ESFs to target endogenous VEGF-A pre-mRNA splicing.
Figure 31:
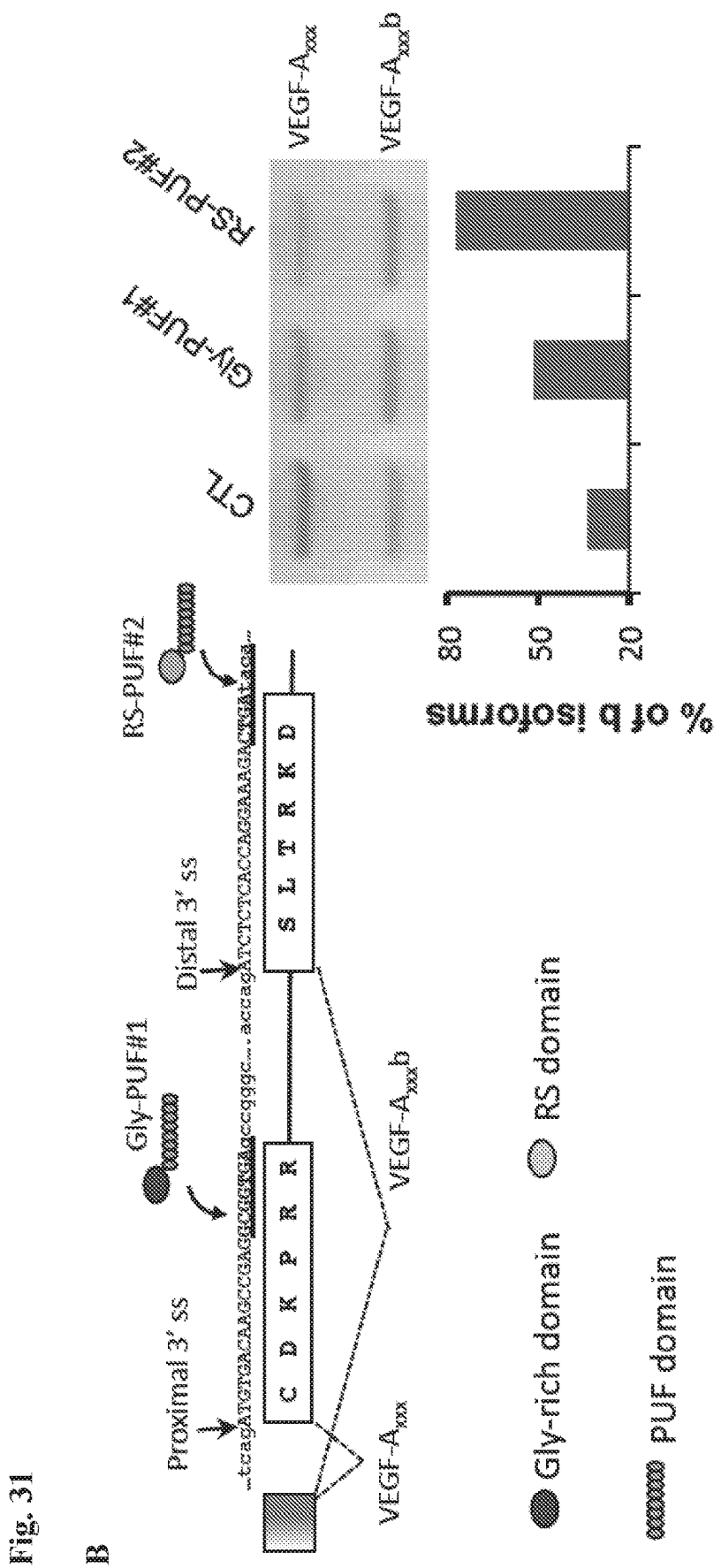

To expand the application of ESFs, ESFs were created that can target C-containing elements by fusing either the Gly-rich domain of hnRNP A1 or the RS domain of ASF/SF2 with the PUF-R6(SYxxR) domain that specifically recognizes UGCAUAUA. This ESF was tested by co-transfecting 293T cells with plasmids expressing the ESF and a splicing reporter containing the cognate 8-nt target sequence in an alternatively spliced cassette exon. Changes in alternative splicing were analyzed using body-labeled RT-PCR (FIG. 31, Panel A) (16). As designed, the Gly-PUF-R6(SYxxR) ESF repressed the inclusion of the cassette exon containing a UGCAUAUA target sequence, whereas the RS—PUF-R6(SYxxR) ESF increased exon inclusion (FIG. 31, Panel A, lanes 2 and 3). Splicing modulation is sequence specific, as control ESFs with non-cognate PUF domains had little effect on exon inclusion (FIG. 31, Panel A, lanes 4 and 5).

ESFs were designed to control the splicing of an endogenous gene using recognition of a C-containing target sequence. The alternative splicing of VEGF-A, an important mediator of angiogenesis and a key anti-tumor target, was chosen for manipulation. The VEGF-A gene contains 8 exons that undergo extensive alternative splicing to produce multiple isoforms. One newly discovered class of isoforms (b isoforms) has anti-angiogenic activity that is opposite to canonical VEGF-A isoforms (29,30). Most solid cancers are associated with a switch from the VEGF-A b isoforms to the pro-angiogenic a isoforms to promote angiogenesis. Thus, restoring the normal splicing balance to the b isoforms may have potential as a new anti-VEGF cancer therapy.

The two classes of VEGF-A isoforms are generated by the alternative use of a 3' splice site (ss) in exon 8 (FIG. 31, Panel B). Pro-angiogenic isoforms are spliced with a proximal 3' ss, and the anti-angiogenic b isoforms are spliced with a distal 3' ss. The choice of alternative 3' ss is generally controlled by regulatory cis-elements between the proximal and distal splice sites and/or inside the "core" exonic region. Therefore, new PUF domains were designed to specifically recognize sequences in these regions.

Two ESFs were designed to modulate VEGF-A alternative splicing: PUF #1 recognized the sequence GCG-GUGAG between the proximal and distal 3' ss and PUF #2 recognized the sequence CUGAUACA downstream of the distal 3' ss (FIG. 31, Panel B). The Gly-PUF #1 ESF should inhibit splicing of pro-angiogenic isoforms (VEGF-$A_{xxx}$), whereas the RS-PUF #2 ESF should promote anti-angiogenic VEGF-$A_{xxx}$ b isoforms, thus both should shift VEGF-A splicing toward the b isoforms. When each ESF was expressed in MDA-MB-231 cells, it was found that either ESF shifted splicing toward the anti-angiogenic isoforms.

The identification of a modular code to recognize cytosine makes it possible to design PUF domains to bind any given sequence and broadens opportunities to create new research tools and therapeutic reagents. This application was demonstrated by developing new ESFs to specifically modulate the alternative splicing of VEGF-A, a key regulator of angiogenesis and cancer growth, and designing PUF domains that recognize pathogenic CUG repeats. Combined with gene delivery tools, such artificial proteins have potential for us as new therapeutic reagents.

References for Example 4

1. Auweter, S. D., Oberstrass, F. C., and Allain, F. H. (2006) *Nucleic Acids Res* 34, 4943-4959
2. Crittenden, S. L., Bernstein, D. S., Bachorik, J. L., Thompson, B. E., Gallegos, M., Petcherski, A. G., Moulder, G., Barstead, R., Wickens, M., and Kimble, J. (2002) *Nature* 417, 660-663
3. Wickens, M., Bernstein, D. S., Kimble, J., and Parker, R. (2002) *Trends Genet* 18, 150-157
4. Dubnau, J., Chiang, A. S., Grady, L., Barditch, J., Gossweiler, S., McNeil, J., Smith, P., Buldoc, F., Scott, R., Certa, U., Broger, C., and Tully, T. (2003) *Curr Biol* 13, 286-296
5. Schweers, B. A., Walters, K. J., and Stern, M. (2002) *Genetics* 161, 1177-1185
6. Ye, B., Petritsch, C., Clark, I. E., Gavis, E. R., Jan, L. Y., and Jan, Y. N. (2004) *Curr Biol* 14, 314-321
7. Chen, G., Li, W., Zhang, Q. S., Regulski, M., Sinha, N., Barditch, J., Tully, T., Krainer, A. R., Zhang, M. Q., and Dubnau, J. (2008) *PLoS Comput Biol* 4, e1000026
8. Wang, X., McLachlan, J., Zamore, P. D., and Hall, T. M. (2002) *Cell* 110, 501-512
9. Wang, X., Zamore, P. D., and Hall, T. M. (2001) *Mol Cell* 7, 855-865
10. Lu, G., and Hall, T. M. (2011) *Structure* 19, 361-367
11. Cheong, C. G., and Hall, T. M. (2006) *Proc Natl Acad Sci USA* 103, 13635-13639
12. Ozawa, T., Natori, Y., Sato, M., and Umezawa, Y. (2007) *Nat Methods* 4, 413-419
13. Tilsner, J., Linnik, O., Christensen, N. M., Bell, K., Roberts, I. M., Lacomme, C., and Oparka, K. J. (2009) *Plant J* 57, 758-770
14. Opperman, L., Hook, B., DeFino, M., Bernstein, D. S., and Wickens, M. (2005) *Nat Struct Mol Biol* 12, 945-951
15. Koh, Y. Y., Opperman, L., Stumpf, C., Mandan, A., Keles, S., and Wickens, M. (2009) *RNA* 15, 1090-1099
16. Wang, Y., Cheong, C. G., Hall, T. M., and Wang, Z. (2009) *Nat Methods* 6, 825-830
17. Zhu, D., Stumpf, C. R., Krahn, J. M., Wickens, M., and Hall, T. M. (2009) *Proc Natl Acad Sci USA* 106, 20192-20197
18. Hook, B., Bernstein, D., Zhang, B., and Wickens, M. (2005) *RNA* 11, 227-233
19. Stumpf, C. R., Opperman, L., and Wickens, M. (2008) *Methods Enzymol* 449, 295-315
20. Fox, J. E., Burow, M. E., McLachlan, J. A., and Miller, C. A., 3rd. (2008) *Nat Protoc* 3, 637-645
21. Otwinowski, Z., and Minor, W. (1997) *Methods in Enzymology* 276, 307-326
22. McCoy, A. J., Grosse-Kunstleve, R. W., Adams, P. D., Winn, M. D., Storoni, L. C., and Read, R. J. (2007) *J Appl Crystallogr* 40, 658-674
23. Emsley, P., and Cowtan, K. (2004) *Acta Crystallogr D Biol Crystallogr* 60, 2126-2132
24. Adams, P. D., Afonine, P. V., Bunkoczi, G., Chen, V. B., Davis, I. W., Echols, N., Headd, J. J., Hung, L. W., Kapral, G. J., Grosse-Kunstleve, R. W., McCoy, A. J., Moriarty, N. W., Oeffner, R., Read, R. J., Richardson, D. C., Richardson, J. S., Terwilliger, T. C., and Zwart, P. H. (2010) *Acta Crystallogr D Biol Crystallogr* 66, 213-221
25. Filipovska, A., Razif, M. F. M., Nygård, K. K. A., and Rackham, O. (2011) *Nat Chem Biol* online publication
26. Koh, Y. Y., Wang, Y., Qiu, C., Opperman, L., Gross, L., Tanaka Hall, T. M., and Wickens, M. (2011) *RNA* 17, 718-727
27. Wheeler, T. M., and Thornton, C. A. (2007) *Curr Opin Neurol* 20, 572-576
28. Lee, J. E., and Cooper, T. A. (2009) *Biochem Soc Trans* 37, 1281-1286
29. Harper, S. J., and Bates, D. O. (2008) *Nat Rev Cancer* 8, 880-887
30. Qiu, Y., Hoareau-Aveilla, C., Oltean, S., Harper, S. J., and Bates, D. O. (2009) *Biochem Soc Trans* 37, 1207-1213
31. Schultz, J., Milpetz, F., Bork, P., and Ponting, C. P. (1998) *Proc Natl Acad Sci USA* 95, 5857-5864
32. Letunic, I., Doerks, T., and Bork, P. (2009) *Nucleic Acids Res* 37, D229-232
33. Gerber, A. P., Herschlag, D., and Brown, P. O. (2004) *PLoS Biol* 2, E79
34. Thomson, E., Rappsilber, J., and Tollervey, D. (2007) *RNA* 13, 2165-2174

The abbreviations used are: 3-AT, 3-aminotriazole; VEGF, Vascular endothelial growth factor; ONPG, O-nitrophenol-β-D-galactopyranoside; SMART, Simple modular architecture research tool; EMSA, electrophoretic mobility shift assay; ss, splice site.

The foregoing is illustrative of the present invention, and is not to be construed as limiting thereof. The invention is defined by the following claims, with equivalents of the claims to be included therein. All publications, patent applications, patents, patent publications, sequences identified by GenBank and/or SNP accession numbers, and other references cited herein are incorporated by reference in their entireties for the teachings relevant to the sentence and/or paragraph in which the reference is presented.

TABLE 1

Kinetic parameters of ASRE. Three independent experiments were performed and the results were fitted to Michaelis-Menten kinetics. The average values and the standard deviations of the independent experiments are listed. Since the activities were calculated assuming 100% of ASRE proteins are active, the rate constant ($k_{cat}$) of each ASRE is probably underestimated compared to the real value.

| ASRE | Target sequences | $K_m$ (μM) | $k_{cat}$ (min$^{-1}$) | $k_{cat}/K_m$ (M$^{-1}$min$^{-1}$) |
|---|---|---|---|---|
| Wt | NRE (UGUAUAUA) | 1.1 (±0.3) | 12.0 (±1.0) | 1.1 × 10$^7$ |
| 6-2/7-2 | 7u6g (UugUAUA) | 1.3 (±0.2) | 46.5 (±5.0) | 3.6 × 10$^7$ |
| 6-2/7-2/1-1 | 7u6g1g (UugAUAUg) | 1.6 (±0.8) | 28.7 (±3.0) | 1.8 × 10$^7$ |
| 531 | 5g3g1g (UGUgUgUg) | 2.0 (±1.2) | 5.1 (±3.3) | 2.5 × 10$^6$ |

TABLE 2

Linker Sequences

| Original ID[#] | AA sequence | PDB ID (Amino acids from) | Possible secondary structure | Possible Length (Å) | Result |
|---|---|---|---|---|---|
| 1ayrA_9 | V<u>D</u>T | 1AYR (347-349) | EEE | 7.307 | specific cleavage (weak) |
| 1al04_1 | V<u>D</u>FVGYPRFPAPVEFI (SEQ ID NO: 20) | 1AL0 (63-78) | HHHHTT CCCCCCC HHHH | 10.93 | specific cleavage (non-specific cleavage observed in longer incubation) |
| 1qlaB_1 | V<u>D</u>TG<u>NGS</u> (SEQ ID NO: 21) | 1QLB (105-111) | EECHHH H | 12.098 | specific cleavage |
| 1qaxA_3 | V<u>D</u>MALHARNIA (SEQ ID NO: 22) | 1QAX (381-390) | HHHHTTT HHH | 14.191 | specific cleavage |
| 1sesA_1 | V<u>D</u>LLALDREVQEL* (SEQ ID NO: 23) | 1SES (30-40) | HHHHHH HHHHH | 15.132 | specific cleavage |
|  | LLALDREVQE (SEQ ID NO: 24) |  | HHHHHH HHHH | ? | Weak specific cleavage |
|  | LLALDREVQ (SEQ ID NO: 25) |  | HHHHHH HHH | ? | specific cleavage |
|  | LLALDREV (SEQ ID NO: 26) |  | HHHHHH HH | ? | Non-specific cleavage |
| 1pfkA_2 | V<u>D</u>HIQRGGSP (SEQ ID NO: 27) | 1PFK (247-256) | CGGGGG CSCC | 17.728 | specific cleavage |
| 1doc_1 | V<u>D</u>RRMARDGLVH (SEQ ID NO: 28) | 1DOC (61-72) | CCHHHH HHCEEE | 20.463 | specific cleavage |

DSSP code for secondary structure:
G = 3-turn helix (310 helix). Min length 3 residues.
H = 4-turn helix (α helix). Min length 4 residues.
I = 5-turn helix (π helix). Min length 5 residues.
T = hydrogen bonded turn (3, 4 or 5 turn)
E = extended strand in parallel and/or anti-parallel β-sheet conformation. Minimal length 2 residues.
B = residue in isolated β-bridge (single pair β-sheet hydrogen bond formation)
S = bend (the only non-hydrogen-bond based assignment
*Deletions of one aa (one pitch 3 amino acid) from C-terminus each time to change the relative angle between PIN and PUF
[#]From linker data base
The underlined sequences are changed from original protein sequence to accommodate a SalI restriction site. In 1qlaB_1 the last two aromatic amino acids (W,F) are changed to G and S

TABLE 3

Nucleotide sequences recovered from the Y3H screen. In total 20 independent clones were sequenced and the resulting codons are listed with the encoded amino acid residue in parentheses. The residue at position 1043 (position 2 in the 5-residue RNA-interaction motif) is tyrosine for all clones. Clone #18 did not have an unambiguous sequence for the first codon (indicating either an A or C in the second position) and thus was disregarded in the analyses.

|  | AA position 1043 | AA position 1047 |
|---|---|---|
| Wild type | AAT(Asn) | CAA(Gln) |
| #1 | AGT(Ser) | AGA(Arg) |
| #2 | AGT(Ser) | AGA(Arg) |
| #3 | AGT(Ser) | AGG(Arg) |
| #5 | AGT(Ser) | AGA(Arg) |
| #6 | AGT(Ser) | CGC(Arg) |
| #7 | AGT(Ser) | AGG(Arg) |
| #8 | TCC(Ser) | CGA(Arg) |
| #9 | AGT(Ser) | CGG(Arg) |
| #10 | AGT(Ser) | CGG(Arg) |
| #11 | AGT(Ser) | AGA(Arg) |
| #12 | AGT(Ser) | AGG(Arg) |
| #13 | TCT(Ser) | AGG(Arg) |
| #14 | TCA(Ser) | CGT(Arg) |
| #15 | AAT(Asn) | TAG (stop) |
| #16 | AGT(Ser) | AGG(Arg) |
| #17 | AGT(Ser) | AGA(Arg) |
| #18 | A(A|C)T(Asn|Thr) | CGG(Arg) |
| #19 | AGT(Ser) | AGA(Arg) |
| #20 | AGT(Ser) | AGG(Arg) |

TABLE 4

Oligonucleotides

| Serial Number | Name | Sequence | SEQ ID NO: |
|---|---|---|---|
| 1 | PufEF1 | CACGAATTCAAGGCCGCAGCCGCCTTTTG | 29 |
| 2 | PufSR1 | CACGTCGACCCCTAAGTCAACACCGTTCTTC | 30 |
| 3 | Smg6SF1 | CACGTCGACACCGGCAACGGCTCTCAGATGGAGCTCGAAATCAGACC | 31 |
| 4 | Smg6NR1 | CACGCGGCCGCTTAGCCCACCTGGGCCCAC | 32 |
| 5 | Smg6EF1 | CACGAATTCAACAGATGGAGCTCGAAATCAGACC | 33 |
| 6 | Loop7.3SF1 | CACGTCGACACTCAGATGGAGCTCGAAATC | 34 |
| 7 | Loop_20SF1 | CACGTCGACCGTCGTATGGCTCGTGATGGTCTTGTTCATCATCAGATGGAGCTCGAAATC | 35 |
| 8 | SmSubHF1 | CACAAGCTTCCCTCATTGACTAGAGCTCC | 36 |
| 9 | GUXbR1 | CACTCTAGATGCATGCTCGACTTGGAAAAC | 37 |
| 10 | Puf87621_XhF1 | GGTTCTCGAGAATGTGATAAGTTCGGGC | 38 |
| 11 | Puf6-2/7-21G_XhF | GGTTCTCTCGAGAATTTGATATGTTCGGGC | 39 |
| 12 | pET43.1b_PufEF1 | CACGAATTCTGGCCGCAGCCGCCTTTTG | 40 |
| 13 | GUnested_XbR1 | CACTCTAGACCCTCACCTTGAATTGGGCC | 41 |
| 14 | GUHIF1 | ACCCAAGCTTGGTACCGAGCTTTTTTTTTTTTTTTT | 42 |
| 15 | GUHIF2 | ACCCAAGCTTGGTACCGAGC | 43 |
| 16 | 3'RACE_BamF1 | CACGGATCCGCATATTAGATTGCACCACC | 44 |
| 17 | AdhF1 | GGAGTGTTGTGGTGTAGTC | 45 |
| 18 | AdhR1 | GGACCCACTTCTGCCACCAC | 46 |
| 19 | LacZF1 | CCTGCTGATGAAGCAGCAGAACA | 47 |
| 20 | LacZR1 | AGACGATTCATTGGCACCAT | 48 |
| 21 | FtsZF1 | GAGGATCGCGATGCATTGC | 49 |
| 22 | FtsZR1 | CTTCAGCGACGACTGGTGC | 50 |
| 23 | Smg6-Pinf2 | CACGGATCGAATTCATGGAGCTCGAAATCAGAC | 51 |
| 24 | Smg6-Pinr2 | CACGCTAGCGCCCACCTGGGCCCAC | 52 |
| 25 | C-Puff | CACGCTAGCACCGGCAACGGCTCTGGCCGCAGCCGCTTTTG | 53 |
| 26 | C-PufR | CACGCGGCCGCTTACCCTAAGTCAACACCGTTCTTC | 54 |

TABLE 5

Nomenclature of ASREs and their targets

| Target sequences, mutations are marked in lower case (seq names) | Repeats with mutations in ASRE | ASRE nomenclature |
|---|---|---|
| UGUAUAUA (NRE) | — | Wt |
| UGUAUgUA (3g) | 3 | 3-2 |
| UugAUAUA (7u6g) | 7, 6 | 6-2/7-2 |
| UugAUAUg (7u6g1g) | 7, 6, 1 | 6-2/7-2/1-1 |
| UGUgUgUg (5g3g1g) | 5, 3, 1 | 531 |
| gugAUAag (8g7u6g2a1g) | 8, 7, 6, 2, 1 | 87621 |

What is claimed is:

1. A method of cleaving a target mRNA in a cell, comprising introducing into the cell a synthetic site-specific RNA endonuclease which comprises:
   (i) an RNA binding protein domain that comprises a variant of the human *Pumilio* 1 homology domain, wherein said variant comprises eight 36-mer repeats, wherein each of the eight 36-mer repeats binds to a single nucleotide in an eight-nucleotide target RNA, wherein said eight-nucleotide target RNA comprises at least one cytosine, and wherein said variant comprises all of amino acids 828 to 1176 of SEQ ID NO:149 except for modifications at one or more positions corresponding to:
      (a) positions 863 to 867 of SEQ ID NO:149,
      (b) positions 899 to 903 of SEQ ID NO:149,
      (c) positions 935 to 939 of SEQ ID NO:149,
      (d) positions 971 to 975 of SEQ ID NO:149,
      (e) positions 1007 to 1011 of SEQ ID NO:149,
      (f) positions 1043 to 1047 of SEQ ID NO:149,
      (g) positions 1079 to 1083 of SEQ ID NO:149, and/or
      (h) positions 1122 to 1126 of SEQ ID NO:149,
   wherein said modifications result in the variant comprising, in any combination, SerXXXGlu (SEQ ID NO:1) to bind guanine, (Cys/Ser)XXXGln (SEQ ID NO:66) to bind adenine, AsnXXXGln (SEQ ID NO:3) to bind uracil, and/or SerTyrXXArg (SEQ ID NO:4) to bind cytosine, wherein X is any amino acid;
   (ii) a linker peptide; and
   (iii) a cleavage domain that comprises a PilT N-terminus (PIN) domain of human SMG6, wherein the RNA binding domain is at the amino terminus of the synthetic site-specific RNA endonuclease and the cleavage domain is at the carboxy terminus of the synthetic site-specific RNA endonuclease, and wherein the cleavage domain cleaves upstream and/or downstream of the eight-nucleotide target RNA, and wherein the RNA binding protein domain of the RNA endonuclease is modified to bind the target mRNA, under conditions whereby cleavage of the mRNA occurs, thereby cleaving the target mRNA in the cell.

2. A method of inhibiting expression of a target gene in a cell, comprising introducing into the cell a synthetic site-specific RNA endonuclease which comprises:
   (i) an RNA binding protein domain that comprises a variant of the human *Pumilio* 1 homology domain, wherein said variant comprises eight 36-mer repeats, wherein each of the eight 36-mer repeats binds to a single nucleotide in an eight-nucleotide target RNA, wherein said eight-nucleotide target RNA comprises at least one cytosine, and wherein said variant comprises all of amino acids 828 to 1176 of SEQ ID NO:149 except for modifications at one or more positions corresponding to:
(a) positions 863 to 867 of SEQ ID NO:149,
(b) positions 899 to 903 of SEQ ID NO:149,
(c) positions 935 to 939 of SEQ ID NO:149,
(d) positions 971 to 975 of SEQ ID NO:149,
(e) positions 1007 to 1011 of SEQ ID NO:149,
(f) positions 1043 to 1047 of SEQ ID NO:149,
(g) positions 1079 to 1083 of SEQ ID NO:149, and/or
(h) positions 1122 to 1126 of SEQ ID NO:149,
wherein said modifications result in the variant comprising, in any combination, SerXXXGlu (SEQ ID NO:1) to bind guanine, (Cys/Ser)XXXGln (SEQ ID NO:66) to bind adenine, AsnXXXGlu (SEQ ID NO:3) to bind uracil, and/or SerTyrXXArg (SEQ ID NO:4) to bind cytosine, wherein X is any amino acid;
(ii) a linker peptide; and
(iii) a cleavage domain that comprises a PilT N-terminus (PIN) domain of human SMG6,
wherein the RNA binding domain is at the amino terminus of the synthetic site-specific RNA endonuclease and the cleavage domain is at the carboxy terminus of the synthetic site-specific RNA endonuclease, and wherein the cleavage domain cleaves upstream and/or downstream of the eight-nucleotide target RNA, and wherein the RNA binding protein domain of the RNA endonuclease is modified to bind mRNA encoding a gene product of the target gene, under conditions whereby cleavage of the mRNA occurs, thereby inhibiting expression of the target gene in the cell.

3. The method of claim 1, wherein the RNA endonuclease is introduced into the cell via a viral vector comprising a nucleic acid encoding the RNA endonuclease.

4. The method of claim 3, wherein the viral vector is an adeno associated viral vector.

5. The method of claim 3, further comprising stably integrating the nucleic acid encoding the RNA endonuclease into the genome of the cell.

6. The method of claim 1, wherein the cell is in an organism.

7. The method of claim 6, wherein the organism is a mammal.

8. The method of claim 6, wherein the organism is a human.

9. A method of cleaving a target mRNA in a mitochondrion in a eukaryotic cell, comprising introducing into the cell a synthetic site-specific RNA endonuclease which comprises:
(i) an RNA binding protein domain that comprises a variant of the human *Pumilio* 1 homology domain, wherein said variant comprises eight 36-mer repeats, wherein each of the eight 36-mer repeats binds to a single nucleotide in an eight-nucleotide target RNA, wherein said eight-nucleotide target RNA comprises at least one cytosine, and wherein said variant comprises all of amino acids 828 to 1176 of SEQ ID NO:149 except for modifications at one or more positions corresponding to:
(a) positions 863 to 867 of SEQ ID NO:149,
(b) positions 899 to 903 of SEQ ID NO:149,
(c) positions 935 to 939 of SEQ ID NO:149,
(d) positions 971 to 975 of SEQ ID NO:149,
(e) positions 1007 to 1011 of SEQ ID NO:149,
(f) positions 1043 to 1047 of SEQ ID NO:149,
(g) positions 1079 to 1083 of SEQ ID NO:149, and/or
(h) positions 1122 to 1126 of SEQ ID NO:149,
wherein said modifications result in the variant comprising, in any combination, SerXXXGlu (SEQ ID NO:1) to bind guanine, (Cys/Ser)XXXGln (SEQ ID NO:66) to bind adenine, AsnXXXGln (SEQ ID NO:3) to bind uracil, and/or SerTyrXXArg (SEQ ID NO:4) to bind cytosine, wherein X is any amino acid;
(ii) a linker peptide; and
(iii) a cleavage domain that comprises a PilT N-terminus (PIN) domain of human SMG6,
wherein the RNA binding domain is at the amino terminus of the synthetic site-specific RNA endonuclease and the cleavage domain is at the carboxy terminus of the synthetic site-specific RNA endonuclease, and wherein the cleavage domain cleaves upstream and/or downstream of the eight-nucleotide target RNA, and wherein the RNA binding protein domain of the RNA endonuclease is modified to bind the target mRNA in the mitochondrion and wherein the RNA endonuclease comprises a mitochondrial targeting signal sequence, under conditions whereby cleavage of the target mRNA in the mitochondrion occurs, thereby cleaving the target mRNA in the mitochondrion in the cell.

10. A method of inhibiting expression of a target mitochondrial gene in a eukaryotic cell, comprising introducing into the cell a synthetic site-specific RNA endonuclease which comprises:
(i) an RNA binding protein domain that comprises a variant of the human *Pumilio* 1 homology domain, wherein said variant comprises eight 36-mer repeats, wherein each of the eight 36-mer repeats binds to a single nucleotide in an eight-nucleotide target RNA, wherein said eight-nucleotide target RNA comprises at least one cytosine, and wherein said variant comprises all of amino acids 828 to 1176 of SEQ ID NO:149 except for modifications at one or more positions corresponding to:
(a) positions 863 to 867 of SEQ ID NO:149,
(b) positions 899 to 903 of SEQ ID NO:149,
(c) positions 935 to 939 of SEQ ID NO:149,
(d) positions 971 to 975 of SEQ ID NO:149,
(e) positions 1007 to 1011 of SEQ ID NO:149,
(f) positions 1043 to 1047 of SEQ ID NO:149,
(g) positions 1079 to 1083 of SEQ ID NO:149, and/or
(h) positions 1122 to 1126 of SEQ ID NO:149,
wherein said modifications result in the variant comprising, in any combination, SerXXXGlu (SEQ ID NO:1) to bind guanine, (Cys/Ser)XXXGln (SEQ ID NO:66) to bind adenine, AsnXXXGln (SEQ ID NO:3) to bind uracil, and/or SerTyrXXArg (SEQ ID NO:4) to bind cytosine, wherein X is any amino acid;
(ii) a linker peptide; and
(iii) a cleavage domain that comprises a PilT N-terminus (PIN) domain of human SMG6, wherein the RNA binding domain is at the amino terminus of the synthetic site-specific RNA endonuclease and the cleavage domain is at the carboxy terminus of the synthetic site-specific RNA endonuclease, and wherein the cleavage domain cleaves upstream and/or downstream of the eight-nucleotide target RNA and wherein the RNA binding protein domain of the RNA endonuclease is modified to bind mRNA encoding a gene product of the target mitochondrial gene and wherein the RNA endonuclease comprises a mitochondrial targeting signal sequence, under conditions whereby cleavage of the target mRNA in the mitochondrion occurs, thereby inhibiting expression of the target mitochondrial gene in the cell.

11. The method of claim 9, wherein the RNA endonuclease is introduced into the cell via a viral vector comprising a nucleic acid encoding the RNA endonuclease.

12. The method of claim 11, wherein the viral vector is an adeno associated viral vector.

13. The method of claim 11, further comprising stably integrating the nucleic acid encoding the RNA endonuclease into the genome of the cell.

14. The method of claim 9, wherein the cell is in an organism.

15. The method of claim 14, wherein the organism is a mammal.

16. The method of claim 14, wherein the organism is a human.

17. The method of claim 10, wherein the RNA endonuclease is introduced into the cell via a viral vector comprising a nucleic acid encoding the RNA endonuclease.

18. The method of claim 17, wherein the viral vector is an adeno associated viral vector.

19. The method of claim 17, further comprising stably integrating the nucleic acid encoding the RNA endonuclease into the genome of the cell.

* * * * *

UNITED STATES PATENT AND TRADEMARK OFFICE
CERTIFICATE OF CORRECTION

PATENT NO. : 10,815,476 B2
APPLICATION NO. : 16/021892
DATED : October 27, 2020
INVENTOR(S) : Wang et al.

Page 1 of 1

It is certified that error appears in the above-identified patent and that said Letters Patent is hereby corrected as shown below:

On the Title Page

Item (56) References Cited, OTHER PUBLICATIONS, Page 4, Column 1, Line 23: Please correct "Unjprot Accession No. Q14671" to read -- Uniprot Accession No. Q14671 --

In the Specification

Column 1, Line 25: Please correct "Oct. 29, 20195" to read -- Oct. 29, 2019 --

Column 8, Line 62: Please correct "means of the" to read -- means of the Ψ --

Column 23, Line 1: Please correct "MT-ATPS" to read -- MT-ATP8 --

Column 26, Line 28: Please correct "3-galactosidase" to read -- β-galactosidase --

Column 41, Line 49: Please correct "$(CUG)_1$" to read -- $(CUG)_n$ --

Column 45, Line 40: Please correct "250" to read -- ~250 --

Column 50, Line 8: Please correct "(a2)" to read -- (α2) --

Column 50, Line 10: Please correct "a2" to read -- α2 --

Column 55, Line 61: Please correct "02" to read -- O2 --

Signed and Sealed this
Twenty-third Day of March, 2021

Drew Hirshfeld
*Performing the Functions and Duties of the
Under Secretary of Commerce for Intellectual Property and
Director of the United States Patent and Trademark Office*